(12) United States Patent
Fire et al.

(10) Patent No.: US 8,716,462 B2
(45) Date of Patent: May 6, 2014

(54) LEVELS AND/OR SUSTAINABILITY OF DNA-BASED GENE EXPRESSION

(75) Inventors: Andrew Fire, Washington, DC (US); Lia Gracey, Stanford, CA (US); Weng-Onn Lui, Stockholm (SE)

(73) Assignees: Carnegie Institution of Washington, Washington, DC (US); The Board of Trustees of the Leland Stanford Junior University, Palo Alto, CA (US)

( * ) Notice: Subject to any disclaimer, the term of this patent is extended or adjusted under 35 U.S.C. 154(b) by 1140 days.

(21) Appl. No.: 12/162,243

(22) PCT Filed: Jan. 29, 2007

(86) PCT No.: PCT/US2007/002453
§ 371 (c)(1),
(2), (4) Date: Mar. 20, 2009

(87) PCT Pub. No.: WO2007/089732
PCT Pub. Date: Aug. 9, 2007

(65) Prior Publication Data
US 2009/0311786 A1 Dec. 17, 2009

Related U.S. Application Data

(60) Provisional application No. 60/762,504, filed on Jan. 27, 2006.

(51) Int. Cl.
*C07H 21/04* (2006.01)
*C12N 15/00* (2006.01)
*A61K 48/00* (2006.01)
*A01N 63/00* (2006.01)
*A01N 65/00* (2009.01)

(52) U.S. Cl.
USPC ............... 536/24.1; 435/320.1; 514/44 R; 424/93.1

(58) Field of Classification Search
None
See application file for complete search history.

(56) References Cited

U.S. PATENT DOCUMENTS 6,881,556 B2 * 4/2005 Antoniou et al. ............ 435/69.1
2002/0146824 A1 * 10/2002 Lamb et al. .................. 435/455

OTHER PUBLICATIONS

Fire, et al. (2006) "Unusual DNA Structures Associated with Germline Genetic Activity in *Caenorhabditis elegans*", Genetics, 173: 1259-73.*
Avramova, et al. (May 2002) "Heterochromatin in Animals and Plants. Similarities and Differences", Plant Physiology, 129(1): 40-49.*
Kogan et al. "Gene splice sites correlate with nucleosome psoitions." Gene 352: 57-62, 2005.

* cited by examiner

*Primary Examiner* — Robert M Kelly
(74) *Attorney, Agent, or Firm* — Morgan, Lewis & Bockius LLP

(57) ABSTRACT

The invention encompasses methods for improving the level and/or sustainability of expression for a target nucleic acid in a eukaryotic cell comprising: (a) modifying the target nucleic acid to introduce or to comprise signals that limit or constrain the positions of nucleosome cores, and (b) introducing the modified target nucleic acid into the eukaryotic cell, wherein the modified target nucleic acid has improved levels and/or sustainability of expression compared to original unmodified nucleic acid.

28 Claims, 105 Drawing Sheets

| GENOME | A+T% | PREDICTED BEAD INCIDENCE | | |
|---|---|---|---|---|
| | | UT91 | KWC86 | BMHT91 |
| C. ELEGANS | 64.6% | 3.52% | 0.81% | 2.52% |
| S. CEREVISAE | 61.7% | 0.19% | 0.015% | 0.25% |
| S. POMBE | 63.8% | 0.23% | 0.015% | 0.33% |
| D. MELANOGASTER* | 57.6% | 0.24% | 0.095% | 0.23% |
| A. THALIANA | 64.0% | 0.28% | 0.057% | 0.36% |
| GLOBAL MONTE CARLO* | 64.6% | 0.085% | 0.0045% | 0.17% |
| REPEAT-MASKED C. ELEGANS | 64.8% | 3.20% | 0.71% | 1.65% |

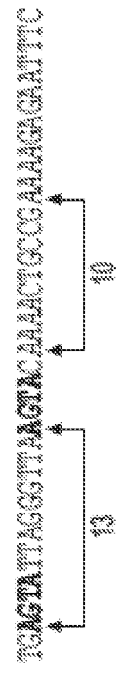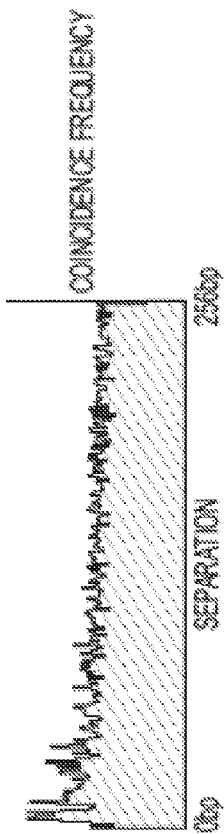
FIG. 3A

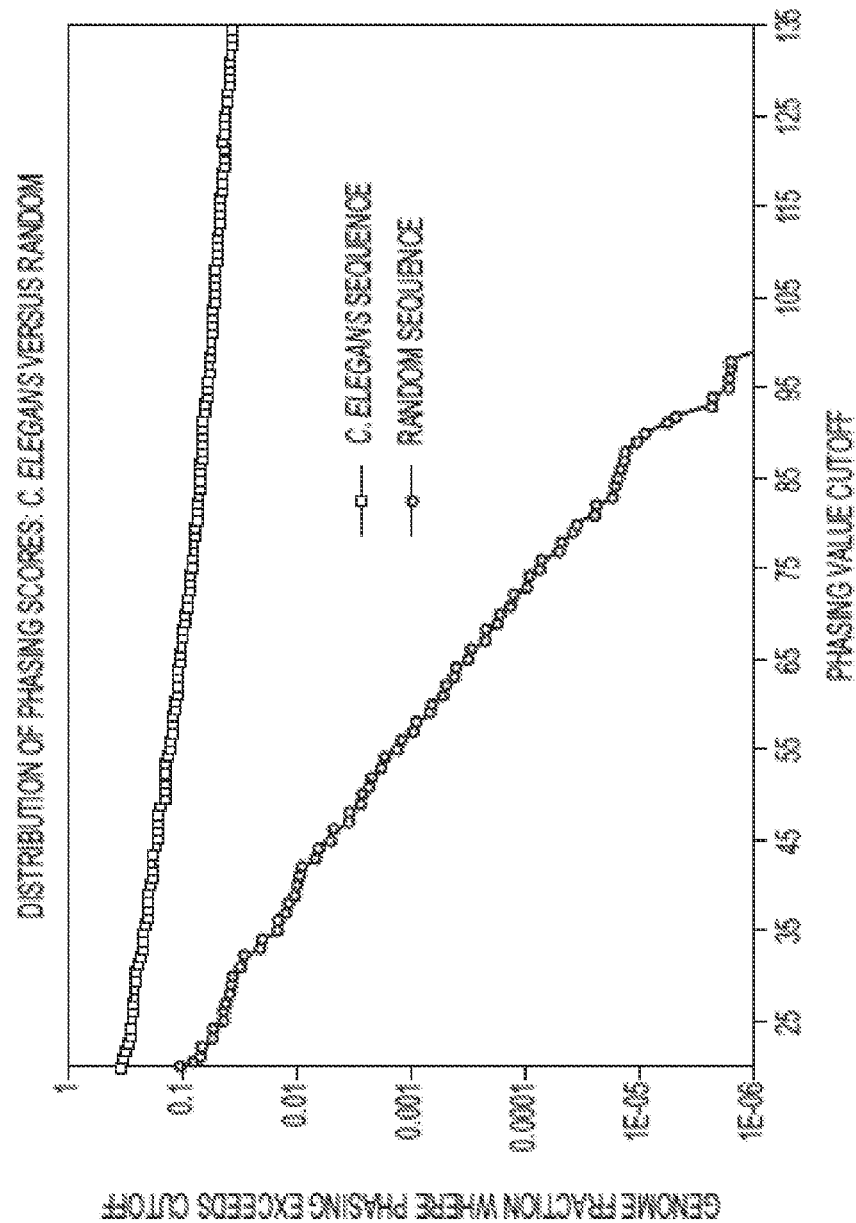

PHASING IN SOME NATURAL AND SIMULATED DNAs

| | |
|---|---|
| C. ELEGANS | 6.14% |
|   INTRONS | 12.88% |
|   EXONS | 0.38% |
|   INTERGENIC | 5.24% |
|   UNIQUE | 5.78% |
|   NON-UNIQUE | 9.27% |
| S. CEREVISIAE | 0.05% |
| S. POMBE | 0.17% |
| D. MELANOGASTER | |
|   EUCHROMATIN | 0.15% |
|   HETEROCHROMATIN | 0.44% |
| A. THALIANA | 0.39% |
| C. BRIGGSAE [DRAFT] | 3.54% |
| C. ELEGANS RANDOM [B] | 0.00016% |
| C. ELEGANS RANDOM [C] | 0.07% |

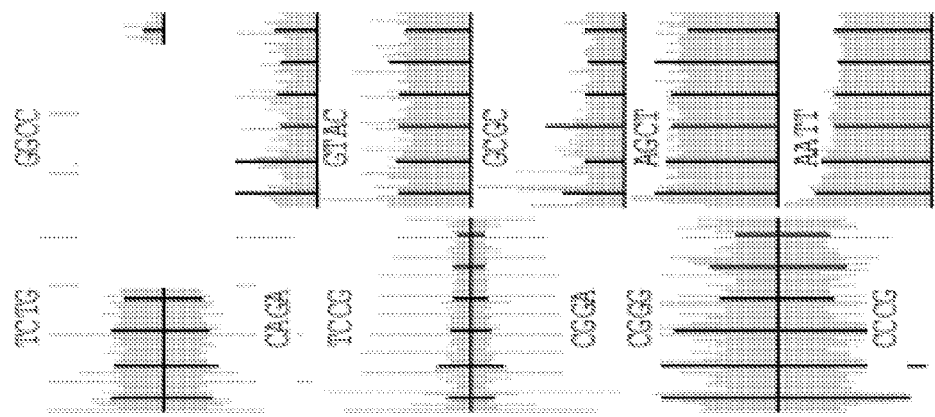
FIG. 8A
CONT.-2
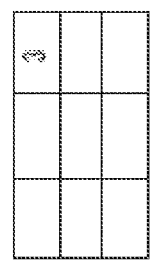

CONT.-3

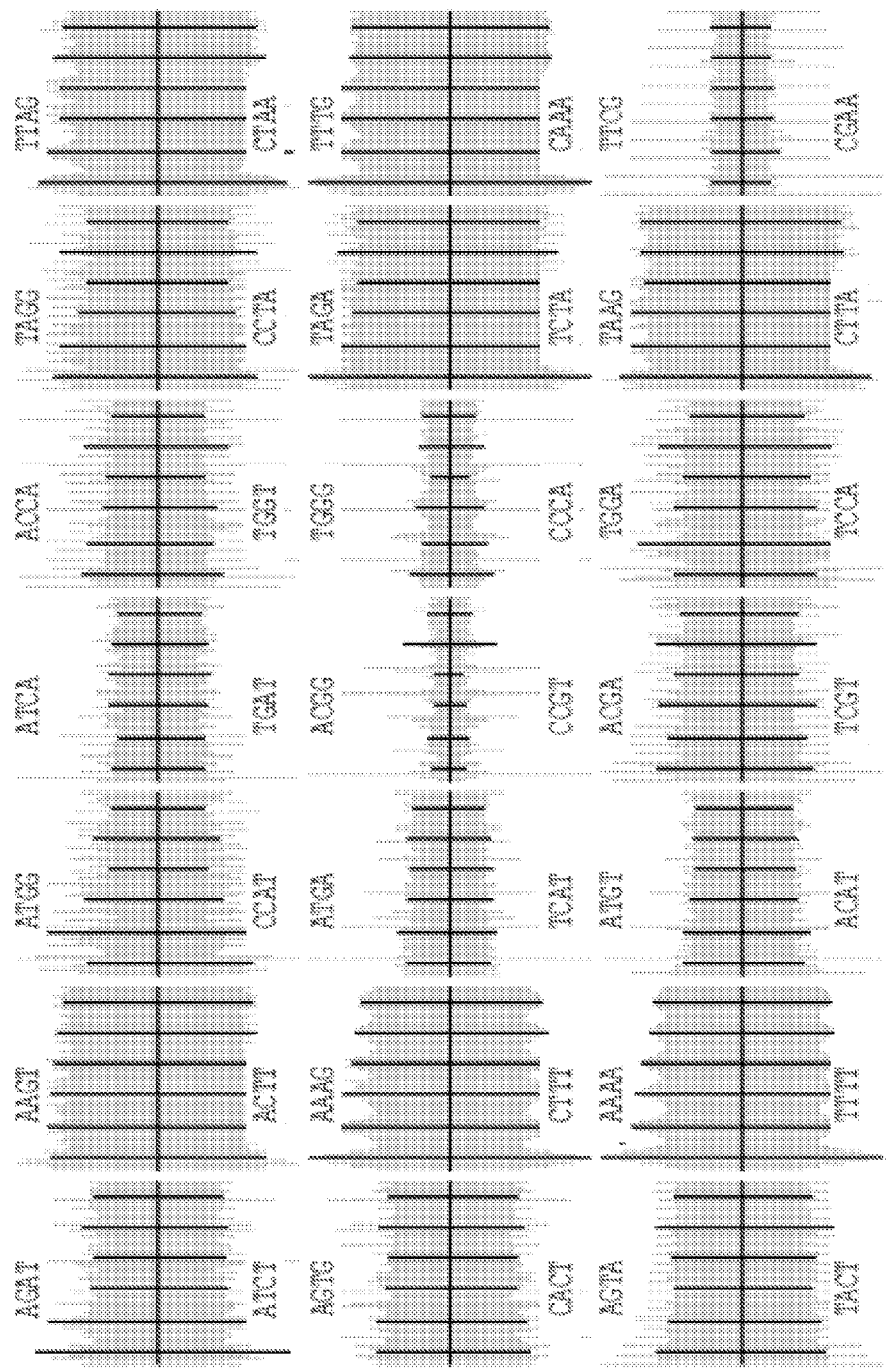
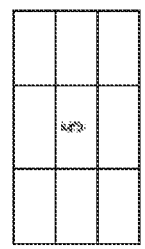
FIG. 8A
CONT.-4

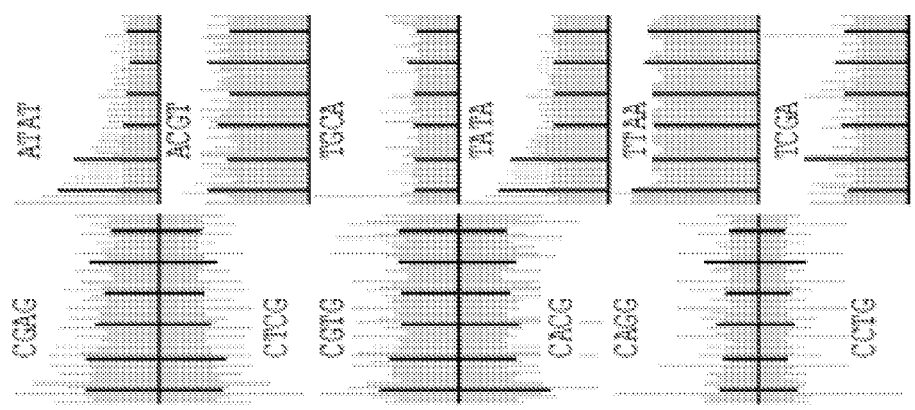
FIG. 8A
CONT.-5
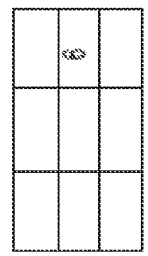

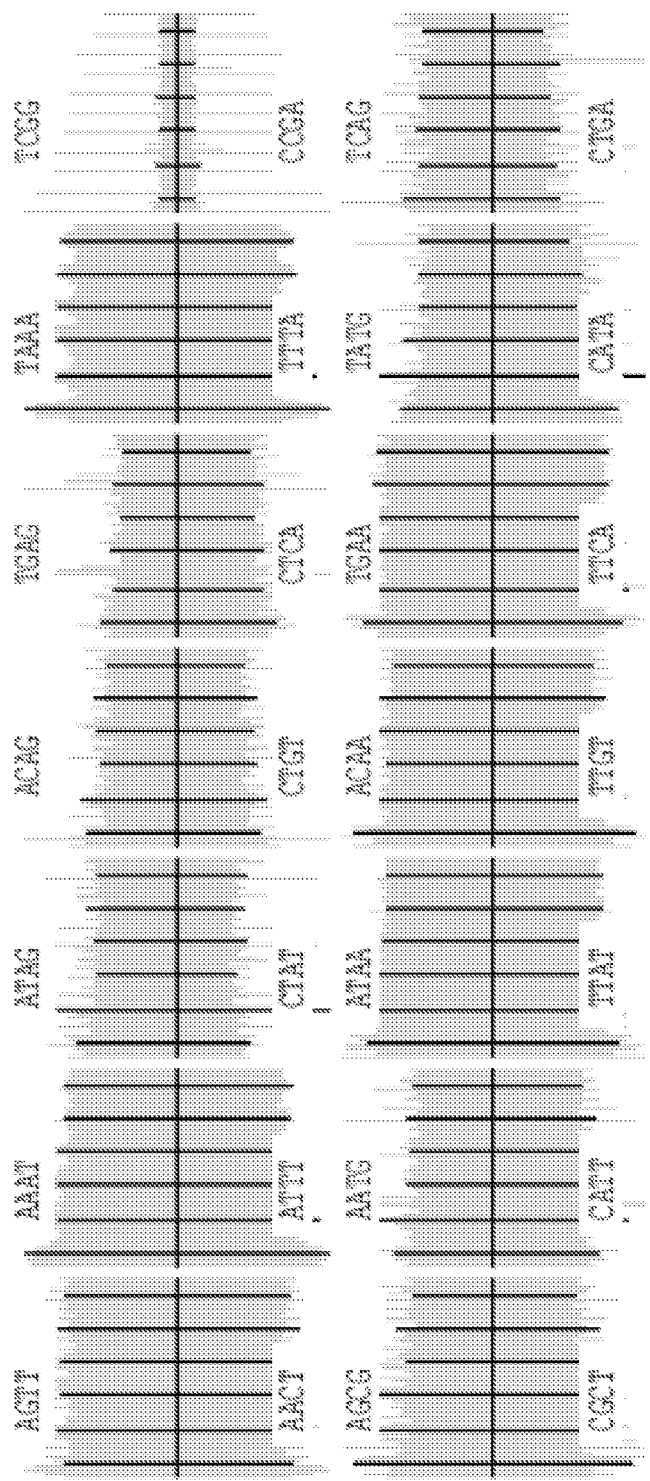
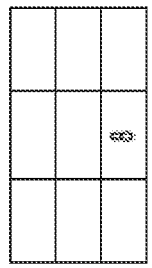
FIG. 8A
CONT.-7

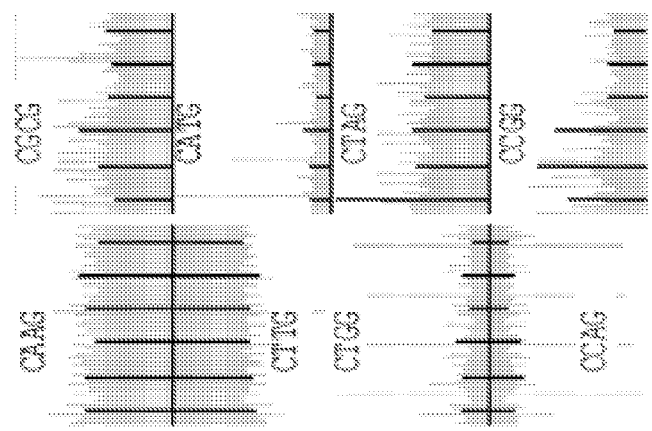
FIG. 8A
CONT.-8
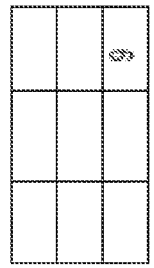

CONT.-1

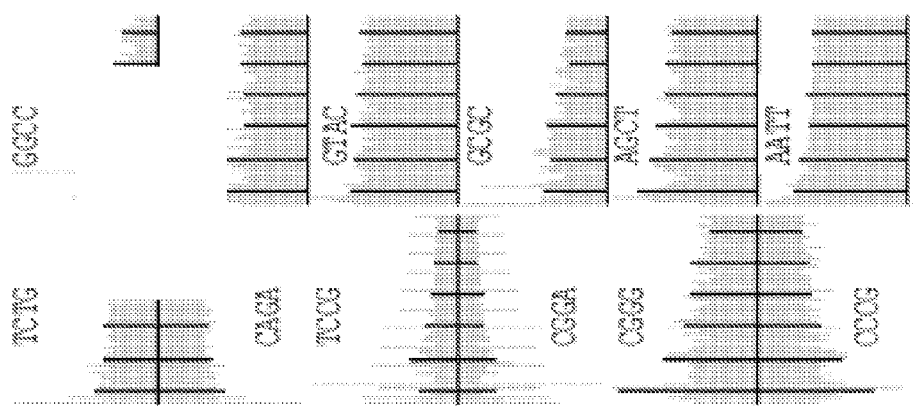
FIG. 8B
CONT.-2
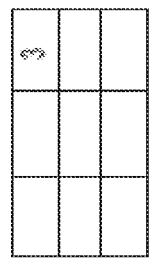

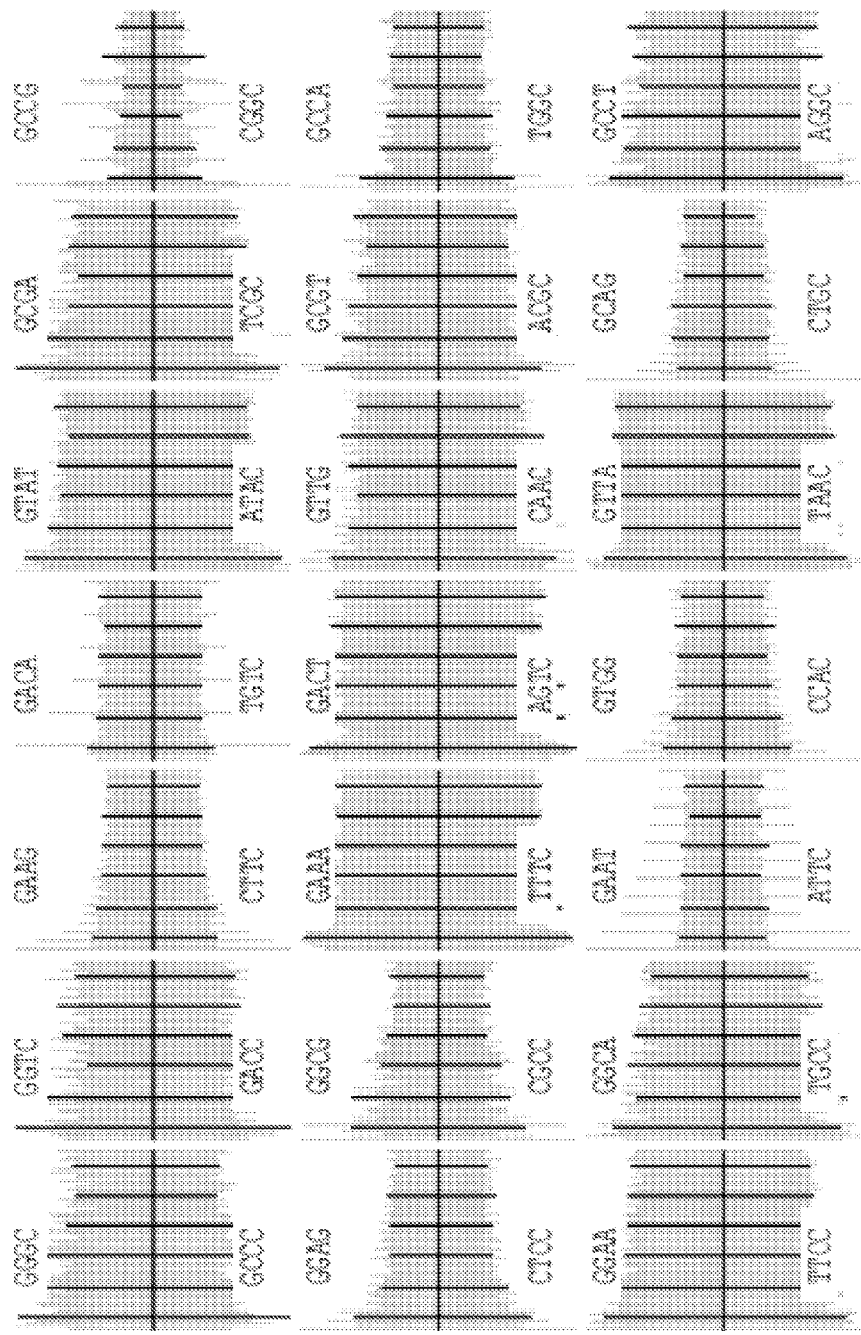
FIG. 8B CONT.-3
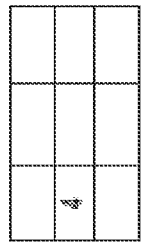

CONT.-4

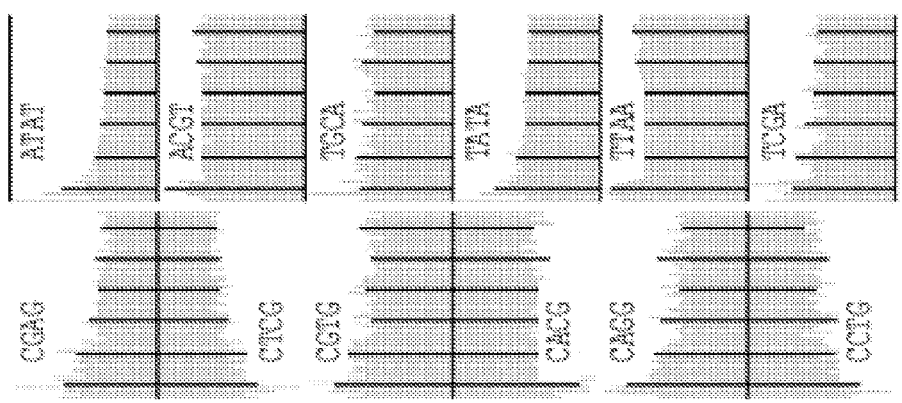
FIG. 8B
CONT.-5
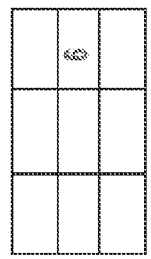

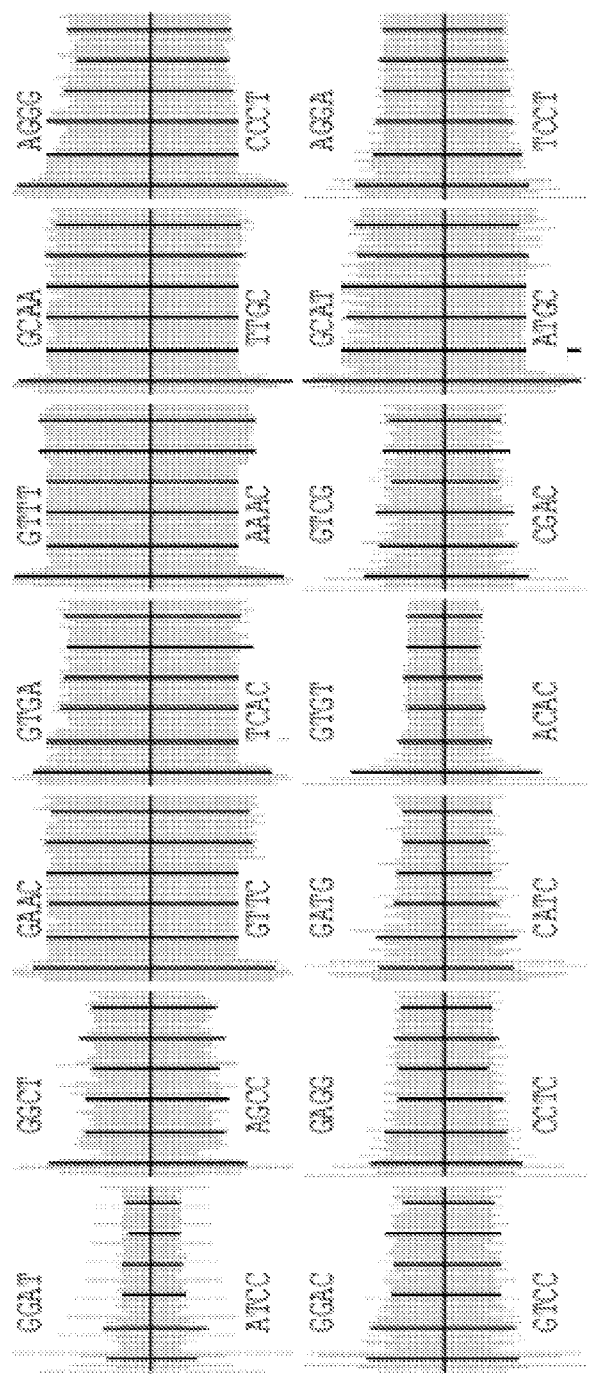
FIG. 8B
CONT.-6
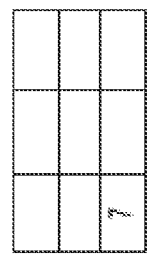

CONT.-7

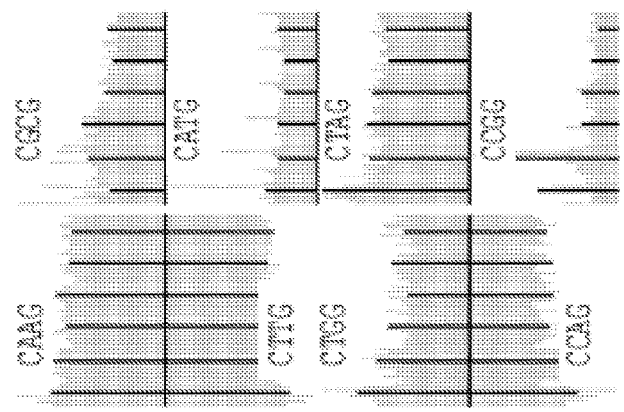
FIG. 8B CONT.-8
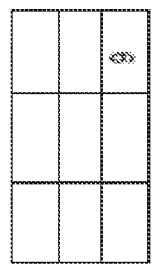

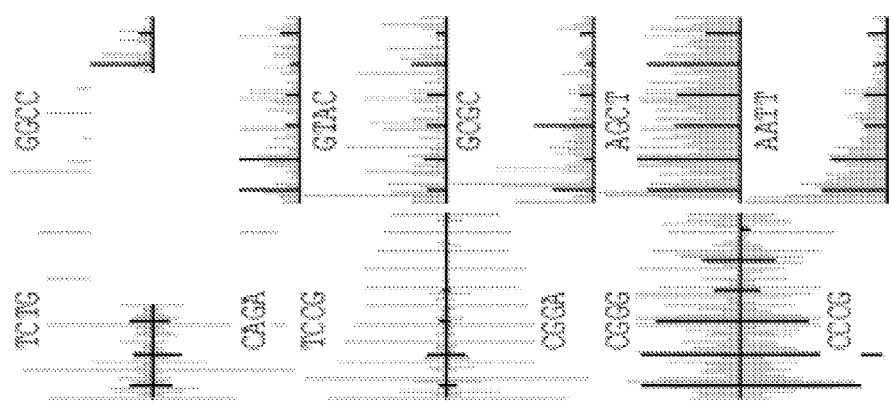

CONT.-3

CONT.-4

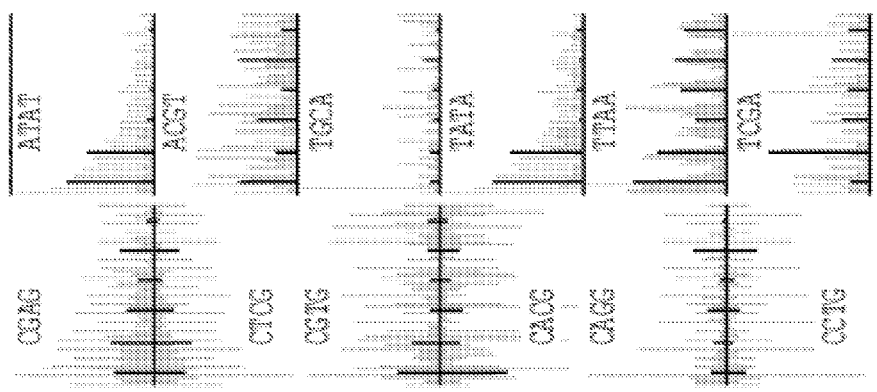
FIG. 8C CONT.-5
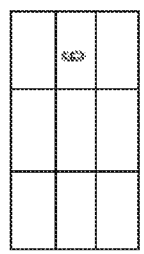

CONT.-6

CONT.-7

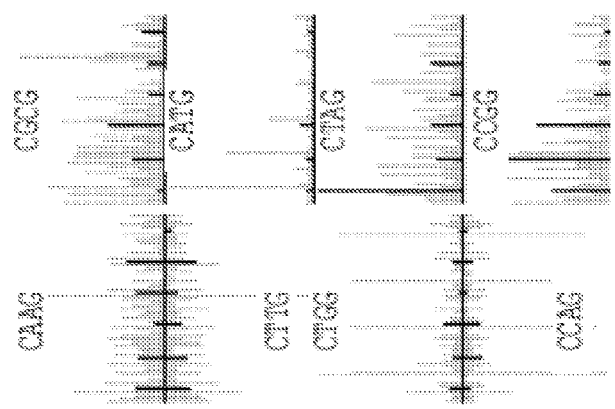

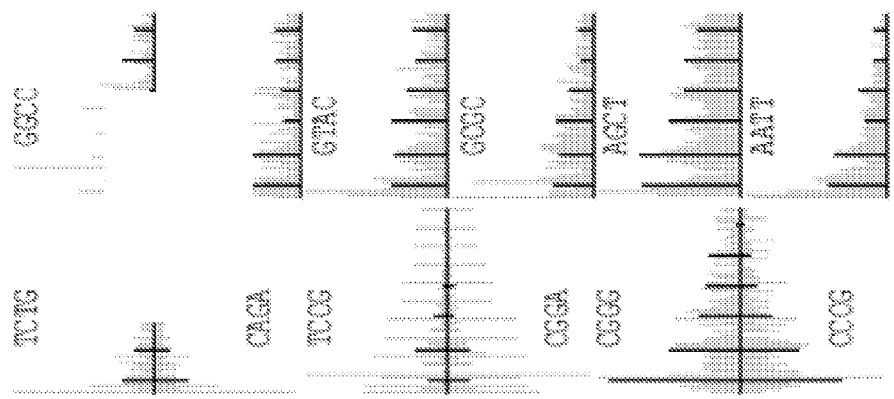
FIG. 8D
CONT.-2

CONT.-3

CONT.-4

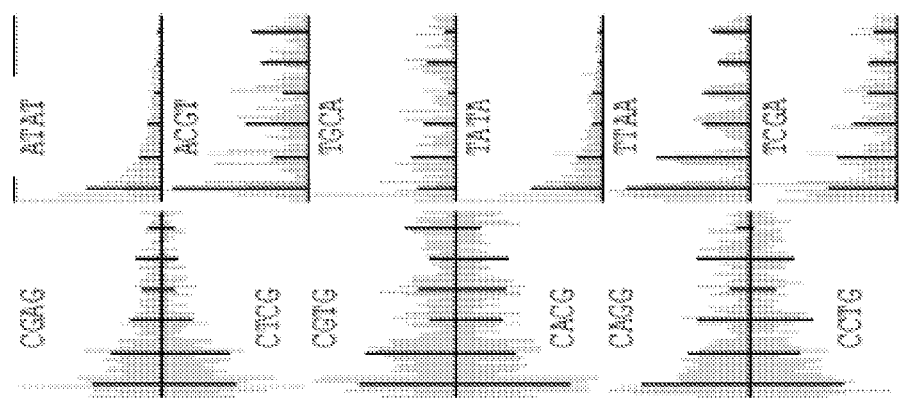
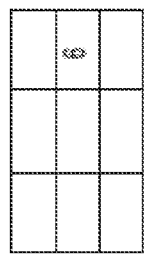
FIG. 8D
CONT.-5

CONT.-6

CONT.-7

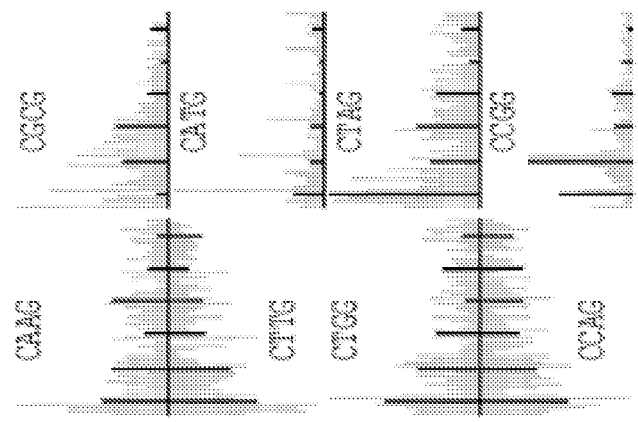
FIG. 8D
CONT.-8
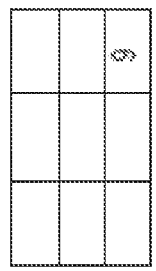

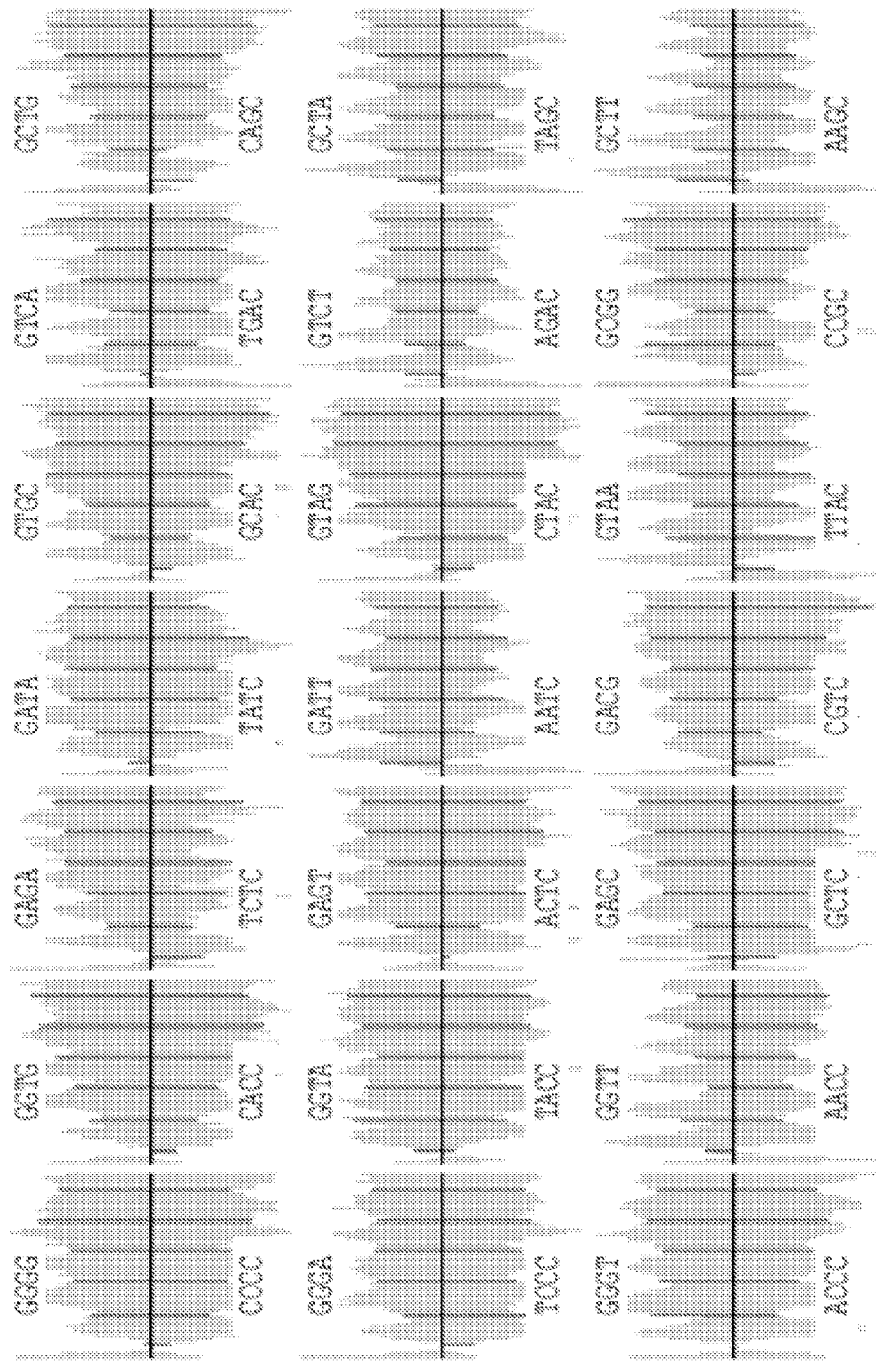
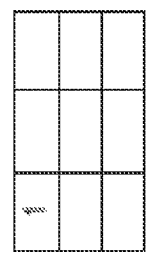
FIG. 9A

CONT.-1

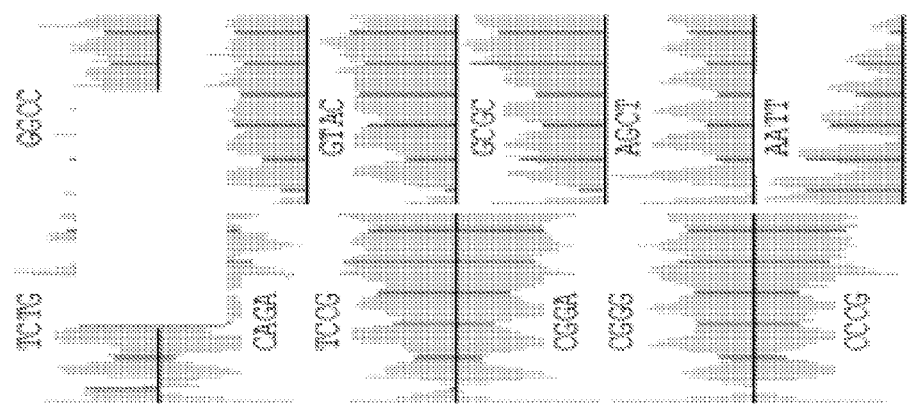
FIG. 9A CONT.-2

CONT.-3

CONT.-4

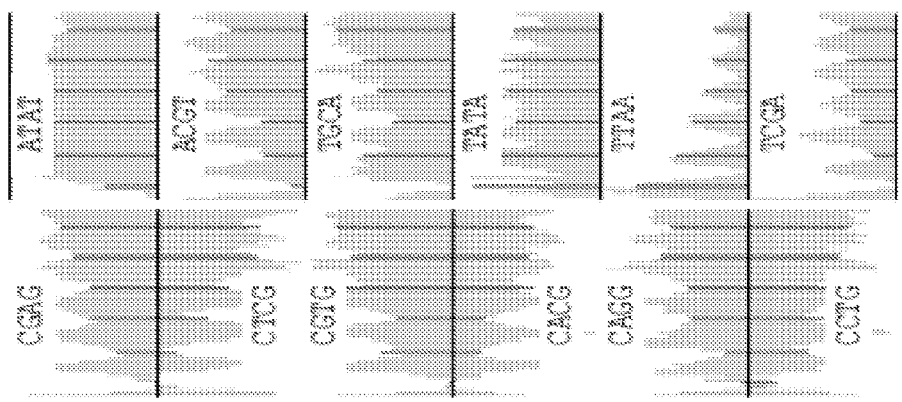
FIG. 9A
CONT.-5
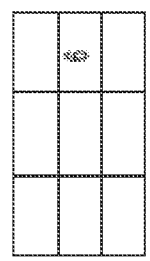

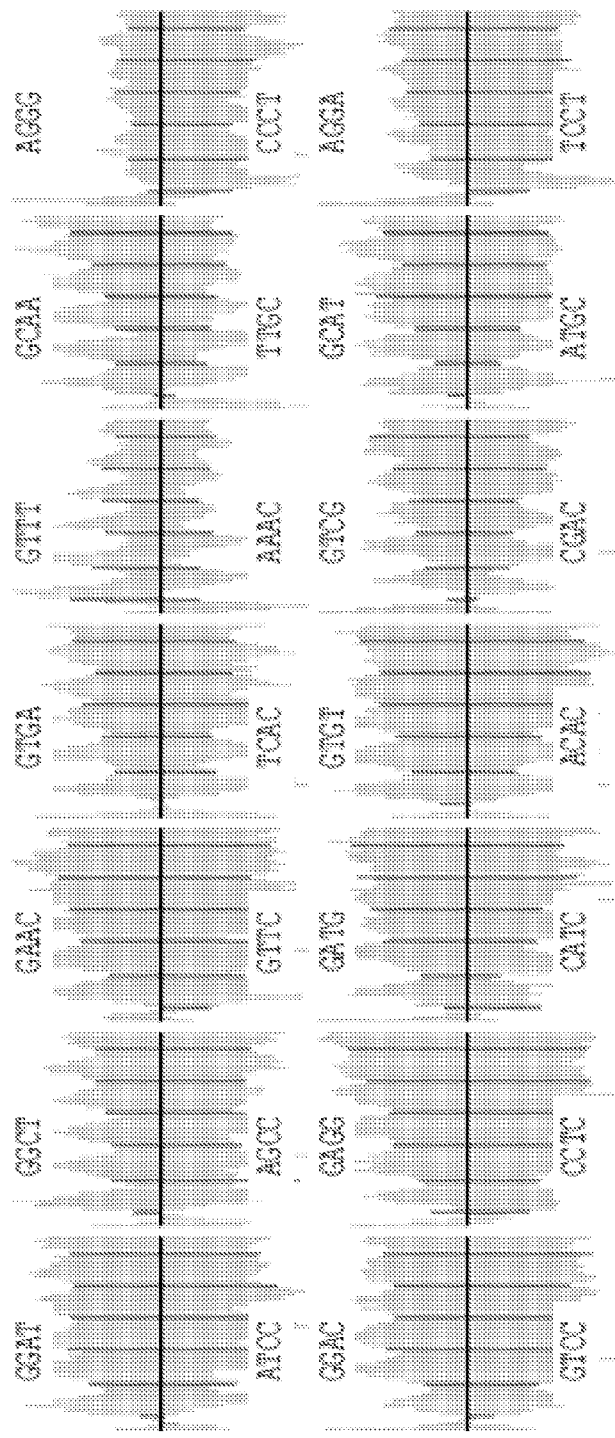
FIG. 9A
CONT.-6

CONT.-7

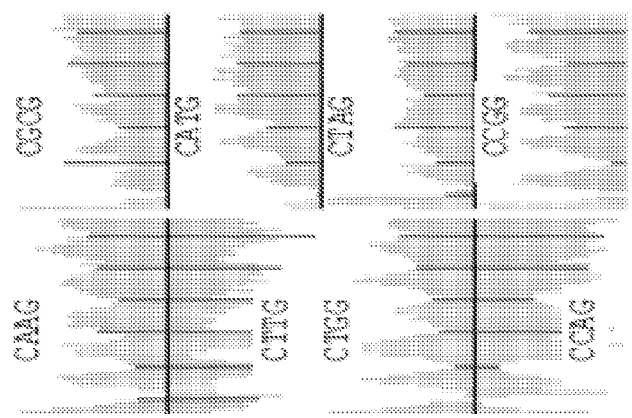
FIG. 9A
CONT.-8
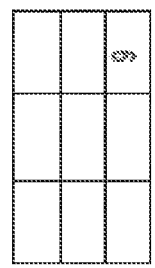

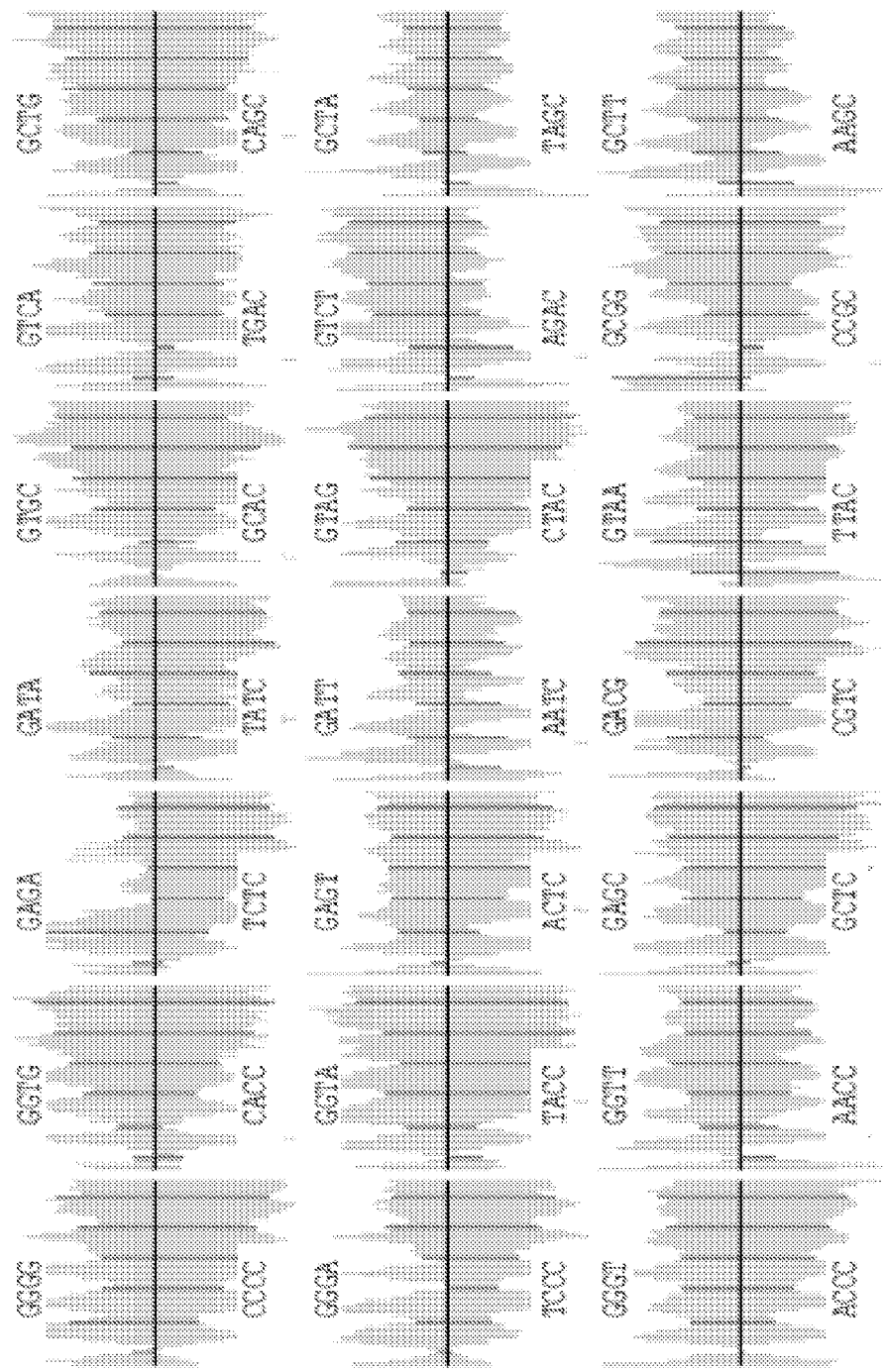
FIG. 9B
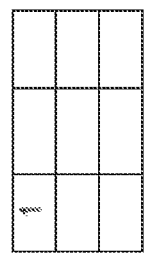

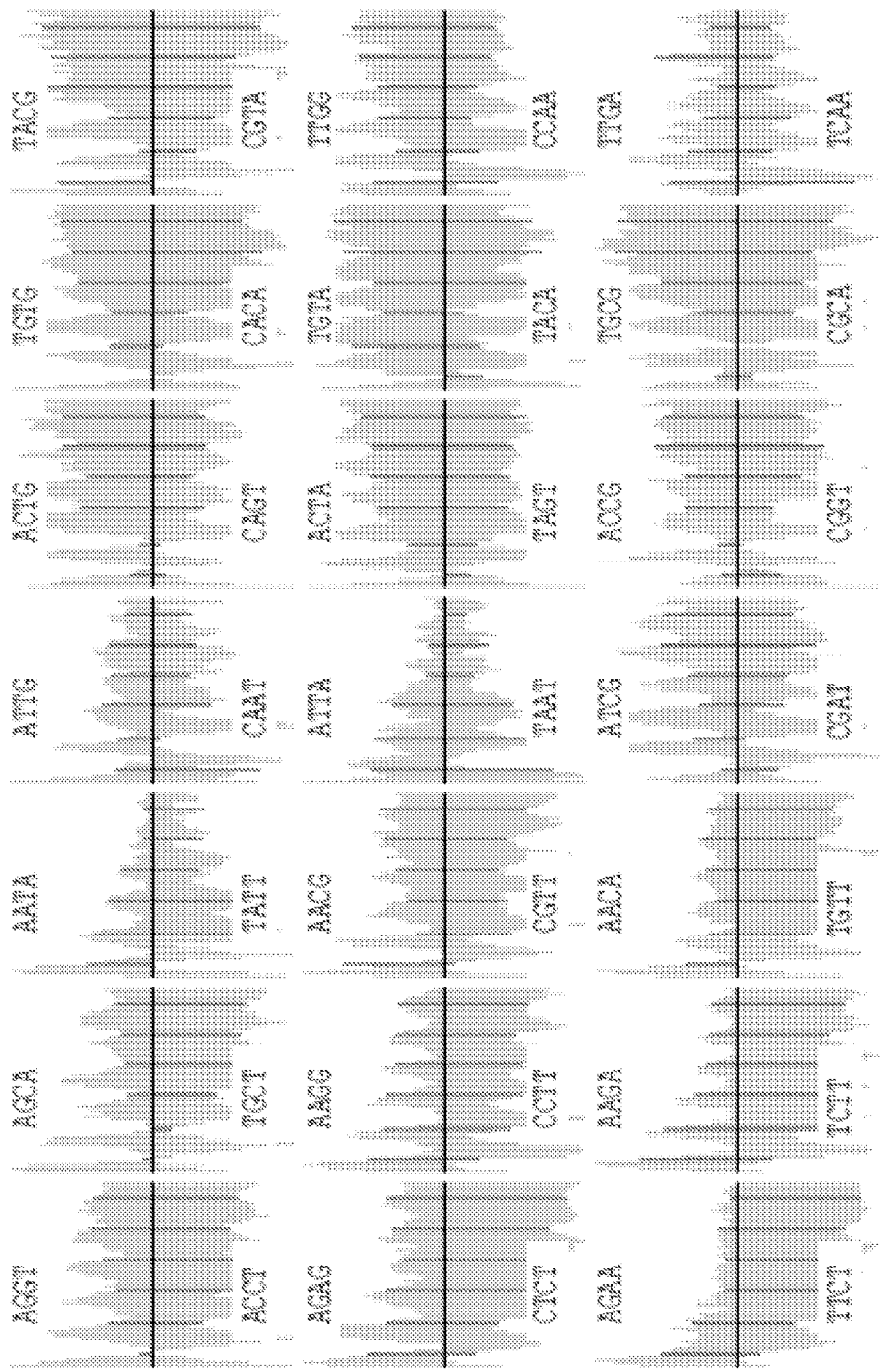
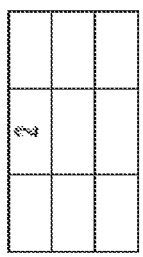
FIG. 9B CONT.-1

CONT.-2

CONT.-3

CONT.-4

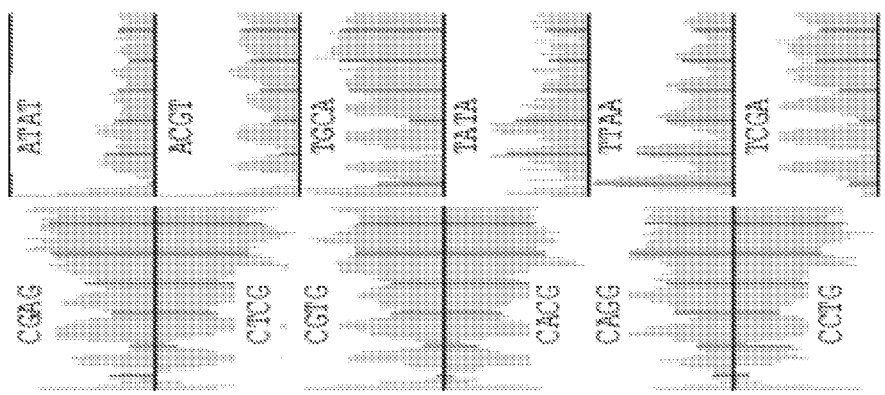
FIG. 9B CONT.-5

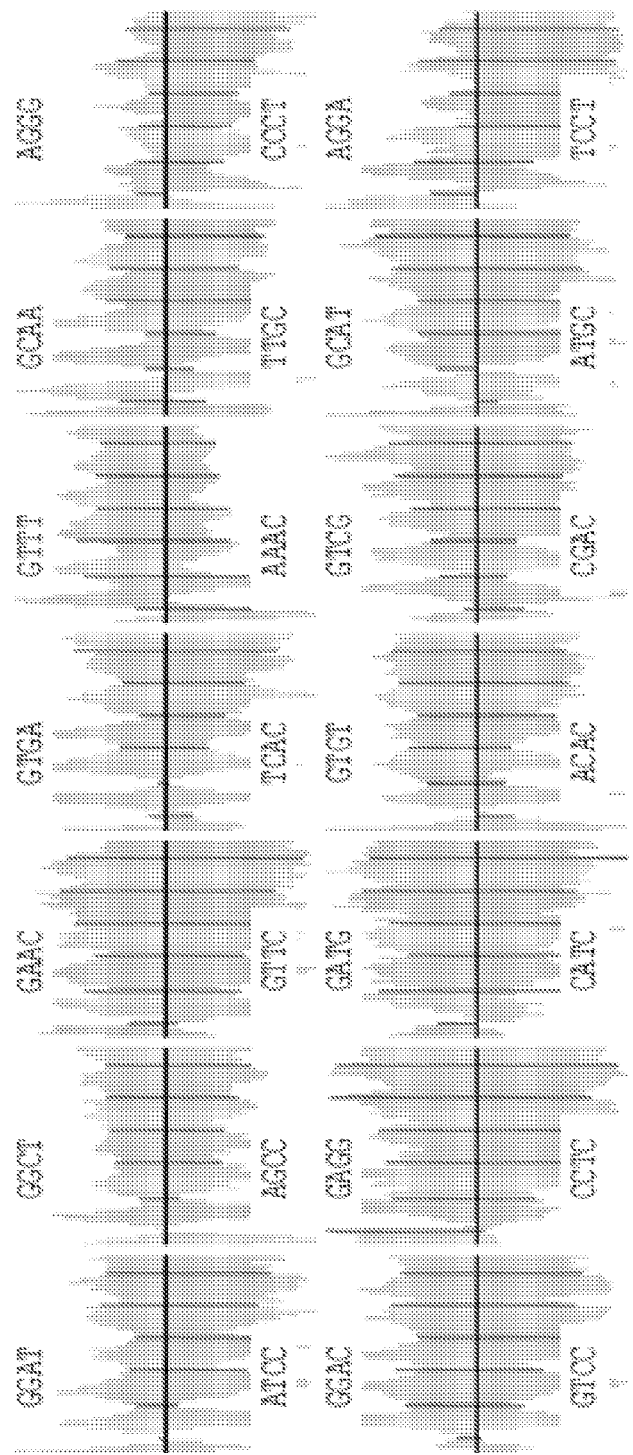
*FIG. 9B CONT.-6*
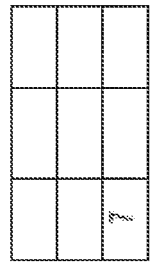

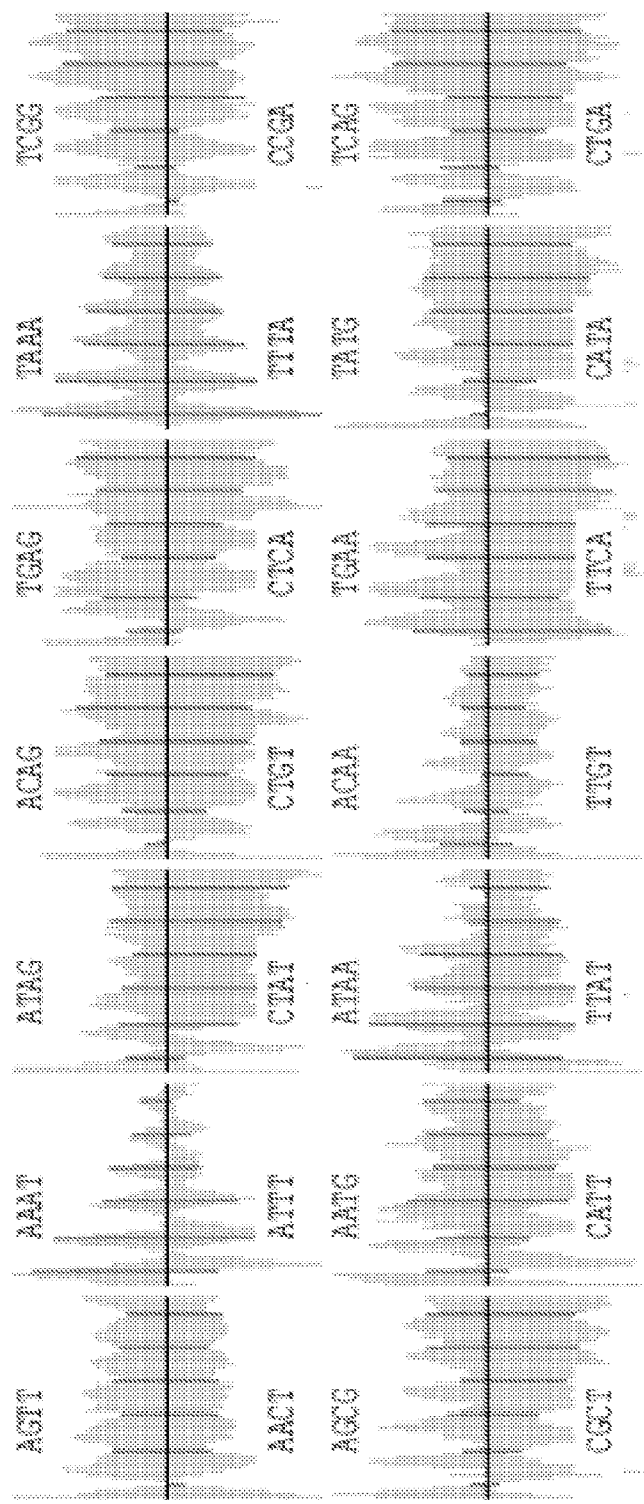
FIG. 9B
CONT.-7
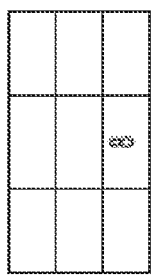

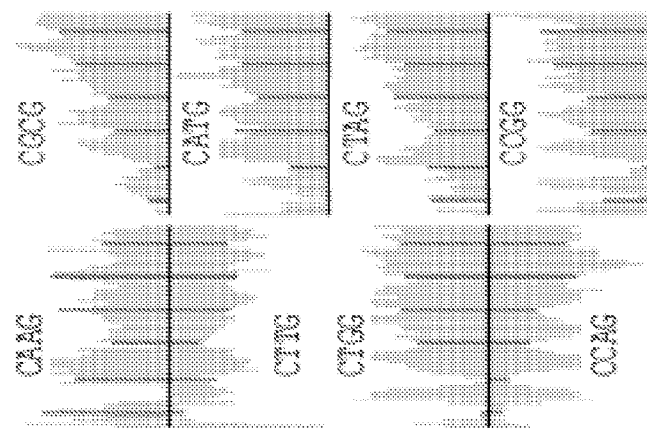
FIG. 9B
CONT.-8
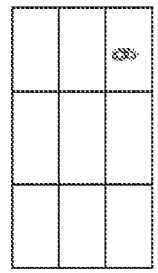

(SEQ ID NO: 2)
ATGTCAAAAGGAGAGGAATTGTTCACCGGCGTCGTTCCAATCCTCGTTGA
ACTCGACGGCGACGTCAACGGGCACAAGTTTTCCGTCTCTGGAGAGGGAG
AGGGAGACGCAACCTACGGCAAATTGACCCTAAATTCATTTGCACCACA
Ggtaagtttcgattttgctatcttttcacgattttactctctttttc
tactaactaacctccttttgaacattttcagGAAAATTGCCAGTTCC
ATGGCCAACATTGGTCACAACCTTCTGTTACGGCGTCCAATGCTTCTCGC
GTTACCCCGATCACATGAAAGGCACGACTTTTTAAATCCGCAATGCCA
GAAGGATACGTACAAGAACGCACAATTTTCTTCAAAGATGACGGAAACTA
CAAGACAAGgtaagttttcccaacttttcggacttttgaccgctttt
tatactaactaacggacttttcgtccttttcagGGCCGAAGTCAAGTT
TGAAGGAGACACCCTCGTCAACCGCATCGAACTTAAAGGAATTGACTTCA
AAGAAGACGGAAACATTCTCGGACACAAACTCGAATACAACTACAATTCT
CACAACGTTTACATAATGGCCGACAAACAAAGAACGGAATCAAGgtaag
tttcgcttttgatgattttggaccattttaggaattttcgatacta
actaactattttgcctgcttttcagGTCAACTTCAAGATTCGTCACAA
CATTGAGGACGGAAGCGTCCAACTTGCTGACCATTACCAGCAAAACACCC
CGATGGCGACGGACCCGTCCTCCTTCCGGACAACCACTACCTCTCAACA
CAGAGCGCCCTCTCGAAAGACCCGAACGAGAAGAGgtaagtttatcgttt
ttcgacgatttttaccattttacgccattttgatactaactaacgcc
ttttaccgattttcagGGACCACATGGTCCTTTTGGAATTTGTTACGG
CCGCAGGCATCACCCACGGCATGGACGAACTCTACAAAtag

FIG. 13

| LINE | PLASMID | PROMOTER | ENHANCER | CODING REGION | EXPRESSION |
|---|---|---|---|---|---|
| JF5474.1 | LT138 | pie-1 (GERMLINE) | pie-1 (GERMLINE) | spgfp-1 | GERM LINE + SOME SOMA (GUT) |
| JF5475.1 | LT138 | pie-1 (GERMLINE) | pie-1 (GERMLINE) | spgfp-1 | GERM LINE + SOME SOMA (GUT) |
| JF5477.1 | LT138 | pie-1 (GERMLINE) | pie-1 (GERMLINE) | spgfp-1 | GERM LINE + SOME SOMA (GUT) |
| JF5478.1 | LT138 | pie-1 (GERMLINE) | pie-1 (GERMLINE) | spgfp-1 | SOME SOMA (GUT) |

| TRANSIENT | | | | | |
|---|---|---|---|---|---|
| | LT129 | unc-54 (BODY MUSCLE) | unc-54 (BODY MUSCLE) | spgfp-1 | BODY MUSCLE |
| PD8211 | LT324 | myo-2 (PHARYNX) | unc-54 (BODY MUSCLE) | spgfp-2 | PHARYNX + BODY MUSCLE |
| PD8212 | LT324 | myo-2 (PHARYNX) | unc-54 (BODY MUSCLE) | spgfp-2 | PHARYNX + BODY MUSCLE |

*FIG. 15*

(SEQ ID NO: 12)

```
GACGG ATCGG GAGAT CTCCC GATCC CCTAT GGTCG ACTCT CAGTA CAATC    50
TGCTC TGATG CCGCA TAGTT AAGCC AGTAT CTGCT CCCTG CTTGT GTGTT   100
GGAGG TCGCT GAGTA GTGCG CGAGC AAAAT TTAAG CTACA ACAAG GCAAG   150
GCTTG ACCGA CAATT GCATG AAGAA TCTGC TTAGG GTAG GCGTT TTGCG    200
CTGCT TGCG ATGTA CGGGC CAGAT ATACG CGTTG ACATT GATTA TTGAC    250
TAGTT ATTAA TAGTA ATCAA TTACG GGGTC ATTAG TTCAT AGCCC ATATA   300
TGGAG TTCCG CGTTA CATAA CTTAC GGTAA ATGGC CCGCC TGGCT GACCG   350
CCCAA CGACC CCCGC CCATT GACGT CAATA ATGAC GTATG TTCCC ATAGT   400
AACGC CAATA GGGAC TTTCC ATTGA CGTCA ATGGG TGGAC TATTT ACGGT   450
AAACT GCCCA CTTGG CAGTA CATCA AGTGT ATCAT ATGCC AAGTA CGCCC   500
CCTAT TGACG TCAAT GACGG TAAAT GGCCC GCCTG GCATT ATGCC CAGTA   550
CATGA CCTTA TGGGA CTTTC CTACT TGGCA GTACA TCTAC GTATT AGTCA   600
TCGCT ATTAC CATGG TGATG CGGTT TTGGC AGTAC ATCAA TGGGC GTGGA   650
TAGCG GTTTG ACTCA CGGGG ATTTC CAAGT CTCCA CCCCA TTGAC GTCAA   700
TGGGA GTTTG TTTTG GCACC AAAAT CAACG GGACT TTCCA AAATG TCGTA   750
ACAAC TCCGC CCCAT TGACG CAAAT GGGCG GTAGG CGTGT ACGGT GGGAG   800
GTCTA TATAA GCAGA GCTCT CTGGC TAACT AGAGA ACCCA CTGCT TACTG   850
GCTTA TCGAA ATTAA TACGA CTCAC TATAG GGAGA CCCAA GCTTG GTACC   900
GGTAG AAAAA ATGTC AAAAG GAGAG GAATT GTTCA CCGGC GTCGT TCCAA   950
TCCTC GTTGA ACTCG ACGGC GACGT CAACG GGCAC AAGTT TTCCG TCTCT  1000
GGAGA GGGAG AGGGA GACGC AACCT ACGGC AAATT GACCC TTAAA TTCAT  1050
TTGCA CCACA Ggtaa gtttc gattt ttgct atctt ttcca cgatt ttac   1100
tctct tttc tacta actaa cctcc ttttt gaaca ttttt tcagG AAAAT    1150
TGCCA GTTCC ATGGC CAACA TTGGT CACA CCTTC TGTTA CGGCG TCCAA    1200
TGCTT CTCGC GTTAC CCGA TCACA TGAAA GGCA GGACT TTTTT AAATC     1250
CGCAA TGCCA GAAGG ATACG TACAA GAACG CACAA TTTTC TTCAA AGATG   1300
ACGGA AACTA CAAGA CAAGg taagt tttc ccaac ttttt cggac ttttt    1350
gacgg ttttt tatac taact aacgg actt ttcgt ccttt tcag GGCCG     1400
AAGTC AAGTT TGAAG GAGAC ACCCT CGTCA ACGC ATCGA ACTTA AGGA     1450
ATTGA CTTCA AAGAA GACGG AAACA TTCTC GGACA CAAAC TCGAA TACAA   1500
CTACA ATTCT CACAA CGTTT ACATA ATGGC CGACA AACAA AAGAA CGGAA   1550
```

FIG. 16

```
TCAAG gtaag ttteg ctttt tgatg atttt tggac cattt ttagg aattt 1600
ttcga tacta actaa ctatt tttgc ctgct ttttc agGTC AACTT CAAGA 1650
TTCGT CACAA CATTG AGGAC GGAAG CGTCC AACTT GCTGA CCATT ACCAG 1700
CAAAA CACCC CGATT GGCGA CGGAC CCGTC CTCCT TCGG ACAAC CACTA 1750
CCTCT CAACA CAGAG CGCCC TCTCG AAAGA CCCGA ACGAG AAGAG gtaag 1800
tttat cgttt ttcga cgatt tttac ccatt tttac gccat ttttg atact 1850
aacta acgcc ttttt acgga ttttt cagGG ACCAC ATGGT CCTTT TGGAA 1900
TTTGT TACGG CCGCA GGCAT CACCC ACGGC ATGGA CGAAC TCTAC AAATA 1950
GCATT CGTAG AATTC GCTAG AGGGC CCTAT TCTAT AGTGT CACCT AAATG 2000
CTAGA GCTCG CTGAT CAGCC TCGAC TGTGC CTTCT AGTTG CCAGC CATCT 2050
GTTGT TTGCC CCTCC CCCGT GCCTT CCTTG ACCCT GGAAG GTGCC ACTCC 2100
CACTG TCCTT TCCTA ATAAA ATGAG GAAAT TGCAT CGCAT TGTCT GAGTA 2150
GGTGT CATTC TATTC TGGGG GGTGG GGTGG GCAG GACAG CAAGG GGAG 2200
GATTG GGAAG ACAAT AGCAG GCATG CTGGG GATGC GGTGG GCTCT ATGGC 2250
TTCTG AGGCG GAAAG AACCA GCTGG GGCTC TAGGG GGTAT CCCCA CGCGC 2300
CCTGT AGCGG CGCAT TAAGC GCGGC GGGTG TGTG GTAC GCGCA GCGTG 2350
ACCGC TACAC TTGCC AGCGC CCTAG CGCCC GCTCC TTTCG CTTTC TTCCC 2400
TTCCT TTCTC GCCAC GTTCG CCGGC TTTCC CCGTC AAGCT CTAAA TCGGG 2450
GCATC CCTTT AGGGT TCCGA TTTAG TGCTT TACGG CACCT CGACC CCAAA 2500
AAACT TGATT AGGGT GATGG TTCAC GTAGT GGGCC ATCGC CCTGA TAGAC 2550
GGTTT TTCGC CCTTT GACGT TGGAG TCCAC GTTCT TTAAT AGTGG ACTCT 2600
TGTTC CAAAC TGGAA CAACA CTCAA CCCTA TCTCG GTCTA TTCTT TTGAT 2650
TTATA AGGGA TTTTG GGGAT TTCGG CCTAT TGGTT AAAAA ATGAG CTGAT 2700
TTAAC AAAAA TTTAA CGCGA ATTAA TTCTG TGGAA TGTGT GTCAG TTAGG 2750
GTGTG GAAAG TCCCC AGGCT CCCCA GCAG GCAGA AGTAT GCAAA GCATG 2800
CATCT CAATT AGTCA GCAAC CAGGT GTGGA AAGTC CCCAG GCTCC CCAGC 2850
AGGCA GAAGT ATGCA AAGCA TGCAT CTCAA TTAGT CAGCA ACCAT AGTCC 2900
CGCCC CTAAC TCCGC CCATC CCGCC CCTAA CTCCG CCCAG TTCCG CCCAT 2950
TCTCC GCCCC ATGGC TGACT AATTT TTTTT ATTTA TGCAG AGGCC GAGGC 3000
CGCCT CTGCC TCTGA GCTAT TCCAG AAGTA GTGAG GAGGC TTTTT TGGAG 3050
```

*FIG. 16*
*CONT.-1*

```
GCCTA GGCTT TTGCA AAAAG CTCCC GGGAG CTTGT ATATC CATTT TGGA   3100
TCTGA TCAAG AGACA GGATG AGGAT CGTTT CGCAT GATTG AACAA GATGG   3150
ATTGC ACGCA GGTTC TCCGG CCGCT TGGGT GGAGA GGCTA TTCGG CTATG   3200
ACTGG GCACA ACAGA CAATC GGCTG CTCTG ATGCC GCCGT GTTCC GGCTG   3250
TCAGC GCAGG GGCGC CCGGT TCTTT TGTC  AAGAC CGACC TGTCC GGTGC   3300
CCTGA ATGAA CTGCA GGACG AGGCA GGGCG GCTAT CGTGG CTGGC CACGA   3350
CGGGC GTTCC TTGCG CAGCT GTGCT CGACG TTGTC ACTGA AGCGG GAAGG   3400
GACTG GCTGC TATTG GGCGA AGTGC CGGGG CAGGA TCTCC TGTCA TCTCA   3450
CCTTG CTCCT GCCGA GAAAG TATCC ATCAT GGCTG ATGCA ATGCG GCGGC   3500
TGCAT ACGCT TGATC CGGCT ACCTG CCCAT TCGAC CACCA AGCGA AACAT   3550
CGCAT CGAGC GAGCA CGTAC TCGGA TGGAA GCCGG TCTTG TCGAT CAGGA   3600
TGATC TGGAC GAAGA GCATC AGGGG CTCGC GCCAG CCGAA CTGTT CGCCA   3650
GGCTC AAGGC GCGCA TGCCC GACGG CGAGG ATCTC GTCGT GACCC ATGGC   3700
GATGC CTGCT TGCCG AATAT CATGG TGGAA AATGG CCGCT TTTCT GGATT   3750
CATCG ACTGT GGCCG GCTGG GTGTG GCGGA CCGCT ATCAG GACAT AGCGT   3800
TGGCT ACCCG TGATA TTGCT GAAGA GCTTG GCGGC GAATG GGCTG ACCGC   3850
TTCCT CGTGC TTTAC GGTAT CGCCG CTCCC GATTC GCAGC GCATC GCCTT   3900
CTATC GCCTT CTTGA CGAGT TCTTC TGAGC GGGAC TCTGG GGTTC GAAAT   3950
GACCG ACCAA GCGAC GCCCA ACCTG CCATC ACGAG ATTTC GATTC CACCG   4000
CCGCC TTCTA TGAAA GGTTG GGCTT CGGAA TCGTT TTCCG GGACG CCGGC   4050
TGGAT GATCC TCCAG CGCGG GGATC TCATG CTGGA GTTCT TGCC  CACCC   4100
CAACT TGTTT ATTGC AGCTT ATAAT GGTTA CAAAT AAAGC AATAG CATCA   4150
CAAAT TTCAC AAATA AAGCA TTTTT TCAC  TGCAT CTAG  TTGTG GTTTG   4200
TCCAA ACTCA TCAAT GTATC TTATC ATGTC TGTAT ACCGT CGACC TCTAG   4250
CTAGA GCTTG GCGTA ATCAT GGTCA TAGCT GTTTC CTGTG TGAAA TTGTT   4300
ATCCG CTCAC AATTC CACAC AACAT ACGAG CCGGA AGCAT AAAGT GTAAA   4350
GCCTG GGGTG CCTAA TGAGT GAGCT AACTC ACATT AATTG CGTTG CGCTC   4400
ACTGC CCGCT TTCCA GTCGG GAAAC CTGTC GTGCC AGCTG CATTA ATGAA   4450
TCGGC CAACG CGCGG GGAGA GGCGG TTTGC GTATT GGGCG CTCTT CCGCT   4500
TCCTC GCTCA CTGAC TCGCT GCGCT CGGTC GTTCG GCTGC GGCGA GCGGT   4550
ATCAG CTCAC TCAAA GGCGG TAATA CGGTT ATCCA CAGAA TCAGG GGATA   4600
ACGCA GGAAA GAACA TGTGA GCAAA AGGCC AGCAA AAGGC CAGGA ACCGT   4650
AAAAA GGCCG CGTTG CTGGC GTTTT TCCAT AGGCT CCGCC CCCCT GACGA   4700
GCATC ACAAA AATCG ACGCT CAAGT CAGAG GTGGC GAAAC CCGAC AGGAC   4750
```

FIG. 16
CONT.-2

```
TATAA AGATA CCAGG CGTTT CCCCC TGGAA GCTCC CTCGT GCGCT CTCCT 4800
GTTCC GACCC TGCCG CTTAC CGGAT ACCTG TCCGC CTTTC TCCCT TCGGG 4850
AAGCG TGGCG CTTTC TCAAT GCTCA CGCTG TAGGT ATCTC AGTTC GGTGT 4900
AGTTC GTTCG CTCCA AGCTG GGCTG TGTGC ACGAA CCCCC CGTTC AGCCC 4950
GACCG CTGCG CCTTA TCCGG TAACT ATCGT CTTGA GTCCA ACCCG GTAAG 5000
ACACG ACTTA TCGCC ACTGG CAGCA GCCAC TGGTA ACAGG ATTAG CAGAG 5050
CGAGG TATGT AGGCG GTGCT ACAGA GTTCT TGAAG TGGTG GCCTA ACTAC 5100
GGCTA CACTA GAAGG ACAGT ATTTG TATC TGCGC TCTGC TGAAG CCAGT 5150
TACCT TCGGA AAAAG AGTTG GTAGC TCTTG ATCCG GCAAA CAAAC CACCG 5200
CTGGT AGCGG TGGTT TTTTT GTTTG CAAGC AGCAG ATTAC GCGCA GAAAA 5250
AAACG ATCTC AAGAA GATCC TTTGA TCTTT TCTAC GGGGT CTGAC GCTCA 5300
GTGGA ACGAA AACTC ACGTT AAGGG ATTTT GGTCA TGAGA TTATC AAAAA 5350
GGATC TTCAC CTAGA TCCTT TTAAA TTAAA AATGA AGTTT TAAAT CAATC 5400
TAAAG TATAT ATGAG TAAAC TTGGT CTGAC AGTTA CCAAT GCTTA ATCAG 5450
TGAGG CACCT ATCTC AGCGA TCTGT CTATT TCGTT CATCC ATAGT TGCCT 5500
GACTC CCCGT CGTGT AGATA ACTAC GATAC GGGAG GGCTT ACCAT CTGGC 5550
CCCAG TGCTG CAATG ATACC GCGAG ACCCA CGCTC ACCGG CTCCA GATTT 5600
ATCAG CAATA AACCA GCCAG CCGGA AGGGC CGAGC GCAGA AGTGG TCCTG 5650
CAACT TTATC CGCCT CCATC CAGTC TATTA ATTGT TGCCG GGAAG CTAGA 5700
GTAAG TAGTT CGCCA GTTAA TAGTT TGCGC AACGT TGTTG CCATT GCTAC 5750
AGGCA TCGTG GTGTC ACGCT CGTCG TTTGG TATGG CTTCA TTCAG CTCCG 5800
GTTCC CAACG ATCAA GGCGA GTTAC ATGAT CCCCC ATGTT GTGCA AAAAA 5850
GCGGT TAGCT CCTTC GGTCC TCCGA TCGTT GTCAG AAGTA AGTTG GCCGC 5900
AGTGT TATCA CTCAT GGTTA TGGCA GCACT GCATA ATTCT CTTAC TGTCA 5950
TGCCA TCCGT AAGAT GCTTT TCTGT GACTG GTGAG TACTC AACCA AGTCA 6000
TTCTG AGAAT AGTGT ATGCG GCGAC CGAGT TGCTC TTGCC CGGCG TCAAT 6050
ACGGG ATAAT ACCGC GCCAC ATAGC AGAAC TTTAA AAGTG CTCAT CATTG 6100
GAAAA CGTTC TTCGG GGCGA AAACT CTCAA GGATC TTACC GCTGT TGAGA 6150
TCCAG TTCGA TGTAA CCCAC TCGTG CACCC AACTG ATCTT CAGCA TCTTT 6200
TACTT TCACC AGCGT TTCTG GGTGA GCAAA AACAG GAAGG CAAAA TGCCG 6250
CAAAA AAGGG AATAA GGGCG ACACG GAAAT GTTGA ATACT CATAC TCTTC 6300
CTTTT TCAAT ATTAT TGAAG CATTT ATCAG GGTTA TTGTC TCATG AGCGG 6350
ATACA TATTT GAATG TATTT AGAAA AATAA ACAAA TAGGG GTTCC GCGCA 6400
CATTT CCCCG AAAAG TGCCA CCTGA CGT
```

FIG. 16
CONT.-3

(SEQ ID NO: 13)

```
GACGG ATCGG GAGAT CTCCC GATCC CCTAT GGTCG ACTCT CAGTA CAATC  50
TGCTC TGATG CCGCA TAGTT AAGCC AGTAT CTGCT CCCTG CTTGT GTGTT 100
GGAGG TCGCT GAGTA GTGCG CGAGC AAAAT TTAAG CTACA ACAAG GCAAG 150
GCTTG ACCGA CAATT GCATG AAGAA TCTGC TTAGG GTTAG GCGTT TTGCG 200
CTGCT TCGCG ATGTA CGGGC CAGAT ATACG CGTTG ACATT GATTA TTGAC 250
TAGTT ATTAA TAGTA ATCAA TTACG GGGTC ATTAG TTCAT AGCCC ATATA 300
TGGAG TTCCG CGTTA CATAA CTTAC GGTAA ATGGC CCGCC TGGCT GACCG 350
CCCAA CGACC CCCGC CCATT GACGT CAATA ATGAC GTATG TTCCC ATAGT 400
AACGC CAATA GGGAC TTTCC ATTGA CGTCA ATGGG TGGAC TATTT ACGGT 450
AAACT GCCCA CTTGG CAGTA CATCA AGTGT ATCAT ATGCC AAGTA CGCCC 500
CCTAT TGACG TCAAT GACGG TAAAT GGCCC GCCTG GCATT ATGCC CAGTA 550
CATGA CCTTA TGGGA CTTTC CTACT TGGCA GTACA TCTAC GTATT AGTCA 600
TCGCT ATTAC CATGG TGATG CGGTT TTGGC AGTAC ATCAA TGGGC GTGGA 650
TAGCG GTTTG ACTCA CGGGG ATTTC CAAGT CTCCA CCCCA TTGAC GTCAA 700
TGGGA GTTTG TTTTG GCACC AAAAT CAACG GGACT TTCCA AAATG TCGTA 750
ACAAC TCCGC CCCAT TGACG CAAAT GGGCG GTAGG CGTGT ACGGT GGGAG 800
GTCTA TATAA GCAGA GCTCT CTGGC TAACT AGAGA ACCCA CTGCT TACTG 850
GCTTA TCGAA ATTAA TACGA CTCAC TATAG GGAGA CCCAA GCTTG GTACC 900
GGTCG CCACC ATGGT GAGCA AGGGC GAGGA GCTGT TCACC GGGGT GGTGC 950
CCATC CTGGT CGAGC TGGAC GGCGA CGTAA ACGGC CACAA GTTCA GCGTG 1000
TCCGG CGAGG GCGAG GGCGA TGCCA CCTAC GGCAA GCTGA CCCTG AAGTT 1050
CATCT GCACC ACCGG CAAGC TGCCC GTGCC CTGGC CCACC CTCGT GACCA 1100
CCCTG ACCTA CGGCG TGCAG TGCTT CAGCC GCTAC CCCGA CCACA TGAAG 1150
CAGCA CGACT TCTTC AAGTC CGCCA TGCCC GAAGG CTACG TCCAG GAGCG 1200
CACCA TCTTC TTCAA GGACG ACGGC AACTA CAAGA CCCGC GCCGA GGTGA 1250
AGTTC GAGGG CGACA CCCTG GTGAA CCGCA TCGAG CTGAA GGGCA TCGAC 1300
TTCAA GGAGG ACGGC AACAT CCTGG GGCAC AAGCT GGAGT ACAAC TACAA 1350
CAGCC ACAAC GTCTA TATCA TGGCC GACAA GCAGA AGAAC GGCAT CAAGG 1400
TGAAC TTCAA GATCC GCCAC AACAT CGAGG ACGGC AGCGT GCAGC TCGCC 1450
GACCA CTACC AGCAG AACAC CCCCA TCGGC GACGG CCCCG TGCTG CTGCC 1500
CGACA ACCAC TACCT GAGCA CCCAG TCCGC CCTGA GCAAA GACCC CAACG 1550
```

FIG. 17

```
AGAAG CGCGA TCACA TGGTC CTGCT GGAGT TCGTG ACCGC CGCCG GGATC 1600
ACTCT CGGCA TGGAC GAGCT GTACA AGTCC GGACT CAGAT CTCGA GCTCA 1650
AGCTT CGAAT TCGCT AGAGG CCCCT ATTCT ATAGT GTCAC CTAAA TGCTA 1700
GAGCT CGCTG ATCAG CCTCG ACTGT GCCTT CTAGT TGCCA GCCAT CTGTT 1750
GTTTG CCCCT CCCCC GTGCC TTCCT TGACC CTGGA AGGTG CCACT CCCAC 1800
TGTCC TTTCC TAATA AAATG AGGAA ATTGC ATCGC ATTGT CTGAG TAGGT 1850
GTCAT TCTAT TCTGG GGGGT GGGGT GGGGC AGGAC AGCAA GGGGG AGGAT 1900
TGGGA AGACA ATAGC AGGCA TGCTG GGGAT GCGGT GGGCT CTATG GCTTC 1950
TGAGG CGGAA AGAAC CAGCT GGGGC TCTAG GGGGT ATCCC CACGC GCCCT 2000
GTAGC GGCGC ATTAA GCGCG GCGGG TGTGG TGGTT ACGCG CAGCG TGACC 2050
GCTAC ACTTG CCAGC GCCCT AGCGC CCGCT CCTTT CGCTT TCTTC CCTTC 2100
CTTTC TCGCC ACGTT CGCCG GCTTT CCCCG TCAAG CTCTA AATCG GGGCA 2150
TCCCT TTAGG GTTCC GATTT AGTGC TTTAC GGCAC CTCGA CCCCA AAAAA 2200
CTTGA TTAGG GTGAT GGTTC ACGTA GTGGG CCATC GCCCT GATAG ACGGT 2250
TTTTC GCCCT TTGAC GTTGG AGTCC ACGTT CTTTA ATAGT GGACT CTTGT 2300
TCCAA ACTGG AACAA CACTC AACCC TATCT CGGTC TATTC TTTTG ATTTA 2350
TAAGG GATTT TGGGG ATTTC GGCCT ATTGG TTAAA AAATG AGCTG ATTTA 2400
ACAAA AATTT AACGC GAATT AATTC TGTGG AATGT GTGTC AGTTA GGGTG 2450
TGGAA AGTCC CCAGG CTCCC CAGGC AGGCA GAAGT ATGCA AAGCA TGCAT 2500
CTCAA TTAGT CAGCA ACCAG GTGTG GAAAG TCCCC AGGCT CCCCA GCAGG 2550
CAGAA GTATG CAAAG CATGC ATCTC AATTA GTCAG CAACC ATAGT CCCGC 2600
CCCTA ACTCC GCCCA TCCCG CCCCT AACTC CGCCC AGTTC CGCCC ATTCT 2650
CCGCC CCATG GCTGA CTAAT TTTTT TTATT TATGC AGAGG CCGAG GCCGC 2700
CTCTG CCTCT GAGCT ATTCC AGAAG TAGTG AGGAG GCTTT TTTGG AGGCC 2750
TAGGC TTTTG CAAAA AGCTC CCGGG AGCTT GTATA TCCAT TTTCG GATCT 2800
GATCA AGAGA CAGGA TGAGG ATCGT TTCGC ATGAT TGAAC AAGAT GGATT 2850
GCACG CAGGT TCTCC GGCCG CTTGG GTGGA GAGGC TATTC GGCTA TGACT 2900
GGGCA CAACA GACAA TCGGC TGCTC TGATG CCGCC GTGTT CCGGC TGTCA 2950
GCGCA GGGGC GCCCG GTTCT TTTTG TCAAG ACCGA CCTGT CCGGT GCCCT 3000
```

FIG. 17
CONT.-1

```
GAATG AACTG CAGGA CGAGG CAGCG CGGCT ATCGT GGCTG GCCAC GACGG 3050
GCGTT CCTTG CGCAG CTGTG CTCGA CGTTG TCACT GAAGC GGGAA GGGAC 3100
TGGCT GCTAT TGGGC GAAGT GCCGG GGCAG GATCT CCTGT CATCT CACCT 3150
TGCTC CTGCC GAGAA ACTAT CCATC ATGGC TGATG CAATG CGGCG GCTGC 3200
ATACG CTTGA TCCGG CTACC TGCCC ATTCG ACCAC CAAGC GAAAC ATCGC 3250
ATCGA GCGAG CACGT ACTCG GATGG AAGCC GGTCT TGTCG ATCAG GATGA 3300
TCTGG ACGAA GAGCA TCAGG GGCTC GCGCC AGCCG AACTG TTCGC CAGGC 3350
TCAAG GCGCG CATGC CCGAC GGCGA GGATC TCGTC GTGAC CCATG GCGAT 3400
GCCTG CTTGC CGAAT ATCAT GGTGG AAAAT GGCCG CTTTT CTGGA TTCAT 3450
CGACT GTGGC CGGCT GGGTG TGGCG GACCG CTATC AGGAC ATAGC GTTGG 3500
CTACC CGTGA TATTG CTGAA GAGCT TGGCG GCGAA TGGGC TGACC GCTTC 3550
CTCGT GCTTT ACGGT ATCGC CGCTC CCGAT TCGCA GCGCA TGGCC TTCTA 3600
TGCCC TTCTT GACGA GTTCT TCTGA GCGGG ACTCT GGGGT TCGAA ATGAC 3650
CGACC AAGCG ACGGC CAACC TGCCA TCACG AGATT TCGAT TCCAC CGCCG 3700
CCTTC TATGA AAGGT TGGGC TTCGG AATCG TTTTC CGGGA CGCCG GCTGG 3750
ATGAT CCTCC AGCGC GGGGA TCTCA TGCTG GAGTT CTTCG CCCAC CCCAA 3800
CTTGT TTATT GCAGC TTATA ATGGT TACAA ATAAA GCAAT AGCAT CACAA 3850
ATTTC ACAAA TAAAG CATTT TTTTC ACTGC ATTCT AGTTG TGGTT TGTCC 3900
AAACT CATCA ATGTA TCTTA TCATG TCTGT ATACC GTCGA CCTCT AGCTA 3950
GAGCT TGGCG TAATC ATGGT CATAG CTGTT TCCTG TGTGA AATTG TTATC 4000
CGCTC ACAAT TCCAC ACAAC ATACG AGCCG GAAGC ATAAA GTGTA AAGCC 4050
TGGGG TGCCT AATGA GTGAG CTAAC TCACA TTAAT TGCGT TGCGC TCACT 4100
GCCCG CTTTC CAGTC GGGAA ACCTG TCGTG CCAGC TGCAT TAATG AATCG 4150
GCCAA CGCGC GGGGA GAGGC GGTTT GCGTA TTGGG CGCTC TTCCG CTTCC 4200
TCGCT CACTG ACTCG CTGCG CTCGG TCGTT CGGCT GCGGC GAGCG GTATC 4250
AGCTC ACTCA AAGGC GGTAA TACGG TTATC CACAG AATCA GGGGA TAACG 4300
CAGGA AAGAA CATGT GAGCA AAAGG CCAGC AAAAG GCCAG GAACC GTAAA 4350
AAGGC CGCGT TGCTG GCGTT TTTCC ATAGG CTCCG CCCCC CTGAC GAGCA 4400
TCACA AAAAT CGACG CTCAA GTCAG AGGTG GCGAA ACCCG ACAGG ACTAT 4450
AAAGA TACCA GGCGT TTCCC CCTGG AAGCT CCCTC GTGCG CTCTC CTGTT 4500
CCGAC CCTGC CGCTT ACCGG ATACC TGTCC GCCTT TCTCC CTTCG GGAAG 4550
```

FIG. 17
CONT.-2

```
CGTGG CGCTT TCTCA ATGCT CACGC TGTAG GTATC TCAGT TGGT GTAGG 4600
TGGTT CGCTC CAAGC TGGGC TGTGT GCACG AACCC CCGT TCAGC CGAC 4650
CGCTG CGCCT TATCC GGTAA CTATC GTCTT GAGTC CAACC CGGTA AGACA 4700
CGACT TATCG CCACT GGCAG CAGCC ACTGG TAACA GGATT AGCAG AGCGA 4750
GGTAT GTAGG CGGTG CTACA GAGTT CTTGA AGTGG TGGCC TAACT ACGGC 4800
TACAC TAGAA GGACA GTATT TGGTA TCTGC GCTCT GCTGA AGCCA GTTAC 4850
CTTCG GAAAA AGAGT TGGTA GCTCT TGATC CGGCA AACAA ACCAC CGCTG 4900
GTAGC GGTGG TTTTT TTGTT TGCAA GCAGC AGATT ACGCG CAGAA AAAAA 4950
GGATC TCAAG AAGAT CCTTT GATCT TTTCT ACGGG GTCTG ACGCT CAGTG 5000
GAACG AAAAC TCACG TTAAG GGATT TTGGT CATGA GATTA TCAAA AAGGA 5050
TCTTC ACCTA GATCC TTTTA AATTA AAAAT GAAGT TTTAA ATCAA TCTAA 5100
AGTAT ATATG AGTAA ACTTG GTCTG ACAGT TACCA ATGCT TAATC AGTGA 5150
GGCAC CTATC TCAGC GATCT GTCTA TTTCG TTCAT CCATA GTTGC CTGAC 5200
TCCCC GTCGT GTAGA TAACT ACGAT ACGGG AGGGC TTACC ATCTG GCCCC 5250
AGTGC TGCAA TGATA CCGCG AGACC CACGC TCACC GGCTC CAGAT TTATC 5300
AGCAA TAAAC CAGCC AGCCG GAAGG GCCGA GCGCA GAAGT GGTCC TGCAA 5350
CTTTA TCCGC CTCCA TCCAG TCTAT TAATT GTTGC CGGGA AGCTA GAGTA 5400
AGTAG TTCGC CAGTT AATAG TTTGC GCAAC GTTGT TGCCA TTGCT ACAGG 5450
CATCG TGGTG TCACG CTCGT CGTTT GGTAT GGCTT CATTC AGCTC CGGTT 5500
CCCAA CGATC AAGGC GAGTT ACATG ATCCC CCATG TTGTG CAAAA AAGCG 5550
GTTAG CTCCT TCGGT CCTCC GATCG TTGTC AGAAG TAAGT TGGCC GCAGT 5600
GTTAT CACTC ATGGT TATGG CAGCA CTGCA TAATT CTCTT ACTGT CATGC 5650
CATCC GTAAG ATGCT TTTCT GTGAC TGGTG AGTAC TCAAC CAAGT CATTC 5700
TGAGA ATAGT GTATG CGGCG ACCGA GTTGC TCTTG CCCGG CGTCA ATACG 5750
GGATA ATACC GCGCC ACATA GCAGA ACTTT AAAAG TGCTC ATCAT TGGAA 5800
AACGT TCTTC GGGGC GAAAA CTCTC AAGGA TCTTA CCGCT GTTGA GATCC 5850
AGTTC GATGT AACCC ACTCG TGCAC CCAAC TGATC TTCAG CATCT TTTAC 5900
TTTCA CCAGC GTTTC TGGGT GAGCA AAAAC AGGAA GGCAA AATGC CGCAA 5950
AAAAG GGAAT AAGGG CGACA CGGAA ATGTT GAATA CTCAT ACTCT TCCTT 6000
TTTCA ATATT ATTGA AGCAT TTATC AGGGT TATTG TCTCA TGAGC GGATA 6050
CATAT TTGAA TGTAT TTAGA AAAAT AAACA AATAG GGGTT CCGCG CACAT 6100
TTCCC CGAAA AGTGC CACCT GACGT
```

FIG. 17
CONT.-3

(SEQ ID NO: 14)
cggtagaaaaaATGGTCTCAAAAGGAGAAGAGCTTTTCACCGGAGTCGTC
CCAATCCTTGTCGAACTTGATGGCGATGTAAACGGACACAAATTCTCCGT
CTCCGGCGAAGGAGAGGGAGATGCTACCTACGGAAAGCTTACCCTTAAAT
TTATCTGCACGACAGgtaagttttgtatactttcgtgtatttccgtga
ttttcatactaactaaccccttttgccactatttcagGAAAACTTCCTG
TCCCTTGGCCAACCCTTGTCACCACCCTTACCTACGGAGTCCAATGCTTC
TCCAGATACCCTGATCACATGAAACAACACGATTTCTTCAAATCCGCTAT
GCCGGAGGGATACGTGCAAGAGAGAACCATCTTCTTCAAAGATGATGGAA
ACTACAAACGAGgtaagttttggcacatttgcgcatatttccaccat
ttactactaactaacagctttgctgcatttcagAGCTGAAGTCAAAT
TCGAAGGAGATACCCTTGTCAATAGAATCGAACTTAAGGAATCGATTC
AAAGAGGATGGAAACATCCTTGGACACAAACTTGAATACAACTACAACTC
CCACAACGTCTACATTATGGCTGATAAACAAAAAAACGGAATCAAAGTCA
ACTTTAAAATAAGgtaagttttcggcaattttgactacatttggctcat
tttcttactaactaacgtcttttcacacacttttcagACACAACATCGAA
GATGGATCCGTCCAACTTGCTGATCACTACCAACAAACACCCCAATCGG
GGATGGCCCGGTCCTTCTTCCGGATAACCACTACCTTTCCACCCAATCCG
CTCTTTCCAAAGATCCAAACGAAAAGAGAGATCACATGGTCCTTCTTGAA
TTTGTCACCGCGGCAGgtaagttttccggactttatggtccttttatgc
catttcctactaactaacggcttttgcgcgccttttcagGAATACCCT
TGGAATGGATGAACTTTACAAAGTTTTCACCGCTCCAAAAAAGAAAAGGA
AGGTTTTGACTGCCCCAAAGAAGAAAAGAAAGGTTTTCGCAGCAAAGCT
GCCAAAGaattc

SEQUENCE LISTING

<160> NUMBER OF SEQ ID NOS: 23

<210> SEQ ID NO 1
<211> LENGTH: 856
<212> TYPE: DNA
<213> ORGANISM: Artificial Sequence
<220> FEATURE:
<223> OTHER INFORMATION: Gene F54C4.1 from C. Elegans

<400> SEQUENCE: 1

| | | | | | | |
|---|---|---|---|---|---|---|
| gtagcggaga | aattgaagaa | aaatcgtcaa | aaaattgatg | aaaaacccga | aaaactcacg | 60 |
| aaaattcatt | aaaatcttaa | aaattgctag | aaattcggaa | aaatgcccaa | aattttagaa | 120 |
| aatgtttaaa | tattgctgag | aaaatgtcaa | aaataccgaa | atttattagt | aaaatcttga | 180 |
| aaattttgcc | aaaaatctgg | aaaaacctgg | aattttcgac | tttttttttc | taaaagtttc | 240 |
| aaaattccca | aataatcatt | caaaaaaaaa | aactttctaa | aaaatctcta | aaattttgc | 300 |
| ggaaattttg | aaaaaattca | ctaaaaaatt | gaaatatccc | cggaaatttc | gagaaaatcc | 360 |
| aaaaatttcg | gaaatacac | aaaaatccg | gttttgctg | aaaagcaca | gagtttgc | 420 |
| gacaaaacct | ttaaaaatct | gtaaatccc | ccaaaaattt | tcaattttt | tctcgaaaaa | 480 |
| ttgcaaaaaa | tgtaaaaatt | ccccaaata | atccgaaaat | ccaaaaaat | tacctaaaaa | 540 |
| tcgggaaaat | tttgaaaaat | ccctgaaaat | tgtcgtaaaa | ataccaaaaa | tttcgctaaa | 600 |
| aatctgaaaa | attgctagaa | attcgaaaaa | aaatgcttaa | aatttcgaa | aatgttaaaa | 660 |
| attcccaaaa | aacatgtaaa | atcttgagaa | aatgtcaaaa | ataccgaaat | ttattagaaa | 720 |
| aatctgaaaa | ctcactgaca | ttttgcgaaa | aattccgaaa | attggttaaa | aaattttttt | 780 |
| aaaaaacctg | gaatttccca | aatttttttt | tctaaaaatt | aaaaaattcc | gaaaaatcct | 840 |
| ttaaaatttc | ttacag | | | | | 856 |

<210> SEQ ID NO 2
<211> LENGTH: 1041
<212> TYPE: DNA
<213> ORGANISM: Artificial Sequence
<220> FEATURE:
<223> OTHER INFORMATION: Spgfp-1 synthetic intron interrupted gfp coding
region

<400> SEQUENCE: 2

| | | | | | | |
|---|---|---|---|---|---|---|
| atgtcaaaag | gagaggaatt | gttcaccggc | gtcgttccaa | tcctcgttga | actcgacggc | 60 |
| gacgtcaacg | ggcacaagtt | ttccgtctct | ggagagggag | agggagacgc | aacctacggc | 120 |
| aaattgaccc | ttaaattcat | ttgcaccaca | ggtaagtttc | gattttgct | atctttttca | 180 |
| cgatttttac | tctcttttc | tactaactaa | cctccttttt | gaacattttt | tcaggaaaat | 240 |
| tgccagttcc | atggccaaca | ttggtcacaa | ccttctgtta | cggcgtccaa | tgcttctcgc | 300 |
| gttaccccga | tcacatgaaa | aggcacgact | ttttaaatc | cgcaatgcca | gaaggatacg | 360 |
| tacaagaacg | cacaattttc | ttcaaagatg | acggaaacta | caagacaagg | taagtttttc | 420 |
| ccaactttt | cggactttt | gaccgctttt | tatactaact | aacggacttt | ttcgtccttt | 480 |
| ttcagggccg | aagtcaagtt | tgaaggagac | accctcgtca | accgcatcga | acttaaagga | 540 |
| attgacttca | agaagacgg | aaacattctc | ggacacaaac | tcgaatacaa | ctacaattct | 600 |
| cacaacgttt | acataatggc | cgacaaacaa | aagaacggaa | tcaaggtaag | tttcgctttt | 660 |
| tgatgatttt | tggaccattt | ttaggaattt | ttcgatacta | actaactatt | tttgcctgct | 720 |
| ttttcaggtc | aacttcaaga | ttcgtcacaa | cattgaggac | ggaagcgtcc | aacttgctga | 780 |

-continued

```
ccattaccag caaaacaccc cgattggcga cggacccgtc ctccttccgg acaaccacta    840
cctctcaaca cagagcgccc tctcgaaaga cccgaacgag aagaggtaag tttatcgttt    900
ttcgacgatt tttacccatt tttacgccat ttttgatact aactaacgcc ttttttaccga   960 tttttcaggg accacatggt cctttttggaa tttgttacgg ccgcaggcat cacccacggc   1020
atggacgaac tctacaaata g                                              1041
```

<210> SEQ ID NO 3
<211> LENGTH: 151
<212> TYPE: DNA
<213> ORGANISM: Artificial Sequence
<220> FEATURE:
<223> OTHER INFORMATION: Spgfp-1 coding region 1

<400> SEQUENCE: 3

```
atgtcaaaag gagaggaatt gttcaccggc gtcgttccaa tcctcgttga actcgacggc    60
gacgtcaacg ggcacaagtt ttccgtctct ggagagggag agggagacgc aacctacggc    120
aaattgaccc ttaaattcat ttgcaccaca g                                    151
```

<210> SEQ ID NO 4
<211> LENGTH: 175
<212> TYPE: DNA
<213> ORGANISM: Artificial Sequence
<220> FEATURE:
<223> OTHER INFORMATION: Spgfp-1 coding region 2

<400> SEQUENCE: 4

```
gaaaattgcc agttccatgg ccaacattgg tcacaacctt ctgttacggc gtccaatgct    60
tctcgcgtta ccccgatcac atgaaaaggc acgactttt taaatccgca atgccagaag    120
gatacgtaca agaacgcaca attttcttca agatgacgg aaactacaag acaag         175
```

<210> SEQ ID NO 5
<211> LENGTH: 160
<212> TYPE: DNA
<213> ORGANISM: Artificial Sequence
<220> FEATURE:
<223> OTHER INFORMATION: Spgfp-1 coding region 3

<400> SEQUENCE: 5

```
ggccgaagtc aagtttgaag gagacaccct cgtcaaccgc atcgaactta aggaattga    60 cttcaaagaa gacggaaaca ttctcggaca caaactcgaa tacaactaca attctcacaa   120
cgtttacata atggccgaca acaaaagaa cggaatcaag                          160
```

<210> SEQ ID NO 6
<211> LENGTH: 158
<212> TYPE: DNA
<213> ORGANISM: Artificial Sequence
<220> FEATURE:
<223> OTHER INFORMATION: Spgfp-1 coding region 4

<400> SEQUENCE: 6

```
gtcaacttca agattcgtca caacattgag gacggaagcg tccaacttgc tgaccattac    60
cagcaaaaca cccgattggc gacggaccc gtcctccttc cggacaacca ctacctctca    120
acacagagcg ccctctcgaa agacccgaac gagaagag                            158
```

<210> SEQ ID NO 7
<211> LENGTH: 73
<212> TYPE: DNA
<213> ORGANISM: Artificial Sequence

```
<220> FEATURE:
<223> OTHER INFORMATION: Spgfp-2 coding region 5

<400> SEQUENCE: 7
ggaccacatg gtccttttgg aatttgttac ggccgcaggc atcacccacg gcatggacga      60
actctacaaa tag                                                        73

<210> SEQ ID NO 8
<211> LENGTH: 83
<212> TYPE: DNA
<213> ORGANISM: Artificial Sequence
<220> FEATURE:
<223> OTHER INFORMATION: Spgfp-1 1VS1-intron 1

<400> SEQUENCE: 8
gtaagtttcg attttttgcta tcttttttcac gatttttact ctctttttct actaactaac    60 ctccttttttg aacatttttt cag                                            83

<210> SEQ ID NO 9
<211> LENGTH: 76
<212> TYPE: DNA
<213> ORGANISM: Artificial Sequence
<220> FEATURE:
<223> OTHER INFORMATION: Spgfp-1 1VS2-intron 2

<400> SEQUENCE: 9
gtaagttttt cccaactttt tcggactttt tgaccgcttt ttatactaac taacggactt      60
tttcgtcctt tttcag                                                     76

<210> SEQ ID NO 10
<211> LENGTH: 82
<212> TYPE: DNA
<213> ORGANISM: Artificial Sequence
<220> FEATURE:
<223> OTHER INFORMATION: Spgfp-1 1VS3-intron 3

<400> SEQUENCE: 10
gtaagtttcg cttttttgatg attttttggac cattttttagg aatttttcga tactaactaa   60 ctattttttgc ctgctttttc ag                                             82

<210> SEQ ID NO 11
<211> LENGTH: 83
<212> TYPE: DNA
<213> ORGANISM: Artificial Sequence
<220> FEATURE:
<223> OTHER INFORMATION: Spgfp-1 1VS4-intron 4

<400> SEQUENCE: 11
gtaagtttat cgttttttcga cgatttttac ccatttttac gccatttttg atactaacta    60
acgccttttt accgatttttt cag                                            83

<210> SEQ ID NO 12
<211> LENGTH: 6428
<212> TYPE: DNA
<213> ORGANISM: Artificial Sequence
<220> FEATURE:
<223> OTHER INFORMATION: Gfp expression vector L7152

<400> SEQUENCE: 12
gacggatcgg gagatctccc gatccccctat ggtcgactct cagtacaatc tgctctgatg     60
ccgcatagtt aagccagtat ctgctcccctg cttgtgtgtt ggaggtcgct gagtagtgcg    120
cgagcaaaat ttaagctaca acaaggcaag gcttgaccga caattgcatg aagaatctgc    180
```

```
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttggtacc    900
ggtagaaaaa atgtcaaaag gagaggaatt gttcaccggc gtcgttccaa tcctcgttga    960
actcgacggc gacgtcaacg ggcacaagtt ttccgtctct ggagagggag agggagacgc   1020
aacctacggc aaattgaccc ttaaattcat ttgcaccaca ggtaagtttc gattttttgct   1080 atcttttttca cgattttttac tctcttttttc tactaactaa cctcctttttt gaacattttt   1140 tcaggaaaat tgccagttcc atggccaaca ttggtcacaa ccttctgtta cggcgtccaa   1200
tgcttctcgc gttaccccga tcacatgaaa aggcacgact tttttaaatc cgcaatgcca   1260
gaaggatacg tacaagaacg cacaattttc ttcaaagatg acggaaacta caagacaagg   1320
taagtttttc ccaactttttt cggactttttt gaccgctttt tatactaact aacggacttt   1380
ttcgtccttt ttcagggccg aagtcaagtt tgaaggagac accctcgtca accgcatcga   1440
acttaaagga attgacttca agaagacgg aaacattctc ggacacaaac tcgaatacaa   1500
ctacaattct cacaacgttt acataatggc cgacaaacaa agaacggaa tcaaggtaag   1560 tttcgctttt tgatgatttt tggaccatttt ttaggaattt ttcgatacta actaactatt   1620
tttgcctgct ttttcaggtc aacttcaaga ttcgtcacaa cattgaggac ggaagcgtcc   1680
aacttgctga ccattaccag caaaacaccc cgattggcga cggacccgtc tccttccgg   1740 acaaccacta cctctcaaca cagagcgccc tctcgaaaga cccgaacgag aagaggtaag   1800
tttatcgttt ttcgacgatt tttacccatt tttacgccat ttttgatact aactaacgcc   1860 ttttttaccga tttttcaggg accacatggt cctttttggaa tttgttacgg ccgcaggcat   1920
cacccacggc atggacgaac tctacaaata gcattcgtag aattcgctag agggccctat   1980
tctatagtgt cacctaaatg ctagagctcg ctgatcagcc tcgactgtgc cttctagttg   2040
ccagccatct gttgtttgcc cctcccccgt gccttccttg accctggaag gtgccactcc   2100
cactgtcctt tcctaataaa atgaggaaat tgcatcgcat tgtctgagta ggtgtcattc   2160
tattctgggg ggtggggtgg ggcaggacag caagggggag gattgggaag acaatagcag   2220
gcatgctggg gatgcggtgg gctctatggc ttctgaggcg aaagaaccca gctgggctc   2280 taggggtat ccccacgcgc cctgtagcgg cgcattaagc gcggcgggtg tggtggttac   2340
gcgcagcgtg accgctacac ttgccagcgc cctagcgccc gctccttttcg ctttcttccc   2400 ttcctttctc gccacgttcg ccggcttttcc ccgtcaagct ctaaatcggg gcatccctttt   2460 agggttccga tttagtgctt tacggcacct cgaccccaaa aaacttgatt agggtgatgg   2520
ttcacgtagt gggccatcgc cctgatagac ggttttttcgc cctttgacgt tggagtccac   2580
```

```
gttctttaat agtggactct tgttccaaac tggaacaaca ctcaaccta tctcggtcta   2640 ttcttttgat ttataaggga ttttggggat ttcggcctat tggttaaaaa atgagctgat   2700
ttaacaaaaa tttaacgcga attaattctg tggaatgtgt gtcagttagg gtgtggaaag   2760
tccccaggct ccccaggcag gcagaagtat gcaaagcatg catctcaatt agtcagcaac   2820
caggtgtgga aagtcccag gctccccagc aggcagaagt atgcaaagca tgcatctcaa   2880
ttagtcagca accatagtcc cgccctaac tccgcccatc ccgccctaa ctccgcccag   2940 ttccgcccat tctccgcccc atggctgact aatttttttt atttatgcag aggccgaggc   3000
cgcctctgcc tctgagctat tccagaagta gtgaggagge ttttttggag gcctaggctt   3060
ttgcaaaaag ctcccgggag cttgtatatc cattttcgga tctgatcaag agacaggatg   3120
aggatcgttt cgcatgattg aacaagatgg attgcacgca ggttctccgg ccgcttgggt   3180
ggagaggcta ttcggctatg actgggcaca acagacaatc ggctgctctg atgccgccgt   3240
gttccggctg tcagcgcagg ggcgcccggt tctttttgtc aagaccgacc tgtccggtgc   3300
cctgaatgaa ctgcaggacg aggcagcgcg gctatcgtgg ctggccacga cgggcgttcc   3360
ttgcgcagct gtgctcgacg ttgtcactga agcgggaagg gactggctgc tattgggcga   3420
agtgccgggg caggatctcc tgtcatctca ccttgctcct gccgagaaag tatccatcat   3480
ggctgatgca atgcggcggc tgcatacgct tgatccggct acctgcccat tcgaccacca   3540
agcgaaacat cgcatcgagc gagcacgtac tcggatggaa gccggtcttg tcgatcagga   3600
tgatctggac gaagagcatc aggggctcgc gccagccgaa ctgttcgcca ggctcaaggc   3660
gcgcatgccc gacggcgagg atctcgtcgt gacccatggc gatgcctgct tgccgaatat   3720
catggtggaa aatggccgct tttctggatt catcgactgt ggccggctgg gtgtggcgga   3780
ccgctatcag gacatagcgt tggctacccg tgatattgct gaagagcttg gcggcgaatg   3840
ggctgaccgc ttcctcgtgc tttacggtat cgccgctccc gattcgcagc gcatcgcctt   3900
ctatcgcctt cttgacgagt tcttctgagc gggactctgg ggttcgaaat gaccgaccaa   3960
gcgacgccca acctgccatc acgagatttc gattccaccg ccgccttcta tgaaaggttg   4020
ggcttcggaa tcgttttccg ggacgccggc tggatgatcc tccagcgcgg ggatctcatg   4080
ctggagttct tcgcccaccc caacttgttt attgcagctt ataatggtta caaataaagc   4140
aatagcatca caaatttcac aaataaagca tttttttcac tgcattctag ttgtggtttg   4200
tccaaactca tcaatgtatc ttatcatgtc tgtataccgt cgacctctag ctagagcttg   4260
gcgtaatcat ggtcatagct gtttcctgtg tgaaattgtt atccgctcac aattccacac   4320
aacatacgag ccggaagcat aaagtgtaaa gcctggggtg cctaatgagt gagctaactc   4380
acattaattg cgttgcgctc actgcccgct ttccagtcgg gaaacctgtc gtgccagctg   4440
cattaatgaa tcggccaacg cgcggggaga ggcggtttgc gtattgggcg ctcttccgct   4500
tcctcgctca ctgactcgct gcgctcggtc gttcggctgc ggcgagcggt atcagctcac   4560
tcaaaggcgg taatacggtt atccacagaa tcaggggata acgcaggaaa gaacatgtga   4620
gcaaaaggcc agcaaaaggc caggaaccgt aaaaaggccg cgttgctggc gttttttccat   4680 aggctccgcc cccctgacga gcatcacaaa aatcgacgct caagtcagag gtggcgaaac   4740
ccgacaggac tataaagata ccaggcgttt ccccctggaa gctccctcgt gcgctctcct   4800
gttccgaccc tgccgcttac cggatacctg tccgcctttc tcccttcggg aagcgtggcg   4860
ctttctcaat gctcacgctg taggtatctc agttcggtgt aggtcgttcg ctccaagctg   4920
ggctgtgtgc acgaaccccc cgttcagccc gaccgctgcg ccttatccgg taactatcgt   4980
```

```
cttgagtcca acccggtaag acacgactta tcgccactgg cagcagccac tggtaacagg    5040
attagcagag cgaggtatgt aggcggtgct acagagttct tgaagtggtg cctaactac     5100 ggctacacta aaggacagt atttggtatc tgcgctctgc tgaagccagt taccttcgga     5160
aaaagagttg gtagctcttg atccggcaaa caaaccaccg ctggtagcgg tggttttttt    5220
gtttgcaagc agcagattac gcgcagaaaa aaggatctc aagaagatcc tttgatcttt     5280
tctacggggt ctgacgctca gtggaacgaa aactcacgtt aagggatttt ggtcatgaga    5340
ttatcaaaaa ggatcttcac ctagatcctt ttaaattaaa aatgaagttt taaatcaatc    5400
taaagtatat atgagtaaac ttggtctgac agttaccaat gcttaatcag tgaggcacct    5460
atctcagcga tctgtctatt tcgttcatcc atagttgcct gactcccgt cgtgtagata     5520 actacgatac gggagggctt accatctggc cccagtgctg caatgatacc gcgagaccca    5580
cgctcaccgg ctccagattt atcagcaata aaccagccag ccggaagggc cgagcgcaga    5640
agtggtcctg caactttatc cgcctccatc cagtctatta attgttgccg ggaagctaga    5700
gtaagtagtt cgccagttaa tagtttgcgc aacgttgttg ccattgctac aggcatcgtg    5760
gtgtcacgct cgtcgtttgg tatggcttca ttcagctccg gttcccaacg atcaaggcga    5820
gttacatgat cccccatgtt gtgcaaaaaa gcggttagct ccttcggtcc tccgatcgtt    5880
gtcagaagta agttggccgc agtgttatca ctcatggtta tggcagcact gcataattct    5940
cttactgtca tgccatccgt aagatgcttt tctgtgactg gtgagtactc aaccaagtca    6000
ttctgagaat agtgtatgcg gcgaccgagt tgctcttgcc cggcgtcaat acgggataat    6060
accgcgccac atagcagaac tttaaaagtg ctcatcattg gaaaacgttc ttcggggcga    6120
aaactctcaa ggatcttacc gctgttgaga tccagttcga tgtaacccac tcgtgcaccc    6180
aactgatctt cagcatcttt tactttcacc agcgtttctg ggtgagcaaa aacaggaagg    6240
caaaatgccg caaaaaaggg aataagggcg acacggaaat gttgaatact catactcttc    6300 cttttcaat attattgaag catttatcag ggttattgtc tcatgagcgg atacatattt     6360
gaatgtattt agaaaaataa acaaataggg gttccgcgca catttccccg aaaagtgcca    6420
cctgacgt                                                            6428
```

<210> SEQ ID NO 13
<211> LENGTH: 6125
<212> TYPE: DNA
<213> ORGANISM: Artificial Sequence
<220> FEATURE:
<223> OTHER INFORMATION: Gfp expression vector L7148

<400> SEQUENCE: 13

```
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
```

```
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttggtacc    900
ggtcgccacc atggtgagca agggcgagga gctgttcacc ggggtggtgc ccatcctggt    960
cgagctggac ggcgacgtaa acggccacaa gttcagcgtg tccggcgagg gcgagggcga   1020
tgccacctac ggcaagctga ccctgaagtt catctgcacc accggcaagc tgcccgtgcc   1080
ctggcccacc ctcgtgacca ccctgaccta cggcgtgcag tgcttcagcc gctaccccga   1140
ccacatgaag cagcacgact tcttcaagtc cgccatgccc gaaggctacg tccaggagcg   1200
caccatcttc ttcaaggacg acggcaacta caagacccgc gccgaggtga agttcgaggg   1260
cgacaccctg gtgaaccgca tcgagctgaa gggcatcgac ttcaaggagg acggcaacat   1320
cctggggcac aagctggagt acaactacaa cagccacaac gtctatatca tggccgacaa   1380
gcagaagaac ggcatcaagg tgaacttcaa gatccgccac aacatcgagg acggcagcgt   1440
gcagctcgcc gaccactacc agcagaacac ccccatcggc gacggccccg tgctgctgcc   1500
cgacaaccac tacctgagca cccagtccgc cctgagcaaa gaccccaacg agaagcgcga   1560
tcacatggtc ctgctggagt tcgtgaccgc cgccgggatc actctcggca tggacgagct   1620
gtacaagtcc ggactcagat ctcgagctca agcttcgaat tcgctagagg gcccctattct   1680 atagtgtcac ctaaatgcta gagctcgctg atcagcctcg actgtgcctt ctagttgcca   1740
gccatctgtt gtttgcccct cccccgtgcc ttccttgacc ctggaaggtg ccactcccac   1800
tgtcctttcc taataaaatg aggaaattgc atcgcattgt ctgagtaggt gtcattctat   1860 tctgggggt ggggtggggc aggacagcaa ggggaggat tgggaagaca atagcaggca   1920
tgctggggat gcggtgggct ctatggcttc tgaggcggaa agaaccagct ggggctctag   1980
ggggtatccc cacgcgccct gtagcggcgc attaagcgcg gcgggtgtgg tggttacgcg   2040
cagcgtgacc gctacacttg ccagcgccct agcgcccgct cctttcgctt tcttcccttc   2100
ctttctcgcc acgttcgccg gctttccccg tcaagctcta aatcggggca tccctttagg   2160
gttccgattt agtgctttac ggcacctcga ccccaaaaaa cttgattagg gtgatggttc   2220
acgtagtggg ccatcgccct gatagacggt ttttcgccct ttgacgttgg agtccacgtt   2280
ctttaatagt ggactcttgt tccaaactgg aacaacactc aaccctatct cggtctattc   2340
ttttgattta agggattt tggggattc ggcctattgg ttaaaaatg agctgattta   2400 acaaaaattt aacgcgaatt aattctgtgg aatgtgtgtc agttagggtg tggaaagtcc   2460
ccaggctccc caggcaggca gaagtatgca aagcatgcat ctcaattagt cagcaaccag   2520
gtgtggaaag tccccaggct ccccagcagg cagaagtatg caaagcatgc atctcaatta   2580
gtcagcaacc atagtcccgc ccctaactcc gcccatcccg ccctaactc gcccagttc   2640 cgcccattct ccgccccatg gctgactaat ttttttttatt tatgcagagg ccgaggccgc   2700
ctctgcctct gagctattcc agaagtagtg aggaggcttt tttggaggcc taggcttttg   2760
caaaaagctc ccgggagctt gtatatccat tttcggatct gatcaagaga caggatgagg   2820
atcgtttcgc atgattgaac aagatggatt gcacgcaggt tctccggccg cttgggtgga   2880
gaggctattc ggctatgact gggcacaaca gacaatcggc tgctctgatg ccgccgtgtt   2940
ccggctgtca gcgcagggc gcccggttct ttttgtcaag accgacctgt ccggtgccct   3000
```

```
gaatgaactg caggacgagg cagcgcggct atcgtggctg gccacgacgg gcgttccttg    3060
cgcagctgtg ctcgacgttg tcactgaagc gggaagggac tggctgctat tgggcgaagt    3120
gccggggcag gatctcctgt catctcacct tgctcctgcc gagaaagtat ccatcatggc    3180
tgatgcaatg cggcggctgc atacgcttga tccggctacc tgcccattcg accaccaagc    3240
gaaacatcgc atcgagcgag cacgtactcg gatggaagcc ggtcttgtcg atcaggatga    3300
tctggacgaa gagcatcagg ggctcgcgcc agccgaactg ttcgccaggc tcaaggcgcg    3360
catgcccgac ggcgaggatc tcgtcgtgac ccatggcgat gcctgcttgc cgaatatcat    3420
ggtggaaaat ggccgctttt ctggattcat cgactgtggc cggctgggtg tggcggaccg    3480
ctatcaggac atagcgttgg ctacccgtga tattgctgaa gagcttggcg gcgaatgggc    3540
tgaccgcttc ctcgtgcttt acggtatcgc cgctcccgat tcgcagcgca tcgccttcta    3600
tcgccttctt gacgagttct tctgagcggg actctggggt tcgaaatgac cgaccaagcg    3660
acgcccaacc tgccatcacg agatttcgat tccaccgccg ccttctatga aaggttgggc    3720
ttcggaatcg ttttccggga cgccggctgg atgatcctcc agcgcgggga tctcatgctg    3780
gagttcttcg cccacccccaa cttgtttatt gcagcttata atggttacaa ataaagcaat    3840
agcatcacaa atttcacaaa taaagcattt ttttcactgc attctagttg tggtttgtcc    3900
aaactcatca atgtatctta tcatgtctgt ataccgtcga cctctagcta gagcttggcg    3960
taatcatggt catagctgtt tcctgtgtga aattgttatc cgctcacaat tccacacaac    4020
atacgagccg gaagcataaa gtgtaaagcc tggggtgcct aatgagtgag ctaactcaca    4080
ttaattgcgt tgcgctcact gcccgctttc cagtcgggaa acctgtcgtg ccagctgcat    4140
taatgaatcg gccaacgcgc ggggagaggc ggtttgcgta ttgggcgctc ttccgcttcc    4200
tcgctcactg actcgctgcg ctcggtcgtt cggctgcggc gagcggtatc agctcactca    4260
aaggcggtaa tacggttatc cacagaatca ggggataacg caggaaagaa catgtgagca    4320
aaaggccagc aaaaggccag gaaccgtaaa aaggccgcgt tgctggcgtt tttccatagg    4380
ctccgccccc ctgacgagca tcacaaaaat cgacgctcaa gtcagaggtg gcgaaacccg    4440
acaggactat aaagatacca ggcgtttccc cctggaagct ccctcgtgcg ctctcctgtt    4500
ccgaccctgc cgcttaccgg atacctgtcc gcctttctcc cttcgggaag cgtggcgctt    4560
tctcaatgct cacgctgtag gtatctcagt tcggtgtagg tcgttcgctc caagctgggc    4620
tgtgtgcacg aacccccccgt tcagcccgac cgctgcgcct tatccggtaa ctatcgtctt    4680
gagtccaacc cggtaagaca cgacttatcg ccactggcag cagccactgg taacaggatt    4740
agcagagcga ggtatgtagg cggtgctaca gagttcttga agtggtggcc taactacggc    4800
tacactagaa ggacagtatt tggtatctgc gctctgctga agccagttac cttcggaaaa    4860
agagttggta gctcttgatc cggcaaacaa accaccgctg gtagcggtgg tttttttgtt    4920
tgcaagcagc agattacgcg cagaaaaaaa ggatctcaag aagatccttt gatcttttct    4980
acggggtctg acgctcagtg gaacgaaaac tcacgttaag ggattttggt catgagatta    5040
tcaaaaagga tcttcaccta gatcctttta aattaaaaat gaagttttaa atcaatctaa    5100
agtatatatg agtaaacttg gtctgacagt taccaatgct taatcagtga ggcacctatc    5160
tcagcgatct gtctatttcg ttcatccata gttgcctgac tccccgtcgt gtagataact    5220
acgatacggg agggcttacc atctggcccc agtgctgcaa tgataccgcg agacccacgc    5280
tcaccggctc cagatttatc agcaataaac cagccagccg aagggccgag cgcagaagt    5340 ggtcctgcaa ctttatccgc ctccatccag tctattaatt gttgccggga agctagagta    5400
```

```
agtagttcgc cagttaatag tttgcgcaac gttgttgcca ttgctacagg catcgtggtg    5460
tcacgctcgt cgtttggtat ggcttcattc agctccggtt cccaacgatc aaggcgagtt    5520
acatgatccc ccatgttgtg caaaaaagcg gttagctcct tcggtcctcc gatcgttgtc    5580
agaagtaagt tggccgcagt gttatcactc atggttatgg cagcactgca taattctctt    5640
actgtcatgc catccgtaag atgcttttct gtgactggtg agtactcaac caagtcattc    5700
tgagaatagt gtatgcggcg accgagttgc tcttgcccgg cgtcaatacg ggataatacc    5760
gcgccacata gcagaacttt aaaagtgctc atcattggaa aacgttcttc ggggcgaaaa    5820
ctctcaagga tcttaccgct gttgagatcc agttcgatgt aacccactcg tgcacccaac    5880
tgatcttcag catcttttac tttcaccagc gtttctgggt gagcaaaaac aggaaggcaa    5940
aatgccgcaa aaaagggaat aagggcgaca cggaaatgtt gaatactcat actcttcctt    6000
tttcaatatt attgaagcat ttatcagggt tattgtctca tgagcggata catatttgaa    6060
tgtatttaga aaaataaaca aatagggggtt ccgcgcacat tccccgaaaa agtgccacct    6120
gacgt                                                                6125
```

<210> SEQ ID NO 14
<211> LENGTH: 1112
<212> TYPE: DNA
<213> ORGANISM: Artificial Sequence
<220> FEATURE:
<223> OTHER INFORMATION: Spgfp-2 synthetic intron interrupted gfp coding region

<400> SEQUENCE: 14

```
cggtagaaaa aatggtctca aaaggagaag agcttttcac cggagtcgtc ccaatccttg      60
tcgaacttga tggcgatgta aacggacaca aattctccgt ctccggcgaa ggagagggag     120
atgctaccta cggaaagctt acccttaaat ttatctgcac tacaggtaag ttttgtatac     180
ttttcgtgta ttttccgtga ttttcatact aactaacccc ttttgccact attttcagga     240
aaacttcctg tcccttggcc aaccctttgtc accaccctta cctacggagt ccaatgcttc     300
tccagatacc ctgatcacat gaaacaacac gatttcttca aatccgctat gccgagggga    360
tacgtgcaag agagaaccat cttcttcaaa gatgatggaa actacaaaac gaggtaagtt    420
ttggcacatt ttgcgcatat tttccaccat tttactacta actaacagct tttgctgcat     480
tttcagagct gaagtcaaat tcgaaggaga taccccttgtc aatagaatcg aacttaaagg     540
aatcgatttc aaagaggatg gaaacatcct tggacacaaa cttgaataca actacaactc     600
ccacaacgtc tacattatgg ctgataaaca aaaaaacgga atcaaagtca actttaaaat     660
aaggtaagtt ttcggcaatt ttgactacat tttggctcat tttcttacta actaacgtct     720
tttcacacac ttttcagaca caacatcgaa gatggatccg tccaacttgc tgatcactac    780
caacaaaaca ccccaatcgg ggatggcccg gtccttcttc cggataacca ctacctttcc    840
acccaatccg ctctttccaa agatccaaac gaaaagagag atcacatggt ccttcttgaa    900
tttgtcaccg cggcagtaa gttttccgga cttttatggt cctttatgc cattttccta     960 ctaactaacg gcttttgcgc gccttttcag gaattaccct tggaatggat gaactttaca    1020
aagttttcac cgctccaaaa aagaaaagga aggttttgac tgccccaaag aagaaaagaa    1080
aggttttcgc agcaaaagct gccaaagaat tc                                  1112
```

<210> SEQ ID NO 15
<211> LENGTH: 154
<212> TYPE: DNA

<213> ORGANISM: Artificial Sequence
<220> FEATURE:
<223> OTHER INFORMATION: Spgfp-2 coding region 1

<400> SEQUENCE: 15

```
atggtctcaa aaggagaaga gcttttcacc ggagtcgtcc caatccttgt cgaacttgat      60
ggcgatgtaa acggacacaa attctccgtc tccggcgaag gagagggaga tgctacctac     120
ggaaagctta cccttaaatt tatctgcacg acag                                 154
```

<210> SEQ ID NO 16
<211> LENGTH: 175
<212> TYPE: DNA
<213> ORGANISM: Artificial Sequence
<220> FEATURE:
<223> OTHER INFORMATION: Spgfp-2 coding region 2

<400> SEQUENCE: 16

```
gaaaacttcc tgtcccttgg ccaacccttg tcaccaccct tacctacgga gtccaatgct      60
tctccagata ccctgatcac atgaaacaac acgatttctt caaatccgct atgccggagg    120
gatacgtgca agagagaacc atcttcttca agatgatgg aaactacaaa acgag          175
```

<210> SEQ ID NO 17
<211> LENGTH: 177
<212> TYPE: DNA
<213> ORGANISM: Artificial Sequence
<220> FEATURE:
<223> OTHER INFORMATION: Spgfp-2 coding region 3

<400> SEQUENCE: 17

```
agctgaagtc aaattcgaag gagatacccct tgtcaataga atcgaactta aaggaatcga     60
tttcaaagag gatggaaaca tccttggaca caaacttgaa tacaactaca actcccacaa    120
cgtctacatt atggctgata acaaaaaaa cggaatcaaa gtcaacttta aataag         177
```

<210> SEQ ID NO 18
<211> LENGTH: 179
<212> TYPE: DNA
<213> ORGANISM: Artificial Sequence
<220> FEATURE:
<223> OTHER INFORMATION: Spgfp-2 coding region 4

<400> SEQUENCE: 18

```
acacaacatc gaagatggat ccgtccaact tgctgatcac taccaacaaa cacccccaat      60
cggggatggc ccgtccttc ttccggataa ccactacctt tccacccaat ccgtctcttc    120
caaagatcca acgaaaaga gagatcacat ggtccttctt gaatttgtca ccgcggcag      179
```

<210> SEQ ID NO 19
<211> LENGTH: 122
<212> TYPE: DNA
<213> ORGANISM: Artificial Sequence
<220> FEATURE:
<223> OTHER INFORMATION: Spgfp-2 coding region 5

<400> SEQUENCE: 19

```
gaattaccct tggaatggat gaactttaca agttttcac cgctccaaaa aagaaaagga      60
aggttttgac tgccccaaag aagaaaagaa aggttttcgc agcaaaagct gccaaagaat    120
tc                                                                   122
```

<210> SEQ ID NO 20
<211> LENGTH: 73
<212> TYPE: DNA

```
<213> ORGANISM: Artificial Sequence
<220> FEATURE:
<223> OTHER INFORMATION: Spgfp-2 1VS1-intron 1

<400> SEQUENCE: 20
gtaagttttg tatacttttc gtgtattttc cgtgattttc atactaacta acccctttg      60 ccactatttt cag                                                         73

<210> SEQ ID NO 21
<211> LENGTH: 73
<212> TYPE: DNA
<213> ORGANISM: Artificial Sequence
<220> FEATURE:
<223> OTHER INFORMATION: Spgfp-2 1VS2-intron 2

<400> SEQUENCE: 21
gtaagttttg gcacattttg cgcatatttt ccaccatttt actactaact aacagcttt       60 gctgcatttt cag                                                         73

<210> SEQ ID NO 22
<211> LENGTH: 74
<212> TYPE: DNA
<213> ORGANISM: Artificial Sequence
<220> FEATURE:
<223> OTHER INFORMATION: Spgfp-2 1VS3-intron 3

<400> SEQUENCE: 22
gtaagttttc ggcaattttg actacatttt ggctcatttt cttactaact aacgtctttt      60
cacacacttt tcag                                                        74

<210> SEQ ID NO 23
<211> LENGTH: 74
<212> TYPE: DNA
<213> ORGANISM: Artificial Sequence
<220> FEATURE:
<223> OTHER INFORMATION: Spgfp-2 1VS4-intron 4

<400> SEQUENCE: 23
gtaagttttc cggactttta tggtccttt atgccatttt cctactaact aacggcttt        60 gcgcgccttt tcag                                                        74
```

LEVELS AND/OR SUSTAINABILITY OF DNA-BASED GENE EXPRESSION

RELATED APPLICATIONS

This application is a U.S. National Phase Application of International Application No. PCT/US2007/002453, filed Jan. 29, 2007, which claims the benefit of U.S. Provisional Application 60/762,504, filed Jan. 27, 2006, all of which are incorporated herein in their entirety.

STATEMENT OF U.S. GOVERNMENT INTEREST

The work described herein was performed under grant NIH-R01-GM37706 of the National Institute of General Medical Science, NIH. The U.S. Government may, therefore, have certain rights with respect to the invention pursuant to said grant.

FIELD OF THE INVENTION

The present invention relates to improving levels and/or sustainability of DNA-based gene expression in eukaryotic cells through the inclusion of defined nucleosome positioning signals and/or periodic clusters of AA::TT dinucleotides.

BACKGROUND OF THE INVENTION

DNA carries biological information on a variety of levels. Some of the information is evident from well-defined sequence features such as the genetic code and certain reproducible transcription factor binding sites. Other (perhaps equally important) information in the genome may involve less precise sequence rules and longer-range interactions that are likely to be more difficult to detect and understand.

One approach to dissecting the information encoded in the genome is to search for non-random character in the DNA sequence. Protein coding constraints, for example, produce a non-random distribution in the utilization of base triplets. Likewise, certain transcription factors have a tendency to recognize multiple target sequences in a short interval, producing a localized increase in the incidence of one or more motifs. An intriguing means to investigate non-random features of DNA sequence involves searches for periodic appearance of specific sequence elements (see Trifonov, 1989; Mirsky 2004, which is herein incorporated by reference in its entirety). Previous analyses of this type have identified, among other non-random features, a strong tendency for 3n repeats in coding sequences (due to non-random usage of the genetic code and of amino acid sequences) and a periodicity of 10-11 bp in occurrence of AA/TT dinucleotides. The latter periodicity has been observed rather strikingly in sequences that display intrinsic curvature in vitro (e.g., Koo et al., 1986; Ulanovsky et al., 1987; Goodsell and Dickerson, 1994, which are herein incorporated by reference in their entireties). AA/TT dinucleotides are also unusual in having less flexibility under certain circumstances than other dinucleotide pairs (e.g., Nelson et al., 1987, which is herein incorporated by reference in its entirety) and in their apparent ability to contribute to the later positioning of nucleosomes along DNA (e.g., Satchwell et al., 1986, which is herein incorporated by reference in its entirety).

Although the bulk genome periodicity analysis has substantial power to detect patterns in the sequence, the biological significance of these patterns has remained somewhat of a mystery, in particular, due to challenges in identifying and finding functional consequences corresponding to individual sequence characteristics. From this perspective, well characterized model systems such as *C. elegans* provide a tool of considerable value. *C. elegans* has been reported to exhibit a strong 10.n base periodicity signal (e.g., VanWye et al., 1991; Widom, 1996; Fukushimna et al., 2002, which are herein incorporated by reference in their entireties) and is among the most extensively characterized both in structure (a complete sequence) and function (both individual genetic studies and whole genome expression and phenotypic analysis).

Notwithstanding extensive study of sequence patterns and their possible effect on biological functions, there remains a substantial area for exploration to determine the implications of sequence patterns and functional activity. The present invention is based on such a study using *C. elegans* as a model system applicable to eukaryotes in general.

SUMMARY OF THE INVENTION

The present invention is based on the finding of a surprisingly prevalent and extensive periodic character in the *C. elegans* genome. Rather than underlying the entire genome sequence, these periodic regions appear enriched in a number of "islands" throughout the genome. These islands are for the most part unique in sequence; strikingly, they appear to delineate transcribed regions for a large group of genes that are expressed in the self-renewing cell population of the *C. elegans* germline.

In one embodiment, the invention provides a method for improving the level and/or sustainability of expression for a target nucleic acid in a eukaryotic cell comprising:
(a) modifying the target nucleic acid to introduce or to comprise signals that limit or constrain the positions of nucleosome cores, and
(b) introducing the modified target nucleic acid into the eukaryotic cell,
wherein the modified target nucleic acid has improved levels and/or sustainability of expression compared to original unmodified nucleic acid.

In some embodiments, the target nucleic acid is an expression vector. In yet a further embodiment, the expression vector comprises a promoter and the coding region for a protein or RNA molecule whose synthesis is desired.

In some embodiments, the coding region encodes an endogenous protein. In other embodiments, the coding region encodes an exogenous protein. In further embodiment, the coding region encodes an RNA shorter than 100 bases.

In some embodiments, expression of the modified nucleic acid is at least 100% greater than that of the original unmodified nucleic acid. In other embodiments, expression of the modified nucleic acid is at least 50% greater than that of the original unmodified nucleic acid. In some embodiments, expression of the modified nucleic acid is at least 10% greater than that of the original unmodified nucleic acid.

In some embodiments, expression of the modified nucleic acid is at least 100% greater than that of the original unmodified nucleic acid after a time period of at least one day has been allowed to pass. In other embodiments, expression of the modified nucleic acid is at least 50% greater than that of the original unmodified nucleic acid after a time period of at least one day has been allowed to pass. In yet another embodiment, expression of the modified nucleic acid is at least 10% greater than that of the original unmodified nucleic acid after a time period of at least one day has been allowed to pass.

In some embodiments, the modifications of the target nucleic acid to introduce signals involve the mutation of at least 10 base pairs in a manner expected to limit or constrain the positions of nucleosome cores. In other embodiments, the modifications to the target nucleic acid involve the mutation of at least 5 base pairs in a manner expected to limit or constrain the positions of nucleosome cores. In yet another embodiment, the modifications to the target nucleic acid involve the mutation of at least 3 base pairs in a manner expected to limit or constrain the positions of nucleosome cores. In some embodiments, the modifications to the target nucleic acid involve at least one insertion of at least 10 base pairs to the target nucleic acid in a manner expected to limit or constrain the positions of nucleosome cores. In further embodiments, the modifications to the target DNA involve at least one insertion of at least 10 base pairs upstream, downstream, or inside the RNA or protein coding region in a manner expected to limit or constrain the positions of nucleosome cores.

In some embodiments, the inserted sequence acts as an intron sequence.

In some embodiments, the modifications made to the target nucleic acid sequence reflect known biases for nucleosome positioning based on analysis of positioned nucleosomes from the biological literature. In other embodiments, the modifications made to the target nucleic acid sequence reflect experimental determination of nucleosome positions on unmodified and modified sequence.

In some embodiments, the modifications to the target nucleic acid sequence result in at least 10 additional AA/TT dinucleotide junctions in a region of 1000 base pairs. In other embodiments, the modifications to the target nucleic acid sequence result in at least 5 additional AA/TT dinucleotide junctions in a region of 1000 base pairs. In yet another embodiment, the modifications to the target nucleic acid sequence result in at least 3 additional AA/TT dinucleotide junctions in a region of 1000 base pairs. In another embodiment, the modifications to the target nucleic acid involve at least one deletion of at least 1 base pair in a manner expected to limit or constrain the positions of nucleosome cores.

In some embodiments, the modifications to the target nucleic acid involve at least one deletion of at least 1 base pair upstream, downstream, or inside the RNA or protein coding region in a manner expected to limit or constrain the positions of nucleosome.

In some embodiments, the target nucleic acid is introduced into the eukaryotic cell by transfection. In other embodiments, the target nucleic acid is a viral vector introduced into the eukaryotic cell by infection.

In some embodiments, the target nucleic acid is introduced into the eukaryotic cell by injection of the cell, or by injection of the target nucleic acid into the organism in which the cell is contained. In other embodiments, the target nucleic acid is introduced into the eukaryotic cell by means of an aerosol.

In some embodiments, the inserted nucleic acid is one which has been shown to constrain nucleosome positions in vitro or in vivo. In other embodiments, the inserted nucleic acid is from a gene with known limitations to nucleosome mobility. In another embodiment, the inserted nucleic acid is from a nematode genome. In further embodiments, the inserted nucleic acid is from a nematode gene that is normally expressed in the nematode germline.

In some embodiments, the eukaryotic cell is grown in cell culture. In other embodiments, the eukaryotic cell is in a living tissue. In further embodiments, the eukaryotic cell is in a human host.

In some embodiment, the eukaryotic cell is infected with a virus. In other embodiments, the eukaryotic cell is part of a tumor.

In some embodiments, the coding region is missing or compromised in function in a genetic disease and the target eukaryotic cell is from a host carrying that disease.

In some embodiments, introduction of the modified target nucleic acid is used to provide a therapy to patients carrying the genetic disease.

In other embodiments, expression of the coding region facilitates an assay for specific biological properties of the target cell or its host organism.

In another embodiment, the invention provides a method for the expression of a target nucleic acid which encodes a protein or RNA molecule of interest in a eukaryotic cell comprising:
(a) modification of the target nucleic acid sequence such that signals that limit or constrain the positions of nucleosome cores are introduced into said target nucleic acid, and
(b) introduction of the modified target nucleic acid into a eukaryotic cell, wherein the modified target nucleic acid expresses the protein or RNA molecule of interest in the eukaryotic cell.

In another embodiment, the invention provides a method for improving the level and/or sustainability of expression for a target nucleic acid in a eukaryotic cell comprising:
(a) modification of the target nucleic acid to introduce at least 10 AA/TT dinucleotides in positions where a majority of distances in base pairs between adjacent AA/TT dinucleotides in the modified nucleic acid are in the range of 1-3, 10-13, 20-23, 30-33, 40-43, or 50-53 nucleotides, and
(b) introducing said modified target nucleic acid into a eukaryotic cell, wherein the modified target nucleic acid has improved levels and/or sustainability of expression compared to original unmodified nucleic acid. Improved levels of expression of a modified target nucleic acid refers to an increase in the levels of target RNA and/or protein in a cell. Sustainability of expression of a modified target nucleic acid refers to maintaining the endogenous level of target RNA and/or protein in a cell.

In another embodiment, the invention provides a method for improving the level and/or sustainability of expression for a target nucleic acid in a eukaryotic cell comprising:
(a) modification of the target nucleic acid to introduce at least 5 AA/TT dinucleotides in positions where 80% or greater of the adjacent AA/TT dinucleotide separations that are a result of the modification are in the range of 1-3, 7-13, 17-23, 27-33, 37-43, or 47-53 nucleotides, and
(b) introducing the modified target nucleic acid into a eukaryotic cell, wherein the modified target nucleic acid has improved levels and/or sustainability of expression compared to original unmodified nucleic acid.

In another embodiment, the invention provides a method for improving the level and/or sustainability of expression for a target nucleic acid in a eukaryotic cell comprising:
(a) modification of the target nucleic acid to introduce at least 10 AA/TT dinucleotides in positions where 80% or greater of the adjacent AA/TT dinucleotide separations that are a result of the modification are in the range of 1-3, 7-13, 17-23, 27-33, 37-43, or 47-53 nucleotides, and
(b) introducing the modified target nucleic acid into a eukaryotic cell, wherein the modified target nucleic acid has improved levels and/or sustainability of expression compared to original unmodified nucleic acid.

In another embodiment, the invention provides a method for improving the level and/or sustainability of expression for a target nucleic acid in a eukaryotic cell comprising:

(a) modification of the target nucleic acid to introduce at least 20 AA/TT dinucleotides in positions where 80% or greater of the adjacent AA/TT dinucleotide separations that are a result of the modification are in the range of 1-3, 7-13, L7-23, 27-33, 37-43, or 47-53 nucleotides, and
(b) introducing the modified target nucleic acid into a eukaryotic cell, wherein the modified target nucleic acid has improved levels and/or sustainability of expression compared to original unmodified nucleic acid.

In yet another embodiment, the invention provides a method for improving the level and/or sustainability of expression for a target nucleic acid in a eukaryotic cell comprising:
(a) modification of the target nucleic acid to introduce at least 30 AA/TT dinucleotides in positions where 80% or greater of the adjacent AA/TT dinucleotide separations that are a result of the modification are in the range of 1-3, 7-13, 17-23, 27-33, 37-43, or 47-53 nucleotides, and
(b) introducing the modified target nucleic acid into a eukaryotic cell, wherein the modified target nucleic acid has improved levels and/or sustainability of expression compared to original unmodified nucleic acid.

In another embodiment, the invention provides a method for improving the level and/or sustainability of expression for a target nucleic acid in a eukaryotic cell comprising:
(a) modification of the target nucleic acid by inserting sequences derived from a nematode into said target nucleic acid, and
(b) introducing the modified target nucleic acid into a target eukaryotic cell, wherein the modified target nucleic acid has improved levels and/or sustainability of expression compared to original unmodified nucleic acid.

In yet another embodiment, the inserted sequence is from a gene that is normally expressed in the *C. elegans* germline.

In another embodiment, the invention provides a method for expressing an RNA or protein molecule of interest in a eukaryotic cell comprising:
(a) synthesizing a nucleic acid molecule that is interrupted by one or more intron sequences that have signals capable of constraining or limiting the positions of nucleosomes and which nucleic acid molecule carries information sufficient to encode the RNA or protein molecule of interest,
(b) introducing said nucleic acid molecule into an expression vector, and
(c) introducing the expression vector comprising said nucleic acid into the eukaryotic cell, wherein the expression vector comprising said nucleic acid expresses the RNA or protein molecule of interest in the eukaryotic cell.

In another embodiment, the invention provides a method for expressing an RNA or protein molecule of interest in a eukaryotic cell comprising:
(a) synthesizing a nucleic acid molecule that is interrupted by heterologous intron sequences or flanked by sequences within 1000 base pairs where the intron or flanking nucleic acid sequence contains one or more synthetic or biologically-derived segment with at least one 50 base sub-segment with at least 10 AA/TT base pairs where the DNA helix can be modeled as a straight molecule with 10-11 base periodicity so that at least 70% of the AA/TT base pairs are visible by an observer looking laterally at the DNA helix and which nucleic acid carries information sufficient to encode the RNA or protein molecule of interest,
(b) introducing said nucleic acid molecule into an expression vector, and
(c) introducing the expression vector comprising said nucleic acid into the eukaryotic cell, wherein the expression vector comprising said nucleic acid expresses the RNA or protein molecule of interest in the eukaryotic cell.

In some embodiments, the synthetic nucleic acid molecule comprises at least one intron sequence selected from the group consisting of SEQ ID NO: 8-11 and 20-23.

In another embodiment, the synthetic nucleic acid molecule comprises at least 30 consecutive base pairs of a nucleotide sequence selected from the group consisting of SEQ ID NO: 8-11 and 20-23. In other embodiments, the synthetic nucleic acid molecule comprises at least 40 consecutive base pairs of a nucleotide sequence selected from the group consisting of SEQ ID NO: 8-11 and 20-23. In further embodiments, the synthetic nucleic acid molecule comprises at least 50 consecutive base pairs of a nucleotide sequence selected from the group consisting of SEQ ID NO: 8-11 and 20-23. In yet further embodiments, the synthetic nucleic acid molecule comprises at least 60 consecutive base pairs of a nucleotide sequence selected from the group consisting of SEQ ID NO: 8-11 and 20-23. In yet another embodiment, the synthetic nucleic acid molecule comprises a nucleotide sequence selected from the group consisting of SEQ ID NO: 8-11 and 20-23.

In some embodiments, the invention provides a method of positioning nucleosomes for a target nucleic acid in a eukaryotic cell comprising: modifying the target nucleic acid to introduce or to comprise signals that limit or constrain the positions of nucleosome cores, wherein the introduction of the signals positions nucleosomes on the target nucleic acid.

In some embodiments the target nucleic acid comprises DNA.

DESCRIPTION OF THE DRAWINGS

The foregoing summary, as well as the following detailed description of the invention, will be better understood when read in conjunction with appended FIGS. 1 to 26. For the purpose of illustrating the invention, shown in the figures are embodiments which are presently preferred. It should be understood, however, that the invention is not limited to the precise arrangements, examples and instrumentalities shown.

FIGS. 1A-B: High incidence of predicted static blends in *C. elegans* DNA. As shown in FIG. 1A, genomes of the indicated species were analyzed using the algorithms of Ulanovsky and Trifonov (1987) ("UT87"), Koo et al. (1986) ("KWC86"), and Bolshoy et al. (1991) ("BMHT91"), which are herein incorporated by reference in their entireties. The UT87 and BMHT91 algorithms predict a trajectory of the DNA through three dimensional space based on perturbations to the helix from specific dinucleotide sequences. The KWC86 algorithm predicts static bends at the borders of longer stretches of An or Tn. For the Koo and Crothers algorithm, it has been assumed that a four base segment (AAAA or TTTT) is required to produce bonds at each end; under these conditions, this algorithm is much more stringent than the two dinucleotide-based algorithms. Relaxing the stringency of the Koo and Crothers algorithm to require only three consecutive A's or T's gives a much closer apposition of the results from this algorithm to those from the UT87 algorithm. Values reported above are the fraction of residues in the genome sequence which lie within some window of 61 bp with a predicted overall bend angle of <84.3° [cos(ø)0.1]. Versions of the genomes used were the most current NCBI or organism-specific database assemblies as of the following dates: *Caenorhabditis elegans* (November 2002), *Sacchromyces cerevisae* (October 2002), *Schizosacchromyces pombe* (October 2002), *Drosophila melanogaster* (October 2002; Euchromatin), *Arabidopsis thaliana* (October 2002). "Global Monte Carlo" represents a random sequence of $10^8$ base pairs was assembled with the A+T composition of the *C. elegans* genome. "Repeat-masked" *C. elegans* represents the genome of *C. elegans* from which each segment of ≥25 nucleotides that is repeated more than one time is ignored using the Reputer algorithm of Kurtz and Schleiermacher (1999), which is herein incorporated by reference in its entirety.

FIG. 1B shows the differences between bending predictions as a function of algorithm parameters. Each line in the graph shows the distribution of bend angles for bases in the *C. elegans* genome (November 2002) as a function of specific parameters used in the UT87 algorithm. The parameters that can easily be examined on the graph are the length of the segment window (SW) used to calculate a maximum bend (31, 61, 121, 241), and angle used as an arbitrary cutoff to distinguish "bent" from "unbent" DNA.

FIG. 2: An exemplary segment of highly bent DNA in *C. elegans*. This Figure shows a unique sequence of 856 bp from the *C. elegans* genome with strongly bent character. This segment is from the fourth intron of gene F54C4.1, expected to encode the *C. elegans* ortholog of mitochondrial ribosomal protein L28 (Consortium, 1998, which is herein incorporated by reference in its entirety). Runs of AAA and TTT are colored accordingly and the sequence is arranged in columns with each line representing 10 bp of sequence. The phasing is evident in the columnar character of the coloring seen in the vertically arranged sequence.

FIGS. 3A-E. Periodicity of individual tetranucleotides in the *C. elegans* genome. FIG. 3A shows a schematic diagram of the procedure used to evaluate periodicity for individual tetranucleotides in the *C. elegans* genome. Briefly, a histogram is set up with zero in each bin from 1 to 256. A four-base-wide window is then "slid" along the genome. At each point, the program examines the sequence for the previous 256 base pairs looking for occurrences of the same tetranucleotide sequence. If an identical sequence is found n base pairs upstream, we add one to bin n in the histogram. For this figure, the "relative coincidence frequency" is a value derived from dividing the raw number of coincidences by the number that would be expected for a randomized genome with identical base composition to that of *C. elegans*. FIGS. 3B and 3C show the separation spectrum for AAAA/TTTT tetranucleotides using a dataset that is the complete *C. elegans* genome (FIG. 3B) and a version from which annotated coding regions and sequences of ~25 nt that appear more than once have been removed (FIG. 3C). The sequence files used for this analysis were derived from the 1999 version of Jim Kent and Alan Zahler's "intronerator" database (Kent and Zahler, 2000, which is herein incorporated by reference in its entirety); masking of repeats was performed using the algorithms of Kurtz and Schleiermacher (1999), which is herein incorporated by reference in its entirety. FIG. 3D (unfiltered) and FIG. 3E (filtered) show equivalent profiles for the tetranucleotide GCCG.

FIGS. 4A-B: An algorithm for detecting local AnTn periodicity. FIG. 4A shows a schematic description of the 'PATC' algorithm for detecting and assigning a score to periodic $A_n/T_n$ clusters in the *C. elegans* genome. A window of 1280 bp slides along the DNA sequence. Starting from the end of this window, the algorithm begins to define a series of "steps" of 9-12 base pairs backward along the DNA sequence. Each step identifies the center of a 5-base segment of the DNA that is scored for clustering of AA/TT junctions follows: segments with four AA/TT junctions (the maximum for a 5-base segment) are scored 30, segments with three, two, one, and zero AA/TT junctions are scored 20, 10, 0, and −5 respectively. A cost is then assessed based on the length of each step: 10 base steps (canonical helical pitch for DNA) scores are assessed at the lowest rate (8 points), while non canonical steps (9, 11, 12) are assessed at higher rates (16, 16, and 32 points respectively). The algorithm continues to work backward along the DNA sampling all possible combinations of the next three steps, until a stopping point is reached for which no combination of the next three backward-reaching steps would increase the score. In practice the computational load of the algorithm is limited in that the stopping point is generally reached within a few helical turns for DNA sequence which is not strongly structured. The phasing score assigned to any given base is the maximum value for all combinations of steps that extend through the base in question. Parameters for this algorithm were set essentially by trial-and-error, starting with statistical costs based on occurrence of features in randomized DNA sequence (each difference of 20 points was designed to reflect a roughly 10-fold difference in background probability). Slight modifications were then made to minimize overweighting of certain simple features in DNA sequence (e.g. A or T homopolymer tracks). Reassuringly, rather significant deviations in parameters for the program produced only marginal differences in distribution of apparent phasing for the *C. elegans* genome (data not shown). Note, however, that long near homopolymeric A or T tracts (>40 bp) will generate a high score with this algorithm. The rarity of such tracts in the *C. elegans* genome ensures that the algorithm truly fulfils the goal of identifying periodic segments. To ensure that this is the case for other scanned genomes, the program maintains a list of the 10 most highly periodic genome segments that have been identified in a DNA sample. Manual inspection of this list after running a novel genome is useful to assess the suitability of the algorithm in the corresponding analysis.

FIG. 4B shows computed distributions of PATC scores above specific values for the *C. elegans* genome (May 2005 version from wormbase) and from a randomized sequence with identical AT content. Y axis numbers are the fraction of total bases in the genome (or random control sequence) with PATC values above the number represented by the X axis coordinant.

FIG. 6A. Distribution of periodic structures in the *C. elegans* genome. Fractions of sequences that fall within segments with a phasing score of 95 or greater using the PATC algorithm described in FIG. 4A. *C. elegans* intron and exon sequences are from a duplicate-filtered set of individual gene sequences derived from Wormbase annotation in May 2005. Intergenic regions are derived from "Intronerator" annotation (1999 version). Unique and repeated sequences were derived from the genbank version of November 2002 in which "repeated" represents those sequences that are contained in a segment of >25 bp that is repeated more than once in the genome. S. cerevisiae, S. pombe, A. thaliana, and C. briggsae genome drafts were as described in FIG. 1. D. melanogaster sequences used for this analysis represent the most current versions available as of September 2005. C. elegans random (b) sequence represents a random string of 108 bases assembled using an algorithm in which the each base in the sequence is added at random using probability weights based on AT/GC ratios for the entire genome. C. elegans random (c) sequence was a sequence of comparable length assembled using a fifth order random Markov model as described by Lowe and Eddy (1999), which is herein incorporated by reference in its entirety, and was a kind gift of Dr. Eddy.

Figure 4A:
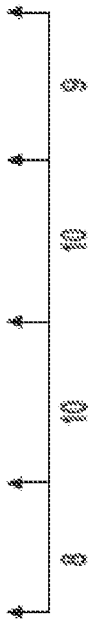
Figure 7B:
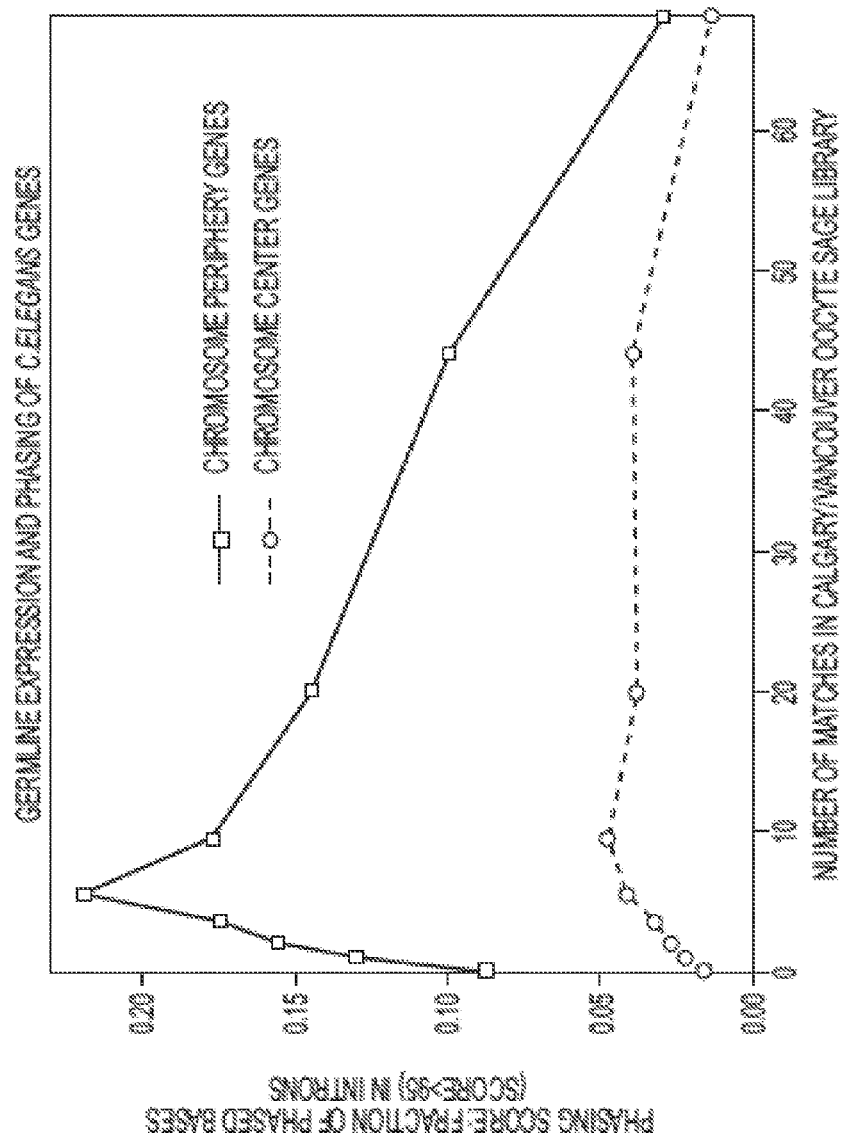
FIG. 7B. Association between phasing character and germline expression based oil data from Serial Analysis of Gene Expression [SAGE]. Sage data from the UBC genome center (see Experimental Procedures) was extracted May 2005, requesting only unambiguous tags assigned to mRNA transcripts. Data were pooled so that the total number of tags from a given gene were summed (file: longsummed.txt; only data from long-sage experiments was utilized). A gene list was then derived representing unique gene names for only those genes that were represented at least once (for any tissue) in the long SAGE data set (file: longsummedlistttxt). Duplicate gene models were eliminated from these set by keeping only a single model (alphabetically the first) for any group with the numerical character *###*#.#.# (e.g. Y134G5.3.1, Y134G5.3.2, etc) or *###*#.#* (e.g. Y134G5.1a, Y134G5.1b, etc.). This data was combined with gene-by-gene measurements of phasing within intron sequences, using the May 2005 version of the C. elegans gene list from which we filtered out a number of artefactual gene models that were misannotated as covering most of a chromosome.

The graph in FIG. 7B shows correspondence between prevalence of SAGE clones in the 10 ngSAGE oocyte library from wild type animals and fraction of phasing in introns (cutoff score 95, FIG. 4). Genes were separated into two partitions based on location as in FIG. 7A.

Figure 7C:
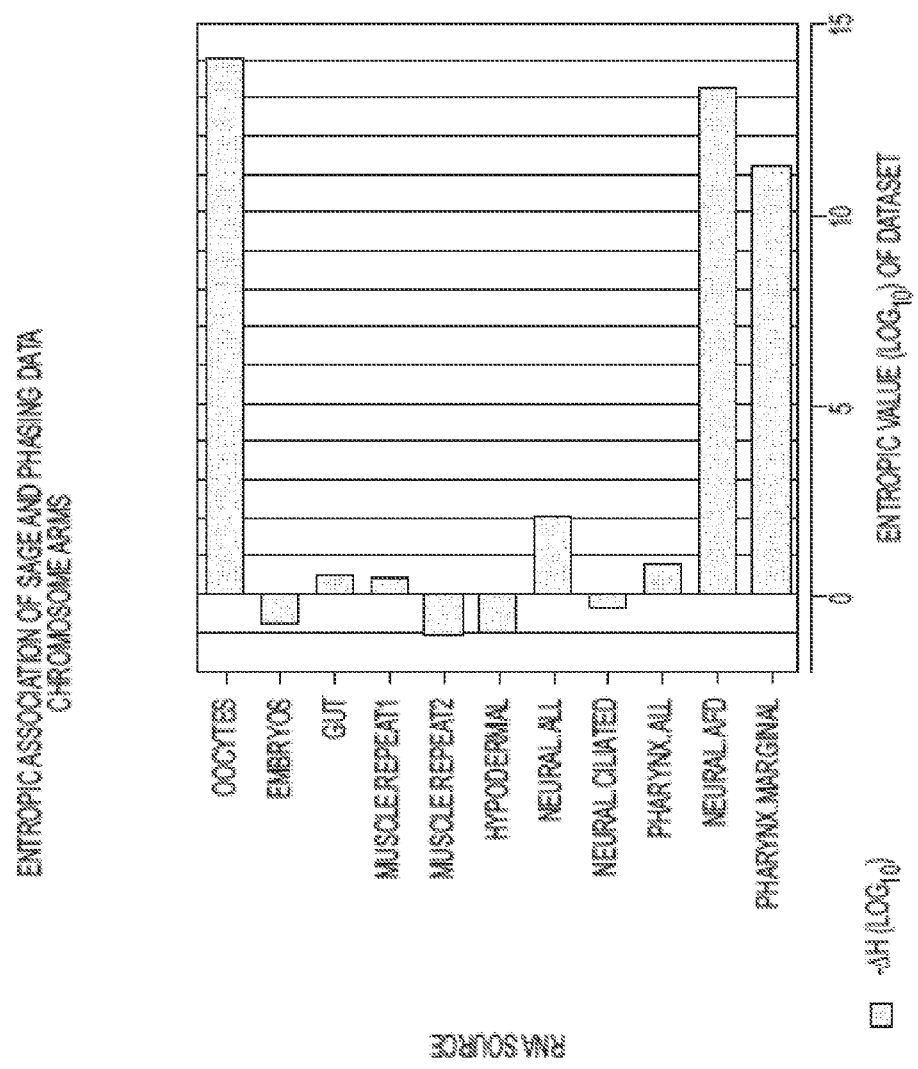
FIG. 7A. Association between phasing character and germline expression. This figure presents an initial comparison of phasing properties among a subset of C. elegans genes for which specific biological functions had been assigned by classical genetic means. To obtain a set of genes which had been characterized independently of genome-wide approaches, we focused on a list of genes which were first isolated using classical genetic screens. In most cases, extensive phenotypic and molecular analysis of these loci was carried out independently of whole-genome expression analysis tools that have been available in the last few years. Genes were also separated on the basis of position within the genome into a strongly-periodic subset (upper part of the figure; roughly the terminal of each autosome plus the left tip of X) and the remaining component of the genome (lower part of figure). At left are shown the highest ranked genes (in terms of intron phasing) in each set. The fully unperiodic group of genes in each genome partition is quite large (several thousand genes in each set show no detectable phasing in introns, exons, or flanking DNA). To avoid any systematic bias in this group, we selected at random within the unperiodic set, listing in the figure only those genes that meet the criteria for classical genetic characterization described above. Although the expression and activity pattern for these 139 genes are by no means completely known, a considerable body of information from gene-specific investigations is available for each gene. This information, referenced through wormbase and open-access literature articles therein, was scanned for indications of any of the following properties: (a) A mutant phenotype which appeared likely to reflect a need for germ line expression of the wild-type gene (e.g. maternal effects on embryogenesis) (b) Evidence for germline expression from antibody staining or in situ hybridization (c) Expression of trans gene reporter constructs in germline tissue (note that such experiments frequently fail to show germline expression for unknown reasons, so that negative results in trans gene assays are not particularly indicative). Although all of these criteria have certain caveats and biases, they are certainly among the best available based on current technologies. We note also here that our gene-by-gene literature-based annotation of germline expression information was likely to be somewhat imperfect. Of the 139 genes in the original scanned set, subsequent conversations with colleagues working on two of the genes (sex-1 [Barbara Meyer] and smu-1 [Robert Herman]) indicated that we had missed subtle points in the original literature). Given the nature of the analysis, this type of error is almost certain to underestimate the number of germline expressed genes in each set. Similarly, it should be stressed that currently published analysis of any given gene is always expected to be incomplete; thus we would certainly expect that additional genes from these lists will eventually be shown to express in germline tissue.
Figure 7D:
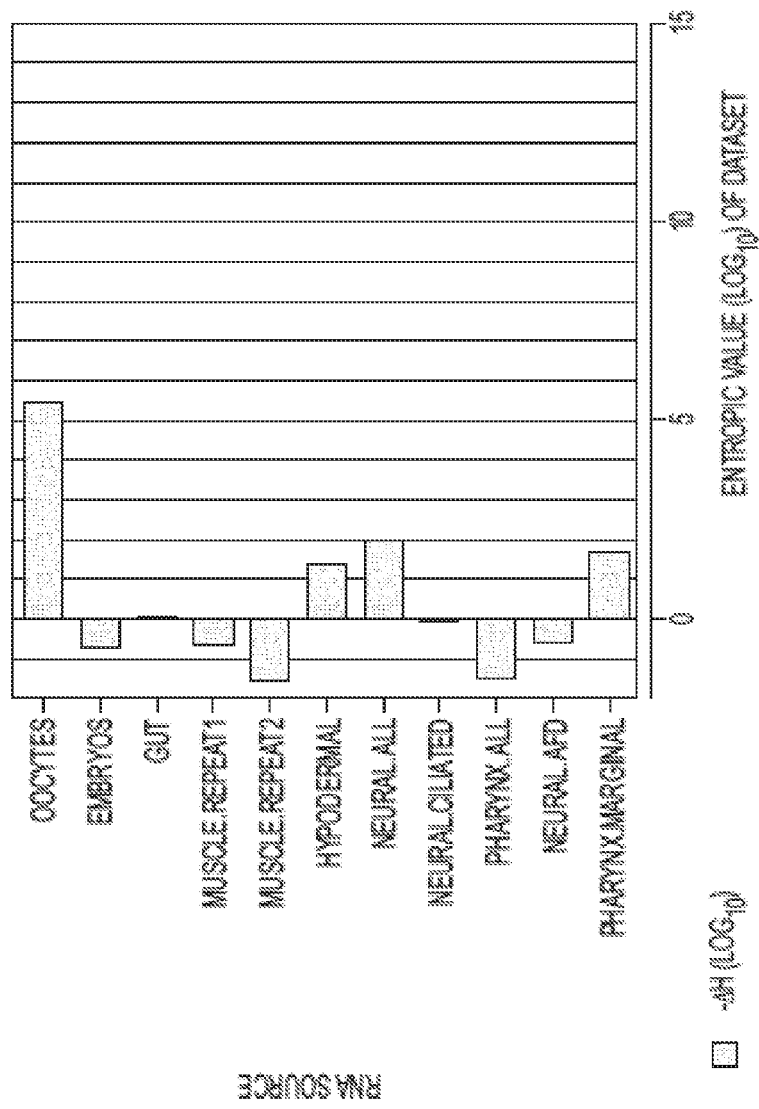

FIG. 7C-D. Quantitative measurement of SAGE-phasing association for different tissues. For each tissue for which highly specific "long-SAGE" data was available from the UBC/GenomeCanada dataset, we calculated a statistical association with intron phasing scores (fraction of intronic bases showing a PATC score above 95). Quantitation of probability association was done using an entropic measure: specifically of the degree to which knowing the SAGE levels in a given group of genes decreases the entropy associated with periodic/non-periodic character in intron sequences. Entropy contributions were arbitrarily weighted relative to total length of intron sequences within a gene. Formulaically, the Entropy Release upon contribution of SAGE data is calculated as $$-\Delta H = \Sigma_{genes} I_g/I_a * (F_g * \log_{10}(F_s/F_a) + (1-F_g) * \log_{10}((1-F_s)/(1-F_a))) = \Sigma_{genes} I_g/I_a * X_g$$

Where
$I_g$ Number of intronic bases in gene "g"
$I_a$ = Average number of intronic bases in all tested genes
$F_g$ = Fraction of intronic sequences in gene "g" with above-threshold phasing (PATC score ≥95)
$F_s$ = [Number of periodic (PATC score ≥95) intronic bases in all genes except "g" with an equivalent [*] SAGE signal to that seen with gene "g"]/[total number of intronic bases in these genes].
$F_a$ = Fraction of intronic sequences (in all genes) with above-threshold phasing [PATC≥95].

This calculation can also be described in terms of a Bayesian value expressing the relatively likelihood of two different datasets (e.g. Sage Data) providing optimal prediction of a non-independent value (in this case the phasing fraction) or as a value related to a size-weighted Cross-Entropy (Kullback and Lieber, 1951).

*These models would show some degree of unintended noise with Sage data due to the volatility of phasing estimates for large SAGE values. To get around this, we stabilized the SAGE→Phasing estimates for large values of the SAGE hit number (S) by averaging the phasing percentage with genes with adjacent values of S. Unless there are at least 10 genes with a similar S score, the algorithm would does a running average by collecting genes with lower and higher S values until each category has at least 10 genes; 7C: phasing scores from chromosome arms; 7D: phasing scores from chromosome centers.

FIG. 8A-D. Periodicities of individual tetranucleotides in the C. elegans genome. Plots of coincidence frequency versus separation for each of the 256 nucleotides in the C. elegans genome. Data was obtained using identical methods and datasets to that of FIG. 3.

Figure 8A:
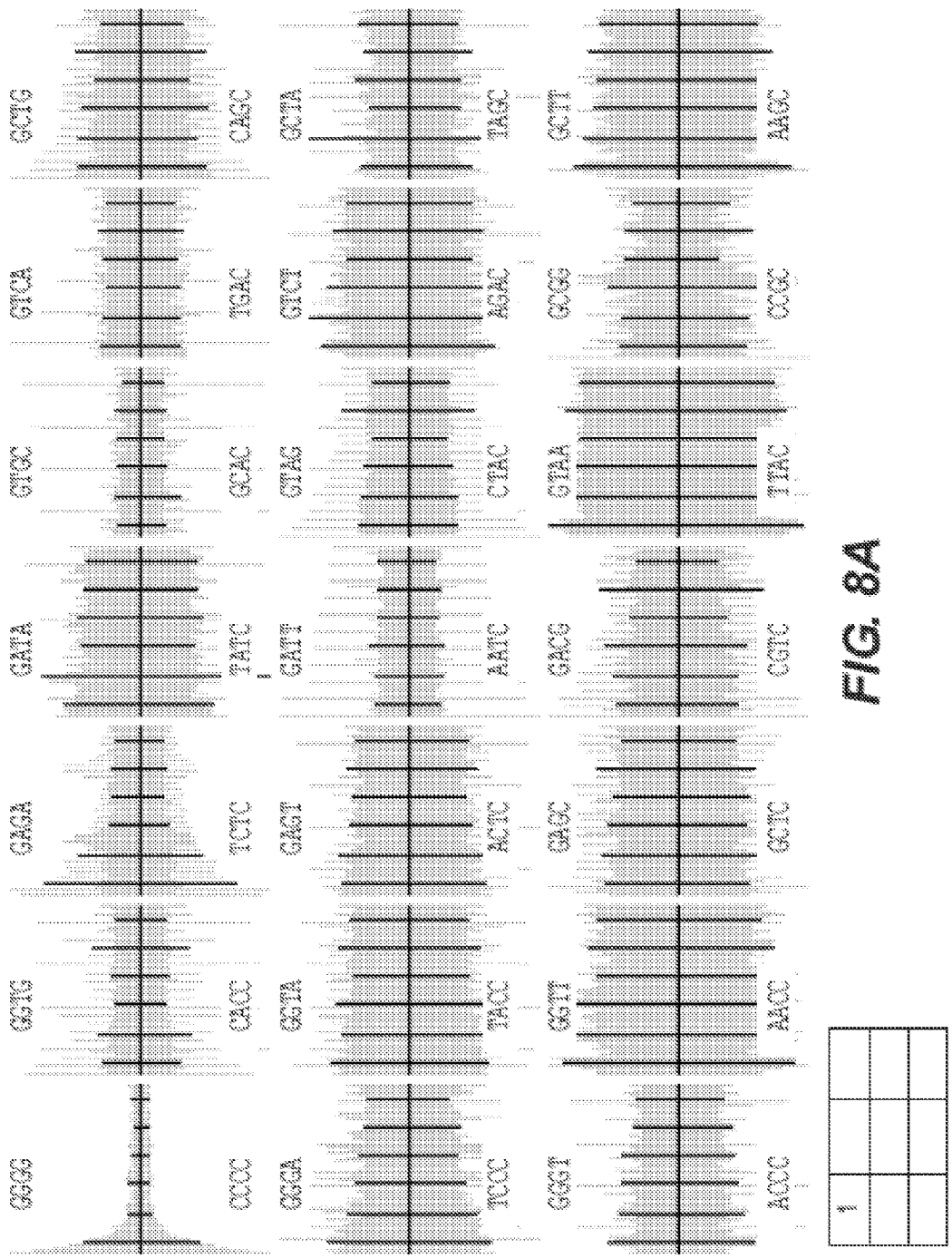
Figure 8A:
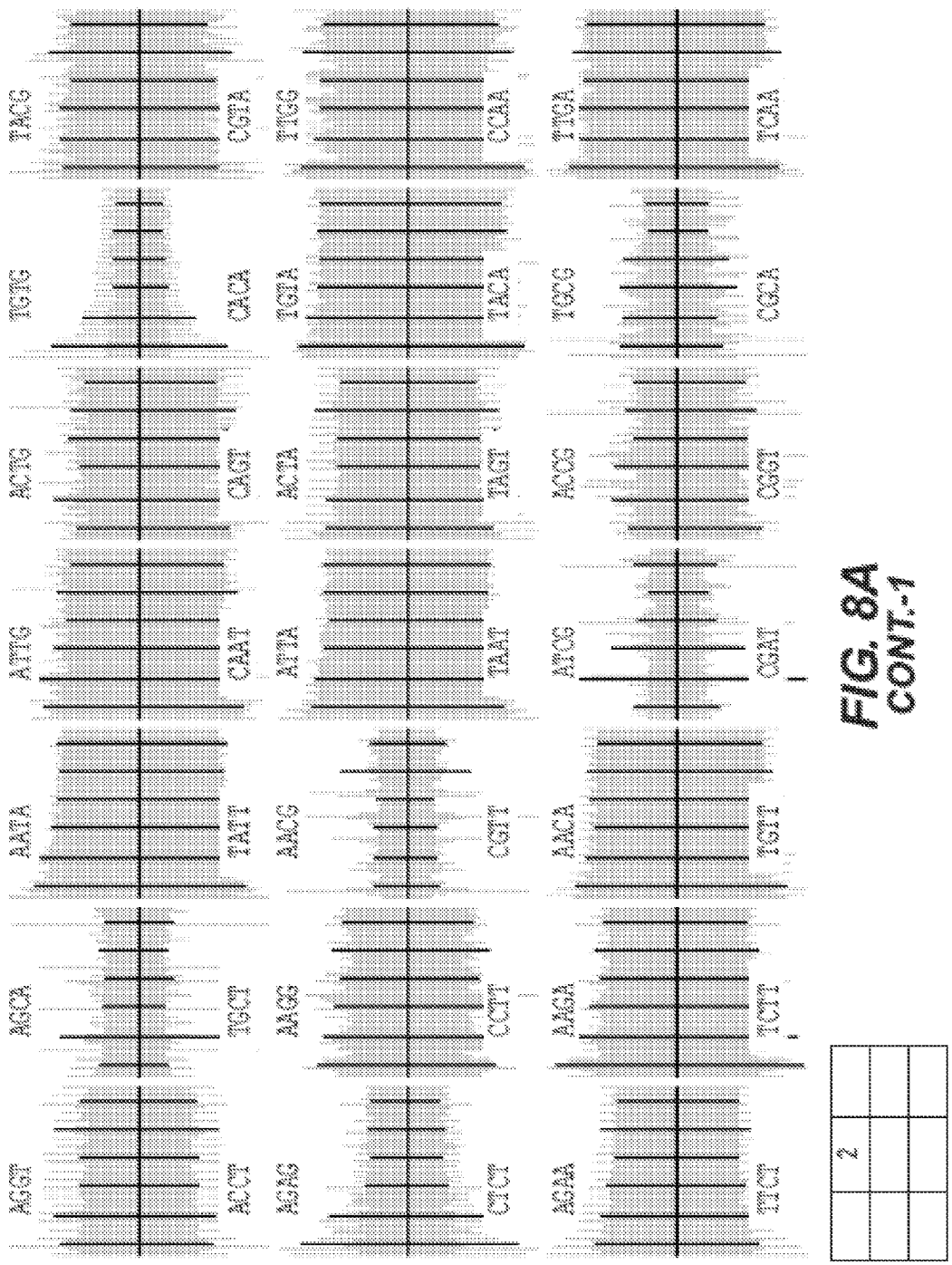
Figure 8A:
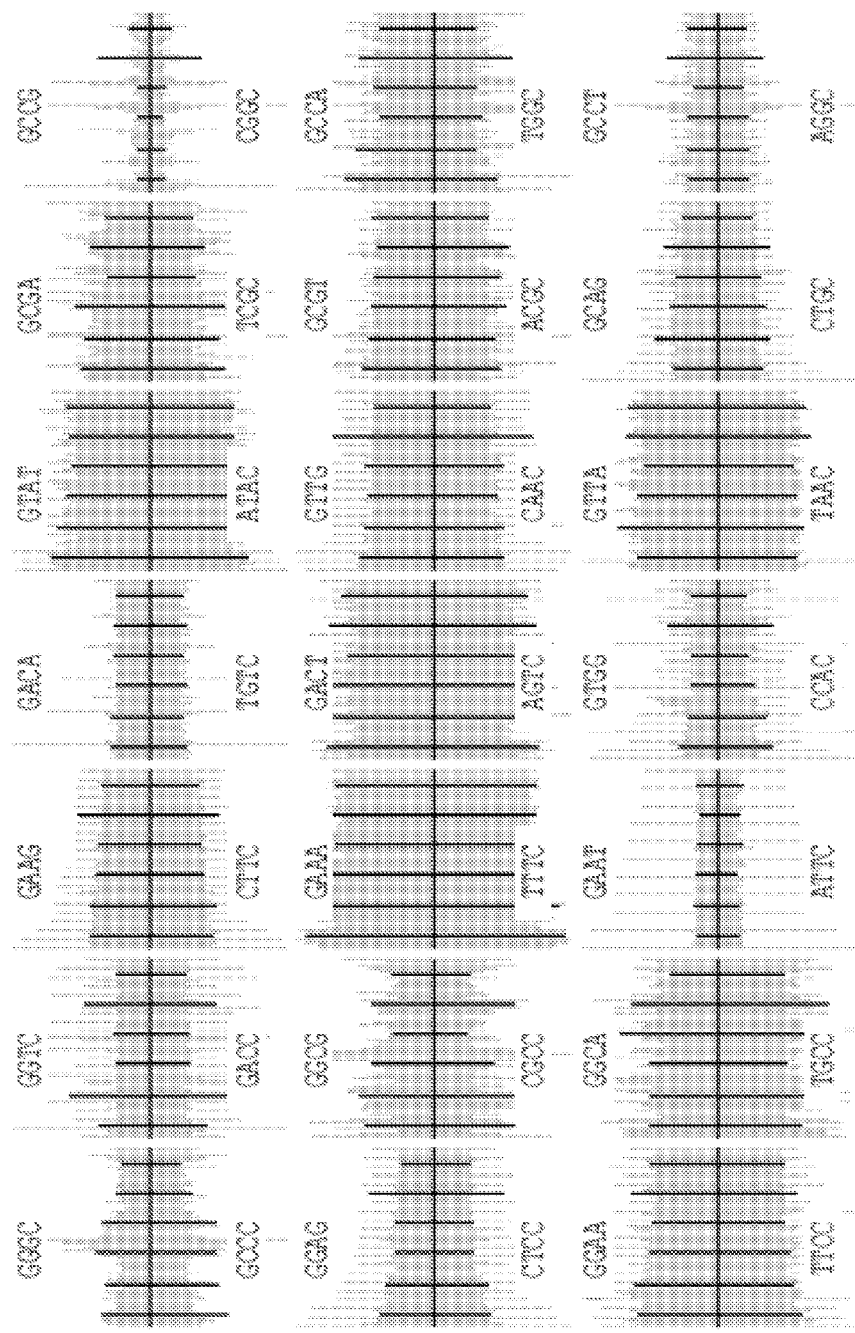
Figure 8A:
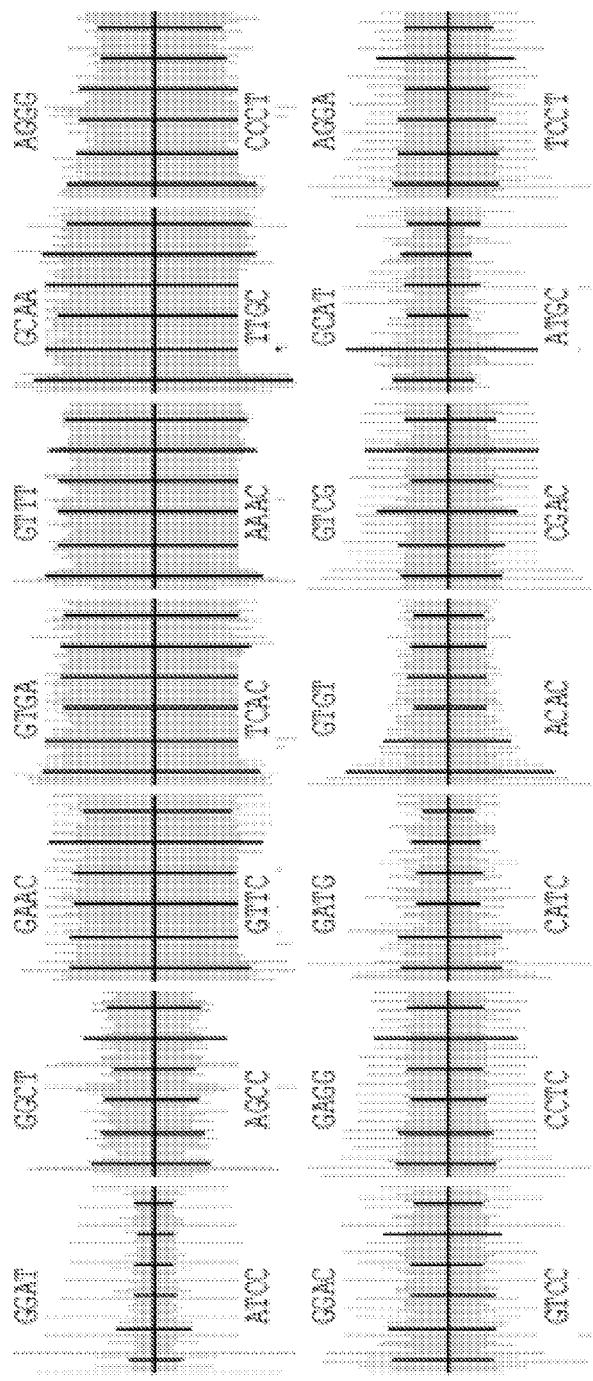
Figure 8B:
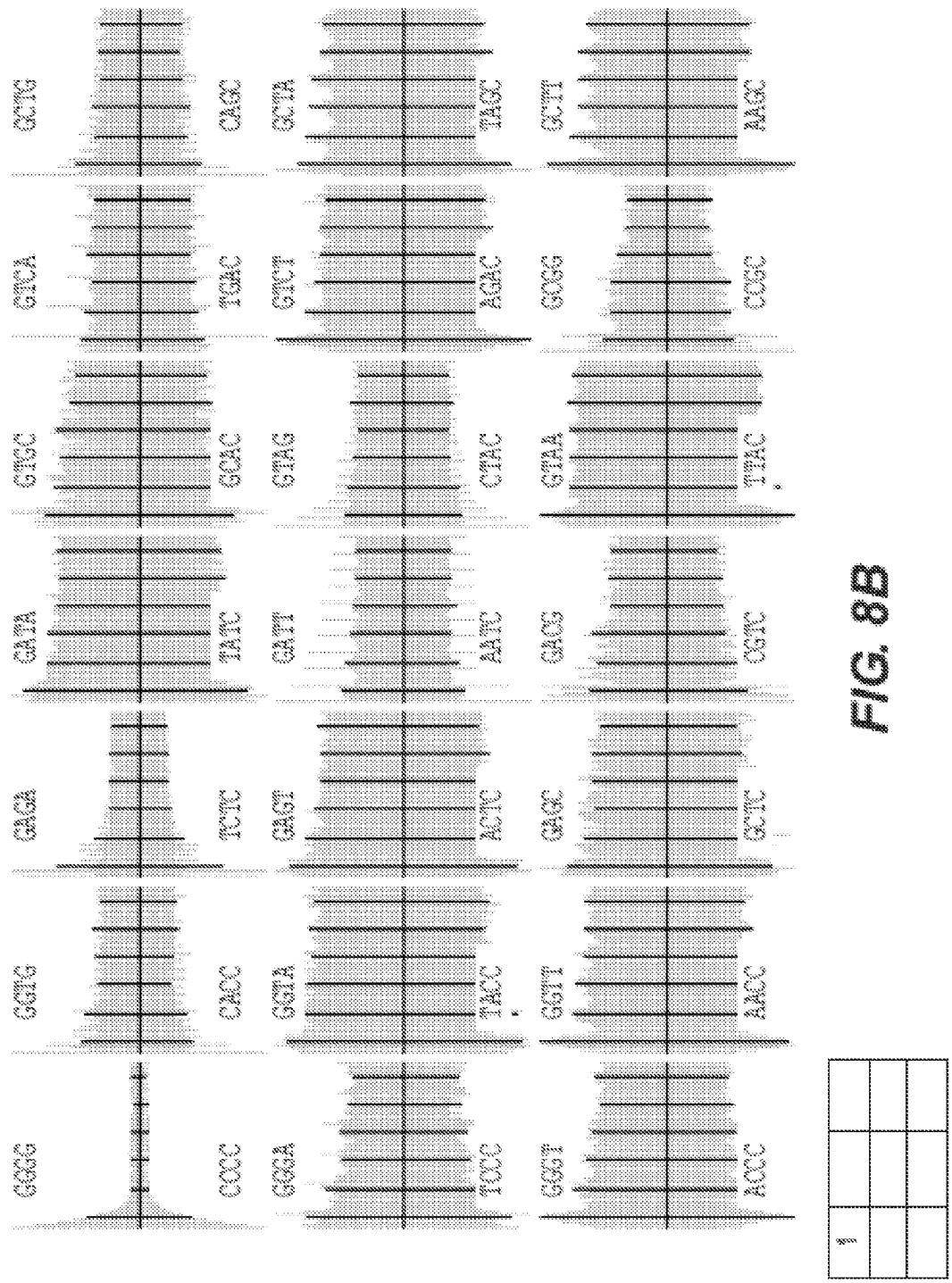
Figure 8B:
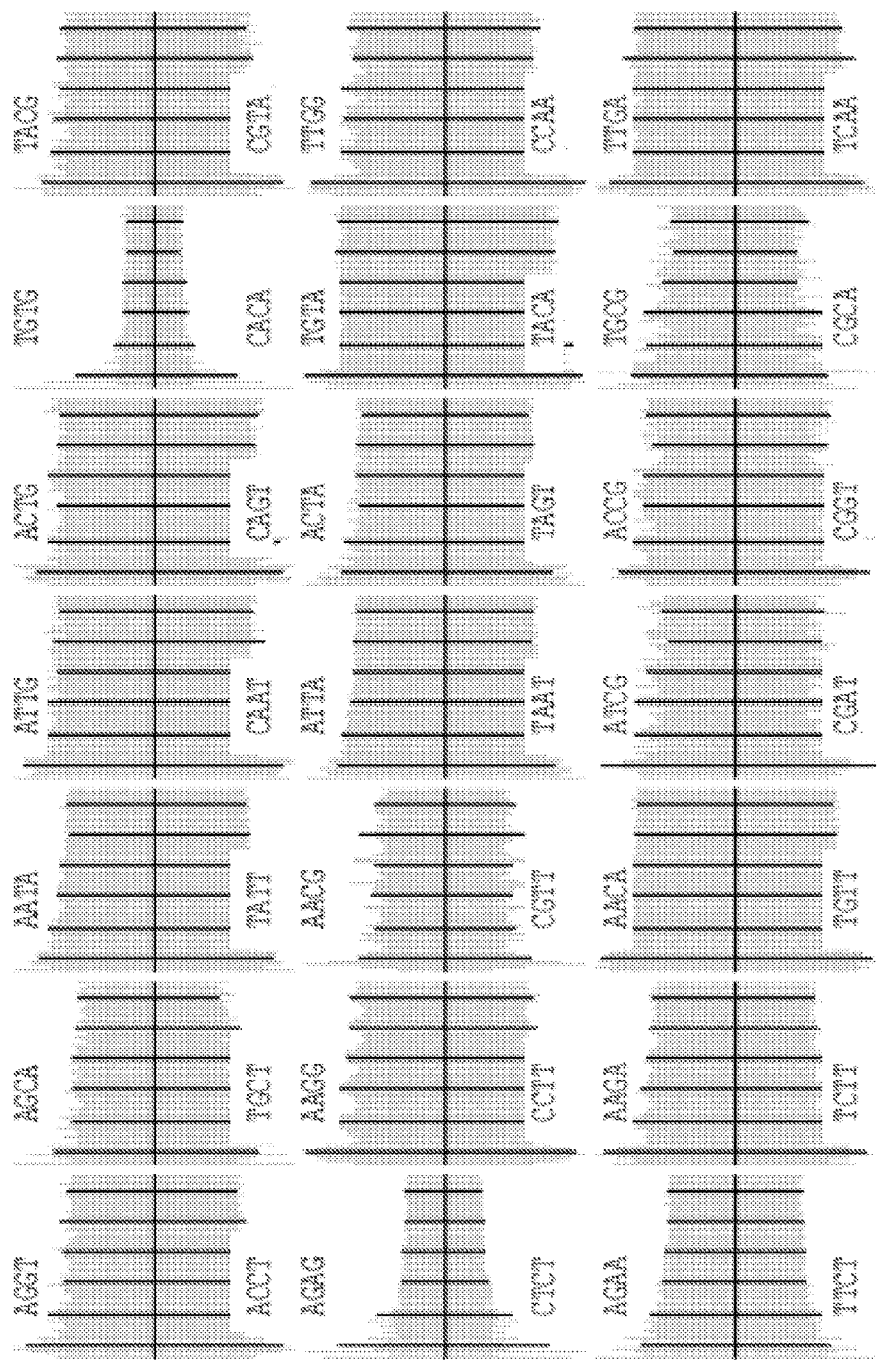
Figure 8B:
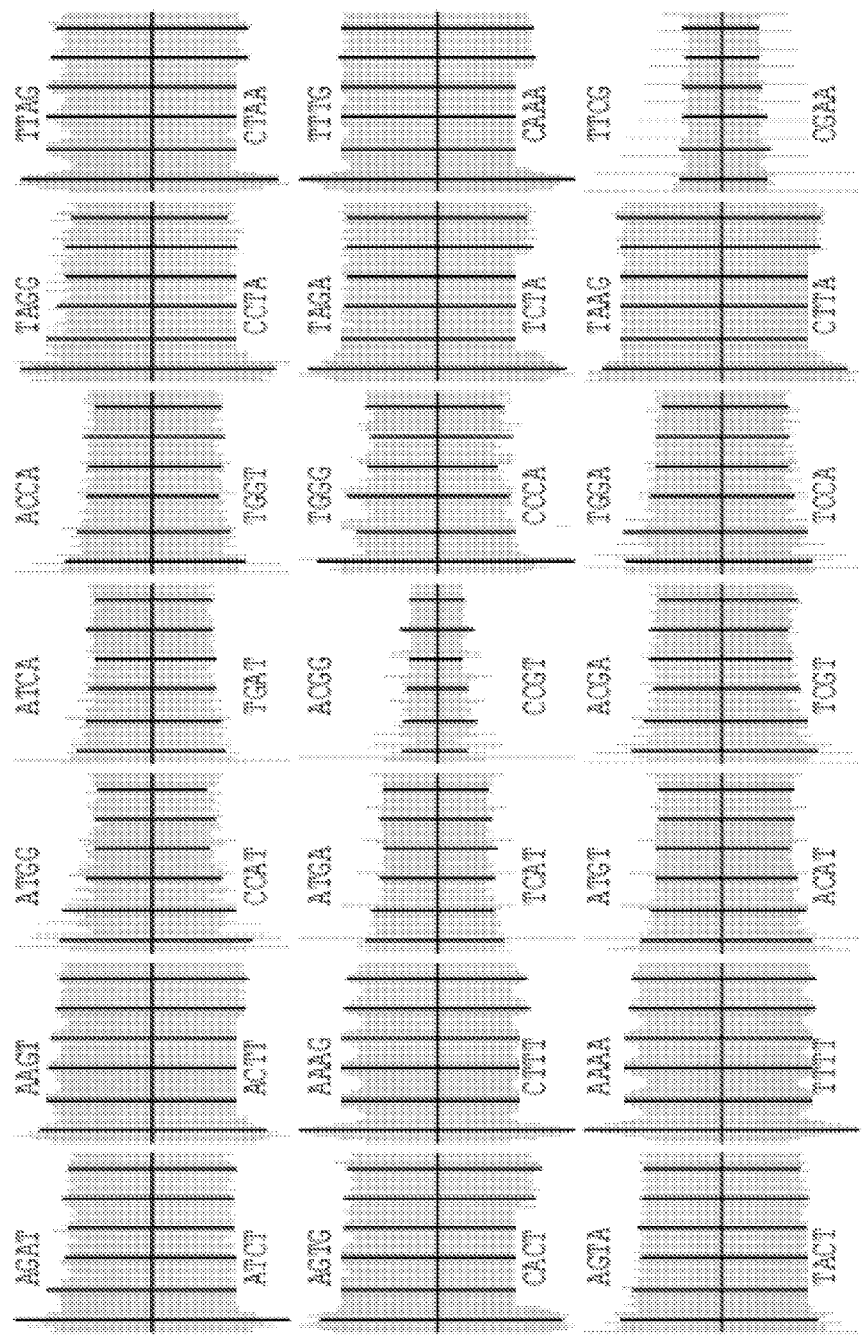
Figure 8B:
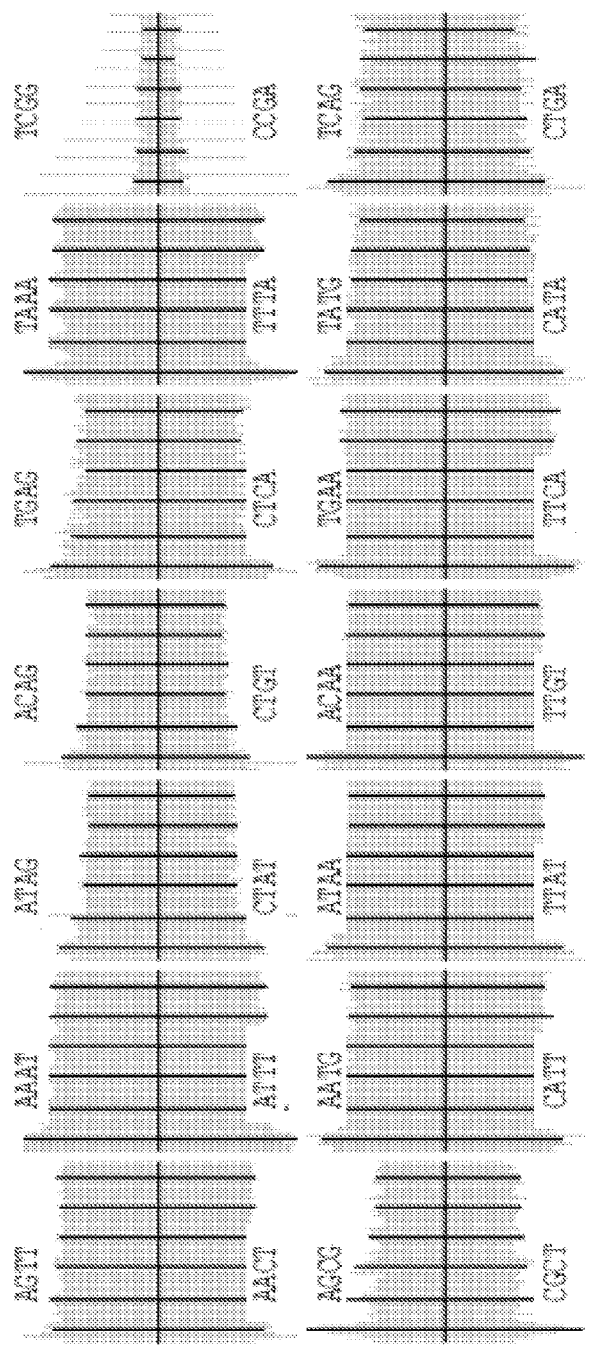
Figure 8C:
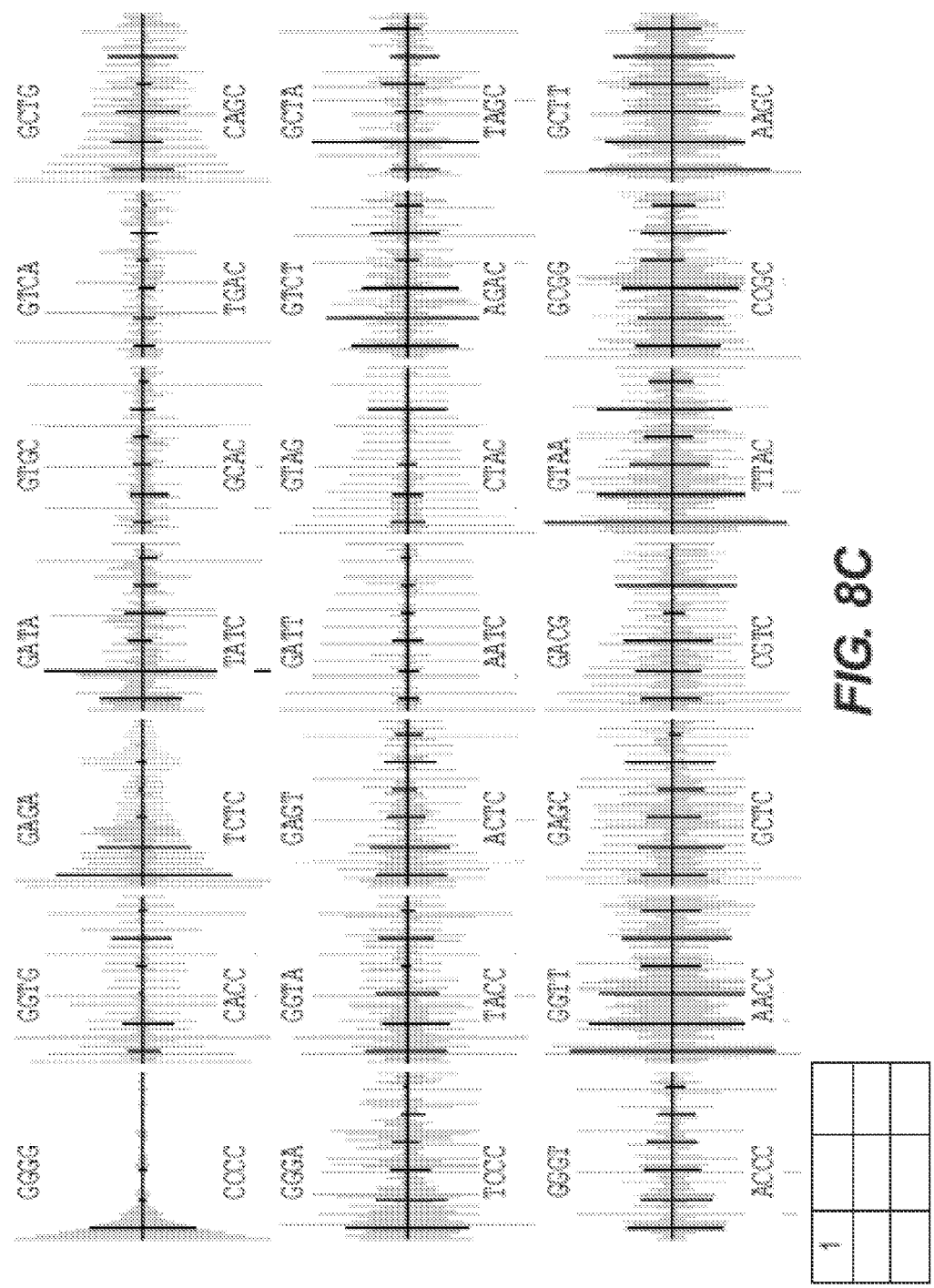
Figure 8C:
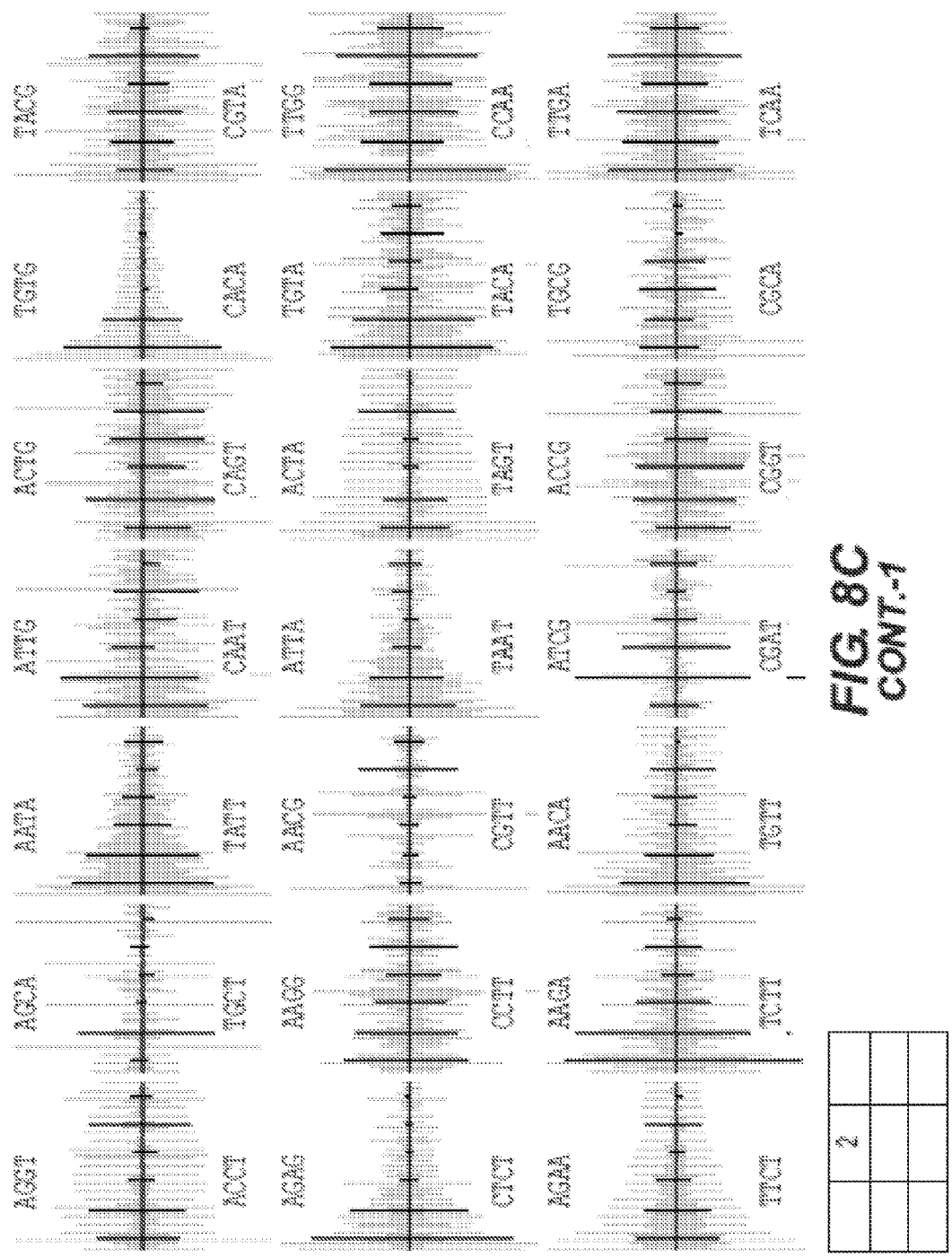
Figure 8C:
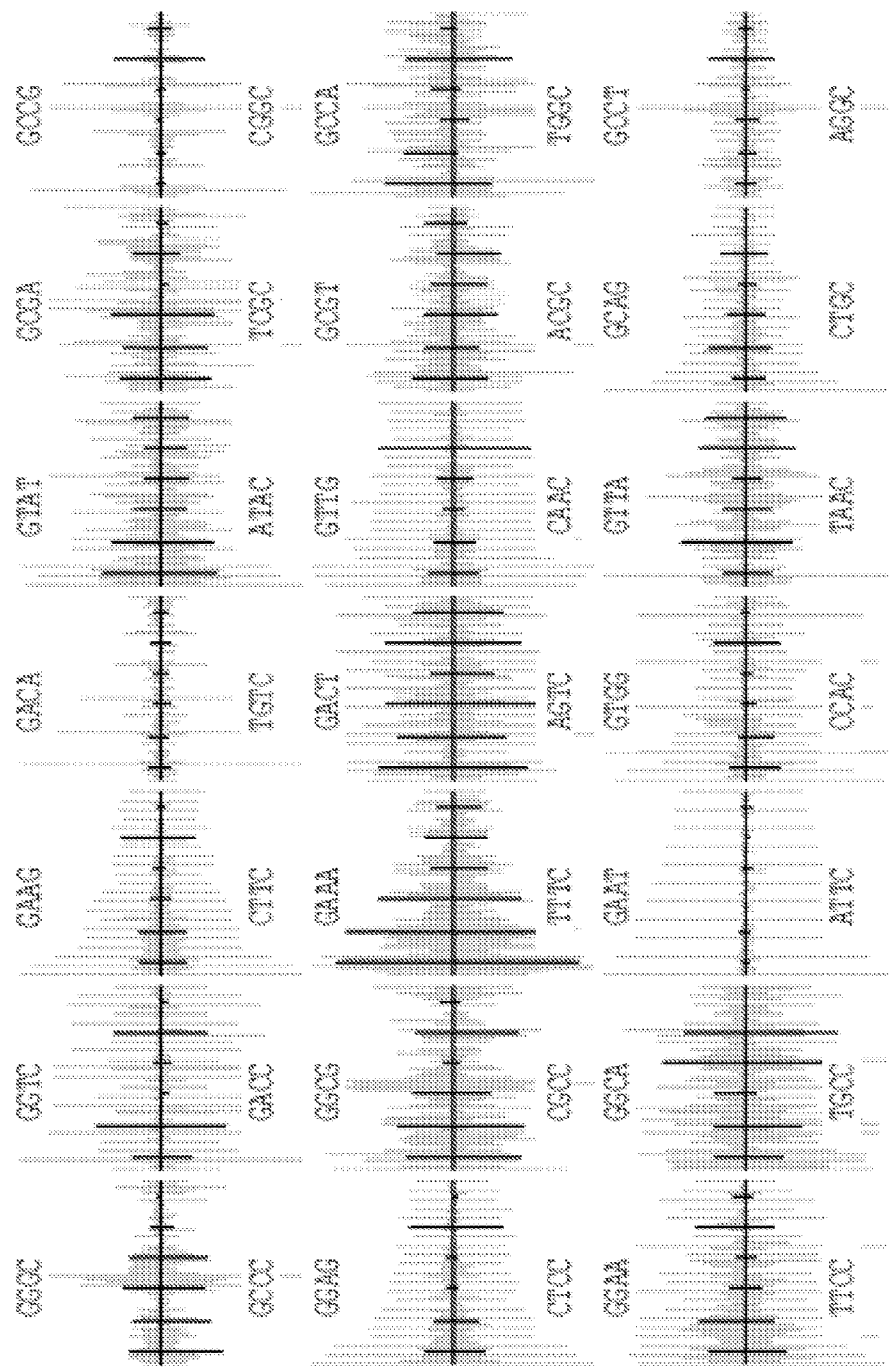
Figure 8C:
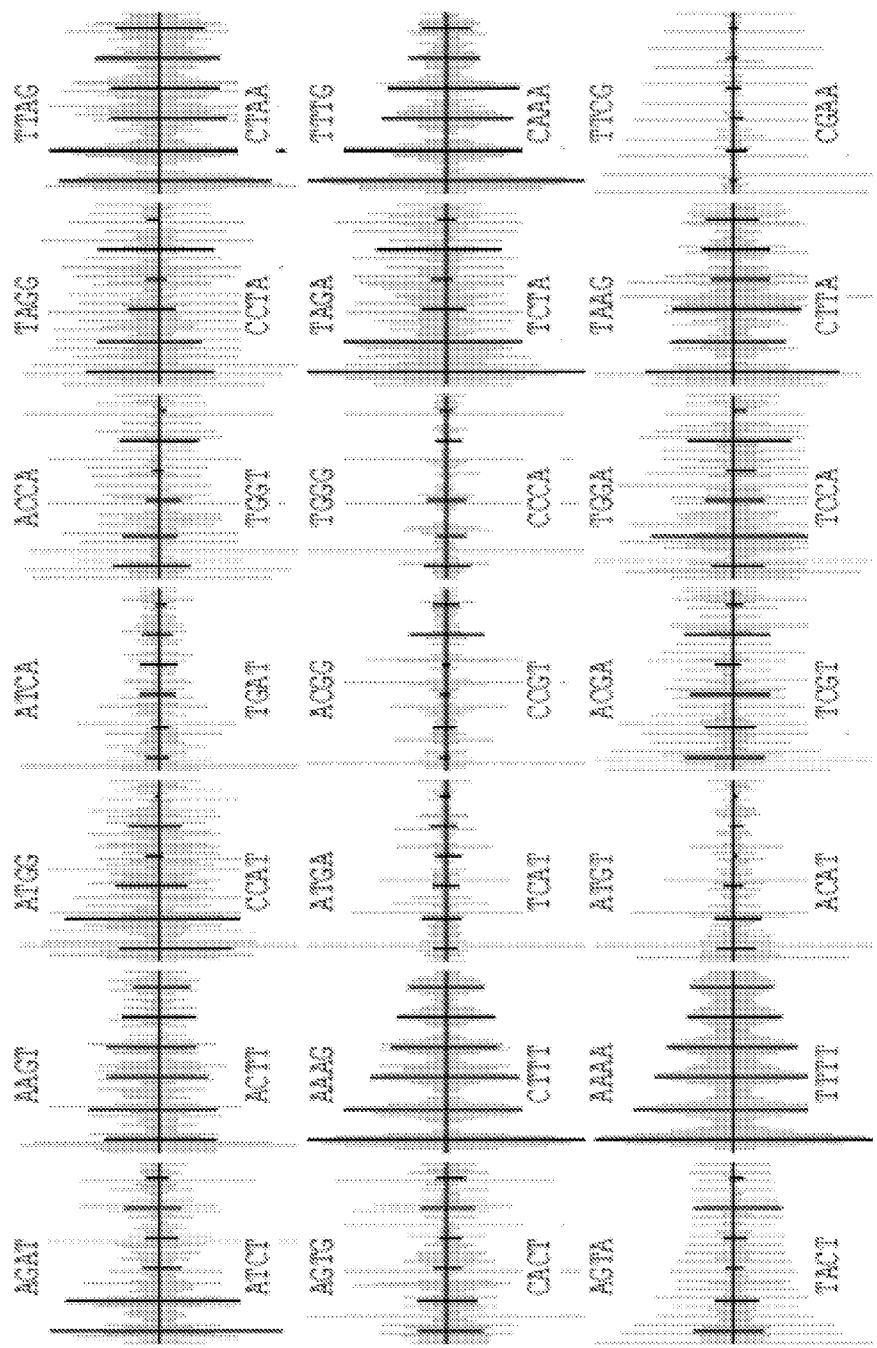
Figure 8C:
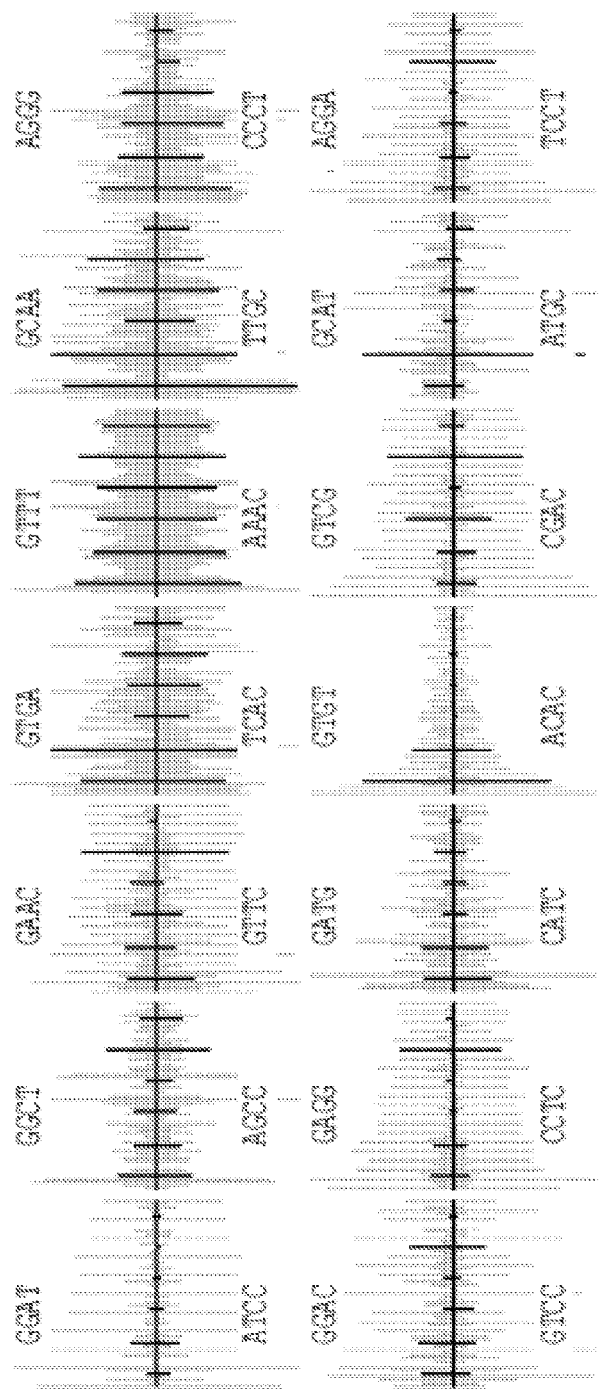
Figure 8C:
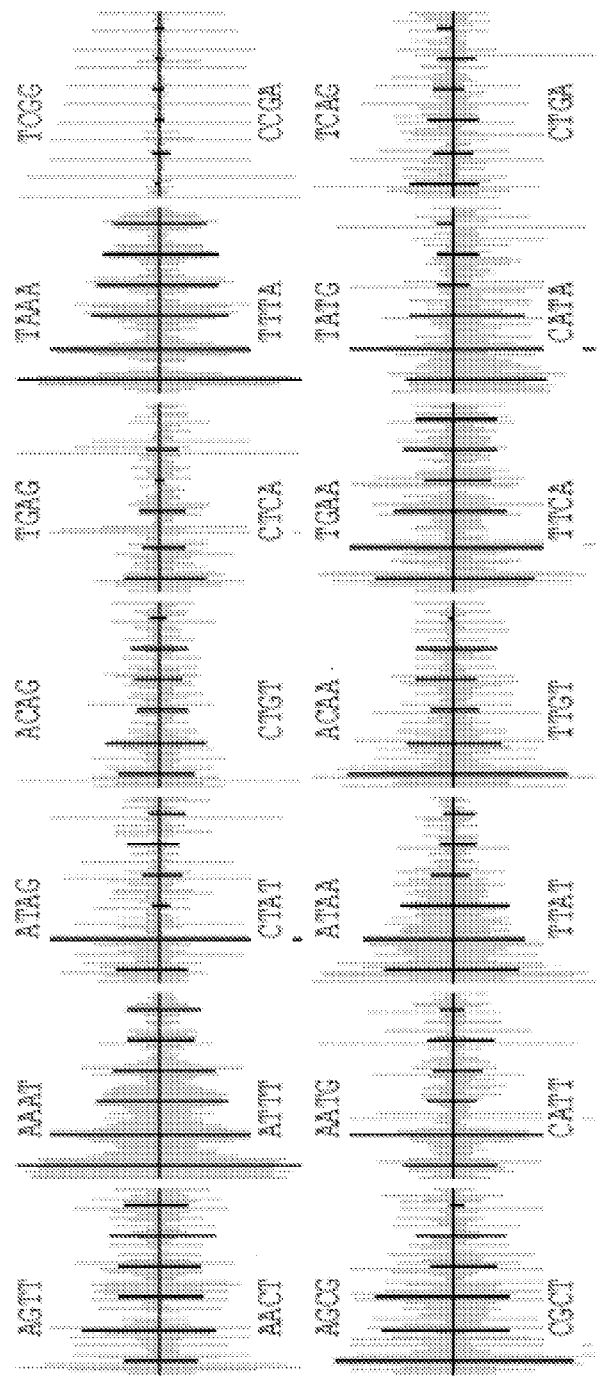
Figure 8D:
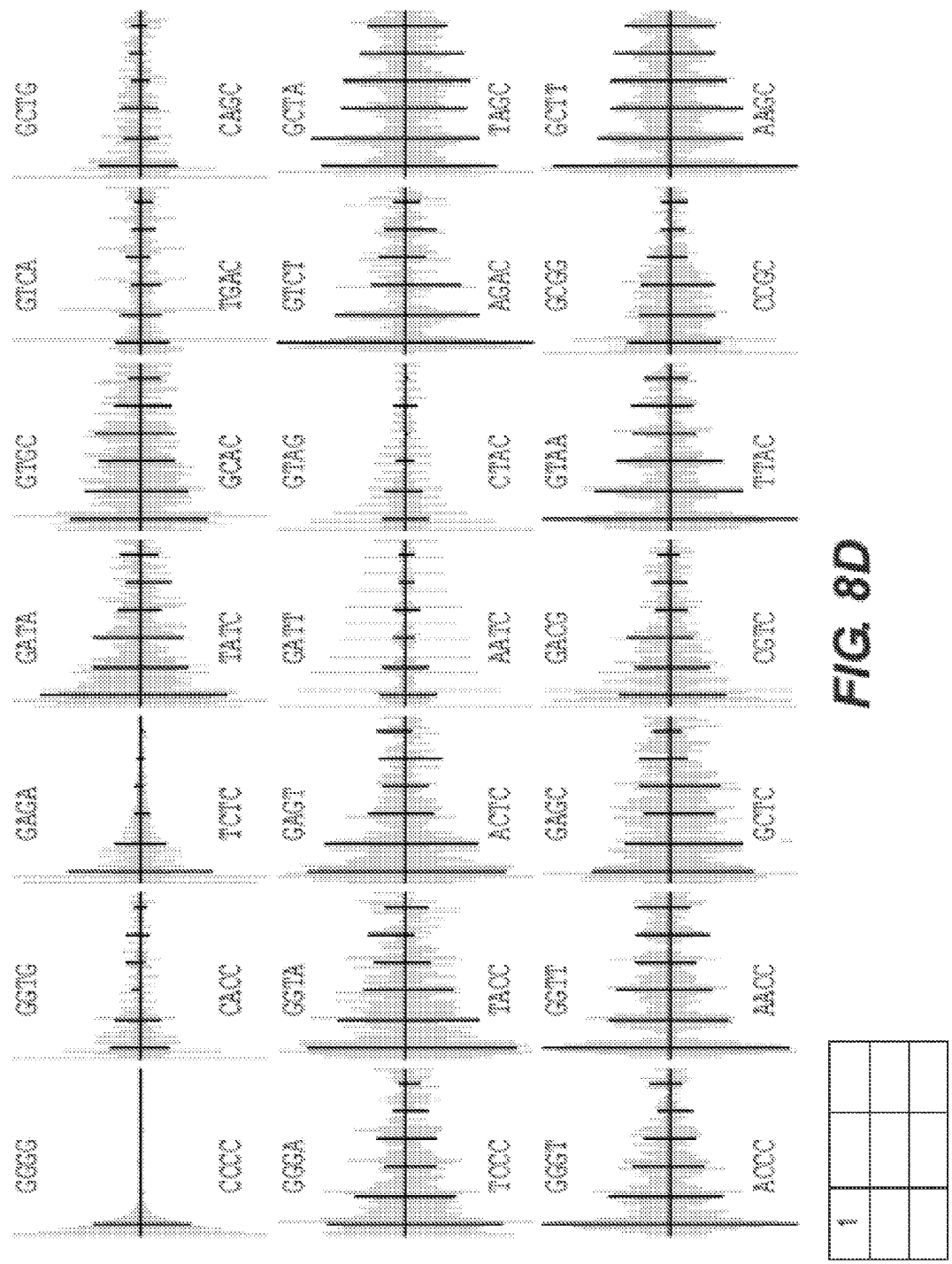
Figure 8D:
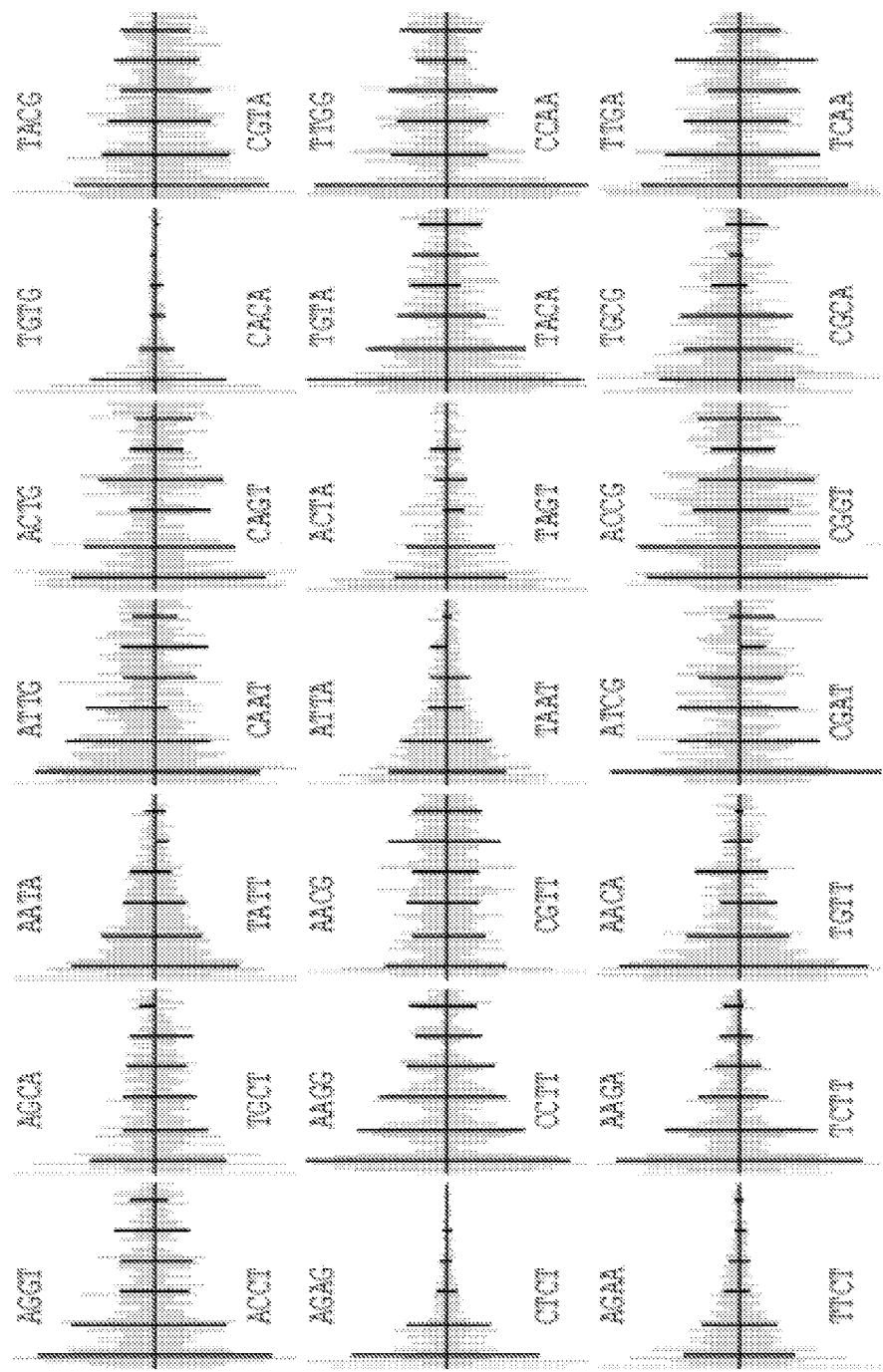
Figure 8D:
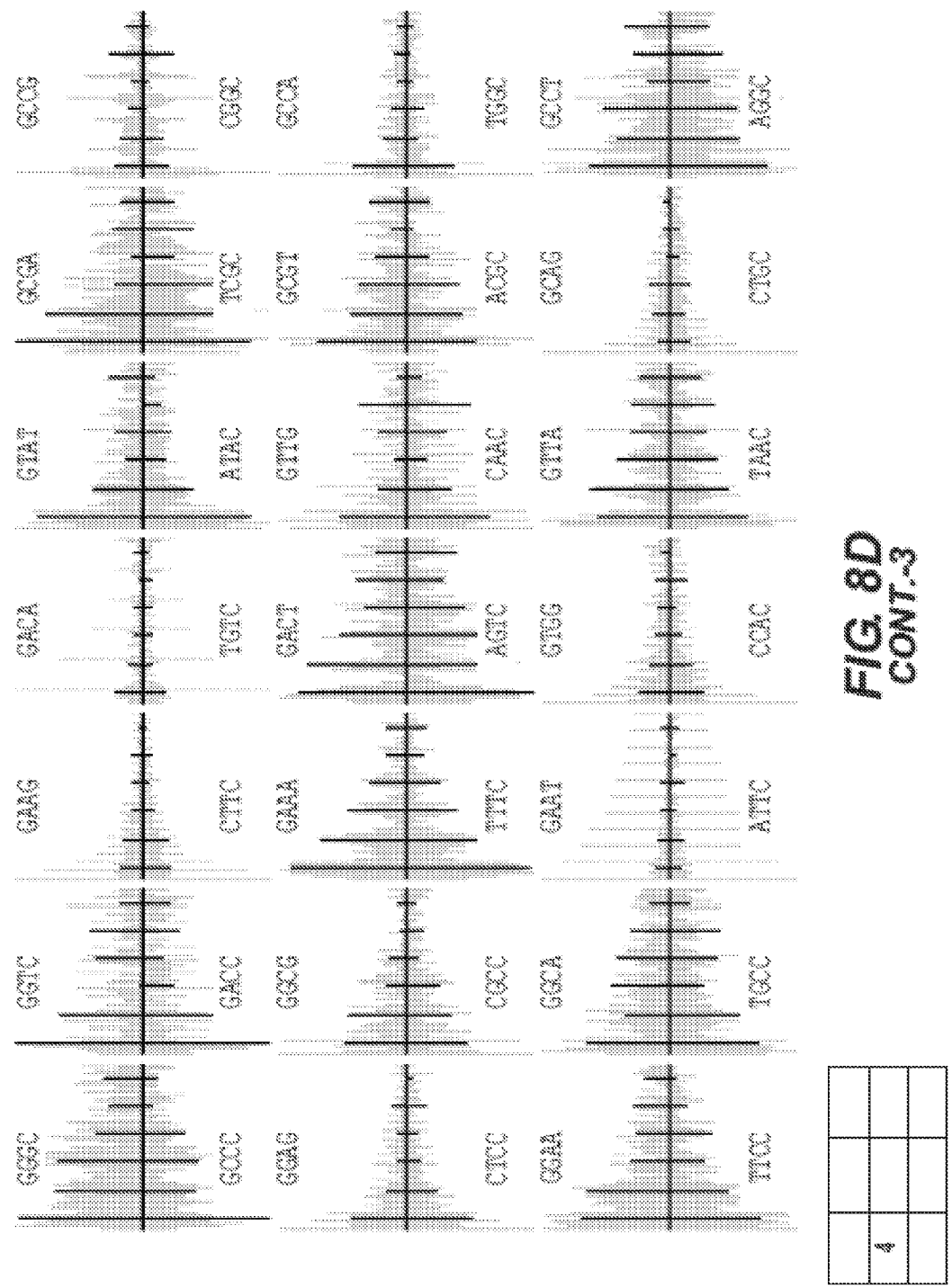
Figure 8D:
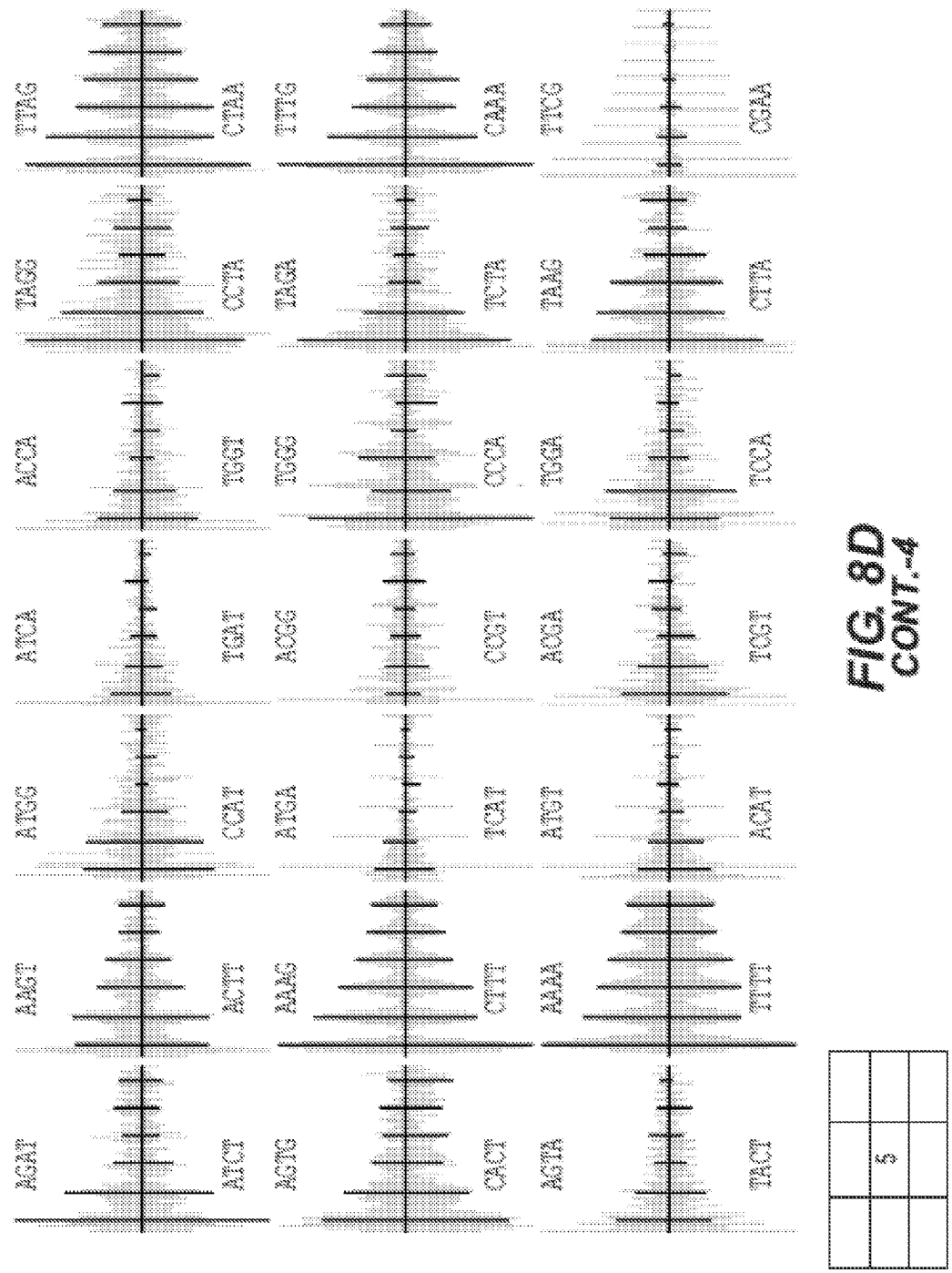
Figure 8D:
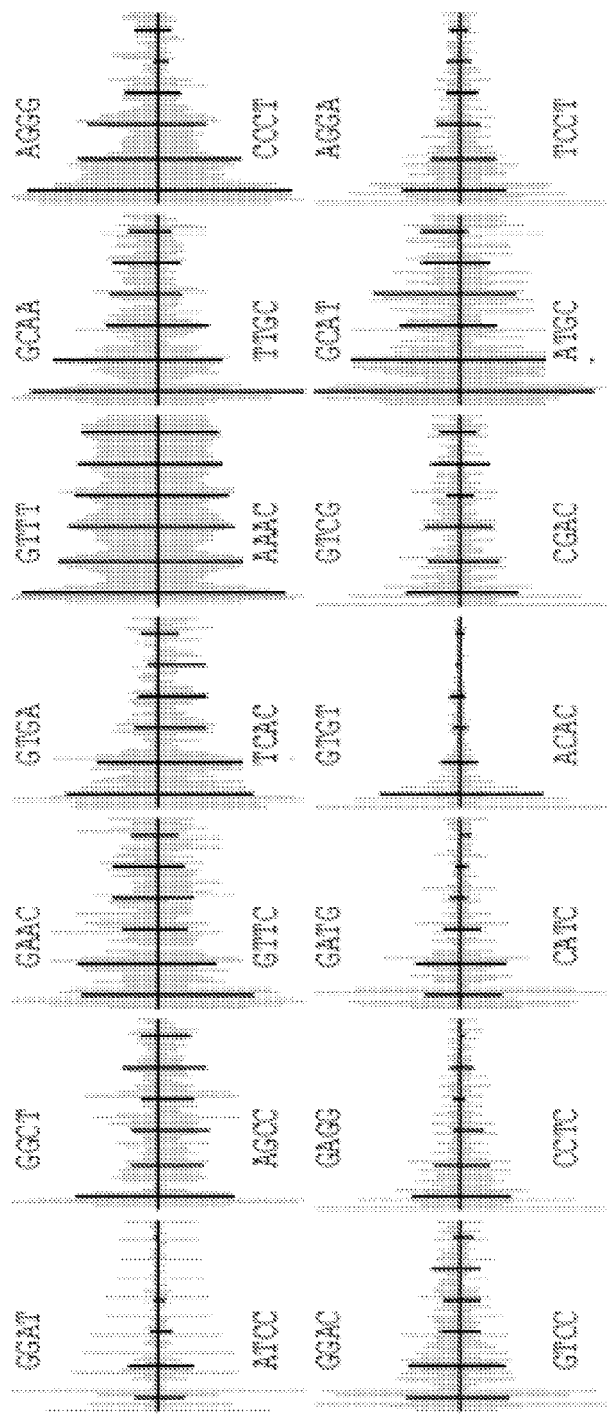
Figure 8D:
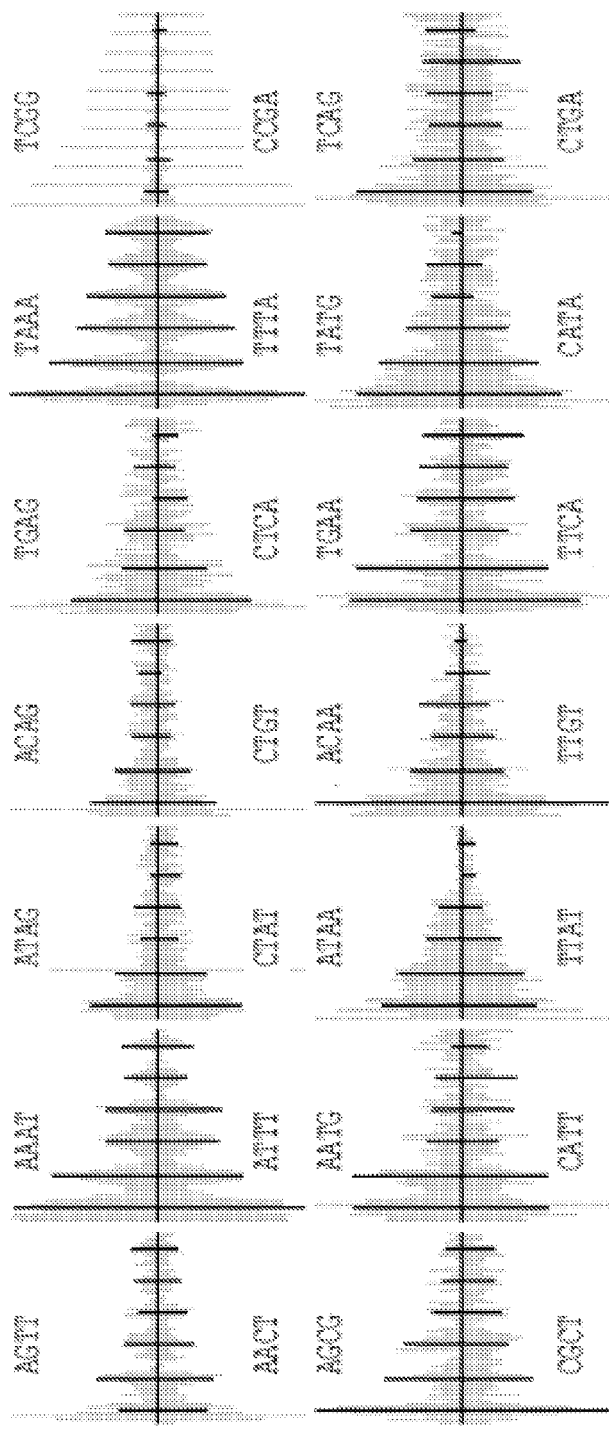

Complementary dinucleotides (e.g. AAGG/CCTT) are shown in vertical mirror symmetry. Distinct coloring of vertical lines every 10 base pairs has been added periodicities to be compared to helical repeat of DNA. The first vertical dark line in each graph corresponds to a separation of 10 bp. Three different types of normalization can be carried out for the graphs. First (and in all cases), the number of coincidences is divided by the total number of cases in which there is an opportunity for two tetranucleotides to be separated by n bases. For unmasked sequences, this is close to the length of the sequence. For masked sequences, this number varies as a function of the density of masked regions. Second (and for all curves shown), each graph has been scaled so that the maximum value for each histogram corresponds to the upper bound of the micropanel (this allows display of graphs with widely different maximal values on the same figure). Third, for figures labeled "scaled" (8C and 8D) the lower bound has been (smallest number of coincidences for a given tetranucleotide) has been arbitrarily set to the zero-point on the Y axis. The latter normalization aids in identifying periodicities in the sequence but confounds somewhat the comparison of periodicities for different datasets or from different tetranucleotides. Thus FIGS. 8A and 8B provide a somewhat better means to compare datasets and tetranucleotides for periodicity, 8C and 8D provide better means to detect subtle periodicities.

Figure 9A:
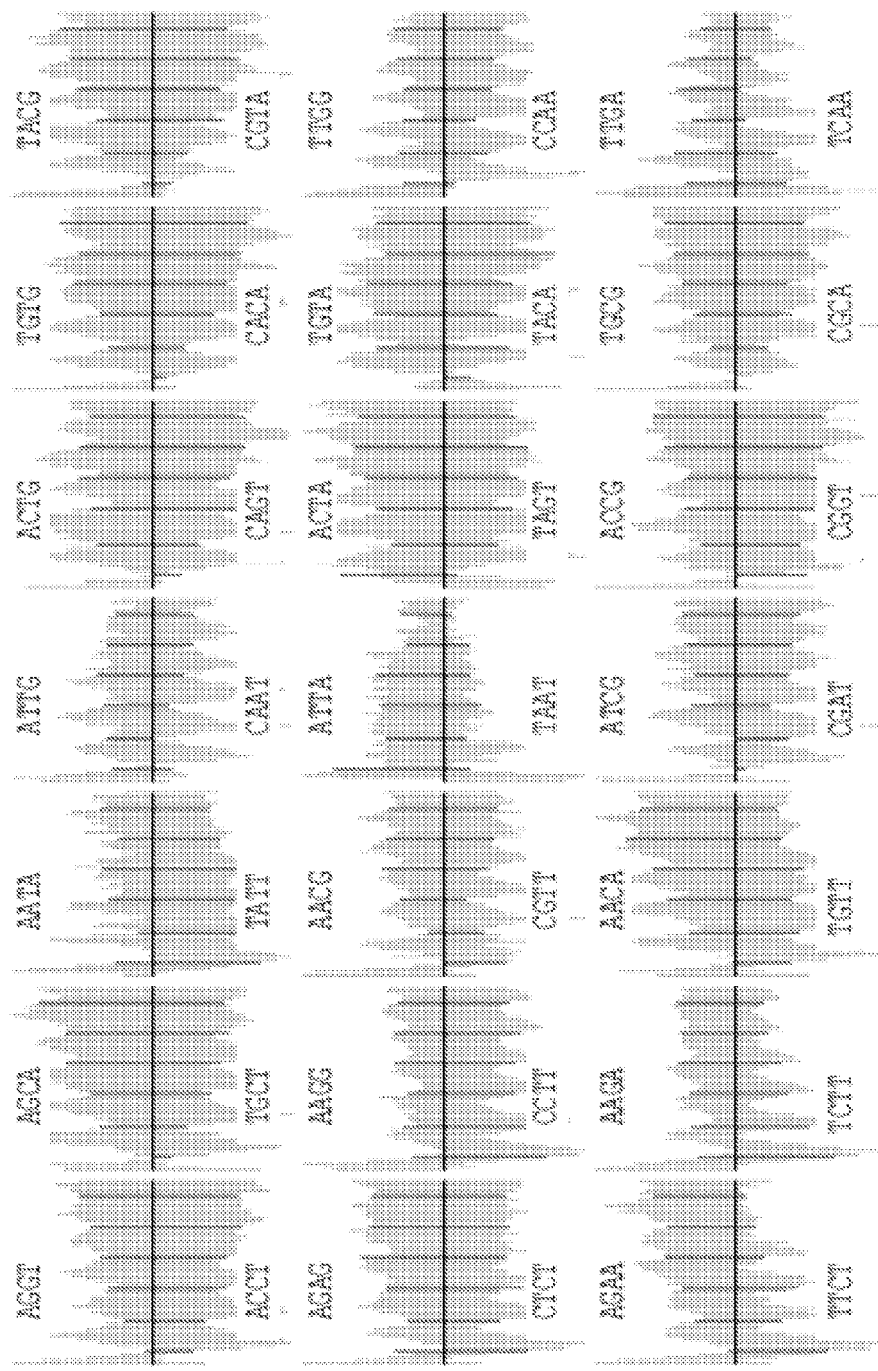
Figure 9A:
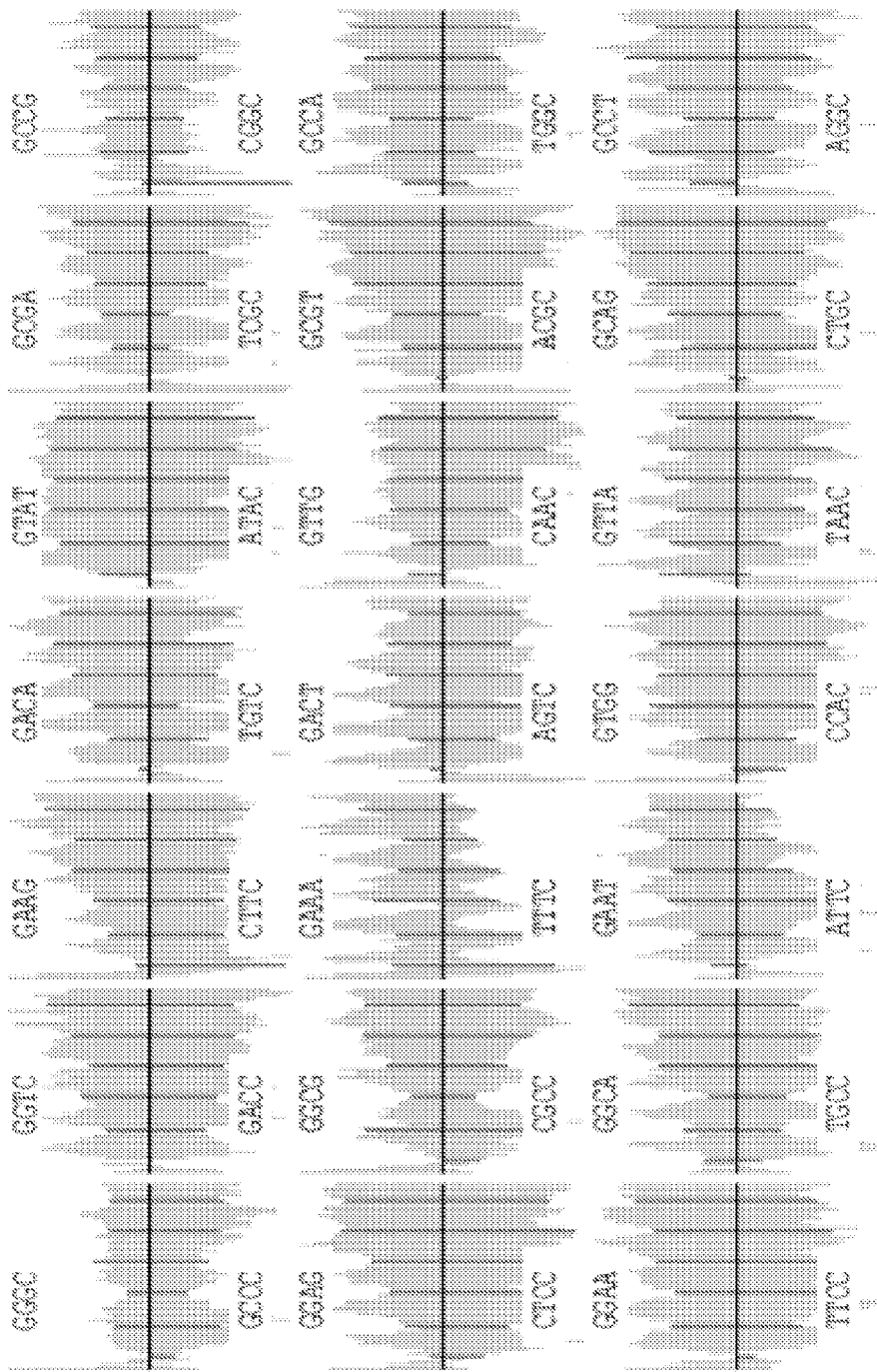
Figure 9A:
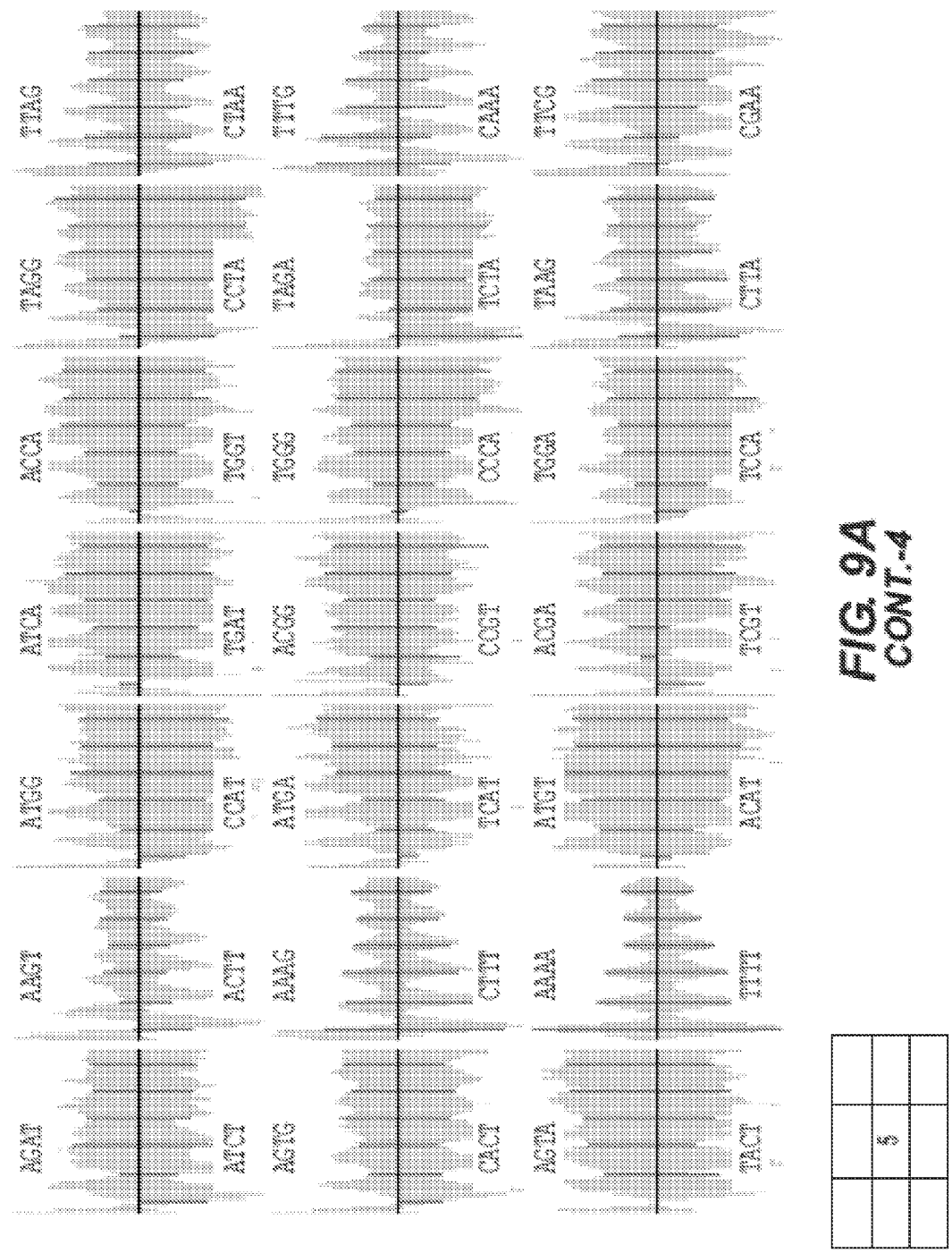
Figure 9A:
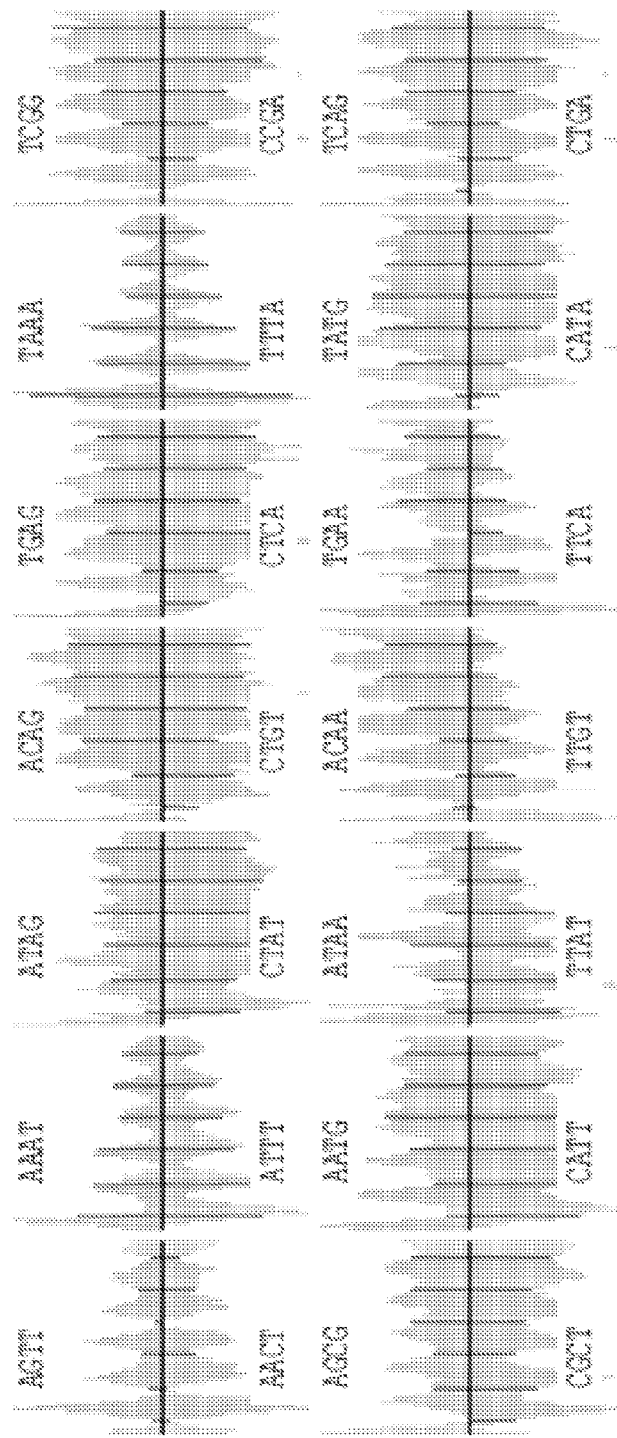
Figure 9B:
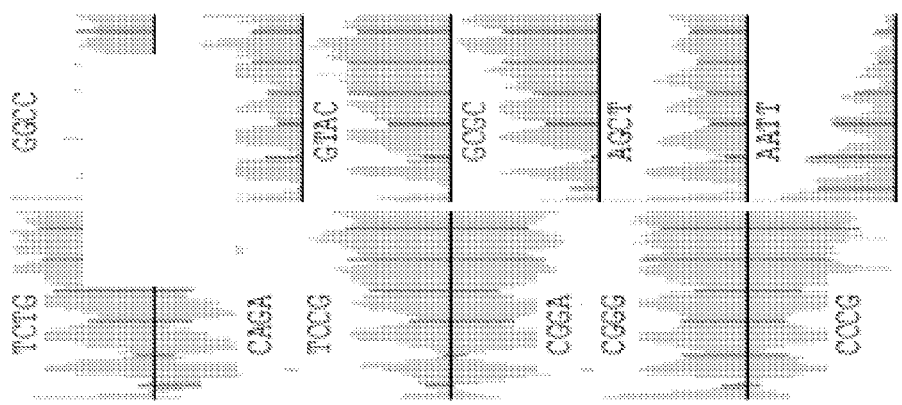
Figure 9B:
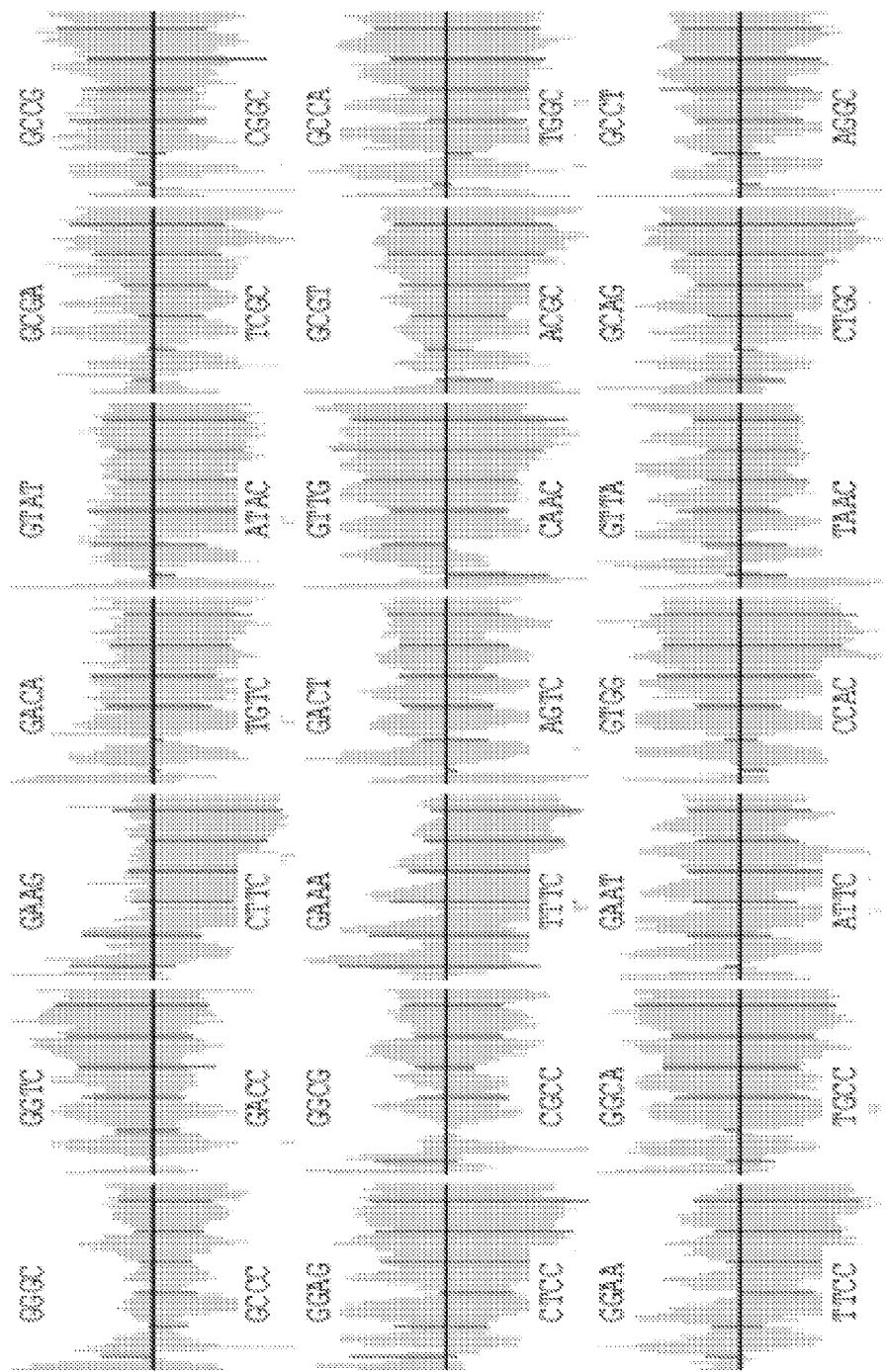
Figure 9B:
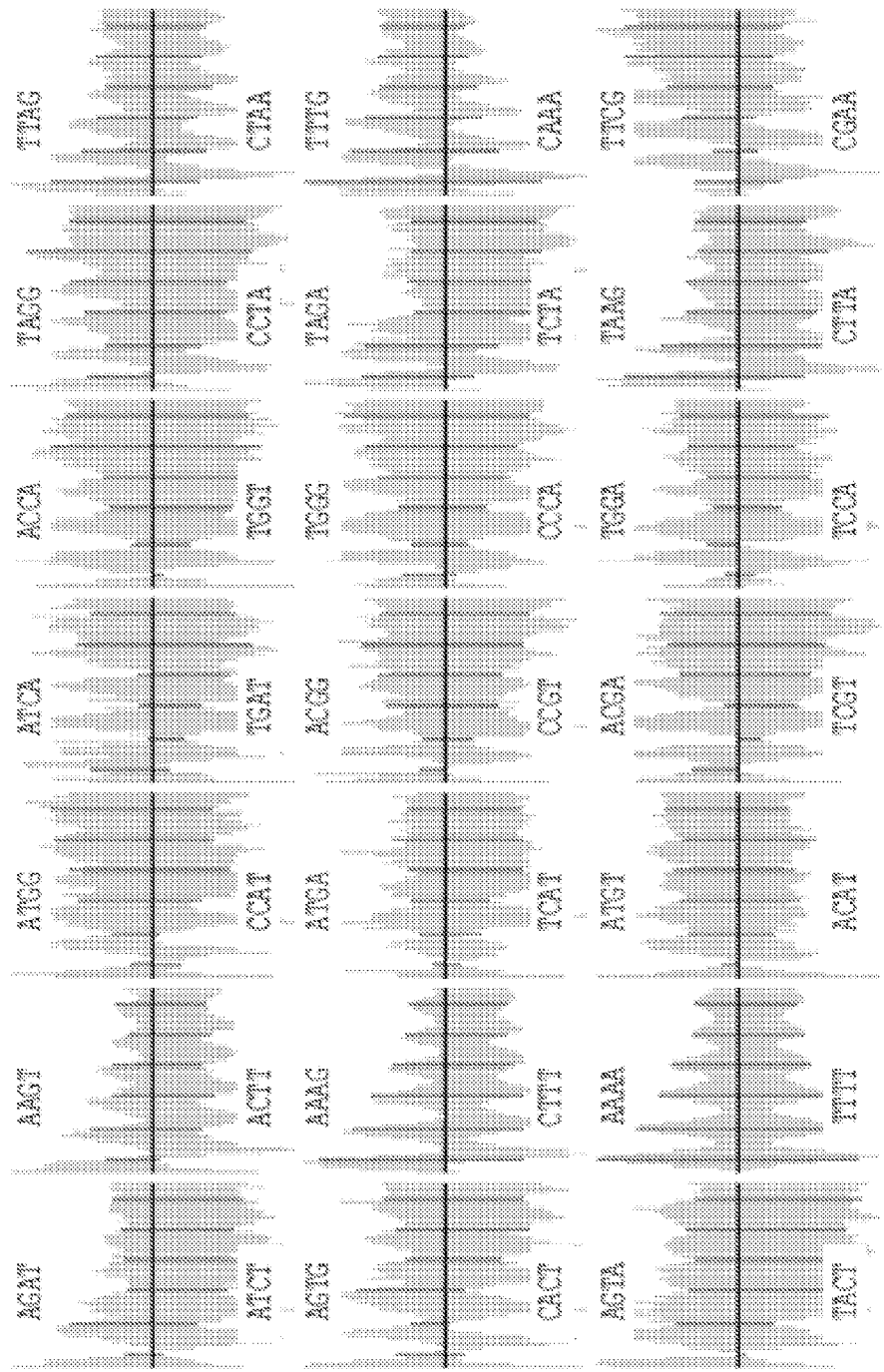

FIG. 9A-B. Separation profiles between arbitrary tetranucleotides and the phasing enriched tetranucleotide AAAA/TTTT. These profiles were prepared as for FIG. 8 except that the profiles shown denote the profile of separations between TTTT and a subsequent unique tetranucleotide (as shown on each graph) (Panel A) or between AAAA and a subsequent unique tetranucleotide (Panel B). Complementary unique tetranucleotides are shown in upward-downward pairs to allow comparison. A strong lack of symmetry can be noted in many cases for the two paired graphs, due to the non-equivalence of motif pairs such as $TTTT(X)_n GGAA$ and $TTTT(X)_n TTCC$. These profiles were prepared from unfiltered genome files obtained from wormbase upward-downward pairs to allow comparison. A strong lack of symmetry can be noted in many cases for the two paired graphs, due to the non-equivalence of motif pairs such as $TTTT(X)_n GGAA$ and $TTTT(X)_n TTCC$. These profiles were prepared from unfiltered genome files obtained from wormbase (Spieth et al., 2005, which is herein incorporated by reference in its entirety) as a May 2005. (Spieth et al., 2005, which is herein incorporated by reference in its entirety) as a May 2005.

Figure 10A:
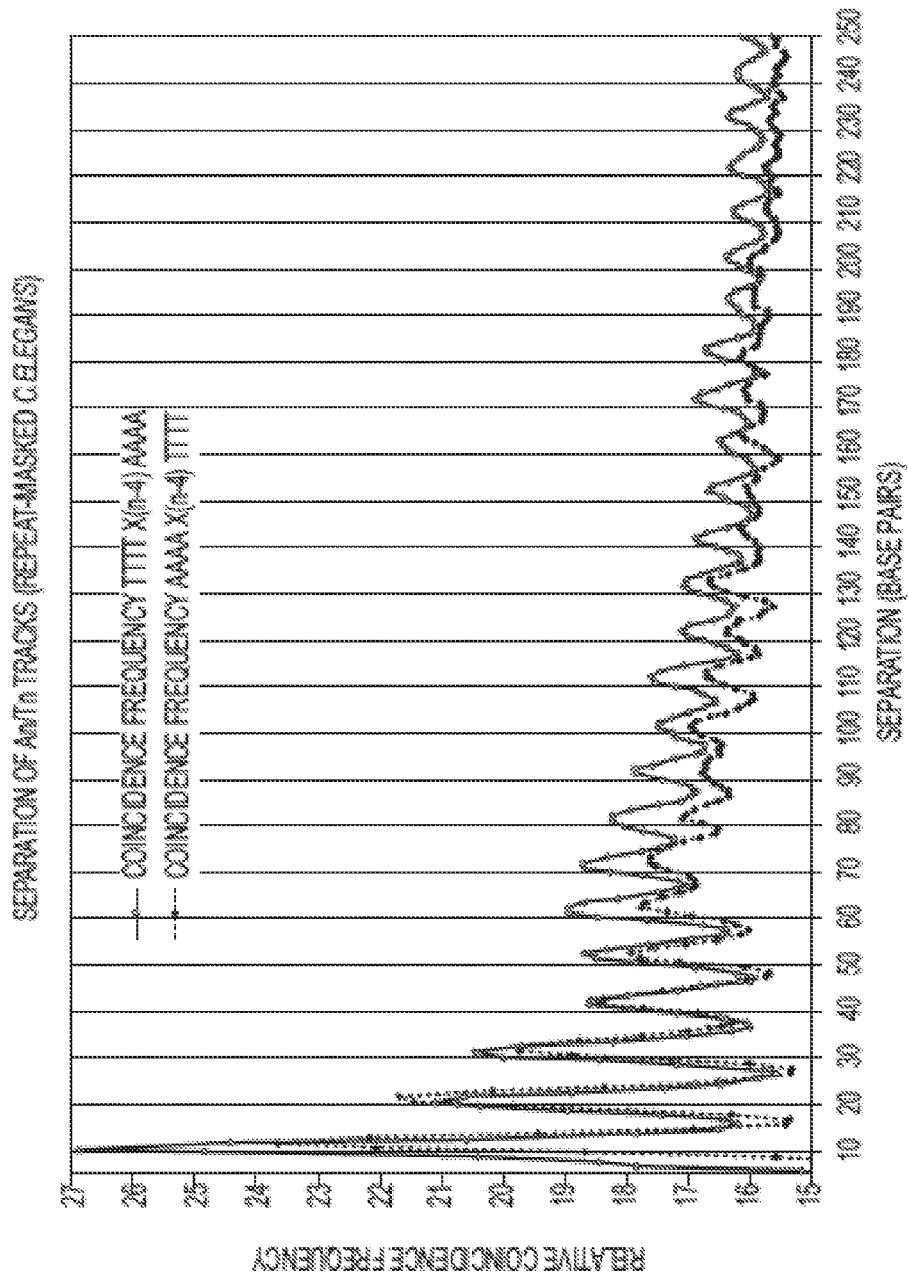
Figure 10B:
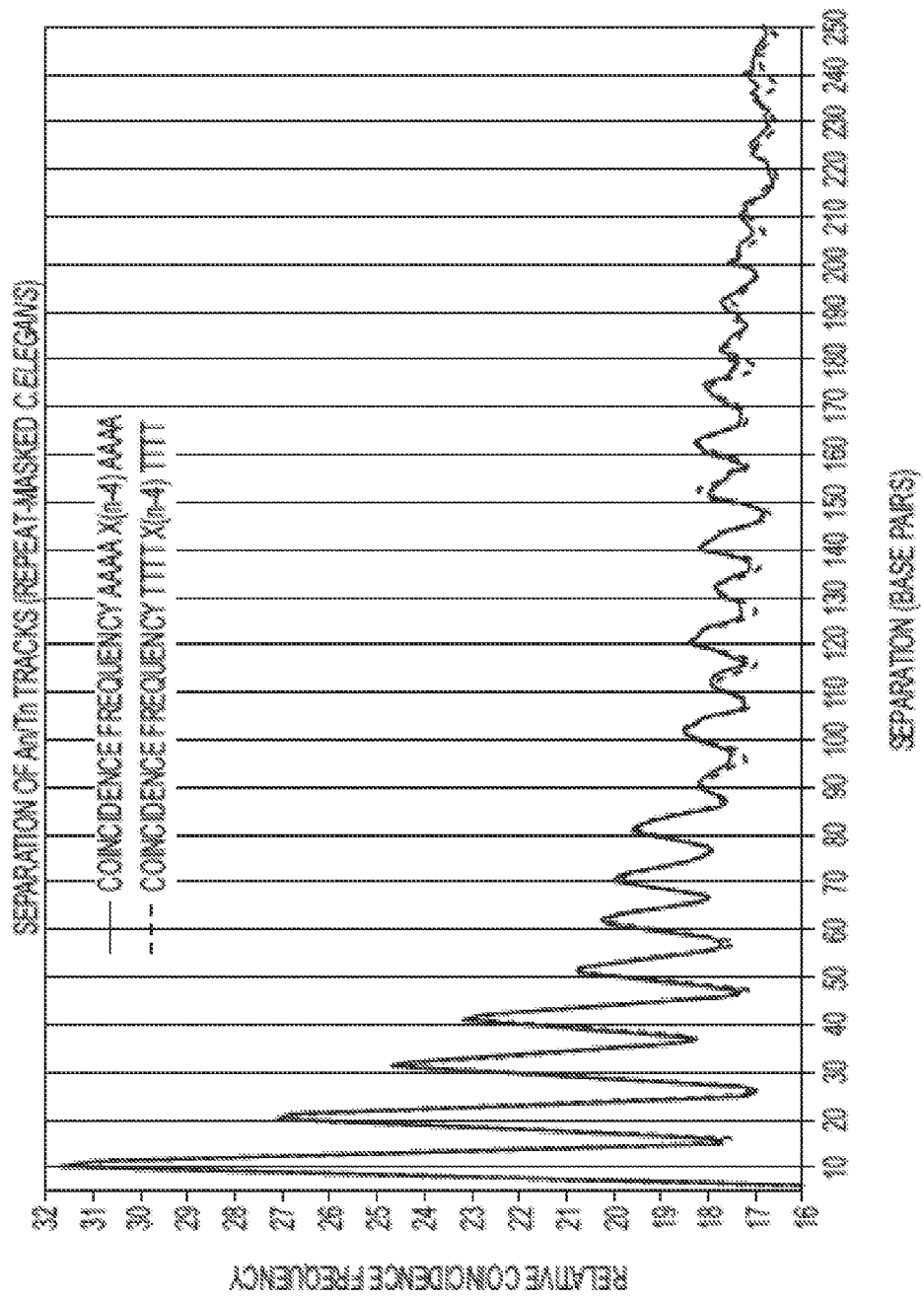

FIG. 10A-B. Asymmetry in periodic distribution of AAAA/TTTT tetranucleotides in the C. elegans genome. FIG. 10A shows two distinct separation profiles prepared from C. elegans genomic DNA. The blue graph shows distributions of separation distance between a TTTT word and a subsequent (downstream) AAAA word in the genome. The superimposed red graph shows distribution of separations between an AAAA word and subsequent TTTT word. Particularly notable are differences in peak positions between the red and blue curves (e.g. peaks at 10 [blue] and 11 bp [red]) and in the overall periodicity of the curves (e.g., 88-100 bp and 140-250 bp). As a reference to indicate magnitudes of differences due to stochastic fluctuations in genome orientation (Dai et al., 2005, which is herein incorporated by reference in its entirety), we compared $AAAA(X_{n-4})AAAA$ to $TTTT(X_{n-4})TTTT$ separation in the genome (FIG. 10B). Unlike the curves in FIG. 10A, those in FIG. 10B represent complementary sequence arrangements; the curves in FIG. 9B would thus be expected to correspond closely (as they do) with any fluctuations of a limited quantitative nature. These profiles were prepared from unfiltered genome files obtained from wormbase as of May 2005 and are normalized and scaled as described in FIG. 3.

Figure 11A:
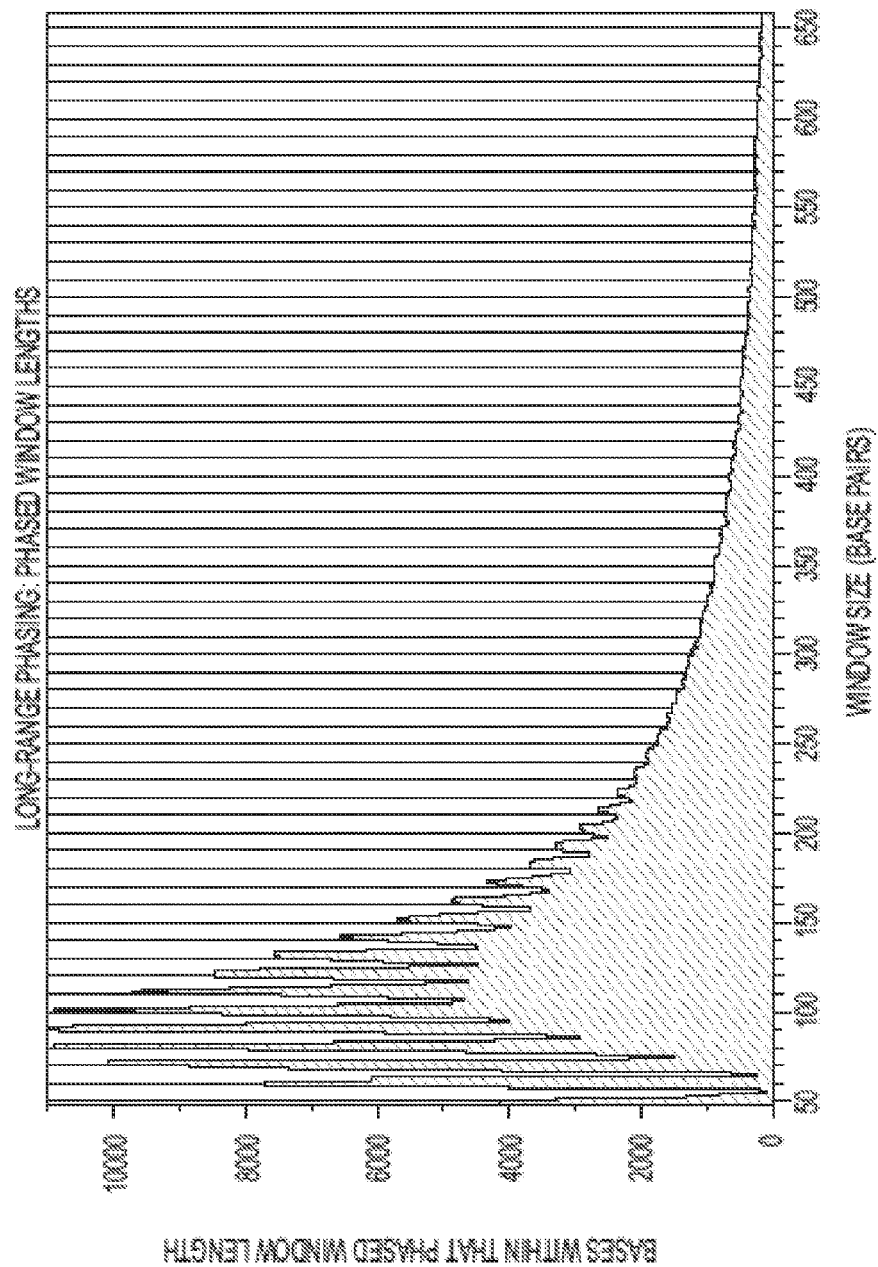
Figure 11B:
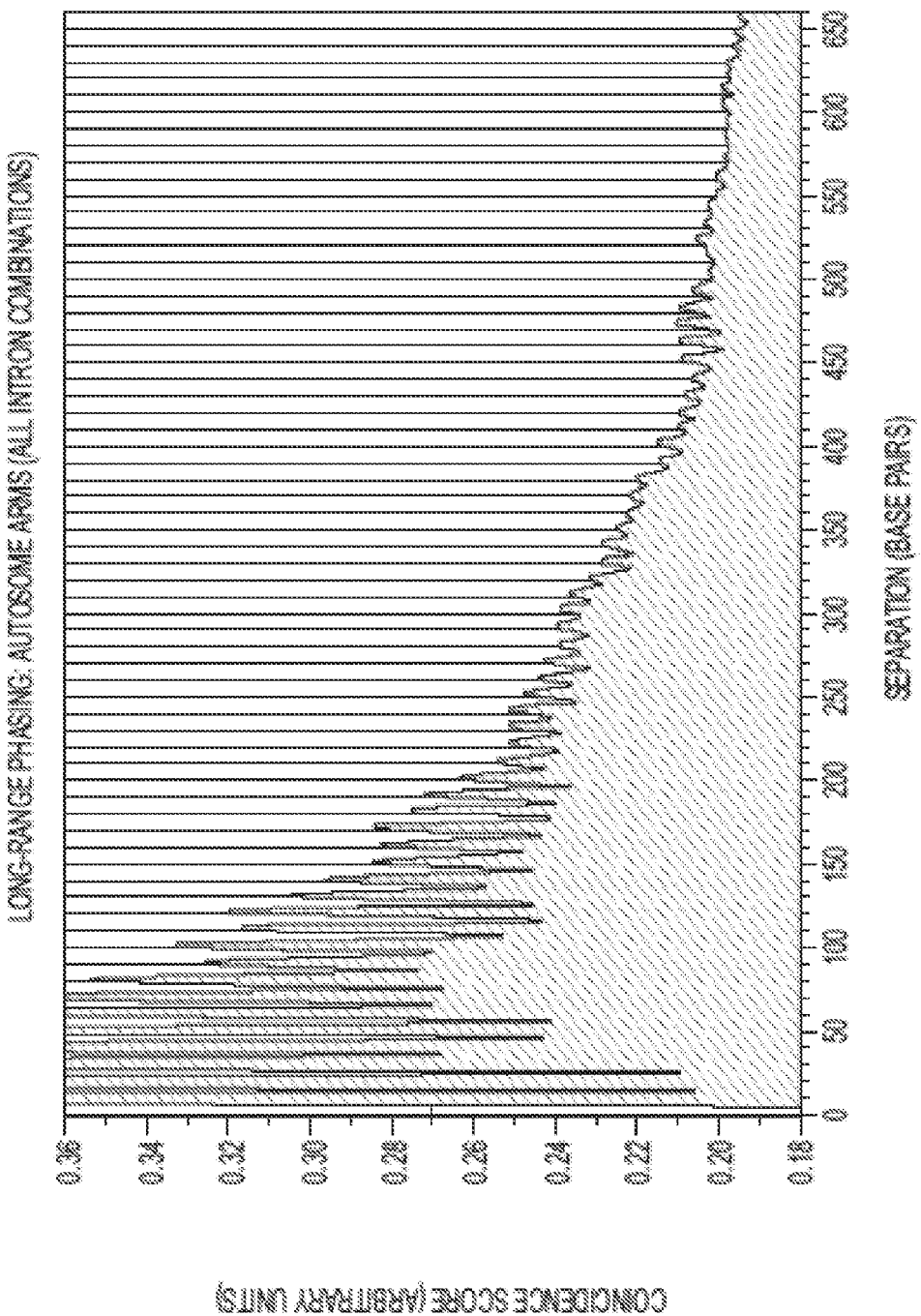
Figure 11C:
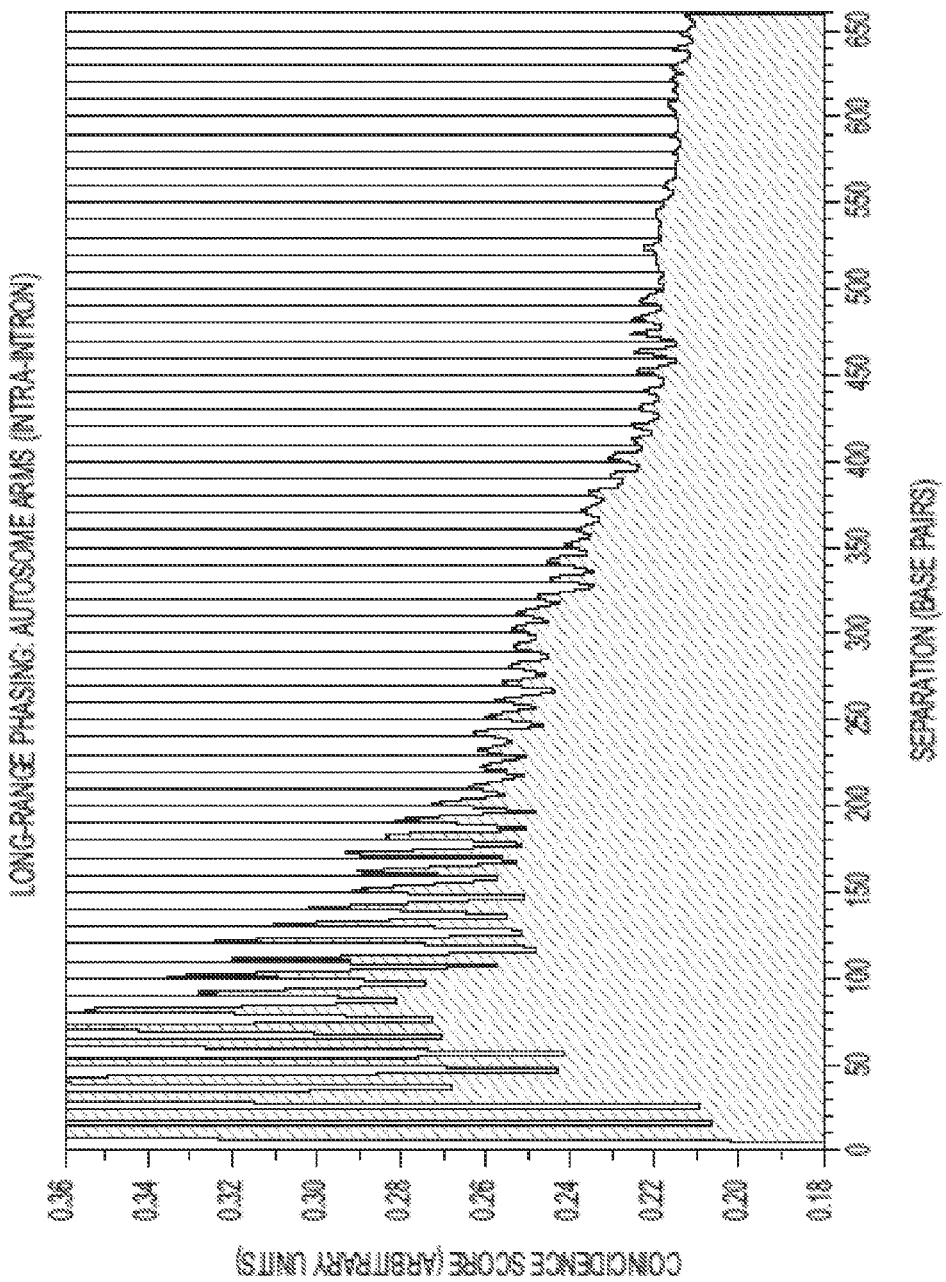
Figure 11D:
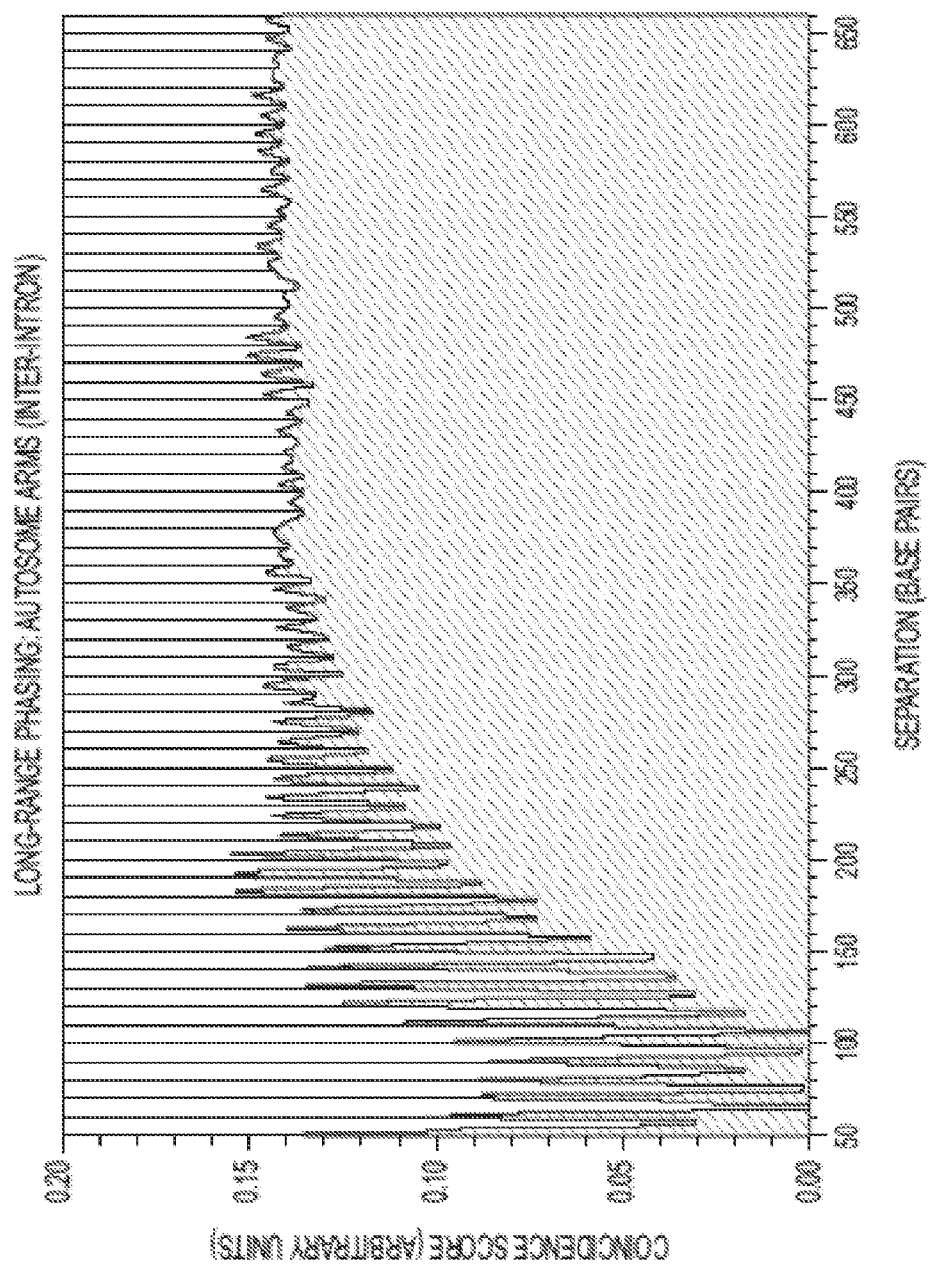
Figure 11E:
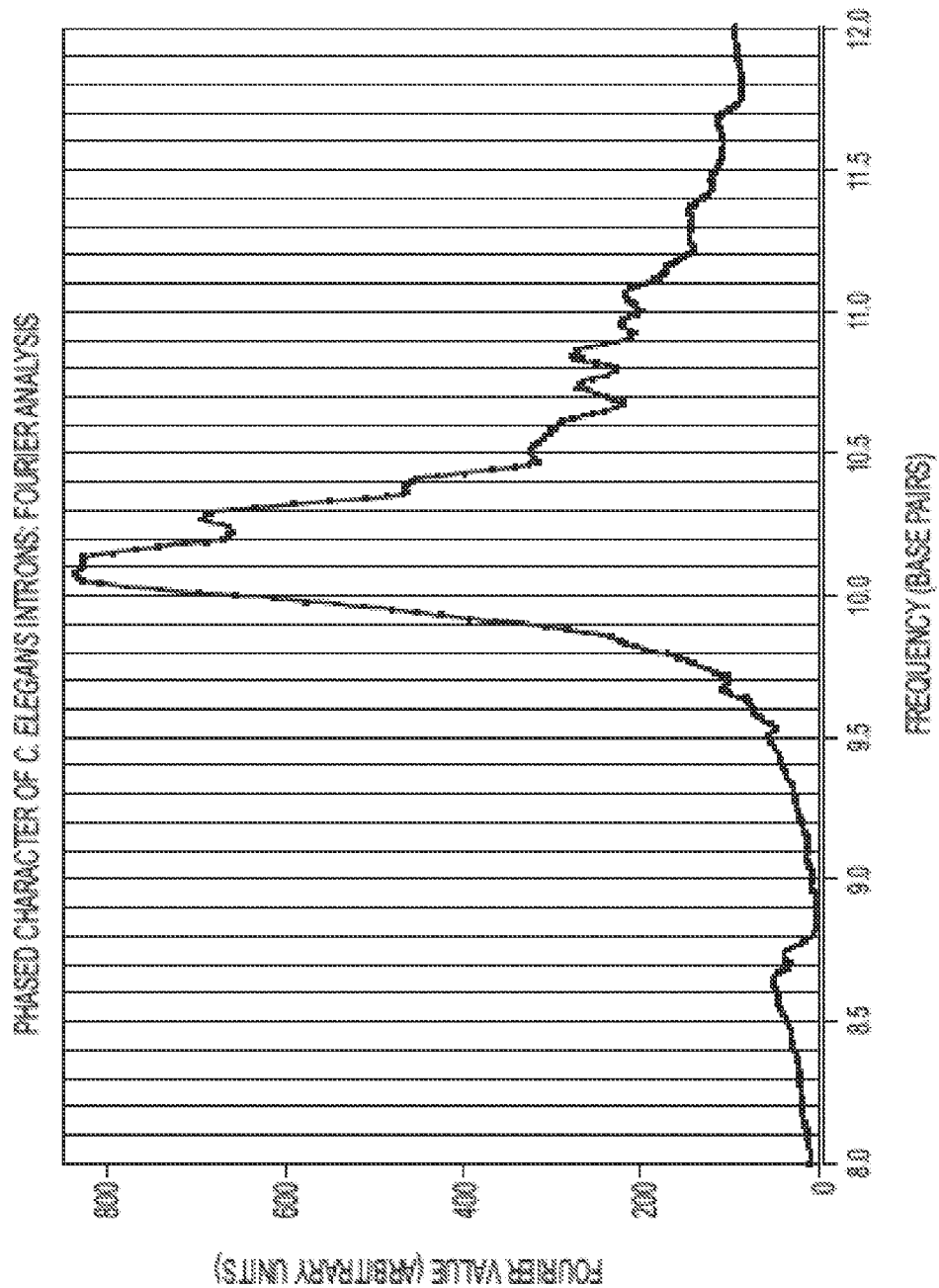

FIGS. 11A-E. Long range phasing measures of the C. elegans genome. FIG. 11A shows how many bases in the genome are present in periodic regions of a specified length, with phasing determined as in FIG. 4A using a cutoff value of 95. FIGS. 11B, C, D, E use a measurement of long range correlation described as follows: For each five base word we define a phasing contribution "Pc" as follows: Pc=−0.2 if there are no AA/TT dinucleotides, Pc=−1 if there is one AA/TT dinucleotide, Pc=1 if there are two AA/TT dinucleotides, and Pc=2 if there are three or four AA/TT dinucleotides. For each possible separation (n bases, X axis), a base-by-base sum is prepared of $\Sigma_{all\ points}$ in genome (x)Pc(x)*Pc(x−n). For each n, the resulting sum is normalized by dividing by the number of individual cases in which two words of any type are separated by n base pairs. FIG. 11B shows this sum prepared for all intron sequences which fall within the autosomal arms (i.e. excluding all but the tip of the X chromosome and the arms of each autosome). FIG. 11C shows a corresponding figure in which only sequences within a single intron are allowed to contribute to the histogram. FIG. 11D shows a comparable plot in which only sequences in different introns within the same gene were allowed to contribute (thus requiring at least one exon separate the two words to be assayed). FIG. 11E shows a Fourier analysis of data in FIG. 6B. Values in FIG. 6E were calculated according to the formula $V(B)=[\Sigma_{all\ expressions\ n}\ \sin(2\pi n/B)\Omega(n)]^2 + [\Sigma_{allseperationsn} \cos(2\pi n/B)\Omega(n)]^2$. Where B is the separation being tested as a potential resonance (in this each multiple of 0.01 between 8 and 12 base pairs), n are different separations (5-1280) for which the long-range correspondence was calculated, and $\Omega(n)$ is the correspondence value for n reported in FIG. 11B.

Figure 12:
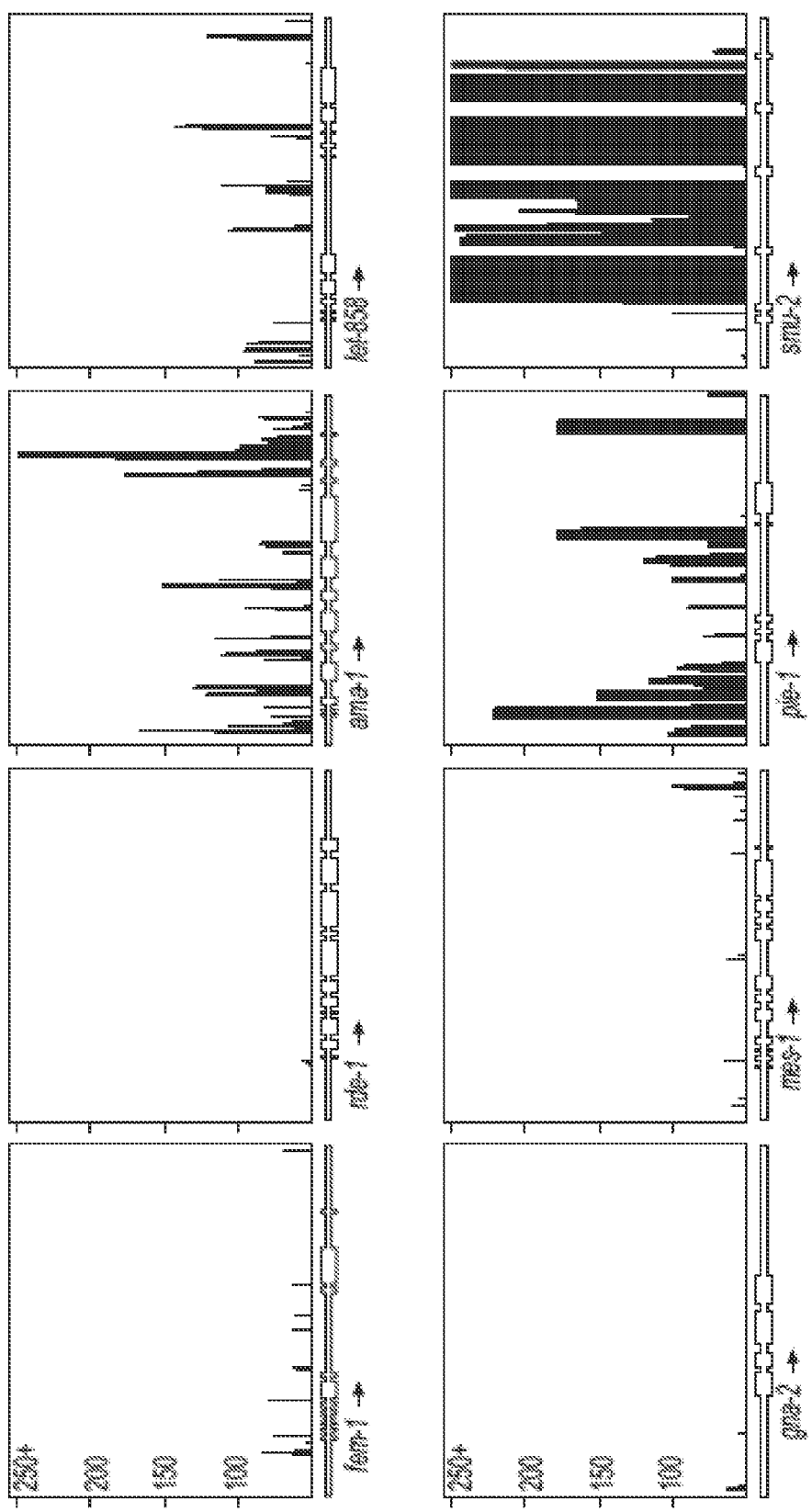
Figure 12:
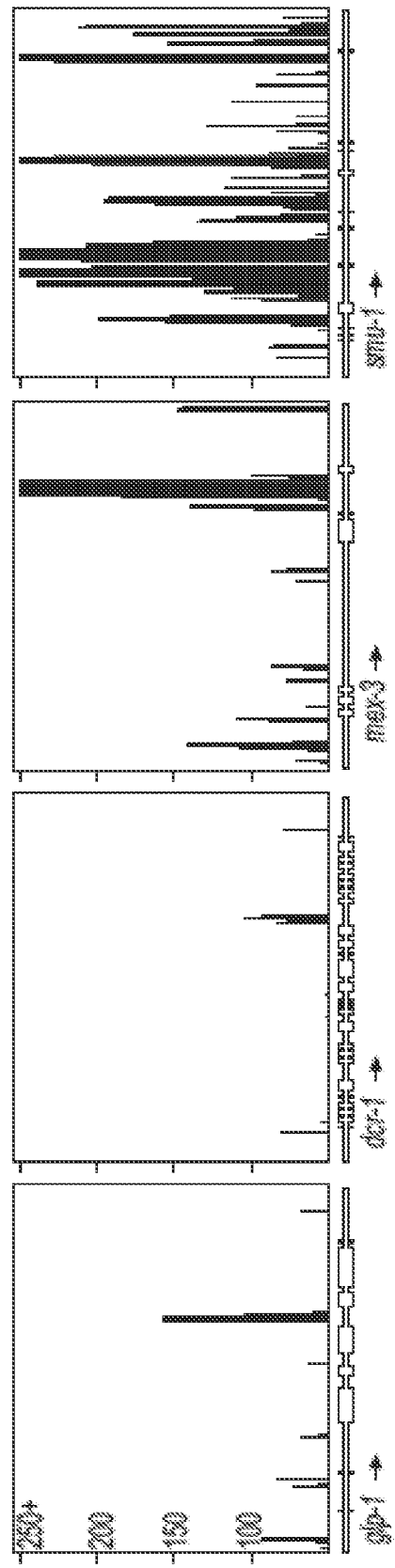

FIG. 12. Phasing profiles for 12 germline-expressed genes that have been investigated for possible adaptation to produce extrachronosomal expression vectors. For each of these genes, we show a schematic diagram of exons (wide bars) and introns (intervening narrow bars), annotated 5' and 3' UTR sequences as well as 1 kb of upstream and downstream sequence annotated as non-transcribed (all annotations as of November 2005 in worm base). Plots above each gene diagram show fraction of bases within a given 50-base region showing above threshold phasing (PATC≥95). Five of these six genetic regions (fem-1, rde-1, mes-1, glp-1, and dcr-1) were incapable of driving reporter expression in either simple tandem array transgenes (as described by Stinchcomb et al., 1995) or complex array trans genes (Kelly et al., 1997). Although some functionality of each transgene construct was confirmed by rescue of the corresponding null mutation with the original (pre-tagging) DNA clone, there was no confirmation that this expression was in the germline. No germline reporter activity (GFP fluorescence) was observed for any of these five gfp-tagged constructs.

FIG. 13. DNA sequence of spgfp-1. Shown is the DNA sequence of spgfp-1, a synthetic intron-interrupted gfp coding region. Coding regions are indicated in boldface capitalized letters while intronic sequences are indicated by non-boldface lower case letters.

Figure 14:
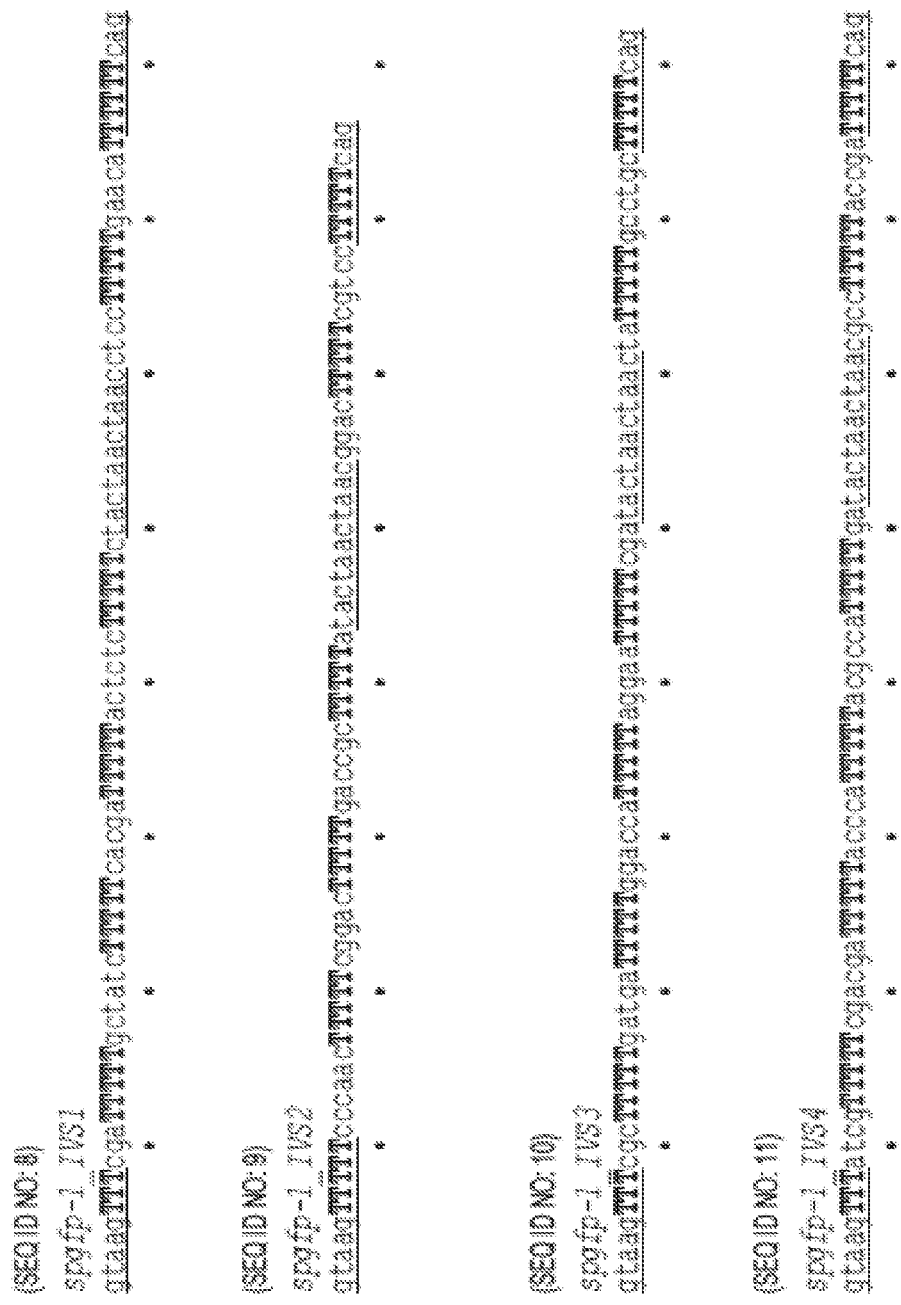

FIG. 14. Intronic sequences in spgfp-1. Shown are the four intronic sequences of 83, 76, 82 and 83 bases, respectively, that are present in spgfp-1. Underlined nucleotides indicate splice site consensus sequences. Boldface capital "T" nucleotides indicate the location of six segments of nucleotides that contain a stretch of five "T" nucleotides arranged at 10-11 base intervals.

FIG. 15. Expression constructs tested in C. elegans. In each case, the indicated promoter (and enhancer if noted) were placed upstream of the noted spgfp coding region and transgenic animals produced by microinjection as described (Mello et al., 1991, which is herein incorporated by reference in its entirety). Transgenic animals were selected using visibly scored markers (including rol-6, which causes the animals to exhibit a clear rolling phenotype). Where line numbers are noted, transgenic lines were obtained before examining animals by fluorescence microscopy. "Transient" indicates a set of experiments in which descendants of the injected animals were analyzed directly in a mass population.

FIG. 16. Structure of Superperiodic GFP expression vector L7152. This figure shows the nucleotide sequence of the vector that carries the spgfp-1 coding region which is driven by the CMV immediate early promoter. Also indicated is the location of landmarks and unique restriction enzyme sites.

FIG. 17. Structure of control GFP expression vector L7148. This figure shows the nucleotide sequence of the vector that carries the standard EGFP coding region which is driven by the CMV immediate early promoter. Also indicated is the location of landmarks and unique restriction enzyme sites.

Figure 18:
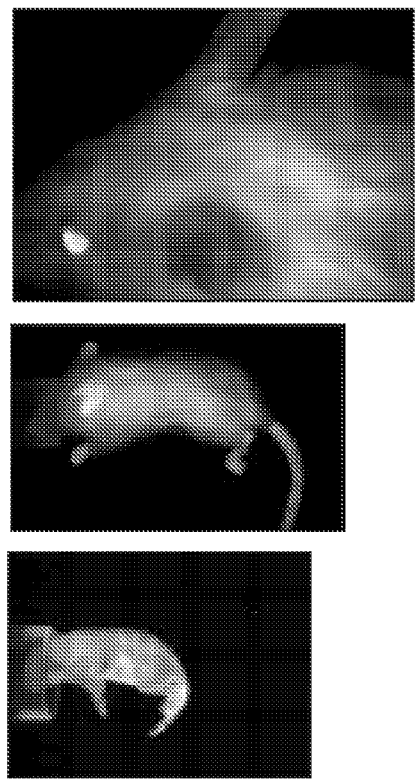

FIG. 18. GFP expression in transgenic mice. Mice derived from standard pronuclear injection of the CMV::spgfp-1 fusion construct are shown here photographed using fluorescence optics. Green tissues correspond to expression of the spgfp-1 transgene. Hair covering the bulk of the adult and 21 day-old animals (white in the image) would presumably obscure any GFP expression outside of exposed surfaces of the ears, eyes, feet, and tail. Parental mice were FVB/N (albino) with transgenesis achieved by standard methods of pronuclear injection (Taketo et al., 1991, which is herein incorporated by reference in its entirety).

Figure 19:
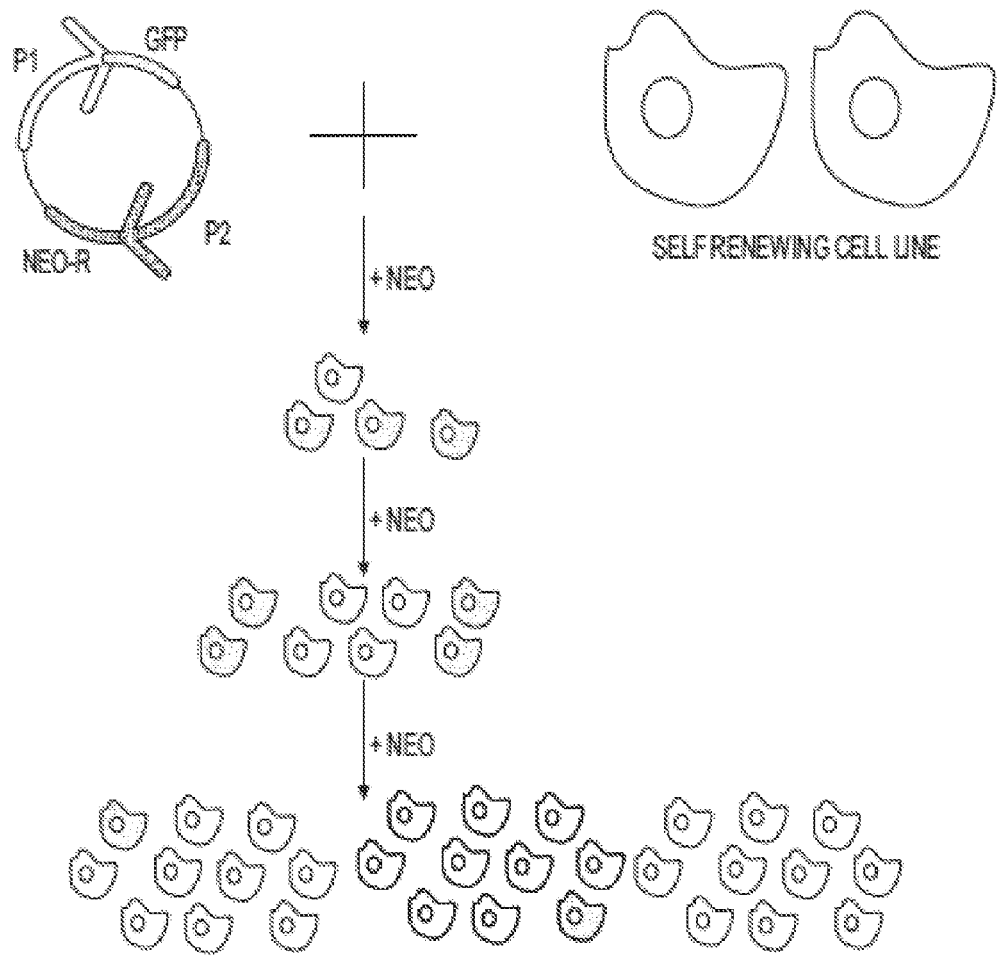

FIG. 19. General scheme for assaying long-term persistence of GFP expression in transfected cell populations. The initial plasmid L7152, described in detail in FIG. 16, is transfected into a self-renewing tissue culture line, and derived cells subjected to positive antibiotic selection (using antibiotic G418 (Davies et al., 1980, which is herein incorporated by reference in its entirety) to select for the neomycin phosphoribosyl transferase gene in the plasmid backbone). The drug resistance gene is driven by promoter the SV40 promoter [P2']). Promoter P1 (from Cytomegalovirus) drives expression of the relevant gfp coding region. The expression vectors were derived from pCDNA3 (pCDNA3 documentation; Sambrook et al., 1989, which is herein incorporated by reference in its entirety) and carry 3' ends for each coding region (Bovine growth hormone gene cleavage/polyA_addition signal for P1 and SV40 cleavage/polyA_addition signal for P2.). Plasmid features are not drawn to scale in this diagram and details of precise base sequence of plasmids are provided in FIGS. 16 and 17.

Figure 20A:
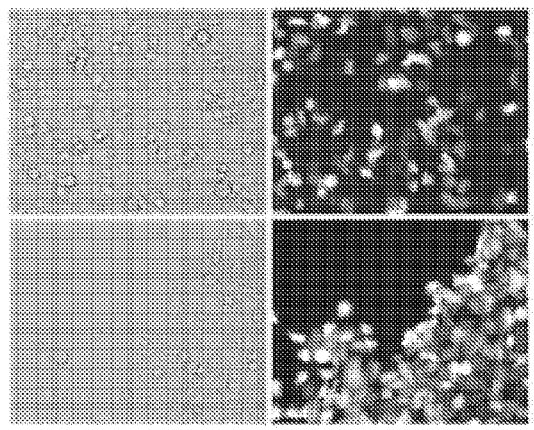
Figure 20B:
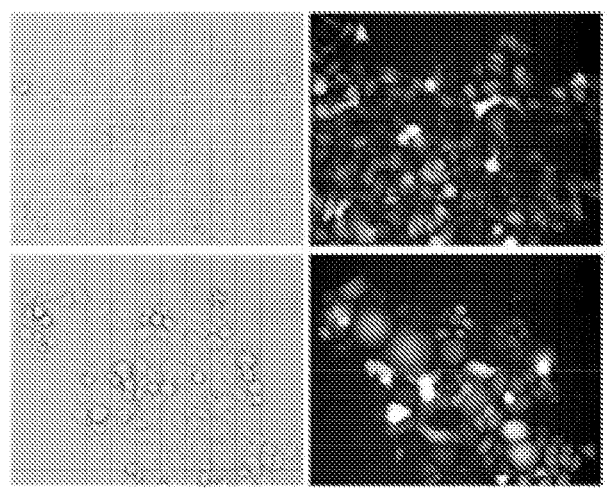
Figure 20C:
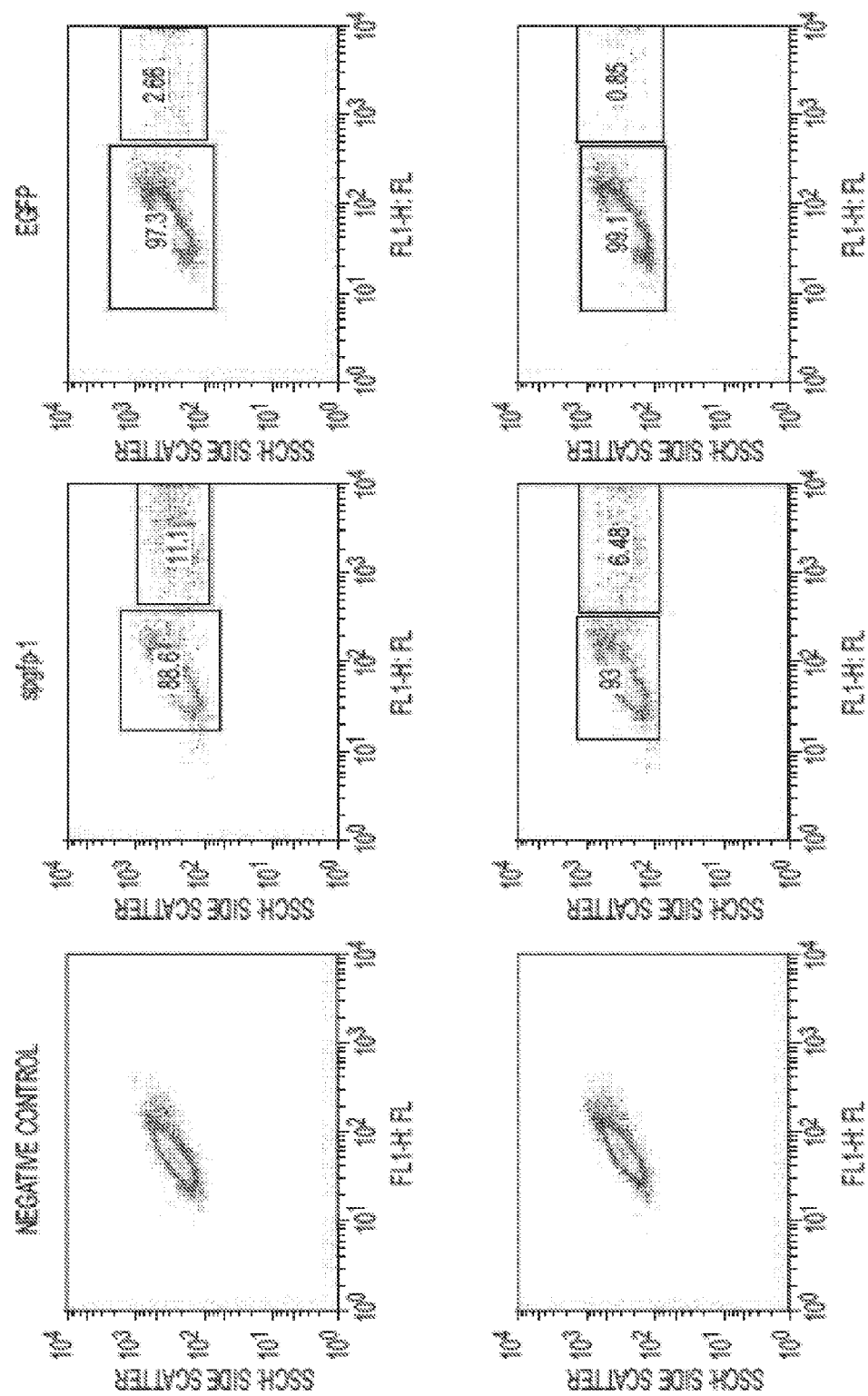
Figure 20C:
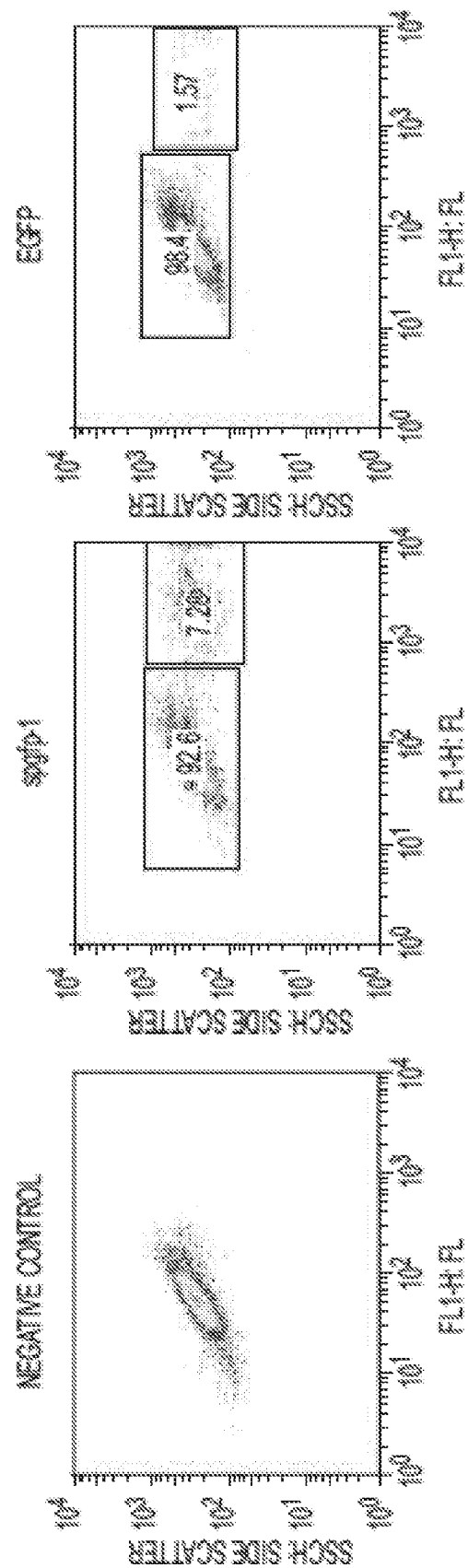

FIGS. 20A-C. GFP activity in transfected cells. FIG. 20A contains exemplary fluorescence micrographs of ME-180 tissue culture cells (a cell line derived from a human cervical tumor) transfected with experimental construct L7152 (FIG. 16). The images were taken after the cells had been cultured in medium with G418 for 2 weeks. Left panel: Transmission light micrographs showing cell outlines, Right panel: Epifluorescence micrographs showing bright signals in gfp-positive cells. FIG. 20B contains exemplary fluorescence micrographs of ME-180 tissue culture cells (a cell line derived from a human cervical tumor) transfected with control (EGFP) construct L7148 (FIG. 17). The images were taken after the cells had been cultured in medium with G418 for 2 weeks. Left panel: Transmission light micrographs showing cell outlines, Right panel: Epifluorescence micrographs showing bright signals in gfp-positive cells. FIG. 20C contains exemplary FACS profiles of Caski tissue culture cells transfected with L7152 (center column) and L7148 (right column). The FACS analysis was performed after the cells had been cultured in medium with G418 for 7 weeks. Non-transfected cells (without antibiotic selection) were used to generate the reference profiles ('Negative Control') shown in the left column.

Figure 21:
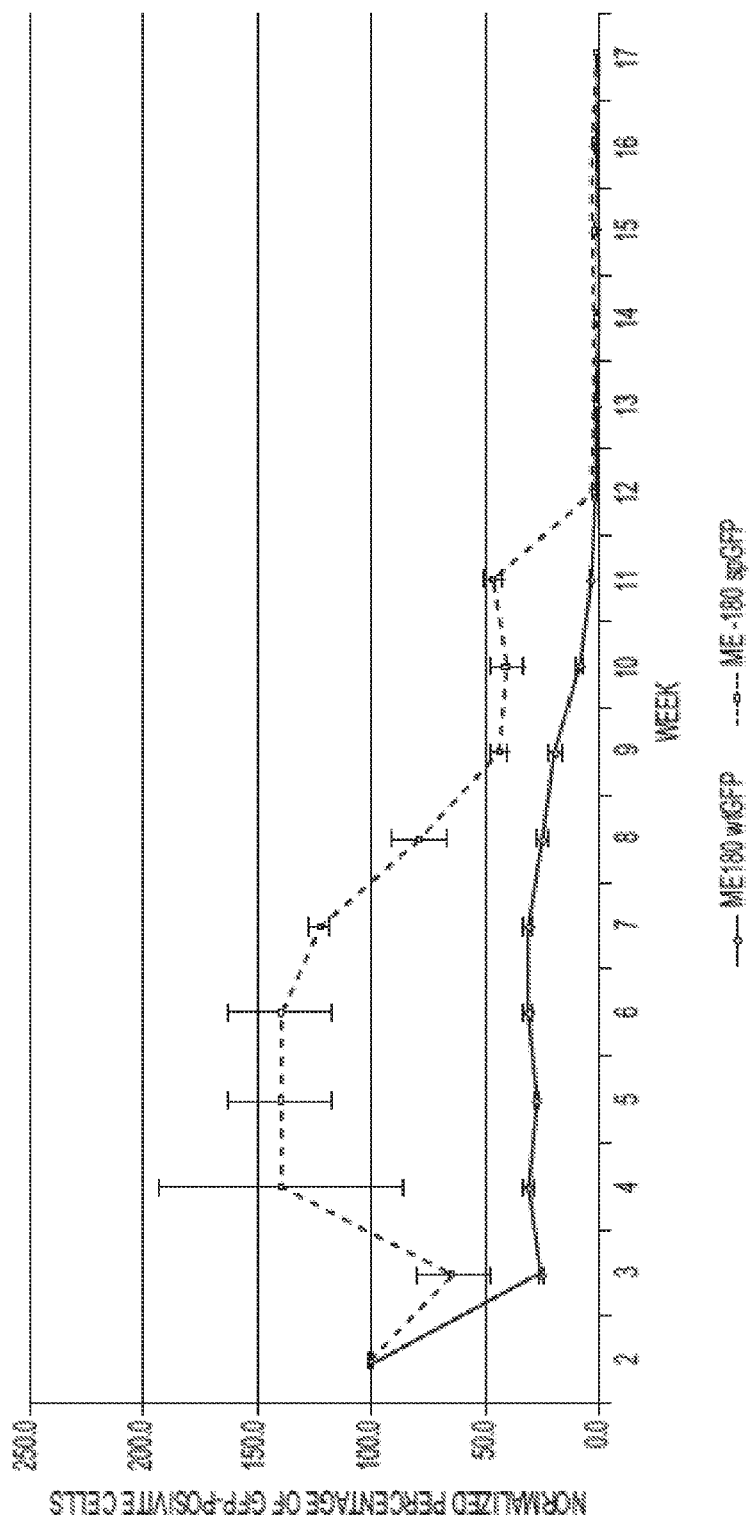

FIG. 21. Persistence of GFP fluorescene following transfection of ME180 cells. ME180 cells, a human cervical cancer line (Sykes et al., 1970, which is herein incorporated by reference in its entirety), were transfected with L7152 (spgfp) and L7148 (wtGFP) constructs. Each time point represents the average and standard deviation derived from following three independent cultures that were each passaged at twice-weekly intervals. For these curves, the activity levels were normalized to the values obtained as the measurements were taken at the first time point (week 2).

Figure 22:
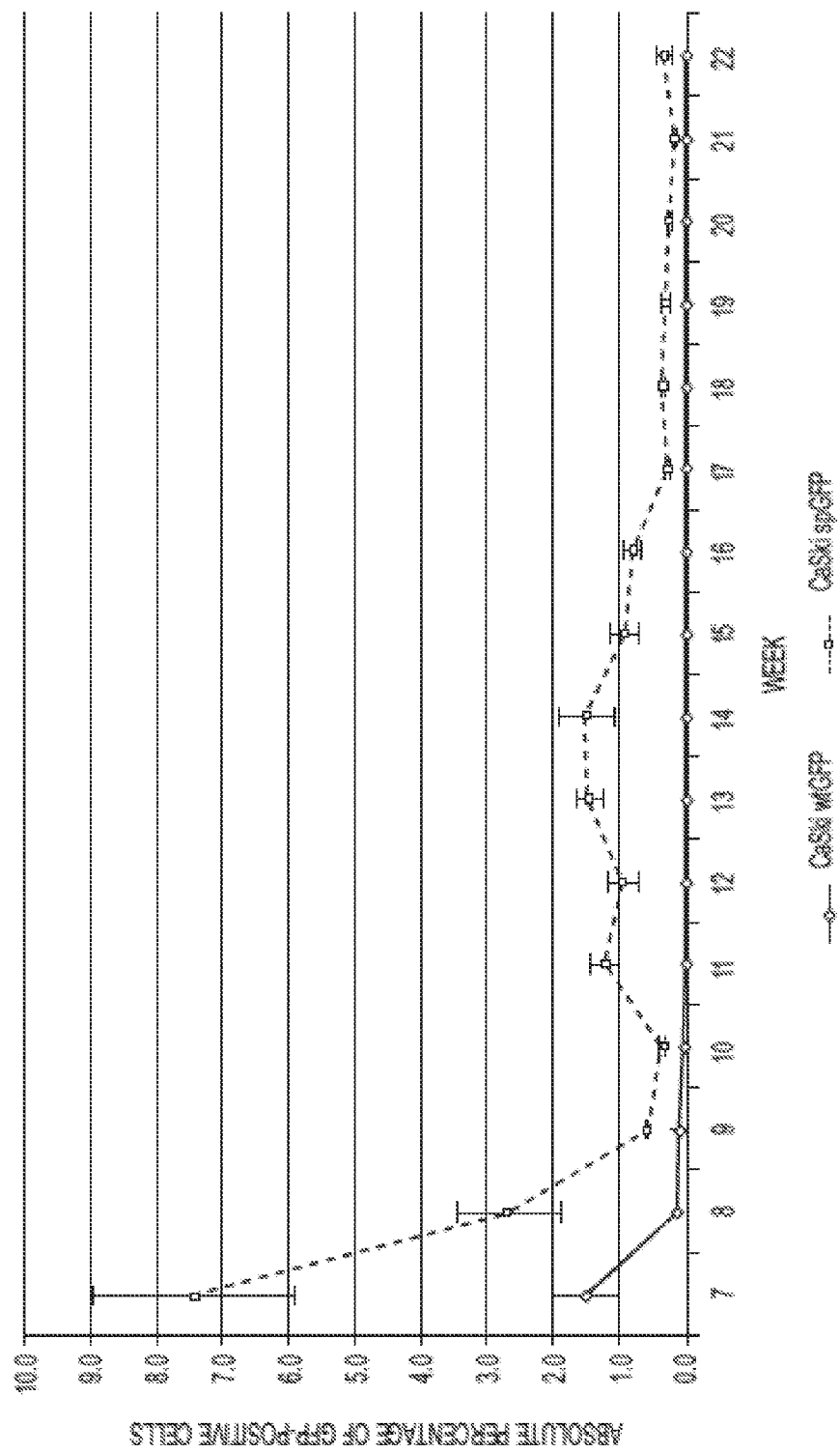

FIG. 22. Persistence of GFP fluorescence following transfection of the Caski strain of tissue culture cells. The Caski strain of tissue culture cells were transfected with L7152 (spgfp) and L7148 (wtGFP) constructs. Each time point represents the average and standard deviation derived from following three independent cultures that were each passaged at twice-weekly intervals. For these curves, the activity levels are reported as the absolute fraction of GFP-positive cells.

Figure 23:
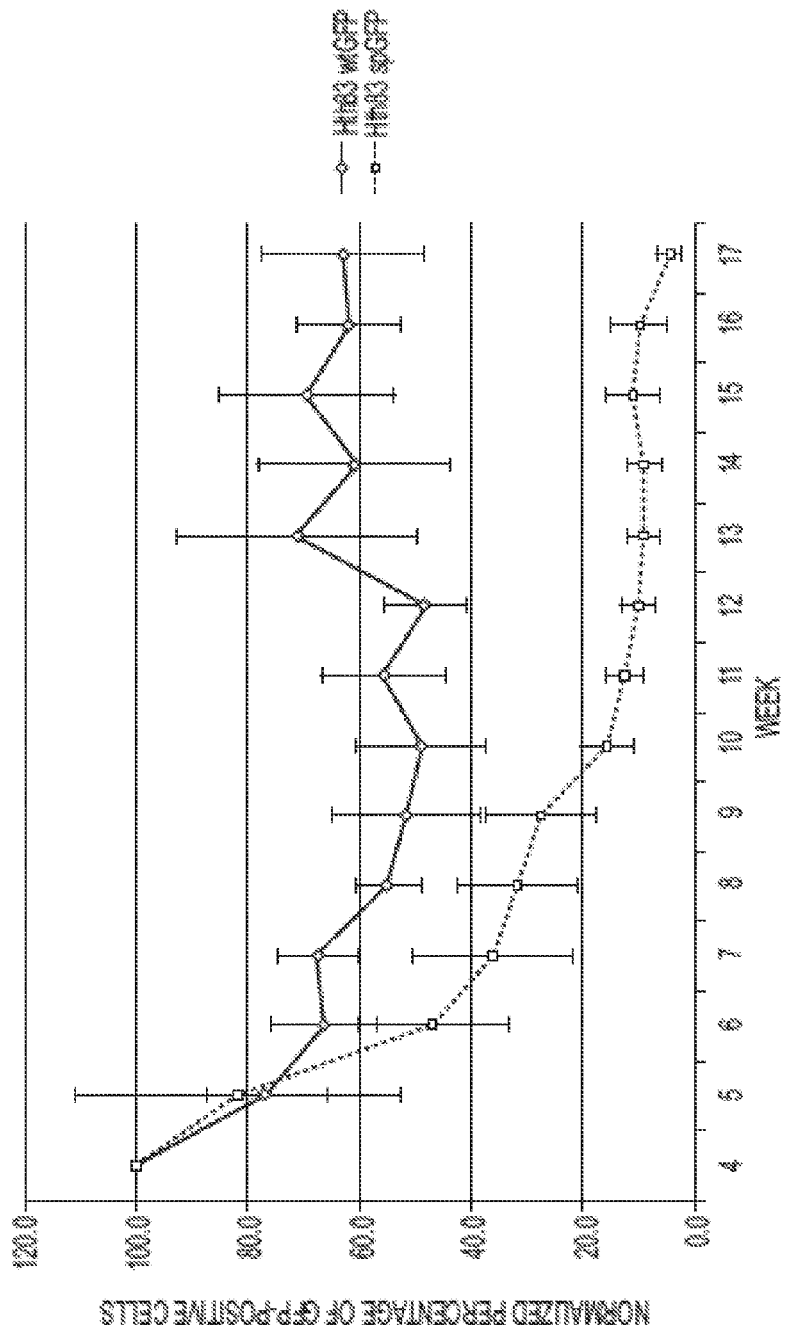

FIG. 23. Persistence of GFP fluorescence following transfection of the Hth83 strain of tissue culture cells. The Hth83 strain of tissue culture cells (derived from a human thyroid tumor) were transfected with L7152 (spgfp) and L7148 (wtGFP) constructs. Each time point represents the average and standard deviation derived from following three independent cultures that were each passaged at twice-weekly intervals. For these curves, the activity levels were normalized to the values obtained as the measurements were taken at the first time point (week 4).

FIG. 24. DNA sequence of spgfp-2. Shown is the DNA sequence of spgfp-2, a synthetic intron-interrupted gfp coding region. Coding regions are indicated in boldface capitalized letters while intronic sequences are indicated by non-boldface lower case letters.

Figure 25:
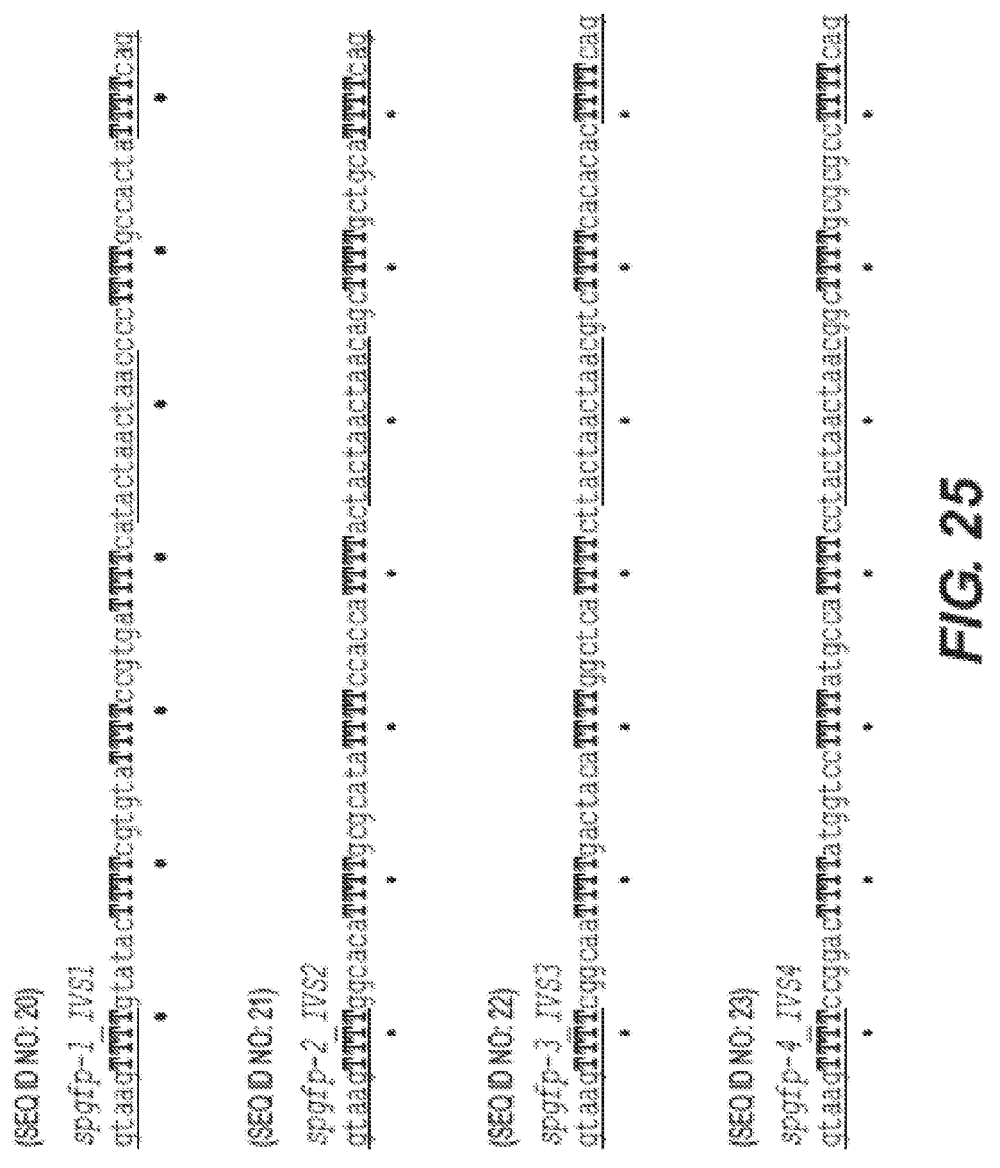

FIG. 25. Intronic sequences in spgfp-2. Shown are the four intronic sequences of 73, 73, 74 and 74 bases, respectively, that are present in spgfp-2. Underlined nucleotides indicate splice site consensus sequences. Boldface capital "T" nucleotides indicate the location of six segments of nucleotides that contain a stretch of four "T" nucleotides arranged at 10-11 base intervals.

Figure 26:
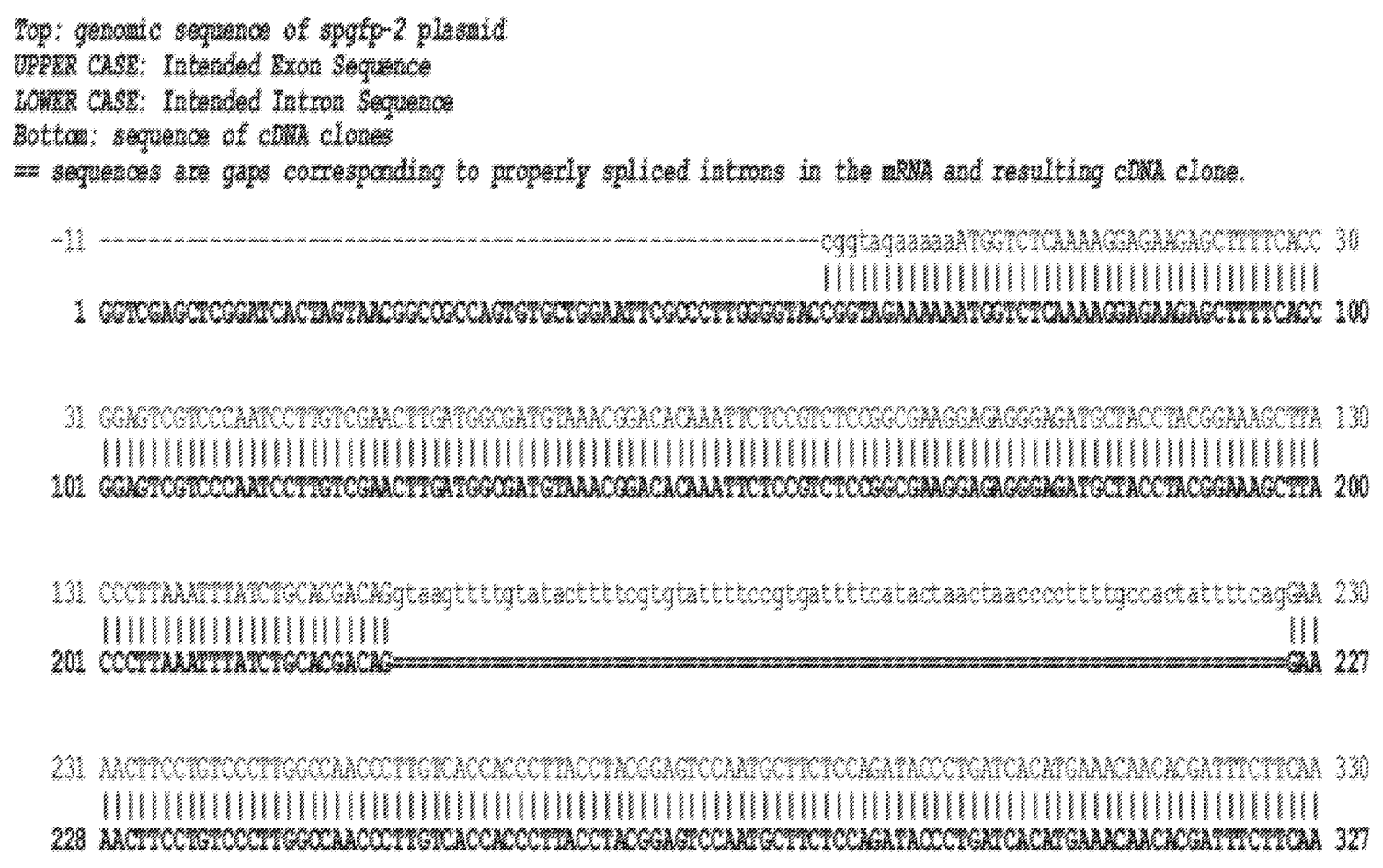
Figure 26:
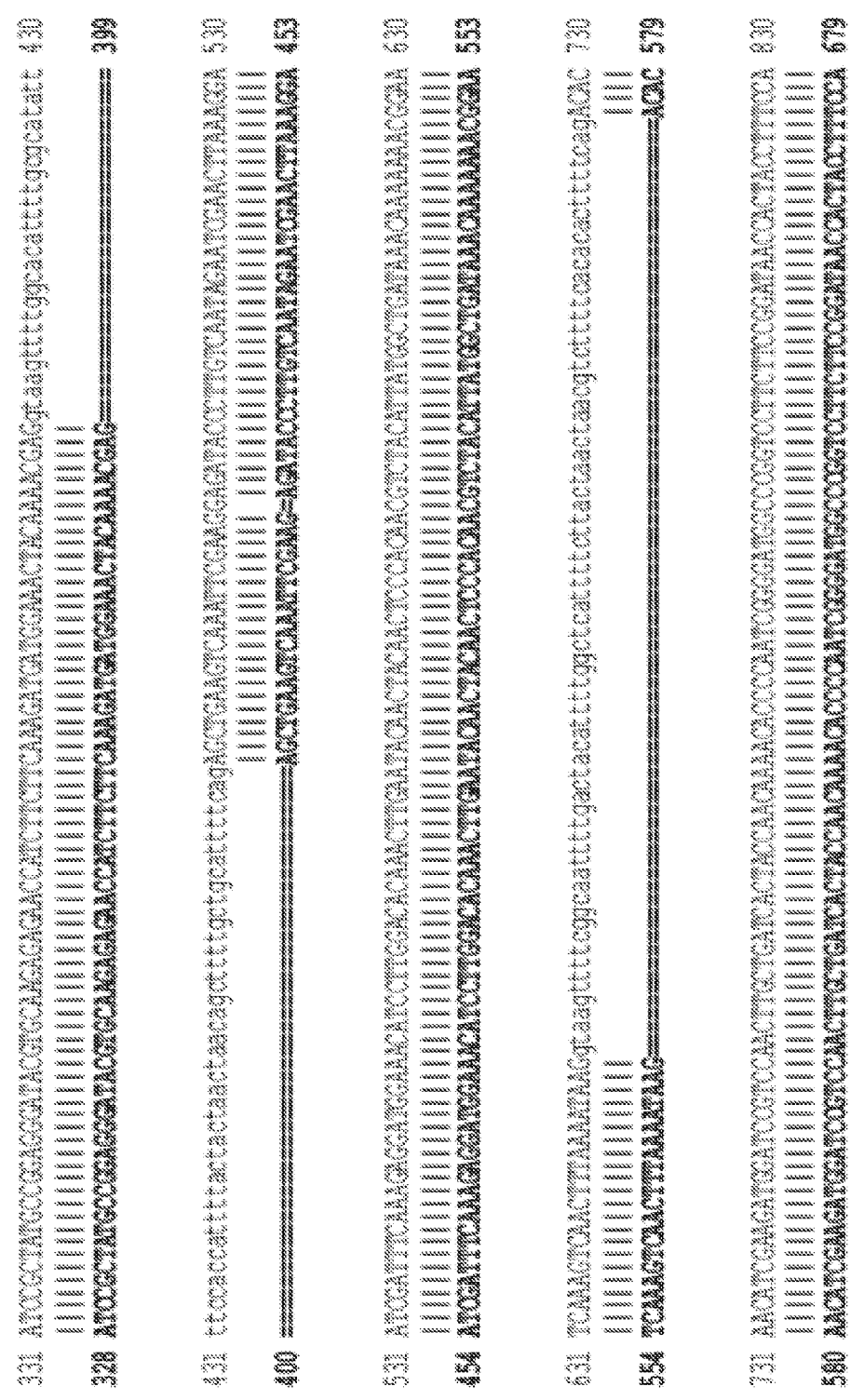
Figure 26:
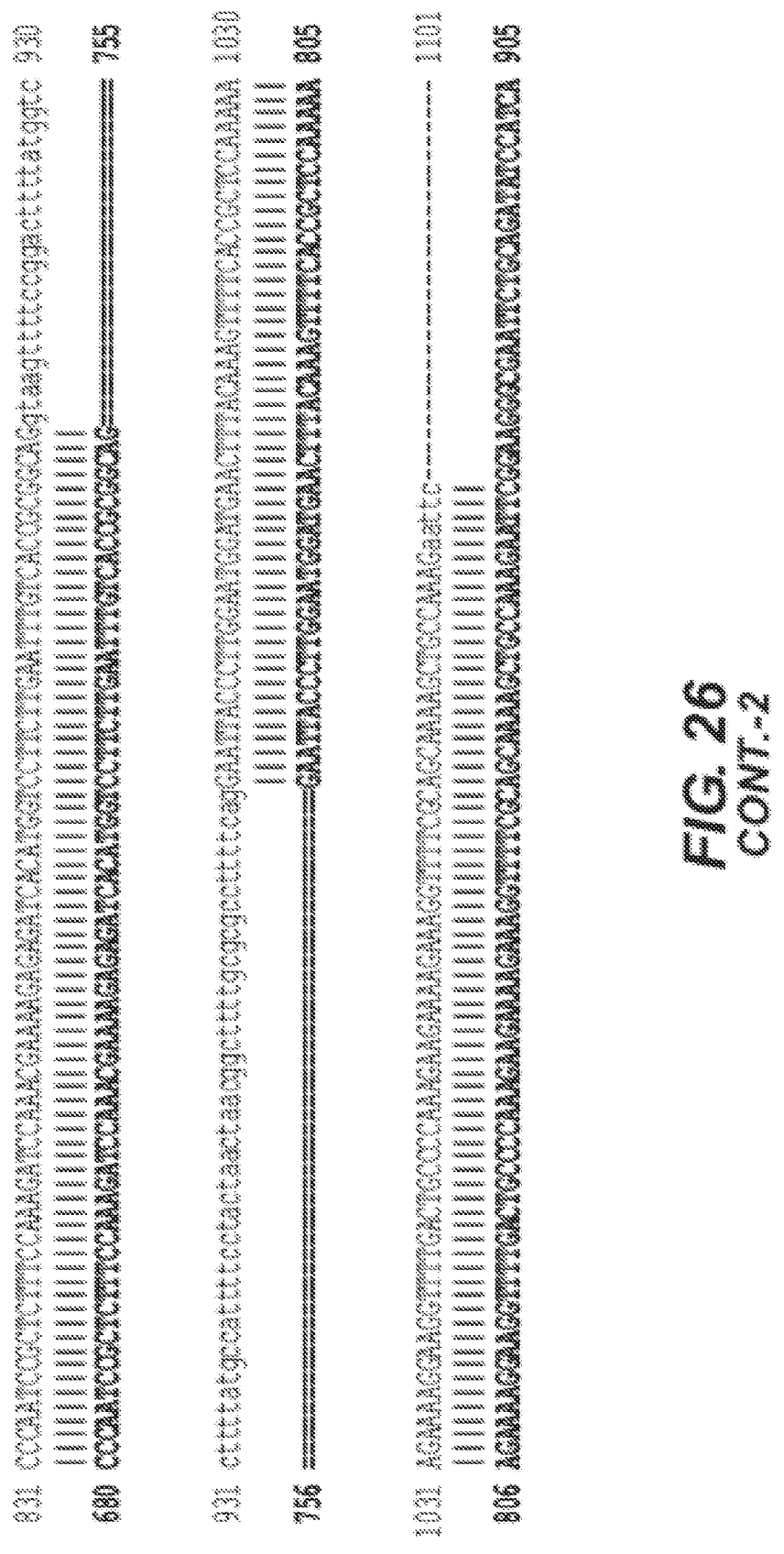

FIG. 26. Confirmation of Expression of spgfp-2 in *C. elegans* by Reverse-transcription PCR. In this experiment, the coding region for spgfp-2 was driven by the unc-54 enhancer and myo-2 promoter in a transgenic *C. elegans* line produced as described (Mello et al., 1991, which is herein incorporated by reference in its entirety). RNA was extracted, reverse transcribed, and amplified by PCR followed by sequencing. Experiments that detect a fully translatable RNA in the background of numerous aberrant products can be complicated by the preferential stabilization of "normal" translatable message over aberrant messages which are likely to harbor premature stops (Pulak et al., 1993; Okkema et al., 1993, which are herein incorporated by reference in their entireties). For this experiment, a single base deletion in the spgfp-2 coding region suffices to avoid any preferential translation, by insuring that neither "normal" nor "aberrant" messages have a major stability advantage. This mutation was present in the DNA (deletion at base 495) of the injected construct (L7198), which is otherwise comparable to the functional construct L7324 described in FIG. 16. The spgfp-2 DNA sequence (orange below) is aligned below with the cDNA sequence (blue), demonstrates the existence of a mRNA population with the appropriate splice junctions. This could only have been produced by transcription and splicing of the primary mRNA transcript.

DETAILED DESCRIPTION

The present invention herein provides methods for improving the level and/or sustainability of expression for a target nucleic acid in a eukaryotic cell which comprises modifying the target nucleic acid sequence to introduce signals that limit or constrain the positions of nucleosome cores and then introducing the thus modified target nucleic acid into a target eukaryotic cell. This embodiment of the invention is based on the concept that restricting the number and/or position of the nucleosome cores is important towards improving the level and/or sustainability of nucleic acid expression.

DEFINITIONS

Unless defined otherwise, all technical and scientific terms used herein have the same meaning as commonly understood by one of ordinary skill in the art to which this invention belongs.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters. In addition, the terms "gene" and "recombinant gene" also refer to nucleic acid molecules comprising an open reading frame encoding an EMP-1 protein, preferably a mammalian EMP-1 protein.

As used herein, the phrase "improved levels of expression of a modified target DNA" refers to an increase in the levels of target RNA and/or protein in a cell.

As used herein, the term "isolated" nucleic acid sequence refers to a nucleic acid sequence which is essentially free of other nucleic acid sequences, e.g., at least about 20% pure, preferably at least about 40% pure, more preferably about 60% pure, even more preferably about 80% pure, most preferably about 90% pure, and even most preferably about 95% pure, as determined by agarose gel electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semi-synthetic, synthetic origin, or any combinations thereof.

As used herein, the phrase "modified target DNA" refers to a nucleotide sequence that has been modified to comprise phased nucleotide sequences that are capable of positioning nucleosomes.

As used herein, the phrase "pharmaceutically acceptable" refers to materials and compositions that are physiologically tolerable and do not typically produce an allergic or similar untoward reaction, such as gastric upset, dizziness and the like, when administered to a human. Typically, as used herein, the term "pharmaceutically acceptable" means approved by a regulatory agency of the Federal or a state government or listed in the U.S. Pharmacopeia or other generally recognized pharmacopeia for use in animals, and more particularly in humans.

As used herein, the phrase "physiologically effective amount" is that amount delivered to a subject to give the desired palliative or curative effect. This amount is specific for each drug and its ultimate approved dosage level.

As used herein, the term "signals" refers to any nucleotide or nucleotide sequence that could potentially position a nucleosome. Signals may comprise AA/TT dinucleotide pairs, or more or less of such dinucleotides, in positions where at least 80%, more preferably 90% and most preferably 100% of the adjacent AA/TT dinucelotide separations are in the range of 1-3, 7-13, 17-23, 27-33, 37-43 or 47-53 nucleotides.

As used herein, the term "subject" can be a human, a mammal, or an animal. The subject being treated is a patient in need of treatment.

As used herein, the term "target nucleic acid" refers to a nucleotide sequence that encodes for a protein or fragment thereof of interest.

As used herein, the term "vector" refers broadly to any plasmid, phagemid or virus encoding an exogenous nucleic acid. The term is also be construed to include non-plasmid, non-phagemid and non-viral compounds which facilitate the transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, *Proc. Natl. Acad. Sci. U.S.A.* 94:12744-12746, which is herein incorporated by reference in its entirety). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057-3063; International Patent Application No. WO 94/17810, published Aug. 18, 1994; International Patent Application No. WO 94/23744, published Oct. 27, 1994, which are herein incorporated by reference in their entireties). Examples of non-viral vectors include, but are not limited to, liposomes, polyamine derivatives of DNA, and the like.

As used herein, the terms "nucleic acid," "nucleic acid molecule," or "polynucleotide" refer to deoxyribonucleotides or ribonucleotides and polymers thereof in either single- or double-stranded form. Unless specifically limited, the terms encompass nucleic acids containing analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605-2608; Cassol et al. (1992); Rossolini et al. (1994) Mol. Cell. Probes 8:91-98, which are herein incorporated by reference in their entireties). The term nucleic acid is used interchangeably with gene, cDNA, and mRNA encoded by a gene. As used herein, the terms "nucleic acid," "nucleic acid molecule," or "polynucleotide" are intended to include DNA molecules (e.g., cDNA or genomic DNA), RNA molecules (e.g., mRNA), analogs of the DNA or RNA generated using nucleotide analogs, and derivatives, fragments and homologs thereof.

Measurement of Target Nucleic Acid Expression

A number of methodologies may be employed to quantitate the level of target nucleic acid expression. Those skilled in the art will appreciate that the methods indicated below represent some of the preferred ways in which the level of target nucleic acid expression may be quantitated and in no manner limit the scope of methodologies that may be employed. Those skilled in the art will be able to determine operative and optimal assay conditions for each determination by employing routine experimentation. As examples, target nucleic acid expression can be quantitated according to the techniques below.

RNA Based Assays.

Target nucleic acid expression may be determined by methods which detect particular mRNAs in cells. These include, hybridization assays using complementary DNA probes (such as in situ hybridization, Northern blot and related techniques) and various nucleic acid amplification assays (such as RT-PCR using complementary primers specific for the target gene, and other amplification type detection methods, such as, for example, branched DNA, SISBA, TMA and the like). Protocols for the detection of specific mRNAs in a sample are well known in the art (Sambrook et al., (1990) Molecular Cloning—A Laboratory Manual, Cold Spring Harbor Laboratory Press; Ausubel et al., (1998) Current Protocols in Molecular Biology, Wiley, which are herein incorporated by reference their entireties).

In one embodiment of the present invention, target gene expression is quantified at the RNA level by amplification of target gene RNA by, for example, reverse transcription polymerase chain reaction (RT-PCR) and resolution/quantification of the reaction products by gel electrophoresis (e.g., slab, capillary, etc.) and product measurement (e.g., by scanning, laser, etc.). Those of skill in the art will appreciate that many variations of the technique are possible.

In another embodiment of the present invention, target nucleic acid expression is measured by a real-time quantitative RT-PCR based method. Methods for carrying out quantitative PCR are known in the art. See, for example, U.S. Pat. Nos. 5,210,015 and 5,487,972 and EP 512334B1, which are hereby incorporated by reference in their entirety. Commercial instruments for carrying out quantitative PCR and RT-PCR are available from PE Applied Biosystems, 850 Lincoln Centre Drive, Foster City, Calif. 94404, from Roche Molecular Systems, Inc., 1145 Atlantic Avenue, Alameda, Calif. 94501, and from Roche Molecular Biochemicals, Indianapolis, Ind.

The primers used for PCR are suitably designed to comprise nucleotide sequences which encode amino acid sequences that are highly conserved within the target gene. Methods to identify nucleotide sequences corresponding to a given amino acid sequence include deduction on the basis of the codon usage of the host cell, and methods of making mixed oligonucleotide sequences using multiple codons (hereinafter referred to as a 'degenerate oligonucleotides'). In the latter case, the multiplicity of oligonucleotides can be reduced by introducing hypoxanthine to their nucleotide sequences.

Primers for PCR amplification of the target gene may comprise a nucleotide sequence designed to anneal with a template chain, the primer being joined to an additional 5' sequence. The choice of such an additional 5' nucleotide sequence is not particularly limited, as long as the primer can be used for PCR or RT-PCR. Such an additional 5' sequence can be, for example, a nucleotide sequence convenient for the cloning operation of a PCR product. Such a nucleotide sequence can be, for example, a restriction enzyme cleavage site or a nucleotide sequence containing a restriction enzyme cleavage site.

Furthermore, in designing of the primer for PCR it is preferred that the sum of the number of guanine (G) and the number of cytosine (C) bases is 40 to 60% of the total number of bases. Furthermore, there is little or no self-annealing for a given primer and, in the case of a pair of primers, little or no annealing between the primers.

The number of nucleotides making up the primer for PCR amplification of the target nucleic acid is not particularly limited, as long as it can be used for PCR. The lower limit of the number is generally 10 to 14 nucleotides, with the upper limit 40 to 60 nucleotides. The primers may be 14 to 40 oligonucleotides in length.

The primers for PCR amplification of the target gene are preferably DNA. Nucleosides in the primer can be deoxy adenosine, deoxy cytidine, deoxy thymidine, and deoxy guanosine, and additionally deoxy inosine. The 5'-position of the nucleoside at the 5'-end of the primer for PCR is suitably a hydroxyl group or a hydroxy group to which one phosphoric acid is bonded by an ester link.

Synthesis of primer for PCR amplification of the target gene can be performed by methods generally used for synthesis of nucleic acids, for example, the phosphoamidite method. An automated DNA synthesizer can be preferably used in such a method. Total RNA can also be used as a template for RT-PCR instead of mRNA.

Relative quantitation of target nucleic acid mRNA may be achieved by means of the ABI Prism 7700 Sequence Detection System (Applied Biosystems, Foster City, Calif.). In TaqMan real-time quantitation technology, the 5'exonuclease activity of the Taq polymerase cleaves and releases a hybridization probe that is labeled with a fluorescent reporter dye. This fluorogenic probe is specific for the target sequence, thereby generating a fluorescence signal that is specific and is directly proportional to the amount of PCR product synthesized. PCR reactions are characterized by the time-point during cycling when amplification of the PCR product is first detected, rather than the amount of product accumulated after a fixed number of cycles. Since the amount of product at the exponential phase of the PCR is proportional to the initial copy number of the target, the more abundant the starting quantity of a target, the earlier will the PCR amplification be detected by means of the fluorescence signal. In this technology, the target quantity is measured by identifying the threshold cycle number ($C_T$), i.e. when the fluorescence signal crosses a preset detection threshold. The laser detector of the Prism 7700 monitors the cycle to cycle change in fluorescence signal on-line. The fewer cycles it takes to reach a detectable level of fluorescence, the greater the initial copy number.

In another embodiment, an oligonucleotide ligation assay (OLA) (U.S. Pat. No. 4,998,617, which is hereby incorporated by reference in its entirety) may be used. The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides hybridize such that their termini abut, and create a ligation substrate. Ligation then permits the labeled oligonucleotide to be recovered using avidin, or another biotin ligand. Nickerson, D. A. et al. ((1990) *Proc. Natl. Acad. Sci. USA* 87:8923-27, which is herein incorporated by reference in its entirety) have described a nucleic acid detection assay that combines attributes of PCR and OLA. In this method, PCR is used to achieve the exponential amplification of target DNA, which is then detected using OLA.

Several techniques based on this OLA method have been developed and are useful for detecting RNA. For example, U.S. Pat. No. 5,593,826, which is hereby incorporated by reference in its entirety, discloses an OLA using an oligonucleotide having 3'-amino group and a 5'-phosphorylated oligonucleotide to form a conjugate having a phosphoramidate linkage. In another variation of OLA described in Tobe et al. ((1996), *Nucleic Acids Res.* 24: 3728, which is herein incorporated by reference in its entirety), OLA combined with PCR may permit the detection and quantification of target gene RNA in a single microtiter well.

In another embodiment, target gene RNA levels are quantified by in situ detection according to standard methods.

In yet a further embodiment of the invention, probes capable of hybridizing specifically to target gene RNA, are attached to a solid phase support, e.g., a "chip," "DNA probe array" or "nucleic acid probe array" and used to quantitate target gene expression. Oligonucleotides can be bound to a solid support by a variety of processes, including lithography. For example, a chip can hold up to about 250,000 oligonucleotides. The solid phase support is then contacted with a test nucleic acid and hybridization to the specific probes is detected. Accordingly, the quantification of numerous samples (e.g., different tissues from the same individual or samples from different individuals) or the profiling of the RNA levels of a gene can be identified in a single hybridization experiment.

Protein Based Assays.

Target nucleic acid expression may be quantified at the protein level using methods known in the art, for example using quantitative enzyme linked immunosorbent assays ("ELISA"). Methods for designing and using quantitative ELISA assays are well known in the art. These methods require use of monoclonal or polyclonal antibodies that are specific for the protein encoded by the target gene.

Suitable monoclonal antibodies may be prepared by standard hybridoma methods, using differential binding assays to ensure that the antibodies are specific for the protein encoded by the target nucleic acid and do not show cross-reactivity between related proteins. Alternatively, suitable monoclonal antibodies may be prepared using antibody engineering methods such as phage display. Methods for obtaining highly specific antibodies from antibody phage display libraries are known in the art, and several phage antibody libraries are commercially available from, for example, MorphoSys (Martinsried, Germany), Cambridge Antibody Technology (Cambridge UK) and Dyax (Cambridge Mass.). Suitable phage display methods are described, for example, in U.S. Pat. Nos. 6,300,064 and 5,969,108, which are hereby incorporated by reference in their entirety. See also, for example "Antibody Engineering," McCafferty et al. (Eds.)(IRL Press 1996), which is herein incorporated by reference in its entirety. Once the antibody heavy and light chain genes are recovered from the phage antibodies, antibodies in any suitable format may be prepared, e.g. whole antibodies, Fab, scFv, etc.

Other antibody preparations may also be used, for example Camelid antibodies, which contain only heavy immunoglobulin chains. See, for example, Muyldermans et al. *J. Biotechnol.* June; 74(4):277-302 (2001), which is herein incorporated by reference in its entirety. Other antibody formats are described, for example in "Antibody Engineering," McCafferty et al. (Eds.)(IRL Press 1996), which is herein incorporated by reference in its entirety.

Polyclonal antibodies specific for protein encoded by the target gene may also be prepared using traditional animal-based methods. Peptides derived from protein encoded by the target gene can be conjugated at their N- or C-termini to carrier proteins such as bovine serum albumin (BSA) or keyhole limpet hemocyanin (KLH) and used to immunize animals, such as rabbits, using well-known immunization regimes. Specific polyclonal antibodies can be obtained from the serum of the animal by, for example, affinity chromatography over a matrix containing the peptide used for immunization bound to a solid support.

An ELISA assay may be used to quantitate the level of target nucleic acid expression. Many ELISA applications and formats have been described. Various sources provide discussion of ELISA chemistry, applications, and detailed protocols (See e.g., Crowther, "Enzyme-Linked Immunosorbent Assay (ELISA)," in Molecular Biomethods Handbook, Rapley et al., pp. 595-617, Humana Press, Inc., Totowa, N.J. (1998); Harlow and Lane (eds.), Antibodies. A Laboratory Manual, Cold Spring Harbor Laboratory Press (1988); Ausubel et al. (eds.), Current Protocols in Molecular Biology, Ch. 11, John Wiley & Sons, Inc., New York (1994); and Laurino et al., Ann. Clin. Lab Sci., 29(3): 158-166 (1999), which are herein incorporated by reference in their entireties.

In one embodiment of the present invention, an ELISA based method is provided in which an antibody specific for the protein encoded by the target nucleic acid is first immobilized on a solid support (e.g. in a microtiter plate well). Protein samples are then added to the plate from either a control or test sample containing the protein encoded by the target gene. The protein encoded by the target nucleic acid is then bound to antibody and can be detected and quantitated by the use of an antibody-enzyme conjugate capable of binding to another region of the protein encoded by the target nucleic acid (not bound by the first antibody) and producing a quantifiable signal. In some embodiments, the amount of antigen present is directly proportional to the amount of enzyme reaction product produced after the addition of an appropriate enzyme substrate.

As indicated previously, enzymes commonly used in ELISAs include horseradish peroxidase (HRPO), urease, alkaline phosphatase, glucoamylase and β-galactosidase. Protocols for the preparation of suitable antibody-enzyme conjugates are well known in the art. The present invention provides methods for the preparation of an antibody-enzyme (i.e., HRPO enzyme) conjugate that specifically recognizes the antigens of interest (i.e., CD4 and CD40) for use in an immunoassay (e.g., ELISA). The method provided herein, as those of skill in the art will recognize other methods for antibody-enzyme conjugation that find use with the present invention.

Conjugation of enzymes to antibodies involves the formation of a stable, covalent linkage between an enzyme (e.g., HRPO or alkaline phosphatase) and the antibody (e.g., the anti-CD4 and anti-CD40 antibodies), where neither the antigen-binding site of the antibody nor the active site of the enzyme is functionally altered.

The conjugation of antibody and HRPO is dependent on the generation of aldehyde groups by periodate oxidation of the carbohydrate moieties on HRPO (Nakane and Kawaoi, J. Histochem. Cytochem., 22:1084-1091 (1988), which is herein incorporated by reference in its entirety. Combination of these active aldehydes with amino groups on the antibody forms Schiff bases that, upon reduction by sodium borohydride, become stable.

Protocols to make antibody-enzyme conjugates using urease or alkaline phosphatase enzymes are also known in the art (Healey et al., Clin. Chim. Acta 134:51-58 (1983); Voller et al., Bull. W. H. O., 53:55-65 (1976); and Jeanson et al., J. Immunol. Methods 111:261-270 (1988), which are herein incorporated by reference in their entireties. For urease conjugation, cross-linking of the urease enzyme (e.g., Urease Type VII, Sigma No. U0376) and antibody using m-maleimidobenzoyl N-hydroxysuccinimide ester (MBS) is achieved through benzoylation of free amino groups on the antibody. This is followed by thiolation of the maleimide moiety of MBS by the cysteine sulfhydryl groups of urease. To prepare an alkaline phosphatase-antibody conjugate, a one-step glutaraldehyde method is the simplest procedure (Voller et al., Bull. W. H. O., 53:55-65 (1976), which is herein incorporated by reference in its entirety. This antibody-alkaline phosphatase conjugation protocol uses an enzyme immunoassay grade of the alkaline phosphatase enzyme.

The end product of an ELISA is a signal typically observed as the development of color or fluorescence. Typically, this signal is read (i.e., quantitated) using a suitable spectrocolorimeter (i.e., a spectrophotometer) or spectrofluorometer. The amount of color or fluorescence is directly proportional to the amount of immobilized antigen. In some embodiments of the present invention, the amount of antigen in a sample (e.g., the amount of protein encoded by the target gene) is quantitated by comparing results obtained for the sample with a series of control wells containing known concentrations of the antigen (i.e., a standard concentration curve). A negative control is also included in the assay system.

It is contemplated that any suitable chromogenic or fluorogenic substrates will find use with the enzyme-conjugated antibodies of the present invention. In some embodiments of the present invention, the substrate p-nitrophenyl phosphate (NPP) in diethanolamine is the preferred substrate for use in colorimetric ELISA methods, and 4-methylumbelliferyl phosphate (MUP) is the preferred alkaline phosphatase substrate in fluorometric ELISA methods. Conjugated antibodies can include radioisotopes, fluorophores, enzymes, luminescers, or visible particles (e.g., colloidal gold and dye particles). These and other labels are well known in the art and are described, for example, in the following U.S. Pat. Nos. 3,766,162; 3,791,932; 3,817,837; 3,996,345; and 4,233,402, which are hereby incorporated by reference in their entirety.

The present invention provides various ELISA protocols for the detection and/or quantitation of target gene expression. In one embodiment, the present invention provides a "direct ELISA" for the detection of target gene expression. In some embodiments, the antigen of interest in a sample (i.e., the protein encoded by the target gene) is bound (along with unrelated antigens) to the solid support (e.g., a microtiter plate well). The immobilized antigen is then directly detected by the antigen-specific enzyme-conjugated antibody, also provided by the present invention. Addition of an appropriate detection substrate results in color development or fluorescence that is proportional to the amount of protein encoded by the target gene present in the well.

In another embodiment, the present invention provides an indirect ELISA for the detection of target nucleic acid expression in a sample. In this embodiment, antigen of interest in a sample is immobilized (along with unrelated antigens) to a solid support (e.g., a microtiter plate well) as in the direct ELISA, but is detected indirectly by first adding an antigen-specific antibody, then followed by the addition of a detection antibody specific for the antibody that specifically binds the antigen, also known as "species-specific" antibodies (e.g., a goat anti-rabbit antibody), which are available from various manufacturers known to one in the art (e.g., Santa Cruz Biotechnology; Zymed; and Pharmingen/Transduction Laboratories).

In another embodiment, the present invention provides "sandwich ELISA" methods, in which the antigen in a sample is immobilized on a solid support by a "capture antibody" that has been previously bound to the solid support. In general, the sandwich ELISA method is more sensitive than other configurations, and is capable of detecting 0.1-1.0 ng/ml protein antigen. As indicated above, the sandwich ELISA method involves pre-binding the "capture antibody" which recognizes the antigen of interest (i.e., the protein encoded by the target gene) to the solid support (e.g., wells of the microtiter plate). In some embodiments, a biotinylated capture antibody is used in conjunction with avidin-coated wells. Test samples and controls are then added to the wells containing the capture antibody. If antigen is present in the samples and/or controls, it is bound by the capture antibody.

In some embodiments, after a washing step, detection of antigen that has been immobilized by the capture antibody is detected directly (i.e., a direct sandwich ELISA). In other embodiments detection of the protein encoded by the target nucleic acid that has been immobilized by the capture antibody is detected indirectly (i.e., an indirect sandwich ELISA). In the direct sandwich ELISA, the protein encoded by the target gene is detected using a target specific enzyme-conjugated antibody. In the indirect sandwich ELISA, the protein encoded by the target gene is detected by using a target protein specific antibody, which is then detected by another enzyme-conjugated antibody which binds the antigen-specific antibody, thus forming an antibody-antigen-antibody-antibody complex. In both the direct and indirect sandwich ELISAs, addition of a suitable detection substrate results in color development or fluorescence that is proportional to the amount of antigen that is present in the well.

In the sandwich ELISA, the capture antibody used is typically different from the second antibody (the "detection antibody"). The choice of the capture antibody is empirical, as some pairwise combinations of capture antibody and detection antibody are more or less effective than other combinations. The same monoclonal antibody must not be used as both the capture antibody and the conjugated detection antibody, since recognition of a single epitope by the capture antibody will preclude the enzyme-conjugated detection antibody from binding to the antigen. However, in some embodiments, two different monoclonal antibodies that recognize different epitopes are used in this assay. In other embodiments, the same polyclonal antibody preparation is used as both the capture antibody and conjugated detection antibody, since multiple epitopes are recognized in the pool of polyclonal antibody species.

Furthermore, it is not intended that the present invention be limited to the direct ELISA and sandwich ELISA protocols particularly described herein, as the art knows well numerous alternative ELISA protocols that also find use in the present invention (See, e.g., Crowther, "Enzyme-Linked Immunosorbent Assay (ELISA)," in Molecular Biomethods Handbook, Rapley et al., pp. 595-617, Humana Press, Inc., Totowa, N.J. (1998); and Ausubel et al. (eds.), Current Protocols in Molecular Biology, Ch. 11, John Wiley & Sons, Inc., New York (1994), which are herein incorporated by reference in their entireties. Thus, any suitable ELISA method including, but not limited to, competitive ELISAs also find use with the present invention.

In yet a further embodiment of the present invention, an ELISA amplification system is provided. These amplification systems produce at least 10-fold, and more preferably, a 500-fold increase in sensitivity over traditional alkaline phosphatase-based ELISAs. In one preferred embodiment of the ELISA amplification protocol, bound alkaline phosphatase acts on an NADPH substrate, whose reaction product initiates a secondary enzymatic reaction resulting in a colored product. Each reaction product from the first reaction initiates many cycles of the second reaction in order to amplify the signal (See e.g., Bio-Rad ELISA Amplification System, Cat. No. 19589-019).

In yet another embodiment of the present invention, target gene expression may be measured and quantitated by Western Blot analysis. Briefly, proteins samples may be electrophoresed on an acrylamide gel and transferred to a membrane such as nitrocellulose or PVDF. The blot is detected with antibody for the protein encoded by the target gene. These primary antibodies are then detected, for example, with labeled secondary antibodies. The fluorescence intensity of the dye is measured for both a test and control sample and the ratio of the intensity indicates the ratio of the two proteins.

In another embodiment of the present invention, target nucleic acid expression may be measured and quantitated by an immunohistochemistry based assay. For example, tissue sections may be treated with an antibody specific to the protein encoded by the target nucleic acid. These primary antibodies may be directly labeled or may be detected with suitable secondary antibodies. Staining intensity can be measured with a charge-coupled device (CCD) camera and the proteins quantitated. The ratio of the staining intensity indicates the ratio of the protein amounts.

In yet a further embodiment of the present invention, a spot/slot blot technique can be employed to measure and quantitate target nucleic acid expression. For example, identical amounts of protein samples may be directly spotted onto a membrane and detected with antibodies specific for the protein encoded by the target nucleic acid as described above.

In another embodiment of the present invention, a biosensor-based method may be used to measure and quantitate target nucleic acid expression. Many types of biosensor-based methods are known in the art and may be used for detecting and quantitating target gene expression. For example, antibody specific to the protein encoded by the target nucleic acid may be bound to the surface of the biosensor such that when the protein encoded by the target nucleic acid binds to the coated surface a detectable change occurs in some property of the surface. Biosensors measure, for example, mass changes at the surface, some measure changes in electrical properties, and some measure changes in optical properties. Each of these methods are well known in the art and are suitable for use in the present methods.

Commercial biosensor-based methods are available from, for example, Biacore (Piscataway, N.J.) and are suitable for use in the present invention for detecting and quantitating changes in target nucleic acid expression. See also, for example, the protein detection methods described in U.S. Pat. No. 6,225,047, the contents of which are hereby incorporated by reference in their entirety, and Davies et al., *Biotechniques* 27(6):1258-61 (1999), which is herein incorporated by reference in its entirety. Commercial protein chip detection methods are available from Ciphergen (Fremont, Calif.).

In another embodiment of the present invention, a mass spectrometric method may be used to measure and quantitate target nucleic acid expression. See, for example, the methods described in U.S. Pat. Nos. 5,719,060, 5,894,063, which are hereby incorporated by reference in their entirety, and Shimizu et al, *J Chromatogr B Analyt Technol Biomed Life Sci* 25; 776(1): 15-30 (2002); Kiernan et al., *Anal Biochem* 301 (1):49-56. (2002); and Pramanik et al., *Protein Sci* (11):2676-87 (2002), which are herein incorporated by reference in their entireties. Mass spectrometry based protein detection methods are also available from Ciphergen (see supra).

Modification of Target Nucleic Acid

Target nucleic acid is modified to introduce signals that position nucleosome cores along the nucleotide sequence to improve or to sustain target nucleic acid expression. Such modification may include the introduction of AA/TT dinucleotides along one face of the helix. In some embodiments, 5 dinucleotides, more preferably 10 dinucleotides and most preferably 30 dinucleotides are introduced to the target nucleic acid.

In other embodiments, 50%, preferably 80%, more preferably 90% and most preferably 100% of the dinucleotides are separated by 1-3, 7-13, 17-23, 27-33, 37-43, or 47-53 nucleotides.

Modifications or variations can be introduced into the target nucleic acid by standard techniques (e.g., site-directed mutagenesis, PCR-mediated mutagenesis, homologous recombination, etc.). Preferably, conservative amino acid substitutions are made at one or more predicted non-essential amino acid residues. Thus, a predicted nonessential amino acid residue in the protein encoded by the target nucleic acid is replaced with another amino acid residue from the same side chain family. Alternatively, in another embodiment, mutations can be introduced randomly by substitutions or insertions along all or part of the target nucleic acid (e.g., by saturation mutagenesis), and the resultant mutants can be screened for biological activity of the protein encoded by the target nucleic acid to identify mutants that retain activity.

Such conservative mutations include but are not limited to mutations that switch one amino acid for another within one of the following groups:
1. Small aliphatic, nonpolar or slightly polar residues: Ala, Ser, Thr, Pro and Gly;
2. Polar, negatively charged residues and their amides: Asp, Asn, Glu and Gln;
3. Polar, positively charged residues: His, Arg and Lys;
4. Large aliphatic, nonpolar residues: Met, Leu, Ile, Val and Cys; and
5. Aromatic residues: Phe, Tyr and Trp.

The types of substitutions selected may be based on the analysis of the frequencies of amino acid substitutions between homologous proteins of different species developed by Schulz et al., Principles of Protein Structure, Springer-Verlag, 1978, pp. 14-16, on the analyses of structure-forming potentials developed by Chou and Fasman, Biochemistry 13, 211, 1974 or other such methods reviewed by Schulz et al., Principles in Protein Structure, Springer-Verlag, 1978, pp. 108-130, which are herein incorporated by reference in their entireties, and on the analysis of hydrophobicity patterns in proteins developed by Kyte and Doolittle, J. Mol. Biol. 157: 105-132, 1982, which is herein incorporated by reference in its entirety.

Methods to Introduce Nucleic Acids Into Cells

A number of methodologies may be employed to introduce the modified target nucleic acid into a cell. Those skilled in the art will appreciate that the methods indicated below represent some of the preferred ways in which the target gene may be introduced into a cell and in no manner limit the scope of methodologies that may be employed. Those skilled in the art will be able to determine operative and optimal assay conditions for each determination by employing routine experimentation. As examples, modified target nucleic acid can be introduced into cells according to the techniques below.

Viral-Based Delivery of Target Nucleic Acid

In one embodiment, gene therapy based methods can be used to deliver the target nucleic acid into a cell. Polynucleotides operably encoding the target nucleic acid can be delivered to a patient either as "naked nucleic acid" or as part of an expression vector. The term vector includes, but is not limited to, plasmid vectors, cosmid vectors, artificial chromosome vectors, or, in some aspects of the invention, viral vectors. Examples of viral vectors include adenovirus, herpes simplex virus (HSV), alphavirus, simian virus 40, picornavirus, vaccinia virus, retrovirus, lentivirus, and adeno-associated virus. Preferably the vector is a plasmid. In some aspects of the invention, a vector is capable of replication in the cell to which it is introduced; in other aspects the vector is not capable of replication. In some preferred aspects of the present invention, the vector is unable to mediate the integration of the vector sequences into the genomic DNA of a cell. An example of a vector that can mediate the integration of the vector sequences into the genomic DNA of a cell is a retroviral vector, in which the integrase mediates integration of the retroviral vector sequences. A vector may also contain transposon sequences that facilitate integration of the coding region into the genomic DNA of a host cell. Furthermore, liposomes containing the modified target DNA may be delivered to a patient.

Selection of a vector depends upon a variety of desired characteristics in the resulting construct, such as a selection marker, vector replication rate, and the like. An expression vector optionally includes expression control sequences operably linked to the coding sequence such that the coding region is expressed in the cell. The invention is not limited by the use of any particular promoter, and a wide variety is known. Promoters act as regulatory signals that bind RNA polymerase in a cell to initiate transcription of a downstream (3' direction) operably linked coding sequence. The promoter used in the invention can be a constitutive or an inducible promoter. It can be, but need not be, heterologous with respect to the cell to which it is introduced.

In one embodiment of the present invention, a method for delivery of the modified target DNA involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a recombinant gene construct that has been cloned therein.

The vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb (Grunhaus et al., 1992, which is herein incorporated by reference in its entirety). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990, which is herein incorporated by reference in its entirety). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

Recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

In nature, adenovirus can package approximately 105% of the wild-type genome (Ghosh-Choudhury et al., 1987, which is herein incorporated by reference in its entirety), providing capacity for about 2 extra kb of DNA. Helper cell lines derived from human cells such as human embryonic kidney cells, muscle cells, hematopoietic cells or other human embryonic mesenchymal or epithelial cells may be used to make the construct. Alternatively, the helper cells may be derived from the cells of other mammalian species that are permissive for human adenovirus. Such cells include, e.g., Vero cells or other monkey embryonic mesenchymal or epithelial cells.

The adenovirus vector may be replication defective, or at least conditionally defective, the nature of the adenovirus vector is not believed to be crucial to the successful practice of the invention. The adenovirus may be of any of the 42 different known serotypes or subgroups A-F.

Adenovirus growth and manipulation is known to those of skill in the art, and exhibits broad host range in vitro and in vivo. This group of viruses can be obtained in high titers, e.g., $10^9$-$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Top et al., 1971), demonstrating their safety and therapeutic potential as in vivo gene transfer vectors.

Adenovirus vectors have been used in eukaryotic gene expression (Levrero et al., 1991; Gomez-Foix et al., 1992, which are herein incorporated by reference in their entireties) and vaccine development (Grunhaus et al., 1992; Graham and Prevec, 1992, which are herein incorporated by reference in their entireties). Animal studies have suggested that recombinant adenovirus could be used for gene therapy (Stratford-Perricaudet and Perricaudet, 1991; Stratford-Perricaudet et al., 1990; Rich et al., 1993, which are herein incorporated by reference in their entireties). Studies in administering recombinant adenovirus to different tissues include trachea instillation (Rosenfeld et al., 1991; Rosenfeld et al., 1992, which are herein incorporated by reference in their entireties), muscle injection (Ragot et al., 1993, which is herein incorporated by reference in its entirety), peripheral intravenous injections (Herz and Gerard, 1993, which is herein incorporated by reference in its entirety) and stereotactic inoculation into the brain (Le Gal La Salle et al., 1993, which is herein incorporated by reference in its entirety).

In another embodiment of the invention, modified target nucleic acid may be delivered through the use of a retroviral expression vector. The retroviruses are a group of single-stranded RNA viruses characterized by an ability to convert their RNA to double-stranded DNA in infected cells by a process of reverse-transcription (Coffin, 1990, which is herein incorporated by reference in its entirety). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990, which is herein incorporated by reference in its entirety).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983, which is herein incorporated by reference in its entirety). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983, which are herein incorporated by reference in their entireties). The media containing the recombinant retroviruses is then collected, optionally concentrated, and used for gene transfer. Retroviral vectors are able to infect a broad variety of cell types. However, integration and stable expression require the division of host cells (Paskind et al., 1975, which is herein incorporated by reference in its entirety).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, packaging cell lines are available that should greatly decrease the likelihood of recombination (Markowitz et al, 1988; Hersdorffer et al., 1990, which are herein incorporated by reference in their entireties).

Adeno-associated virus (AAV) is an attractive vector system for use in the present invention as it has a high frequency of integration and it can infect nondividing cells, thus making it useful for delivery of genes into mammalian cells in tissue culture (Muzyczka, 1992, which is herein incorporated by reference in its entirety). AAV has a broad host range for infectivity (Tratschin, et al., 1984; Laughlin, et al., 1986; Lebkowski, et al., 1988; McLaughlin, et al., 1988, which are herein incorporated by reference in their entireties), which means it is applicable for use with the present invention. Details concerning the generation and use of rAAV vectors are described in U.S. Pat. No. 5,139,941 and U.S. Pat. No. 4,797,368, each of which is incorporated by reference herein.

Studies demonstrating the use of AAV in gene delivery include LaFace et al. (1988); Zhou et al. (1993); Flotte et al. (1993); and Walsh et al. (1994), each of which is herein incorporated by reference in their entireties. Recombinant AAV vectors have been used successfully for in vitro and in vivo transduction of marker genes (Lebkowski et al., 1988; Samulski et al., 1989; Shelling and Smith, 1994; Yoder et al., 1994; Zhou et al., 1994; Hermonat and Muzyczka, 1984; Tratschin et al., 1985; McLaughlin et al., 1988, each of which is herein incorporated by reference in their entireties) and genes involved in human diseases (Flotte et al., 1992; Ohi et al., 1990; Walsh et al., 1994; Wei et al., 1994, each of which is herein incorporated by reference in their entireties). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992, which is herein incorporated by reference in its entirety). In the absence of coinfection with helper virus, the wild-type AAV genome integrates through its ends into human chromosome 19 where it resides in a latent state as a provirus (Kotin et al., 1990; Samulski et al., 1991, each of which is herein incorporated by reference in their entireties). rAAV, however, is not restricted to chromosome 19 for integration unless the AAV Rep protein is also expressed (Shelling and Smith, 1994, which is herein incorporated by reference in its entirety). When a cell carrying an AAV provirus is superinfected with a helper virus, the AAV genome is "rescued" from the chromosome or from a recombinant plasmid, and a normal productive infection is established (Samulski et al., 1989; McLaughlin et al., 1988; Kotin et al., 1990; Muzyczka, 1992, each of which is herein incorporated by reference in their entireties).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild-type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994; Clark et al., 1995, each of which is herein incorporated by reference in their entireties). Cell lines carrying the rAAV DNA as an integrated provirus can also be used (Flotte et al., 1995).

Other viral vectors may be employed as constructs in the present invention. Vectors derived from viruses such as vaccinia virus (Ridgeway, 1988; Baichwal and Sugden, 1986; Coupar et al., 1988, each of which is herein incorporated by reference in their entireties) and herpesviruses may be employed. They offer several attractive features for various mammalian cells (Friedmann, 1989; Ridgeway, 1988; Baichwal and Sugden, 1986; Coupar et al., 1988; Horwich et al., 1990, each of which is herein incorporated by reference in their entireties).

A molecularly cloned strain of Venezuelan equine encephalitis (VEE) virus has been genetically refined as a replication competent vaccine vector for the expression of heterologous viral proteins (Davis et al., 1996, which is herein incorporated by reference in its entirety). Studies have demonstrated that VEE infection stimulates potent CTL responses and has been suggested that VEE may be an extremely useful vector for immunizations (Caley et al., 1997, which is herein incorporated by reference in its entirety). It is contemplated in the present invention, that VEE virus may be useful in targeting breast cells.

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990, which is herein incorporated by reference in its entirety). This suggested that large portions of the genome could be replaced with foreign genetic material.

In still further embodiments of the present invention, the modified target nucleic acid is housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. Such modifications permit specific infection of cancer and/or hyperproliferative cells via specific receptors present on these cells.

For example, targeting of recombinant retroviruses was designed in which biotinylated antibodies against a retroviral envelope protein and against a specific cell receptor were used. The antibodies were coupled via the biotin components by using streptavidin (Roux et al., 1989, which is herein incorporated by reference in its entirety). Using antibodies against major histocompatibility complex class I and class II antigens, they demonstrated the infection of a variety of human cells that bore those surface antigens with an ecotropic virus in vitro (Roux et al., 1989, which is herein incorporated by reference in its entirety).

Non-Viral Delivery of Modified Target Nucleic Ccid

In addition to viral delivery of modified target nucleic acid, the following are additional methods of recombinant gene delivery to a given host cell and are thus considered in the present invention.

Delivery of Modified Target Nucleic Acid by Electroporation

In one embodiment of the present invention, the modified target nucleic acid is introduced into target cells via electroporation. Electroporation involves the exposure of cells (or tissues) and DNA (or a DNA complex) to a high-voltage electric discharge.

Transfection of eukaryotic cells using electroporation has been quite successful. Mouse pre-B lymphocytes have been transfected with human kappa-immunoglobulin genes (Potter et al., 1984, which is herein incorporated by reference in its entirety), and rat hepatocytes have been transfected with the chloramphenicol acetyltransferase gene (Tur-Kaspa et al., 1986, which is herein incorporated by reference in its entirety) in this manner.

It is contemplated that electroporation conditions for cells from different sources may be optimized. One may particularly wish to optimize such parameters as the voltage, the capacitance, the time and the electroporation media composition. The execution of other routine adjustments will be known to those of skill in the art.

Delivery of Modified Target Nucleic Acid by Particle Bombardment

In yet another embodiment of the present invention, a method is provided in which a modified target nucleic acid is delivered into cells through particle bombardment. This method depends on the ability to accelerate nucleic acid-coated microprojectiles to a high velocity allowing them to pierce cell membranes and enter cells without killing them (Klein et al, 1987, which is herein incorporated by reference in its entirety). The microprojectiles used have consisted of biologically inert substances such as tungsten, platinum, or gold beads.

It is contemplated that in some instances nucleic acid precipitation onto metal particles would not be necessary for nucleic acid delivery to a recipient cell using particle bombardment. It is contemplated that particles may contain nucleic acid rather than be coated with nucleic acid. Hence it is proposed that nucleic acid-coated particles may increase the level of nucleic acid delivery via particle bombardment but are not, in and of themselves, necessary.

Several devices for accelerating small particles have been developed. One such device relies on a high voltage discharge to generate an electrical current, which in turn provides the motive force (Yang et al., 1990, which is herein incorporated by reference in its entirety). Another method involves the use of a Biolistic Particle Delivery System, which can be used to propel particles coated with DNA through a screen, such as stainless steel or Nytex screen, onto a filter surface covered with cells in suspension. The screen disperses the particles so that they are not delivered to the recipient cells in large aggregates. It is believed that a screen intervening between the projectile apparatus and the cells to be bombarded reduces the size of projectile aggregates and may contribute to a higher frequency of transformation by reducing the damage inflicted on the recipient cells by projectiles that are too large.

For the bombardment, cells in suspension are preferably concentrated on filters, or alternatively on solid culture medium. The cells to be bombarded are positioned at an appropriate distance below the macroprojectile stopping plate. If desired, one or more screens are also positioned between the acceleration device and the cells to be bombarded.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity or either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. Recently, results from a clinical trial evaluating utility of this delivery system for vaccination were published. The study was designed to determine the safety and immunogenicity in volunteers of a DNA vaccine consisting of a plasmid encoding hepatitis B surface antigen delivered by the PowderJect XR1 gene delivery system into human skin (Tacket et al., 1999, which is herein incorporated by reference in its entirety).

Accordingly, it is contemplated that one may wish to adjust various bombardment parameters in small scale studies to fully optimize the conditions. One may particularly wish to adjust physical parameters such as gap distance, flight distance, tissue distance and helium pressure. One also may optimize the trauma reduction factors by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art.

Delivery of Modified Target Nucleic Acid by Calcium Phosphate Co-Precipitation or DEAE-Dextran Treatment In other embodiments of the present invention, the modified target nucleic acid is introduced into cells using calcium phosphate co-precipitation. Mouse primordial germ cells have been transfected with the SV40 large T antigen, with excellent results (Watanabe et al., 1997, which is herein incorporated by reference in its entirety). Human KB cells have been transfected with adenovirus 5 DNA (Graham and Van Der Eb, 1973) using this technique. Also in this manner, mouse L(A9), mouse C 127, CHO, CV-1, BHK, NIH3T3 and HeLa cells were transfected with a neomycin marker gene (Chen and Okayama, 1987, which is herein incorporated by reference in its entirety), and rat hepatocytes were transfected with a variety of marker genes (Rippe et al., 1990, which is herein incorporated by reference in its entirety).

In another embodiment, the expression construct is delivered into the cell using DEAE-dextran followed by polyethylene glycol. In this manner, reporter plasmids were introduced into mouse myeloma and erythroleukemia cells (Gopal, 1985, which is herein incorporated by reference in its entirety).

Delivery of Modified Target Nucleic Acid by Direct Microinjection or Sonication Loading In yet a further embodiment of the present invention, the modified target nucleic acid is introduced into cells by direct microinjection or sonication loading. Direct microinjection has been used to introduce nucleic acid constructs into *Xenopus* oocytes (Harland and Weintraub, 1985, which is herein incorporated by reference in its entirety), and LTK⁻ fibroblasts have been transfected with the thymidine kinase gene by sonication loading (Fechheimer et al., 1987, which is herein incorporated by reference in its entirety).

Delivery of Modified Target Nucleic Acid by Lipid-Mediated Transformation

In a further embodiment of the invention, the modified target nucleic acid may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991, which is herein incorporated by reference in its entirety). Also contemplated is a gene construct complexed with Lipofectamine (Gibco BRL).

Lipid-mediated nucleic acid delivery and expression of foreign nucleic acid in vitro has been very successful (Nicolau and Sene, 1982; Fraley et al., 1979; Nicolau et al., 1987, which are herein incorporated by reference in their entireties). Wong et al. (1980), which is herein incorporated by reference in its entirety, demonstrated the feasibility of lipid-mediated delivery and expression of foreign DNA in cultured chick embryo, HeLa and hepatoma cells.

Lipid based non-viral formulations provide an alternative to adenoviral gene therapies. Although many cell culture studies have documented lipid based non-viral gene transfer, systemic gene delivery via lipid based formulations has been limited. A major limitation of non-viral lipid based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in lipid vehicle stability in the presence and absence of serum proteins. The interaction between lipid vehicles and serum proteins has a dramatic impact on the stability characteristics of lipid vehicles (Yang and Huang, 1997, which is herein incorporated by reference in its entirety). Cationic lipids attract and bind negatively charged serum proteins. Lipid vehicles associated with serum proteins are either dissolved or taken up by macrophages leading to their removal from circulation. Current in vivo lipid delivery methods use subcutaneous, intradermal, intratumoral, or intracranial injection to avoid the toxicity and stability problems associated with cationic lipids in the circulation. The interaction of lipid vehicles and plasma proteins is responsible for the disparity between the efficiency of in vitro (Felgner et al., 1987, which is herein incorporated by reference in its entirety) and in vivo gene transfer (Zhu et al., 1993; Solodin et al., 1995; Thierry et al., 1995; Tsukamoto et al., 1995; Aksentijevich et al., 1996, which are herein incorporated by reference in their entireties).

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Lipid encapsulation has resulted in a lower toxicity and a longer serum half-life for such compounds (Gabizon et al., 1996, which is herein incorporated by reference in its entirety). Numerous disease treatments are using lipid based gene transfer strategies to enhance conventional or establish novel therapies, in particular therapies for treating cancers.

In certain embodiments of the invention, the lipid vehicle may be complexed with a hemagglutinating virus (HVJ). This has been shown to facilitate fusion with the cell membrane and promote cell entry of lipid-encapsulated DNA (Kaneda et al., 1989, which is herein incorporated by reference in its entirety). In other embodiments, the lipid vehicle may be complexed or employed in conjunction with nuclear non-histone chromosomal proteins (HMG-1) (Kato et al., 1991, which is herein incorporated by reference in its entirety). In yet further embodiments, the lipid vehicle may be complexed or employed in conjunction with both HVJ and HMG-1.

Pharmaceutical Compositions

The present invention provides for improving the level and/or sustainability of expression of a target nucleic acid in a subject by administering to the subject a therapeutically effective amount of a pharmaceutical composition or formulation. The pharmaceutical composition or formulation may comprise the modified target nucleic acid which is capable of improving or sustaining expression of the target nucleic acid. The modified target nucleic acid may comprise signals that could position a nucleosome. Signals may comprise AA/TT dinucleotide pairs, or more or less of such dinucleotides, in positions where at least 80%, more preferably 90% and most preferably 100% of the adjacent AA/TT dinucelotide separations are in the range of 1-3, 7-13, 17-23, 27-33, 37-43 or 47-53 nucleotides.

Improved levels of expression of a modified target nucleic acid involves to an increase in the levels of target RNA and/or protein in a cell. Sustainability of a modified target nucleic acid involves to maintaining the endogenous level of target RNA and/or protein in a cell.

In one embodiment, the modified target gene is contained in an appropriate expression vector. In yet another embodiment, the target gene is contained within a liposome.

Various delivery systems are known and can be used to administer pharmaceutical composition capable of improving the level and/or sustainability of expression of a target nucleic acid in a subject, e.g., encapsulation in liposomes, microparticles, microcapsules, recombinant cells capable of expressing the mutant viruses, receptor mediated endocytosis (see e.g., Wu and Wu (1987) J. Biol. Chem., 262: 4429 4432, which is herein incorporated by reference in its entirety). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g. oral mucosa, rectal and intestinal mucosa, etc.) and may be administered together with other biologically active agents. Administration can be systemic or local. In a preferred embodiment, it may be desirable to introduce the pharmaceutical compositions of the invention into the affected tissues by any suitable route. Pulmonary administration can also be employed, e.g., by use of an inhaler or nebulizer, and formulation with an aerosolizing agent.

As mentioned above for some methods of the invention, topical administration may be used. Any common topical formulation such as a solution, suspension, gel, ointment or salve and the like may be employed. Preparation of such topical formulations are described in the art of pharmaceutical formulations as exemplified, for example, by Gennaro et al. (2000) Remington's Pharmaceutical Sciences, Mack Publishing, which is herein incorporated by reference in its entirety. For topical application, the compositions could also be administered as a powder or spray, particularly in aerosol form. In one embodiment, the compositions of this invention may be administered by inhalation. For inhalation therapy, the active ingredients may be in a solution useful for administration by metered dose inhalers or in a form suitable for a dry powder inhaler. In another embodiment, the compositions are suitable for administration by bronchial lavage.

In a specific embodiment, it may be desirable to administer the pharmaceutical compositions capable of improving the level or sustainability of expression of a target nucleic acid locally to the area in need of treatment; this may be achieved by, for example, and not by way of limitation, local infusion during surgery, topical application, e.g. in conjunction with a wound dressing after surgery, by injection, by means of a catheter, by means of a suppository, or by means of an implant, said implant being of a porous, non porous, or gelatinous material, including membranes, such as sialastic membranes, or fibers. In one embodiment, administration can be by direct injection at the site (or former site) of diseased tissues.

In another embodiment, the pharmaceutical composition can be delivered in a vesicle, in particular a liposome (see, e.g., Langer, 1990 Science 249: 1527-1533; Treat et al., in Liposomes in the Therapy of Infectious Disease and Cancer, Lopez Berestein and Fidler (eds.), Liss, N.Y., pp. 353-365 (1989); Lopez-Berestein, ibid., pp. 317-327; each of which is herein incorporated by reference in their entireties).

In yet another embodiment, the pharmaceutical composition can be delivered in a controlled release system. In one embodiment, a pump may be used (see Langer, supra; Sefton, (1987) CRC Crit. Ref. Biomed. Eng. 14: 201; Buchwald et al., (1980) Surgery 88:507; and Saudek et al., (1989) N. Engl. J. Med. 321: 574, which are herein incorporated by reference in their entireties). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, (1983) J. Macromol. Sci. Rev. Macromol. Chem. 23: 61; see also Levy et al., (1985) Science 228:190;

During et al., (1989) *Ann. Neurol.* 25:351; Howard et al., (1989), *J. Neurosurg.* 71:105, which are herein incorporated by reference in their entireties). In yet another embodiment, a controlled release system can be placed in proximity of the composition's target, i.e., the breast tissue, thus requiring only a fraction of the systemic dose (see, e.g., Goodson, in Medical Applications of Controlled Release, supra, vol. 2, pp. 115-138 (1984), which is herein incorporated by reference in its entirety). Other controlled release systems are discussed in the review by Langer (1990, *Science* 249:1527-1533, which is herein incorporated by reference in its entirety).

The pharmaceutical compositions capable of improving the level and/or sustainability of expression of a target nucleic acid in a subject may further comprise a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the pharmaceutical composition is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin, which is herein incorporated by reference in its entirety. The formulation should suit the mode of administration.

In a preferred embodiment of the present invention, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions capable of improving the level and/or sustainability of expression of a target nucleic acid in a subject can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2 ethylamino ethanol, histidine, procaine, etc.

The amount of the pharmaceutical composition capable of improving the level and/or sustainability of expression of a target nucleic acid in a subject which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose response curves derived from in vitro or animal model test systems. Suppositories generally contain active ingredient in the range of 0.5% to 10% by weight; oral formulations preferably contain 10% to 95% active ingredient.

Methods of Treatment

The present invention includes methods for improving the level and/or sustainability of expression for a target nucleic acid in a subject comprising: contacting said subject with a modified target nucleic acid, wherein the modified nucleic acid constrains the positions of nucleosome cores in the target nucleic acid, thereby improving the level and/or sustainability of expression of a modified target nucleic acid. Preferably the increase in the amount of modified target nucleic acid expression is at least 10%, preferably 25%, more preferably 50%, most preferably 100% above the expression level observed in the subject prior to treatment. Improved levels of expression of a modified target nucleic acid involves to an increase in the levels of target RNA and/or protein in a cell. Sustainability of expression of a modified target nucleic acid involves to maintaining the endogenous level of target RNA and/or protein in a cell.

For the purposes of the present invention, the modified target nucleic acid may be introduced into a subject either ex vivo, (i.e., in a cell or cells removed from the subject) or directly in vivo into the body to be treated.

In one particular class of embodiments, the modified target nucleic acid is introduced into a subject for purposes of therapy. Gene therapy provides methods for combating chronic infectious diseases such as HIV, as well as non-infectious diseases such as cancer and birth defects such as enzyme deficiencies.

In another embodiment, cells can be removed from a subject having a deficiency in target gene expression, and then the modified target nucleic acid is introduced into the cell. These transfected cells will thereby produce functional protein or fragments thereof from the modified target gene and can be reintroduced into the patient. Methods described in U.S. Pat. No. 5,162,215 (Bosselman et al.) demonstrate how to detect the presence and expression of a target gene in target cells. Methods described in U.S. Pat. No. 5,741,486 (Pathak et al.) teach the use of viral vectors in gene therapy. Such methods can be used to introduce the modified target nucleic acid of the present invention, for example in gene therapy.

In some embodiments, the modified target nucleic acid can be introduced into a subject in vivo. The scientific and medical procedures required for human cell transfection are now routine procedures. Administration is by any of the routes normally used for introducing a molecule into cells. The packaged nucleic acids are administered in any suitable manner, preferably with pharmaceutically acceptable carriers. Suitable methods of administering such packaged nucleic acids in the context of the present invention to a patient are available, and although more than one route can be used to administer a particular composition, a particular route can often provide a more immediate and more effective reaction than another route.

Injection solutions and suspensions can be prepared from sterile powders, granules, and tablets of the kind previously described. Cells transduced by the packaged nucleic acid as described above in the context of ex vivo therapy can also be administered intravenously or parenterally as described above. The dose administered to a subject, in the context of the present invention should be sufficient to effect a beneficial therapeutic response in the subject over time, or to inhibit infection by a pathogen. The dose will be determined by the efficacy of the particular transgene employed and the condition of the subject, as well as the body weight or surface area of the subject to be treated. The size of the dose also will be determined by the existence, nature, and extent of any adverse side-effects that accompany the administration of a particular vector, or transduced cell type in a particular subject.

In determining the effective amount of modified target nucleic acid to be administered in the treatment of a disease, the physician or other clinician evaluates symptom or clinical parameters, including the progression of the disease. In general, the dose equivalent of a naked nucleic acid from a vector is from about 1 µg to 100 µg for a typical 70 kilogram. The exact dosage of modified target DNA is dependent upon a variety of factors, including the age, weight, and sex of the subject to be treated, and the nature and extent of the disease or disorder to be treated. Effective doses can be extrapolated from dose-response curves derived from in vitro or animal model test systems.

Administration can be accomplished via single or divided doses. Methods of introduction include, but are not limited to, intradermal, intramuscular, intraperitoneal, intravenous, subcutaneous, intranasal, and oral routes. Administration can be by any convenient route, for example by infusion or bolus injection, by absorption through epithelial or mucocutaneous linings (e.g., oral mucosa, rectal and intestinal mucosa, etc.). In addition, the pharmaceutical compositions can be introduced into the central nervous system by any suitable route, including intraventricular and intrathecal injection; intraventricular injection can be facilitated by an intraventricular catheter, for example, attached to a reservoir, such as an Ommaya reservoir. Administration can be systemic or local. The modified target DNA can be administered together with other biologically active agents.

In some embodiments, the present invention relates to a method of treating patients which underexpress a gene, or in which greater expression of the gene is desired. These methods can be accomplished by introducing a modified target gene, comprising periodic nucleotide sequences (i.e. signals) for the underexpressed gene into an appropriate vector, which is subsequently introduced into the patient.

In some of the foregoing embodiments, it may only be necessary to introduce the genetic or protein elements into only certain cells or tissues. However, in some instances (i.e. tumors), it may be more therapeutically effective and simple to treat all of the patients cells, or more broadly disseminate the vector, for example by intravascular administration.

In another embodiment, ex vivo methods for introducing a modified target nucleic acid into a subject involve transducing the cell ex vivo, and then subsequently introducing the cell into the subject. Transduced cells are prepared for reinfusion according to established methods (See, Abrahamsen et al., *J. Clin. Apheresis* 6:48-53, 1991; Carter et al. *J. Clin. Arpheresis* 4:113-117, 1988; Aebersold et al., *J. Immunol. Methods* 112: 1-7, 1988; Muul et al., *J. Immunol. Methods* 101: 171-181, 1987; and Carter et al., *Transfusion* 27:362-365, 1987, each of which is herein incorporated by reference in their entireties).

All cited patents, patent applications, publications and other documents cited in this application are herein incorporated by reference in their entirety. The present invention is not to be limited in terms of the particular embodiments described in this application, which are intended as single illustrations of individual aspects of the invention. Functionally equivalent methods and apparatus within the scope of the invention, in addition to those enumerated herein, will be apparent to those skilled in the art from the foregoing description and accompanying drawings. Such modifications and variations are intended to fall within the scope of the appended claims.

Without further description, it is believed that one of ordinary skill in the art can, using the preceding description and the following illustrative examples, make and utilize the agents of the present invention and practice the claimed methods. The following working examples are provided to facilitate the practice of the present invention, and are not to be construed as limiting in any way the remainder of the disclosure.

EXAMPLE 1

Materials and Methods

Sequences used for this analysis were downloaded from Genbank (Wheeler et al., 2005, which is herein incorporated by reference in its entirety), Wormbase (Spieth et al., 2005), or the Intronerator (Kent and Zahler, 2000, which is herein incorporated by reference in its entirety) databases at the times noted in describing each experiment. Use of distinct versions of certain sequences was in some cases necessitated by the availability of annotation files of a given type only for those versions. Basic observations (such as the strong enrichment of phasing in the *C. elegans* genome and the propensity for periodic sequences to appear in autosomal arms) have been confirmed for numerous releases of the genome sequence and using several independent software tools with a wide variety of parameters.

SAGE data were obtained from the Genome BC *C. elegans* Gene Expression Consortium hhttp://elegans.bcgsc.bc.ca/.

Stringent repeat masking of genomes was carried out as described by Kurtz and chliermacher using a PC-compatible machine running the Red Hat version of Linux. All other analysis was carried out on Macintosh systems using Pascal-based programming for processor intensive tasks (Metrowerks Code Warrior v. 7). Hypercard-based programming for text-intensive tasks. Several randomized sequences were derived independently from scripts in Perl, Hypercard, and Pascal with no evident differences in phasing properties.

Current Macintosh computers running processor-intensive operations under system 9 (Metrowerks and Hypercard) have somewhat limited capacity for heat and power management.

Figure 1B:
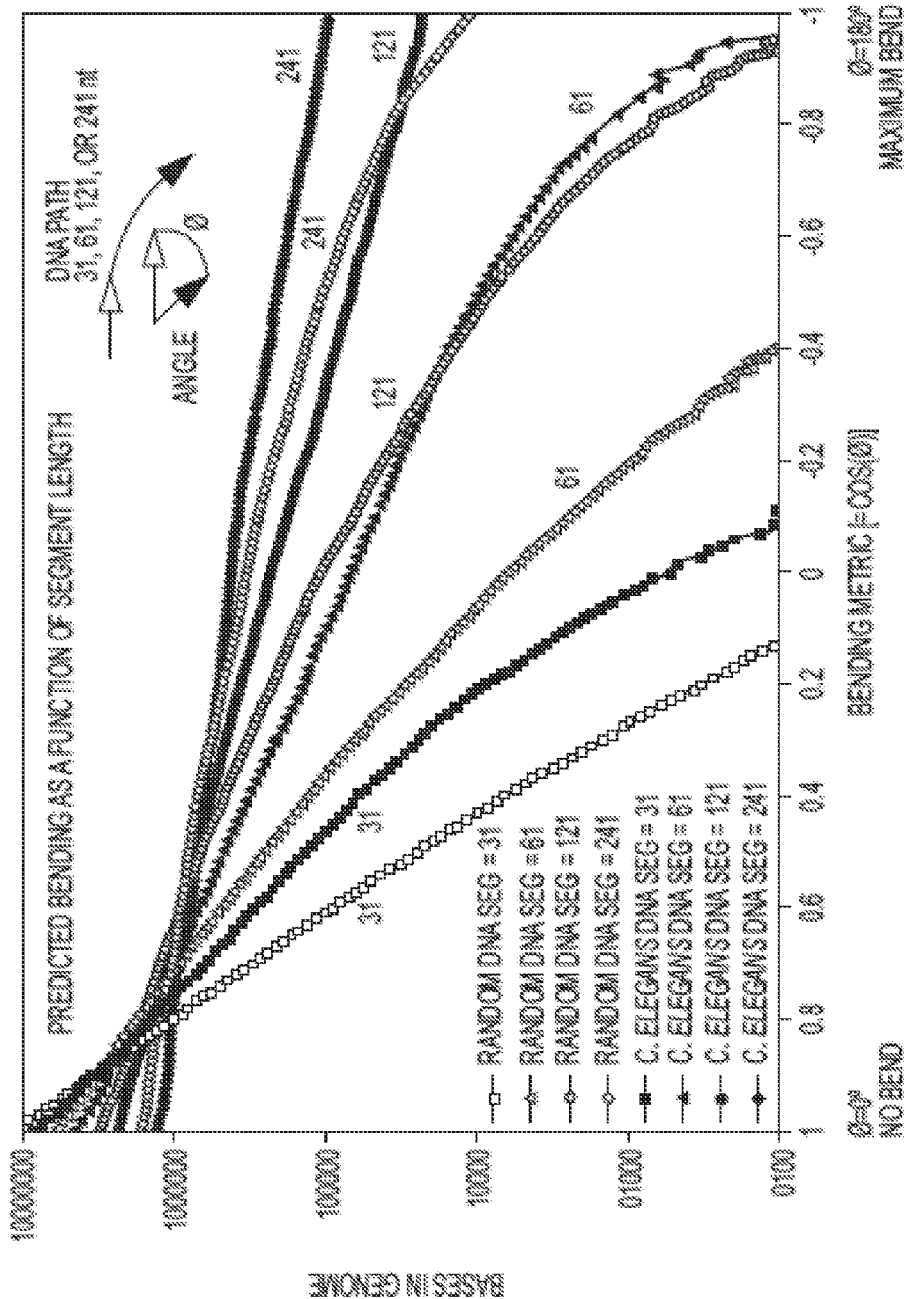

To avoid machine-burnout for such applications, processor speed was turned to a "reduced" mode and machines were situated with both ventilation available both above and below.
Long-Range Structure in a Eukaryotic Genome: A Substantial Fraction of Germline-Active C. elegans Genomic Regions are Specialized for Surface Alignment of DNA The research described herein had its origin from an observation that certain DNA sequences from C. elegans exhibited unusual electrophoretic mobility on agarose gels at low temperature (S. M. White Harrison, J. Fleenor, and A. Fire, unpublished observations). Retarded electrophoresis, seen for DNAs from diverse biological sources, can be induced by specific sequence elements that can produce a static bend in the otherwise straight helix (e.g., Marini et al. 1982, which is herein incorporated by reference in its entirety). Several rather precise models for predicting the three dimensional path of the DNA helix as a function of base sequence (roll, tilt, and helical periodicity) have been published; these models can predict certain anomalies in electrophoretic behavior with considerable sensitivity and specificity (e.g. Goodsell and Dickerson, 1994, which is herein incorporated by reference in its entirety) and indeed all of these algorithms predict strongly bent character in the segments of C. elegans DNA for which we had observed abnormal mobility. The algorithms are readily scaled for high throughput analysis of large numbers of sequences. This analysis revealed a higher overall "bend" density for C. elegans DNA than for other non nematode genomes with a comparable base composition (FIG. 1).

The indicated relatively long range periodicity underlies a substantial fraction (approximately 5-10%) of C. elegans genomic sequence. Extended segments (up to several hundred nucleotides) of the C. elegans genome show a strong bias toward occurrence of AA/TT dinucleotides along one face of the helix while little or no such constraint is evident on the opposite helical face. Segments with this characteristic phasing are significantly enriched in introns and are associated with a large fraction of genes with known germline expression in C. elegans. In addition to altering the path and flexibility of DNA in vitro, sequences of this character have been shown by others to constrain DNA::nucleosome interactions, potentially producing a structure which may limit the sliding of nucleosomes relative to DNA.
Periodicity Analysis of C. elegans DNA While the "bending" analysis above demonstrates a non-random character in the DNA sequence, it is by no means clear that bending per se is the biologically selected basis for this non-randomness. Indeed, the algorithms used above are based on in vitro behavior of DNA at relatively low temperatures (Diekman, 1987, which is herein incorporated by reference in its entirety); using the same in vitro conditions, little or no gel mobility anomaly is generally observed at physiological temperatures. Thus the unusual shapes of DNAs predicted by the algorithms are unlikely to accurately represent the geometric path of the DNA in vivo.

Figure 2:
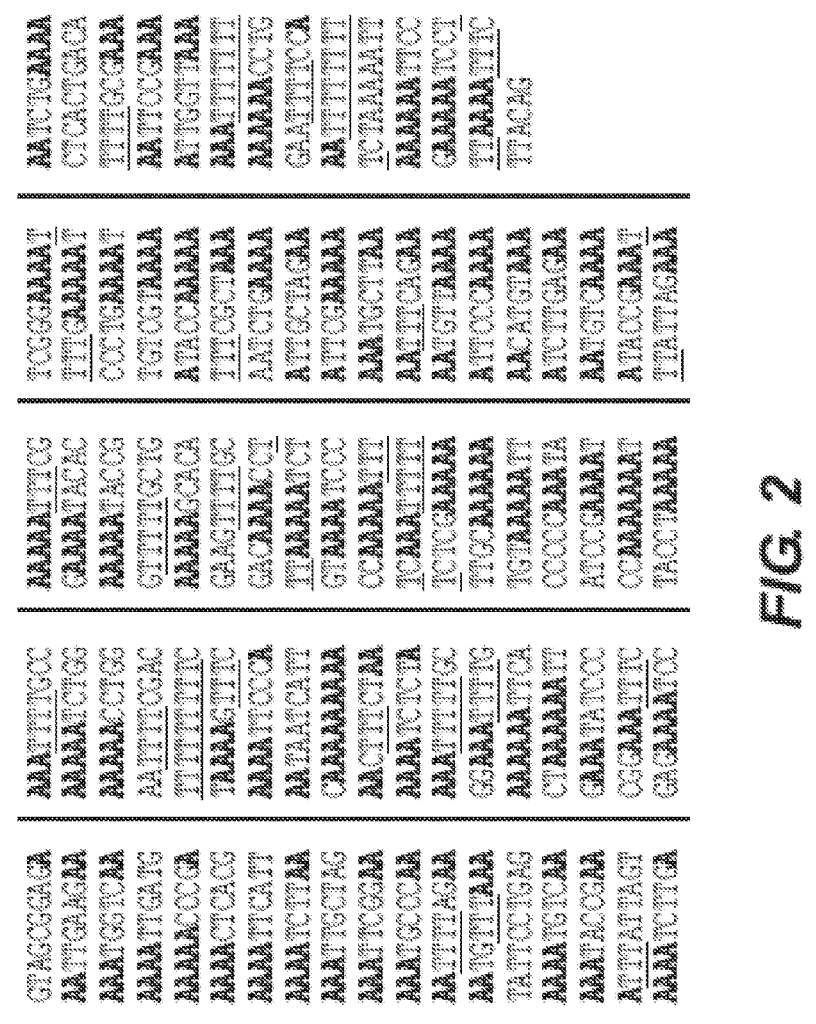

When a set of predicted "bent" sequences from the C. elegans genome were inspected in detail, it was found that the most prominent common feature was a propensity for occurrence of AA or TT dinucleotides on one face of the helix over 10s of base pairs (e.g., FIG. 2). This is consistent with reports in the literature that periodic distributions of AA/TT dinucleotides can produce some of the largest anomalies in DNA structure (e.g., Bolshoy et al., 1991, which is herein incorporated by reference in its entirety). To extend this analysis to the whole genome, a general analysis of periodicity for the C. elegans genome was conducted. FIGS. 3 and 8A-D show such an analysis for each of the 256 tetranucleotide "words". The analysis shown measures the number of times that two occurrences of a given word are separated by each integral number of base pairs.

As expected from previous analyses of periodicity in sequence databases (e.g., Trifonov 1989, which is herein incorporated by reference in its entirety), a variety of different characteristics are evident from the periodicity analysis of C. elegans.

1. For some tetranucleotides (e.g. TGTG), a 2-base periodicity is present, apparently representing segments of the genome with extended runs of alternating purine-pyrimidine.
2. A 3 base periodicity is evident for a number of the tetranucleotides (e.g. GCCT). This type of periodicity is likely to represent the triplet nature of the genetic code combined with non random codon choices and distributions of amino acids.
3. Additional 3n periodicities of 6, 9, 12, etc. presumably reflect (at least in part) coding for protein motifs such as a beta sheet that themselves have a periodic structure.
4. A number of the distributions show a strong and very discrete signal at a unique periodicity (e.g. GCCT). These longer periodicities represent highly repeated tandem sequences in the genome.
5. A ~10 base periodicity is present in "words" containing multiple AA/TT dinucleotides.

Filtering the Genome to Remove Repetitive and Protein Coding Sequences

To avoid the biases of repetitive DNA and coding sequences, a version of the genome sequence was thought in which repetitive sequences were stringently removed and coding sequences (as much as possible) ignored.

Many repeat masking algorithms are very limited in that only repeats from a limited and defined database are masked in the target sequence (e.g. the repeatmasker algorithm of Smit and Green (Thomas et al., 2003, which is herein incorporated by reference in its entirety). This type of operation was at best incomplete for the task at hand. Accordingly, there were used an algorithm and tools developed by Kurtz and Schleiermacher (1999), which is herein incorporated by reference in its entirety, which takes two parameters, window (n) and stringency (m). The reputer algorithm efficiently removes any sequence of n base pairs which is matched in at least m positions to a sequence of n base pairs elsewhere in the genome. There were used n=25, m=25 (i.e. removal of all sequences of 25 base pairs that precisely match another sequence in the genome) and n=28, m=27 (i.e. removal of all sequences of 28 base pairs that match 27/28 to another sequence in the genome) with highly similar results. For the discussion below, the 25/25 genome masks are used.

Removal of coding sequences was a less precise operation. Although numerous attempts have been made to annotate coding sequences in genomes, none are complete. It was, however, possible to obtain a substantial damping of triplet and 3n periodicities by utilizing a version of the genome in which coding sequences annotated by the genome project consortium (Wormbase (Chen et al., 2005, which is herein incorporated by reference in its entirety) had been removed (Chen et al., 2005; Kent and Zahler, 2000, which are herein incorporated by reference in their entireties).

Figure 3B:
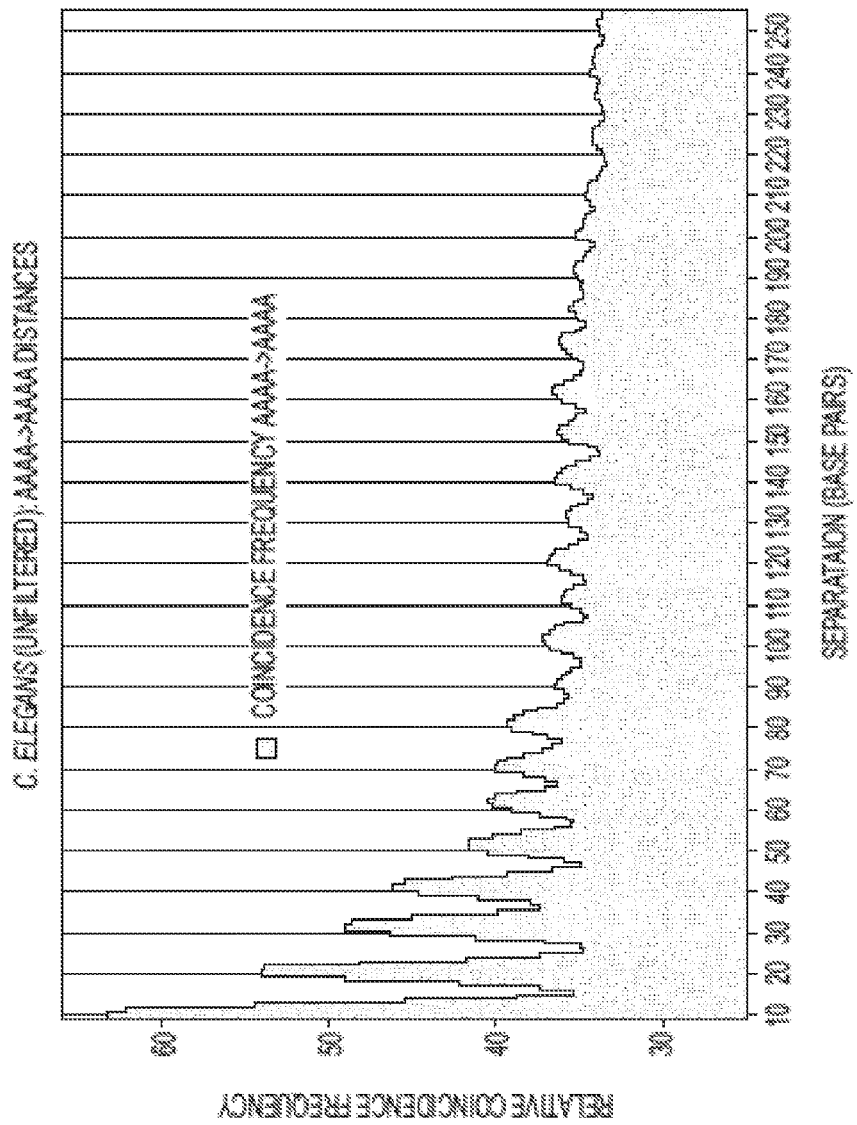
Figure 3C:
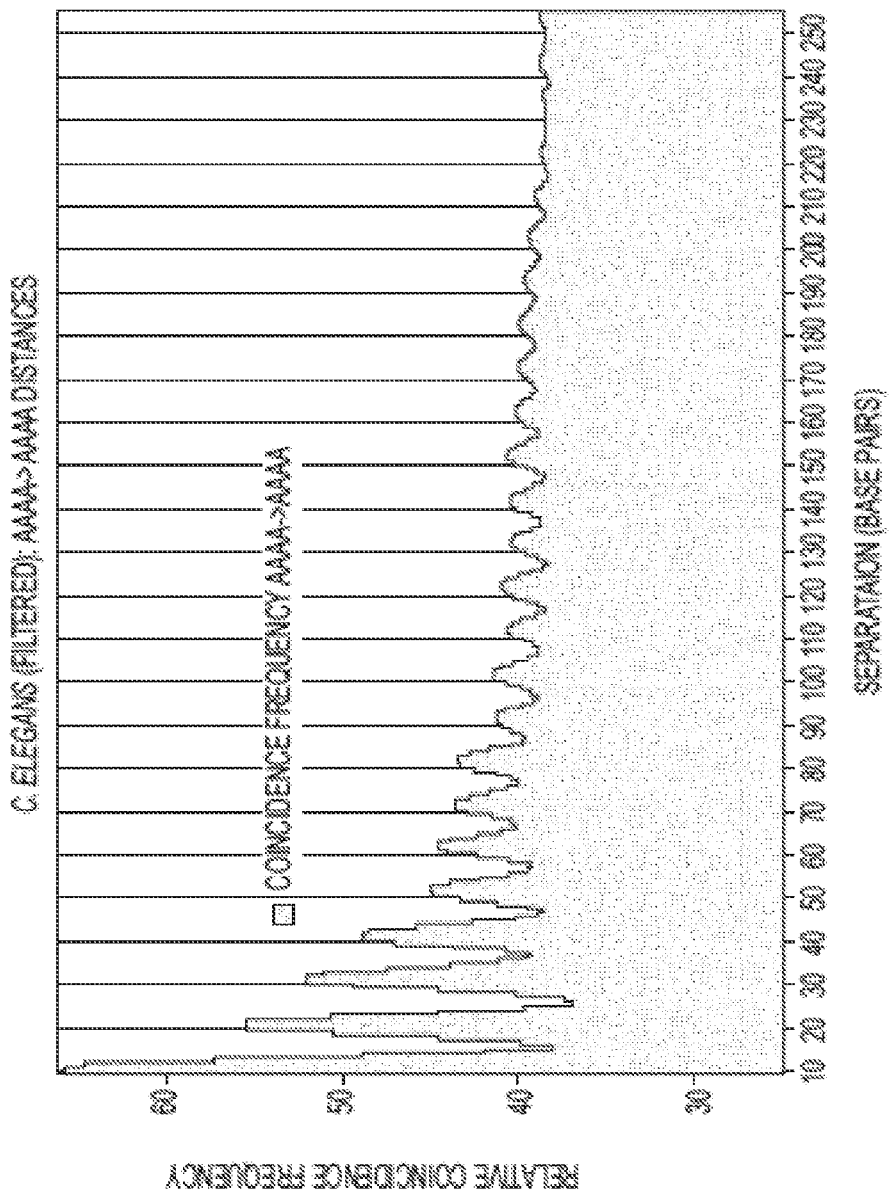
Figure 3D:
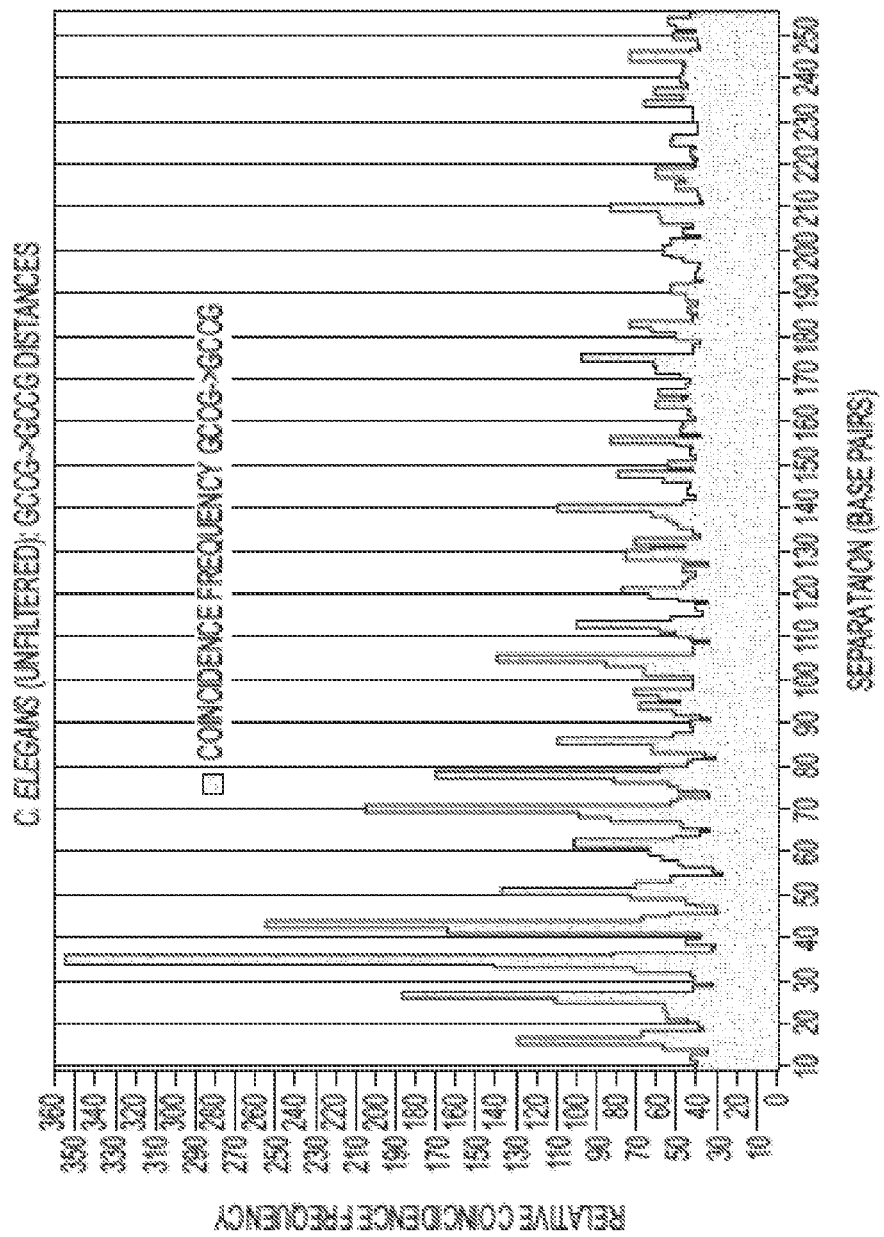
Figure 3E:
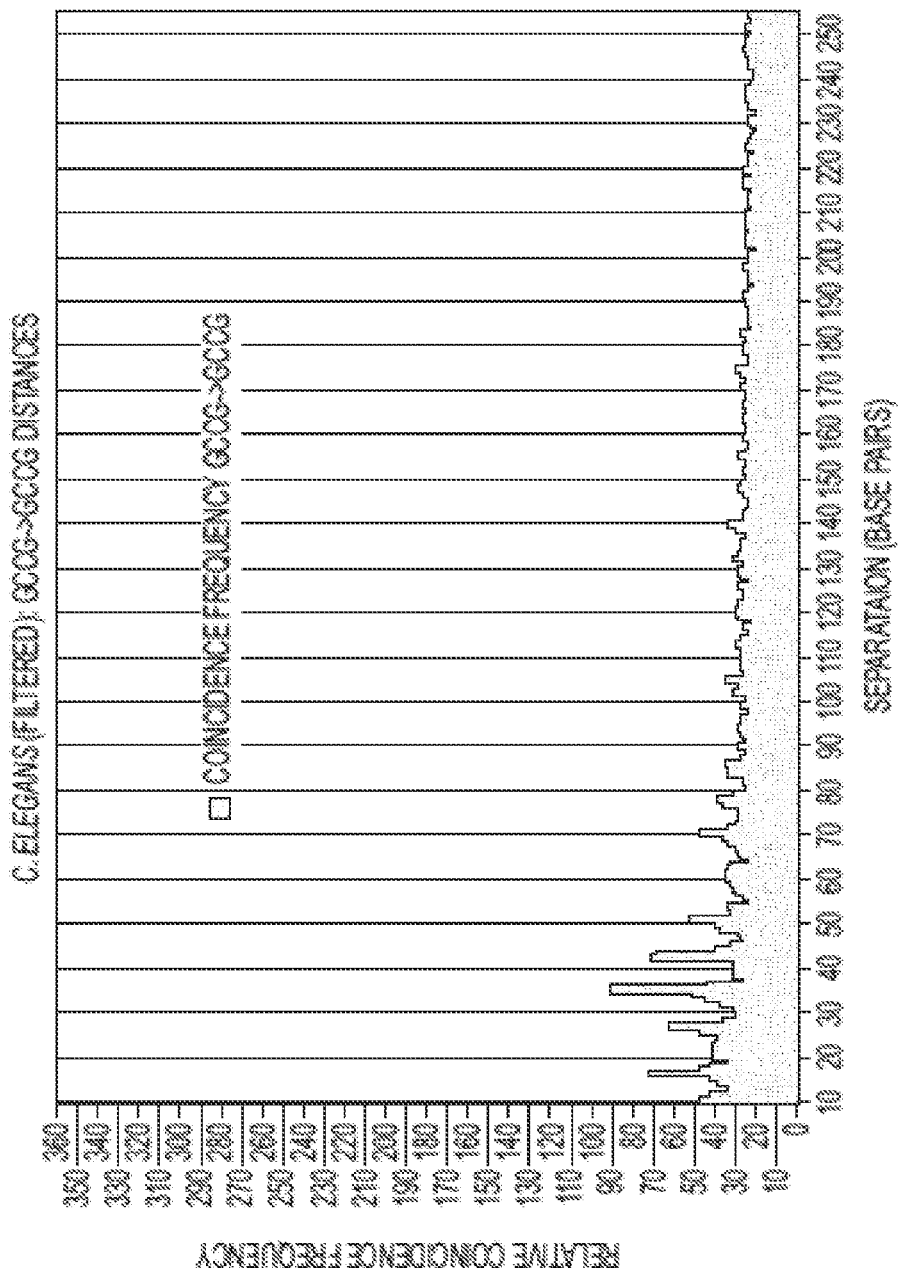

FIGS. 3C, 3E and 8B shows the tetranucleotide periodicity analysis for the repeat subtracted, coding-region-depleted version of the C. elegans genome. Two aspects of the genome emerge from this analysis. First, tetranucleotides rich in AA or TT dinucleotides retain their ~10 base periodicity, and second, the complex set of patterns for other tetranucleotide are substantially or completely removed.

The periodic distribution of AA/TT containing tetranucleotides is consistent with previous observations (e.g., Widom, 1996; Fukushima et al., 2002, which are herein incorporated by reference in their entireties) as well as the above analysis of bending predictions. Not as evident from some of the earlier analyses was the extent to which the periodicities can be detected over relatively long molecular distances. In FIG. 3B, showing the frequencies of AAAA to AAAA distance as a function of base pair separation, a clear periodicity can easily be seen to extend beyond 200 base pairs.

Periodic Regions Demarcate Islands in the *C. elegans* Genome

It will be appreciated that the periodicities discussed above are statistical in nature: even for the most highly periodic of all the tetranucleotides (AAAA/TTTT), there are large numbers of cases in which the separation between instances is not close to an integral multiple of 10.

Given a mixture of highly periodic and non-periodic occurrences of individual sequences, it was conceivable that the phasing signal derived uniformly from the whole genome. Alternatively, the phasing signal might derive from a small number of highly periodic areas or "islands". Some tetranucleotides might be expected to be over-represented in such islands, with other tetranucleotides potentially under-represented. Certainly the phasing would be most easily detected for the overrepresented tetranucleotides. Under this "island" scenario, periodic arrangement of additional tetranucleotides might be detectable by first selecting for an over represented tetranucleotide then looking for distance distributions from other tetranucleotides. Such an analysis is shown in FIG. 9A (distributions of distance between AAAA and an antecedent arbitrary tetranucleotide sequence) and 9B (distributions of distances between AAAA and an subsequent arbitrary tetranucleotide sequence). These analyses indicate a periodic character to virtually all tetranucleotides when located in the vicinity of AAAA/TTTT sequences. The data in FIGS. 9A-B are consistent with a mosaic character to the genome with respect to periodicity. In particular, these data indicate that non-random phasing for many different tetranucleotides can be seen when the analysis is focused on just the AAAA/TTTT-rich component of the genome.

Sequence Characteristics of *C. elegans'* Periodic Regions

The distance histograms in FIGS. 3, 8A-D, and 9A-B provide extensive evidence of both correlation and noise in the genome sequence. Particularly striking is the propensity for AA/TT containing tetranucleotides to concentrate in one face of the helix (e.g. separations 10, 20, 30 from adjacent AAAA/TTTT sequences), while non-AA/TT containing tetranucleotides to concentrate in inter-helical regions (e.g. 5, 15, 25, etc.). This distribution indicates that periodic relationships are not limited to identical tetranucleotide sequences. Rather, many similar tetranucleotides seem to participate in some way in the phasing. As an extreme case, it was conceivable that the phasing would treat all sequences equally based simply on their content of AA/TT dinucleotides. This simple model is refuted by a detailed comparison of two complementary distance histograms with AAAA and TTTT tetranucleotides (FIG. 10A-B). Although these sequences are perfect complements of each other, the distribution of AAAA→TTTT distances need not be equivalent to that of TTTT→AAAA distances (as an extreme example, note that the sequences AAAATTTT and TTTTAAAA are not complementary to each other and have different physical properties (e.g. Ulanovsky et al., 1987, which is herein incorporated by reference in its entirety). Although the AAAA→TTTT and TTTT→AAAA distributions have superficial similarity, significant differences were observed in both period and amplitude for the different peaks (FIG. 10A-B). These differences are indicative of a specific structure reflected in the long-range patterns, of DNA sequence and will be discussed below.

Identification of Individual Periodic Islands in the *C. elegans* Genome

Although the statistical analysis above demonstrates non-random aspects of genome structure, the ability to understand the significance of the unusual structures depends on being able to identify and draw functional correlations between individual structures and genome function. To accomplish this, algorithms were needed that were able to detect a significant fraction (preferably as high as possible) of sequences with strong phasing while showing maximal selectivity in avoiding detection of "false" positives (e.g. predicted highly periodic regions in random DNA sequence). Several different algorithms were evaluated for this purpose including examination of localized sequence trajectories using available models for DNA bending (FIG. 1), variations of a hidden markov model, a localized form of Fourier analysis, and the "PATC" algorithm described below. All of these approaches gave similar results in the incidence and distribution of unusual DNA structures in the *C. elegans* genome, with general agreement on both localized and overall patterns of these structures.

The "PATC" algorithm (FIG. 4A-B) was chosen for detailed analysis as it has been the most straightforward to "tune" toward specific periodic features in the *C. elegans* genome and has thus given somewhat better signal to noise responses. In particular, examination of exemplary sequences such as that in FIG. 2 suggested a tolerance for degeneracy in phase (9-12 base pairs per turn) as well as sequence in the individual helical steps that form the unusual structure. From analysis of exemplary cases and statistical considerations, a scoring system was developed whereby the number of AA or TT dinucleotides in a 5-base segment is assigned a score, as are the sequence displacements (9-12 bp) between AA/TT clusters. The algorithm then consists of following a window along the DNA sequence while determining the number and quality of An/Tn clusters that occur on the single face of the predicted duplex. The degeneracy in the intrinsic exact AA/TT dinucleotides as well as in the precise periodicity of the helix needs to be accommodated as the window is "slid" along the DNA by testing different helical periods (9, 10, 11, 12) for each turn. Defining such a window optimally at every point in the genome has the potential to be a computation ally demanding task. However, this was addressed by using a localized optimization strategy similar to that used by programs designed to play chess: at each point an optimal decision is made based on optimizing consequences at a distance of several moves. With the parameters described above, a "look ahead" window of four "moves" appeared sufficient to detect the majority of periodic regions.

To make use of the algorithm, one additional parameter was needed: a cut-off score allowing regions to be defined as either periodic or unperiodic. By evaluating a randomized (and AT-content matched) genome-length sequence for *C. elegans*, we were able to obtain a distribution of optimization scores. For the ensuing analysis, the cutoff score was arbitrarily set to exclude 99.999% of the random sequence from the definition of "periodic". Based on this cutoff score (which has an arbitrary numerical value of 95), 6.14% of the *C. elegans* genome is categorized as "periodic". This sequence motif is referred to as a "Periodic An/Tn Cluster" (or PATC).

Figure 5:
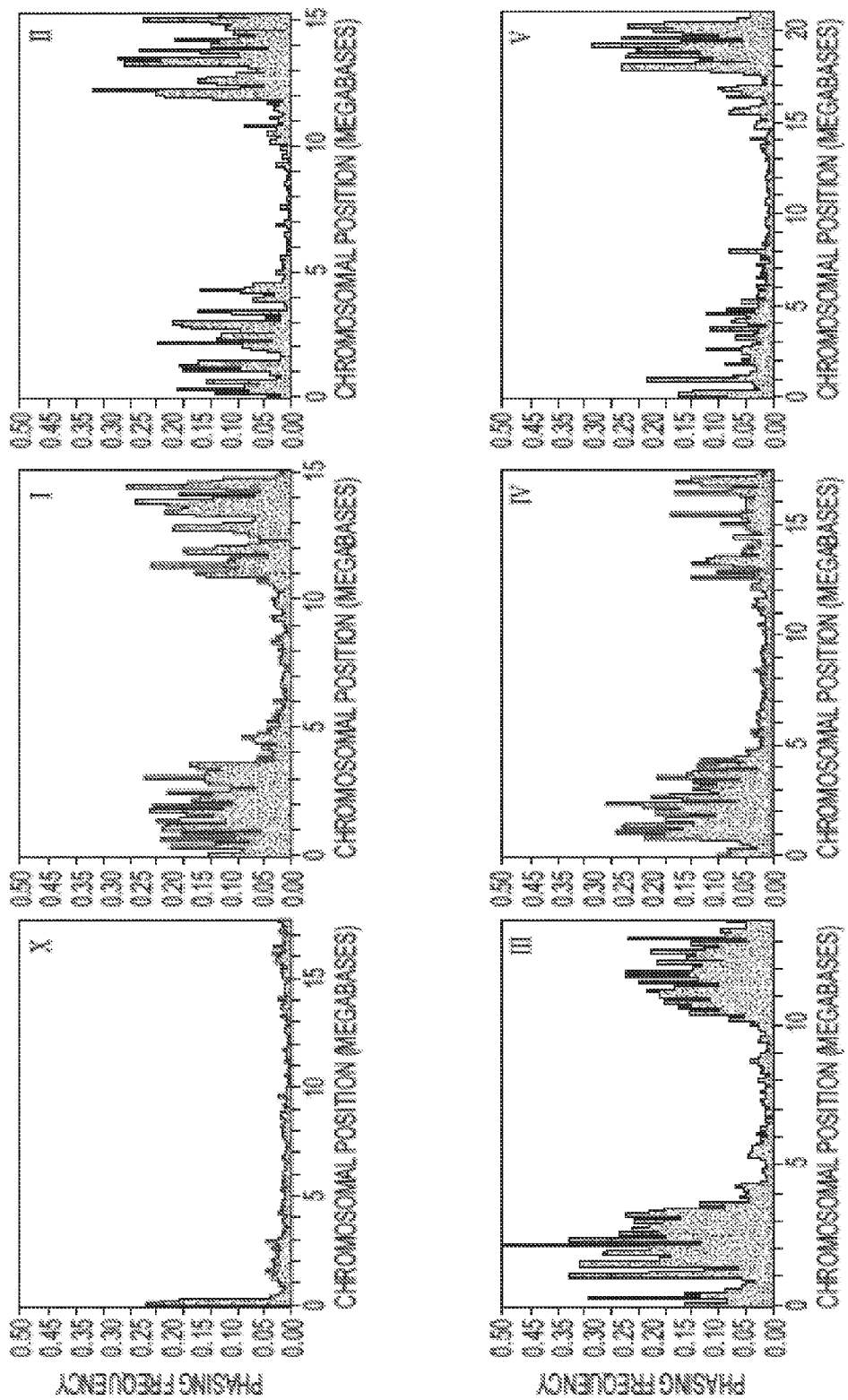
FIG. 5. Distribution of periodic segments within the *C. elegans* genome. The six graphs shown represent the fraction of bases with above-average phasing score as a function of position in the *C. elegans* genome. Phasing scores for each base in the *C. elegans* genome were calculated as described in FIG. 4A. For each 'bin' of 100,000 bp, we plotted the fraction of base pairs with PATC scores that were greater than 95. Lengths of the six *C. elegans* chromosomes vary slightly from 13.8 to 20.9 MB; plots in this figure are normalized so that each chromosome has an identical horizontal span. Left-right orientation for the chromosomes conforms to the standard (and arbitrary) assignments from Brenner (1974), which is herein incorporated by reference in its entirety. Data source for these calculations is the complete *C. elegans* genome as downloaded from wormbase as of May 2005.

PATC motifs show a striking global pattern within the genome (FIG. 5). Abundant phasing is observed on the terminal ~⅓ of each autosome, and on the extreme left tip of the X chromosome. Autosomal centers and the bulk of the X chromosome were, by comparison, relatively deficient in periodic clusters. *C. elegans* autosomes are known to have distinct central and peripheral characteristics, with genes more densely packed in the center and recombination and the occurrence of certain transposons higher in peripheral regions (Brenner, 1974; Barnes et al., 1995, Consortium, 1998; Duret et al., 2000, which are herein incorporated by reference in their entireties).

Figure 6B:
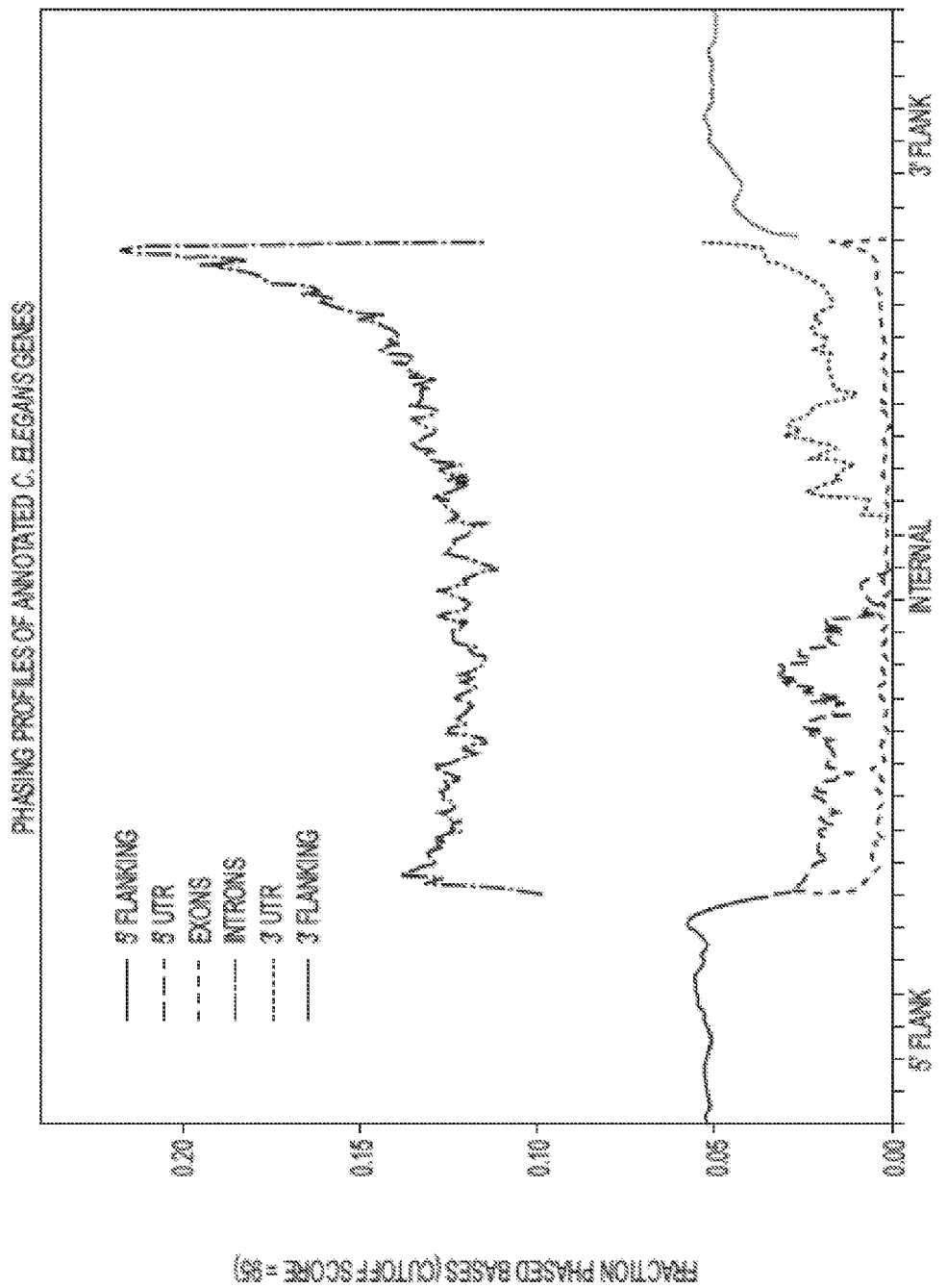
FIG. 6B: Distributions of phasing in the vicinity of C. elegans coding regions. Shown in the graph are aggregate phasing fractions for intron, exon, 5' and 3' noncoding transcribed sequence, and 5' and 3' flanking sequence for 20919 unique gene models derived from wormbase gene annotations as of May 2005. Following a download of the entire set of C. elegans gene models from wormbase, we first needed to remove a small number of clearly incorrect models with incorrect endpoints (these appeared upon comparison with the individual gene annotations to be simple typographical errors; although few in number they represent large regions of DNA and were thus potentially confounding for further analysis). Subsequently, we removed all but one model for each individual gene (taking the first alphabetical example in each case). Each gene model was downloaded with 1000 bases of upstream sequence and 1000 bp of downstream sequence as well as the putative transcribed region. Importantly, most genes are only annotated in terms of protein coding sequences and corresponding introns. Thus true 5' untranslated intron and exon sequences are rarely annotated or included in this list and only a fraction of 3' UTRs are included. Thus the database of 5' and 3' transcribed nontranslated sequence is quite incomplete while the database of immediate 5' and 3' flanking non-transcribed sequences will contain substantial components of noncoding intron, exon, and outtron (Blumenthal and Gleason, 2003, which is herein incorporated by reference in its entirety) sequence. In addition, the choice of a single gene model for each putative coding region (required for the database to be non-redundant) means that some 5' and 3' flanking sequences will actually be coding and intron sequences for differentially spliced isoforms (or correct models) for individual genes. Despite these concerns, the wormbase annotations are likely to represent (at least for the present) one of the most complete gene annotation sets for any metazoan genome. For the putative 5' and 3' flanking regions (700 bases each), the metric on the X axis is identical for each gene (one tick per hundred base pairs). The dip in each curve as an approach to the junction with translated sequence likely represents constraints of coding DNA that prevent periodic regions from extending into that region (and thus somewhat limit phasing scores). For introns, exons, 5' and 3' transcribed regions, each gene was split proportionally into 200 bins (shown on the graph as 10 bins per tick). This allowed an aggregate calculation of periodic/total bases for each of 200 steps across a canonical gene. The PATC phasing score cutoff used in this analysis was 95.

The genome can be divided along functional lines into coding sequence, introns, and intergenic regions. Combining this distinction with chromosomal position and uniqueness, we obtain several partitions in the genome. As shown in FIG. 6A-B, phasing of unique chromosomal regions is most evident in intron sequences, showing a relatively constant profile over the length of individual genes. A somewhat lower degree of phasing is seen in intergenic regions, while only low levels of phasing is seen in coding regions. It should be noted that intergenic regions are predicted on a very limited data set; it is conceivable that some of these sequences are actually transcribed as part of coding of non-coding RNA transcripts. Thus the possibility that all periodic regions are part of transcribed genes cannot be ruled out. Phasing of 5' and 3' UTR regions is also of interest and is described in FIGS. 6A-B as best could be extracted from current databases. Both 5' and 3' UTR regions clearly show above-background phasing, although with both sets of UTR sequences that current annotation is less complete than that for introns and exons, so that various issues may substantially bias the overall numerical values for phasing of 5' and 3' UTRs.

To understand the functional significance of periodic An/Tn clusters in the *C. elegans* genome, it is very useful to know the extent of the periodic regions. The first approach to determining the extent of periodic segments was simply to examine the AAAA/TTTT phasing plot in FIG. 3C. From this analysis it is clear that the phasing extends beyond 200 base pairs, at which point the noise becomes sufficient to hide any signal. Second, the distribution of extents to which the PATC algorithm described in FIG. 4A can define a periodic face of the helix, was examined. As shown in FIG. 11A, this distribution continues beyond 1000 bp. Because the latter method could fortuitously "fuse" some adjacent periodic regions that happened to be in the same register, a third algorithm was applied to look for phasing correlations over long distance. This algorithm simply assigns a phasing weight to each 5-base word based on the number of AA/TT dinucleotides, then sums the coincidence value as a function of distance (1-1280). As a starting dataset for the latter procedure, the component of the genome most susceptible to phasing was used: intron present on autosomal arms. The resulting plot (FIG. 11B) shows striking albeit imperfect periodicity well beyond 500 bp. Interestingly, if it is required that two intron-contained words be separated not only by n bases, but by at least one exon sequence, the strong phasing is compiled (FIG. 11C). This indicates that the specific phasing can be maintained even through a region of unperiodic exon sequence.

The strong preference for phasing in a subset of transcribed intron sequences raises the question of whether there might be correlation(s) between gene function and periodic character. To address this question, a list of unique gene names associated with the corresponding values for phasing in introns, exons, upstream and downstream segments was compiled (Fire et al. (2006) Genetics 173:1259-1273, and supplementary materials, which are incorporated by reference herein). Given the high degree of phasing in intron-sequences genome-wide, the study focused specifically on the "intron phasing score" for each gene in deriving our initial hypotheses regarding association between phasing and gene function.

Despite the remarkable functional genomic analysis available for *C. elegans*, the majority of the coding regions have been subject to only limited experimental analysis. It was determined to start with the relatively small number of genes for which functional data from classical genetics has been available (generally these are genes with classical genetic nomenclature and references to alleles isolated in forward mutagenic screens). Of the ten most highly periodic genes in this list (sorted by intron phasing), nine (par-2, smu-2, mrt-2, ced-1O, mel-46, sqv-2, hmp-2, ced-2, and apx-1) are known to express and/or function in the adult hermaphrodite germline, while only one gene in this set (ced-1) has not been reported to function in the germline. It should be noted, however, that the observed lack of maternal rescue for by ced-1(+) (Ellis et al., 1991, which is herein incorporated by reference in its entirety) does not necessarily rule out activity or expression during germline development (Kemphues et al., 1988; Spartz et al., 2004; Ahmed and Hodgkin, 2000; Ellis et al., 1991; R. Minasaki and A. Streit, personal communication; Hwang et al., 2003; Costa et. al., 1998; Mello et al., 1994, which are herein incorporated by reference in their entireties). Cross-referencing of a somewhat more extensive subset of this list with data in the *C. elegans* database "Wormbase" and openly available articles in PubMed again revealed an unexpectedly high fraction (46/62) from this class with known roles or expression in the hermaphrodite germline (FIG. 7A). A comparable set of genes culled at random from the least periodic portion of the list included a much lower fraction with known germline roles (14/69). It should be stressed that this analysis is quite imperfect, since annotation of gene expression and function in Wormbase and indeed in the literature as a whole is by nature incomplete.

A more objective assessment of association between periodic character and gene expression should be derivable from expression data that has been obtained as expression measurement methods have been applied on a genome-wide scale. Although microarray assays have been the most frequently employed in such analyses (e.g., Kim et al., 2001, which is herein incorporated by reference in its entirety), the resulting data is complicated by a marginal signal-to-noise ratio among low-level-expressed genes. Another technique, SAGE (Serial Analysis of Gene Expression) offers a somewhat better opportunity to definitively detect rare RNAs in a mixture (Velculescu et al., 1995, which is herein incorporated by reference in its entirety). An extensive set of published and unpublished SAGE data was obtained from the Genome BC *C. elegans* gene expression consortium (McKay et al., 2003, Chen et al., 2005, Blacque et al., 2005, J. McGhee, K. Wong, M. Marra, S. Jones, D. Baillie and D. Moerman, personal communication, which are herein incorporated by reference in their entireties). As shown in FIG. 7B, analysis of RNA from *C. elegans* oocytes shows a clear, albeit nonlinear, association between SAGE oocyte representation level and degree of phasing. At one extreme, low phasing (on average) for genes whose RNAs are not represented in the oocyte SAGE library was observed. It is noted that some genes could be unrepresented in the SAGE library due to inefficient tag production or cloning. Accordingly, FIG. 7B includes only those genes which are actually represented at least once in the equivalent long SAGE libraries prepared from different *C. elegans* tissues by the UBC genome group. As representation in the oocyte library begins to increase, the average phasing level can also be seen to increase substantially. Average phasing scores drop for genes with higher levels of representation in the oocyte SAGE library. Although not necessarily precisely reflective of expression levels, SAGE frequencies are certainly related to the underlying mRNA level. These data thus suggest a "reverse bell curve" association between oocyte expression and periodic character.

Although the analyses in FIG. 7B suggest a relationship between ooctye expression level and phasing, there is no reason to assume that this relationship is exclusive. Indeed many of the genes described as periodic (e.g. FIG. 7A; Fire et al. (2006) Genetics 173:1259-1273, and supplementary materials, which are incorporated by reference herein) are putative housekeeping genes involved in processes such as basal transcription that are essential for all cells. To determine which, if any, tissues were most tightly associated with phasing character, quantitative tools were needed to assess the quality of nonlinear association between phasing scores and expression in a broad range of tissues. The bell-shaped curve of phasing versus expression level in rules out using simple correlation measures to represent the association. Accordingly, a more general measure was used as follows: Each tissue-specific set of SAGE data can be used to generate a model for predicting phasing of *C. elegans* genes. These models "predict" that the phasing will be the average score all other genes with the corresponding tissue-specific SAGE value. If SAGE values for a given tissue are unrelated to phasing, then the resulting model will be useless: no better than simply guessing the all-gene average in each case. Higher association between expression and phasing will produce a more informative prediction based on the SAGE data. The information value of a given model can be assessed using tools from communications signal processing. Quality of a given model is measured as a difference in "entropy" value (Shannon, 1948, which is herein incorporated by reference in its entirety). For oocyte tissue, the total entropy value of the SAGE dataset is greater than 19 logs (base 10). As shown in FIG. 7C, a much less significant entropy value is obtained from the other major tissues (gut, hypodermis, muscle, neurons, pharynx). Better entropy values were obtained from two additional SAGE datasets (pharyngeal marginal cells and AFD neurons). It should be noted that the marginal cell and AFD datasets derive from a much rarer tissue (a small number of cells in each case). Contamination by germline or oocyte RNAs becomes more of a concern under such circumstances, and indeed we observe that several genes which are thought to be germline-specific in their activity are represented in these datasets. It is stressed, however, that no contamination has been demonstrated and thus the possibility remains that these two tissues share considerable portions of their gene expression profiles with the germline. Based on this analysis of the SAGE data, we conclude that oocyte SAGE data representation provides the best associative model for predicting phasing.

The foregoing describes an unusual DNA structure that underlies a significant fraction of the *C. elegans* genome. This structure shares certain features with DNA that has been shown to curve or bend in several biochemical and untrastructural assays (Crothers et al., 1990, which is herein incorporated by reference in its entirety). Nonetheless, it is noted that the unusual sequence characteristics are not accounted for in detail by assumptions of a specific role in producing a bent naked DNA in vivo.

Nature of Periodic Sequences in the *C. elegans* Genome

The long range nature of the periodicities observed in *C. elegans* suggests that the "shadow" of a large nuclear structure is being detected as it is reflected in DNA sequence. The working hypothesis is that the extended regions of phasing correspond with the ability of the DNA to interact with some surface within the nucleus. Extended surfaces in the nucleus include the nuclear envelope, the outer surfaces of nucleosome cores, neighboring DNA duplexes, and a number of other organelles (nuclear granules and speckles, higher order chromatin structures, nuclear scaffolds, etc.) (Taddei et al., 2004, Gruenbaum et al., 2005; Kornberg and Lorch, 1999; Gall et al., 2004, which are herein incorporated by reference in their entireties).

Among the various nuclear structures, the outer surface of the nucleosome core provides perhaps the most fertile speculation. In particular, it is this surface that is thought to associate most prominently with the bulk of nuclear DNA (Kornberg and Lorch, 1999, which is herein incorporated by reference in its entirety). AA/TT dinucleotides have been suggested to be involved in specific positioning of nucleosomes through a preference for their minor groove to interact the core (e.g. Calladine and Drew, 1986, which is herein incorporated by reference in its entirety). Although the contributions of individual AA/TT dinucleotides to energy of binding may be relatively small, nucleosome conformations for which many AA/TT dinucleotides face minor-groove-inward would provide a substantial free energy benefit. Such structural interactions have been proposed to be capable of constraining nucleosomes by impeding their ability to slide along the DNA (e.g., Richmond and Davey, 2003, which is herein incorporated by reference in its entirety).

Nucleosome positioning is likely to be a rather complex reflection of nucleosome core sequence/structure preferences, non-nucleosomal proteins that bind in a genomic neighborhood, and positioning of nearby nucleosomes. AA/TT dinucleotides contribute only a subset to the intrinsic preferences. Nonetheless, their specific nucleosome interactions may under certain circumstances have a rather substantial thermodynamic effect (e.g., Satchwell et al., 1986, which is herein incorporated by reference in its entirety). Although no direct measurements are available, kinetic impedance of nucleosome translocation by these sequences would also be expected to be substantial.

Several observations support the suggestion the PATC clusters reflect nucleosomal positioning in *C. elegans*. First, *C. elegans* DNA is associated in bulk with nucleosomes and nucleosomal components and modification complexes are critical in setting up appropriate patters of gene expression in the germline (Dixon e al., 1990; Shin and Mello, 2003; Ahringer, 2000, which are herein incorporated by reference in their entireties). Second, distance versus sequence plots can be used (e.g. in FIG. 11B) to calculate a "best fit" period for the underlying structure. This period is 10.06 bp (FIG. 11E). By comparison, the reported average periodicities for B form DNA in solution and on nucleosomes are approximately 10.5 and 10.0 respectively (e.g., Klug and Lutter, 1981; Hayes et al., 1991, which are herein incorporated by reference in their entireties). Third, the minor peaks in the Fourier plot in FIG. 11E and the observation in FIG. 4A-B that AAAA→TTTT separations have a distinct profile from TTTT→AAAA separations is consistent with previous reports of non-symmetric dinucleotide preferences and non-uniform helical repeat at different positions within a nucleosome (e.g., see Ioshekhes et al., 1996, Hayes et al., 1991, which are herein incorporated by reference in their entireties).

Although these data are certainly consistent with a nucleosomal connection to the structural anomaly in PATC sequences, several caveats are noted: (1) that regions of the DNA may adopt different protein associations under distinct cellular conditions, thus the association in some tissue with nucleosomes does not demonstrate that this is always the case; (2) that helical periodicities of DNA have not been determined for potential alternative models (e.g. for nuclear envelope associated DNA); (3) that differences and heterogeneity in TT versus AA dinucleotide distribution might also be expected for other physical interactions, either as a result of intrinsic structure and flexibility or as a result of specific protein binding.

One feature of the sequence anomalies that initially seems unexpected based on nucleosomal models is the persistence of periodic structure. Individual nucleosomes would be expected to cover only 146-147 bp of DNA, with some additional sequence potentially added by linker proteins. Two situations could potentially extend this footprint: first, an array of tandemly arranged nucleosomes could potentially produce a longer periodicity, assuming that the spacing between nucleosomal cores was such that the 10.# base periodicity was maintained (Widom, 1992, which is herein incorporated by reference in its entirety). Second, as has been proposed for a number of systems, a region of DNA might be specialized based on constraining one or more nucleosomes not to a single position but rather to a quantized set of positions, e.g., to impede its movement on DNA. Such a situation might involve a larger region of DNA than would be covered by these nucleosomes, just as a bicycle chain is much longer than the gears that it connects with.

For purposes of discussion of functionality and evolution, reference is made in the remainder of this discussion to the unknown surfaces that align the periodic regions as "nucleosomes". It is noted, however, that all of the subsequent arguments could equally apply to another type of subnuclear surface. It is expected that the identity of the surface associated with periodic structures in the *C. elegans* genome will become clear as the physical environment of periodic sequences from the *C. elegans* genome in their natural context in the animal is examined.

Functional Correlates of Strong Periodic Character in the *C. elegans* Genome

The strong bias for phasing of intron sequences in a discrete subset of genes suggests a functional commonality amongst these genes. The most striking feature that is observed as being associated with the phasing is expression in the hermaphrodite germline. Manual annotation of gene lists and objective comparisons of genomic data confirm a statistically significant association between germline activity and phasing predictions. Nonetheless, it should be stressed that this correlation could be secondary and that the functional link could be a complex one, for example involving another cell type with similar expression profiles to the hermaphrodite germline of some metabolic process that is simply more effective in these cells. In terms of functionality, it is expected over the next several years that additional data from the *C. elegans* community will address the degree of correlation between phasing and tissue specificity. For potential mutagenic origins of the sequence, we note that any process that contributes directly to maintenance or formation of periodic regions must occur within the germline of the animal. If the mutagenic process is biased (e.g., Shieferstein and Thoma, 1996; Holmquist, 1994, which are herein incorporated by reference in their entireties), then the biasing structure must affect germline DNA at some stage.

The *C. elegans* germline passes through a rather dramatic series of transitions during development. Examining the lists of genes that show phasing character, we note that the majority of highly periodic genes are likely to be active in meiotic cells of the distal adult germline which act simultaneously as oocytes-in-training and as nurse cells for the ocytes that are actually at the terminal stages of maturity. Interestingly, no strong phasing was observed in a trio of genes (him-I 7 (Reddy and Villeneuve, 2004, which is herein incorporated by reference in its entirety), spa-II (Dernberg et al., 1998, which is herein incorporated by reference in its entirety), and rad 51 (Colaiacovo et al., 2003, which is herein incorporated by reference in its entirety) that are located on autosomal arms and are thought to be active at premeiotic stages in germline function. Likewise, no strong phasing was observed in a large group of genes (many on the X chromosome) that are activated in a late burst of transcription during the last stages of oocyte maturation (Kelly et al., 2002, which is herein incorporated by reference in its entirety). Spermatogenesis also has a characteristic pattern of gene expression (L'Hernault and Roberts, 1995, which is herein incorporated by reference in its entirety), and we see no evidence for unusual phasing of the majority of genes active in this aspect of germline development. These observations are consistent with the hypothesis that phasing character is associated with expression at a stage of germline development in which oocyte precursors slowly traverse the early stages of meiosis.

Given the strongly non-random character of periodic sequences in the *C. elegans* genome, it is expected that considerable evolutionary pressure must have been present for their origin. Two possible (and not necessarily exclusive) modes for this pressure are envisioned: macroscopic (organismal selection) and microscopic (nonrandom mutagenesis and or repair).

One could certainly imagine, whatever the role of periodic character in the *C. elegans* genome, that the strongly periodic regions could be the result of natural selection at the organismal phenotype level. For this to be the case, periodic segments which are sufficiently unusual to be absent in random DNA would need to each contribute in some way to the phenotypic fitness of the animal. Such contributions might be relatively subtle, so that no single base might produce a phenotype demonstrable in the laboratory. Otherwise, one might expect to uncover a set of mutations whose phenotypic effects might be difficult to explain based on standard aspects of DNA and RNA structure during classical genetic screens for mutations that alter specific phenotypes. Such mutations have been rarely if ever reported in the *C. elegans* literature, although biases for examining mutations with stronger phenotypes and biases in choices of mutagen may have masked such events. Estimates of total periodic material in the *C. elegans* genome are rather substantial (with on the order of $10^6$ non-coding bases showing nonrandom identity related to these structures). Spontaneous mutation rates in *C. elegans* ($\sim 10^8$/base/generation) are such that this would pose a slight but evolutionarily significant burden on the species. At the same time, the likely non-lethal character of individual mutations which affect only one or a few periodic regions raises some interesting population genetic questions in terms whether simple selection could allow highly periodic structures to be fixed and maintained within in a population.

A "macroscopic" evolutionary basis for periodic sequences in *C. elegans* could contribute to the modulation of nearby genetic elements in a number of ways. The most attractive hypothesis is that these sequences impede nucleosome rearrangement in genes for which germline expression is important. By doing so, the energy and time that would be need to wrap these regions into higher order (and potentially silenced) chromatin structures may be greatly increased. Such a situation might serve to protect a subset of genes from active and somewhat indiscriminant silencing mechanisms that normally protect the germline from unwanted expression of genes whose expression might be harmful. Harmful genes might include both somatic specification and differentiation components and selfish DNAs such as transposons or viruses.

Although the forces that shape patterns of heterochromatin in the genome are not fully understood, they are almost certain to involve nucleation events (de novo initiation of heterochromatin structures) combined with a tendency of heterochromatin structures to spread laterally in a stepwise and somewhat deliberate manner until sequences that prevent their spread are encountered (Richards and Elgin, 2002, which is herein incorporated by reference in its entirety). Initiation events involve a mixture of triggers: specific DNA sequence elements that are targeted by interaction with proteins that initiate heterochromatic silencing, repeated structures in DNA that may be recognized by meiotic or recombination machinery, parasitic genetic elements, and certain types of modulatory RNA (Turker and Bestor, 1997; Hsieh and Fire, 2000; Selker, 2002, which are herein incorporated by reference in their entireties). Interestingly, the outer autosomal regions where many of the periodic genes in C. elegans reside are enriched in repeated DNA and putative selfish elements (C. elegans sequencing consortium, 1998, which is herein incorporated by reference in its entirety). One model would be that these elements contribute to a relatively inhospitable genomic environment for those genes whose activity in the germline is important. This might necessitate the ability of such genes to evolve mechanisms to resist the encroachment of heterochromatic structure (which could potentially render them useless for the germline). As noted above, it is certainly conceivable that regions of the DNA for which nucleosome rearrangements are impeded may be refractory to higher order heterochromatin assembly. This might afford a considerable degree of protection to these sequences.

As a (non-exclusive) alternative to models proposing an organismal selection for periodic regions in DNA, it is conceivable that such structures arise due to biases in mutagenesis and repair at the level of individual genomic regions. Biased mutagenesis and repair processes have certainly been documented in numerous systems and could certainly reflect both nucleosome positioning and transcriptional properties (e.g., Schieferstein and Thoma, 1996; Mellon, 2005, which are herein incorporated by reference in their entireties). Such processes have frequently been proposed to underlie nonrandom character in DNA sequences. The observed phasing in C. elegans DNA could be explained if a number of conditions were met.

First, certain sequences in the genome (those transcribed at specific stages of germline development) would either (1) have distinct sensitivity to mutagenic hits or (2) be repaired with altered efficiency or specificity after such hits. The most likely scenario here would be for transcription in germline tissue to be associated with altered mutability characteristics. The relatively stable early meiotic states slowly traversed by oocyte precursors in the distal germline make a good candidate for the tissue of interest here since these chromosomes persist in an unusual state for a considerable time period. Another possibility would be targeting of specific regions of chromatin that are accessible in diapause (e.g. dauer) animals, again at a stage where cells persist for a long period.

Second, the mutagenic processes in the animal would need to be influenced by local structural characteristics of the chromosome and its environment. Most attractive as a model here would be to propose that nucleosome interactions might influence the distribution of mutagenic hits and/or the spectrum of repair functions. Such influences have been hypothesized (Holmquist, 1994, which is herein incorporated by reference in its entirety) and demonstrated in model systems (Schieferstein and Thoma, 1996, which is herein incorporated by reference in its entirety). In the C. elegans particular case, the nucleosome positions would need to alter mutagenic consequences on a base-by-base level, skewing the eventual spectrum of mutations such that AA/TT dinucleotides would form more frequently on one face of a surface contacting the DNA. This type of bias would result in the appearance of a "nucleosome shadow" in certain regions of the DNA sequence.

Numerous mutational events would be required to produce a periodic structure. Assuming these hits occurred over considerable evolutionary time, one must also assume for this model that some force must constrain the nucleosome. One possibility would be a constraint of nucleosomes independent of the AA/TT phasing so that the A/VT phasing just appears as a shadow of this underlying positional constraint. Alternatively, the AA/TT phasing itself may work to constrain nucleosome positions, so that positioning of nucleosomes may become more and more constrained as further point mutations are accumulated. The latter model works under the interesting constraint that biases in mutagenesis and repair serve to reinforce current nucleosome positioning. This would certainly be the case is mutagenic lesions that produce A/VTT dinucleotides with their minor grooves facing into the nucleosome were more frequently formed or fixed in the DNA sequence. Curiously, this set of conditions would set up a situation where strong nucleosome positioning signals could coalesce 'de novo' in DNA sequence through an increasingly energetically favorable and self-reinforcing process.

There is relatively little information available from which to speculate on potential mutagenic processes that might produce the types of nonrandomness observed as phasing in the C. elegans genome. Certainly virtually any point mutagen that was sensitive to DNA structure or context could produce such a bias. Likewise almost any repair process could be biased for or against events that occur on surface-associated micro-regions in the DNA. For exemplary purposes, we note the following aspects of ultraviolet-induced mutagenesis: (a) UV has been shown to preferentially induce lesions at TT dimmers, (b) repair can proceed by either a error-free mechanism (photoreactivation) or an error prone mechanism (excision and gap repair), (c) it is certainly conceivable that gap repair would predominate on the outer (exposed) surface of nucleosomes while photoreactivation would predominate on inner (sterically protected) faces. Combining this with other mutagenic processes that might result in formation of A- or T-rich segments in transcriptionally accessible regions of the genome, one might expect the types of structures that we observe in nematodes.

Proposals that the strong phasing seen in the C. elegans genome might reflect a combination of structural constraints and mutagenesis/repair biases lead to a plausible hypothesis that the resulting anomalies may have no particular fitness value for the organism. While this would certainly be a valid hypothesis, an attractive alternative would be to propose that the aggregate changes occurring in certain germline-active genomic regions would confer structural characteristics that would confer a fitness advantage for the organism. One possible modality for this advantage would be the formation over evolutionary time of certain germline active chromatin regions that would be protected from encroachment by processes that enforce epigenetic silencing (as described above). Other potential roles for these sequences could be envisioned in chromosome structure, replication, recombination, segregation, or maintenance. Whatever the role in the function of the organism, the unexpected suggestion here is that mutagenic and repair functions in the nematode phylum have been tuned over evolutionary time so that beneficial changes to certain regions of the genome accumulate without any immediate selection for the individual events. Such processes, if they truly benefit the phylum, may be one of many factors that account for the remarkable prevalence (and hence fitness) of this very successful phylum.

The proposal that organisms might evolve to manage their own evolutionary change is by no means original to this system (e.g. McClintock, 1984, which is herein incorporated by reference in its entirety). As additional nematode genomes are sequenced and functionally characterized, we expect that further information about the large scale processes directing their change to become clearer.

Organisms use numerous mechanisms to protect themselves from activities and encroachment by various forms of selfish or unwanted information (transposons, viruses, etc.). These mechanisms include silencing of repeated DNA, meiotic silencing of unpaired DNA, RNAi, recognition and clearance of extended regions of ssDNA and untranslated RNA, and gatekeeping processes that prevent nuclear export of unspliced RNAs (Fire, 2006, which is herein incorporated by reference in its entirety). Even with these numerous defense mechanisms, we have clear evidence for the ability of certain sequences to enter the genome uninvited and potentially to cause deleterious effects.

Unusual structural characteristics of germline expressed genes could potentially provide a species with an additional level of protection. Foreign DNAs (whether viral, transposon, or from another species or phylum) would generally lack such characteristics and might thus be recognized as foreign. In the case of the periodic character of many germline-expressed genes in *C. elegans*, an ability of periodic sequences to resist encroachment of silencing would allow the organism to employ a highly aggressive process for spreading of germline heterochromatin into unprotected regions of the genome. The vast majority of sequences which entered the genome from outside sources would then be subject to effective silencing for germline expression during their first few generations in the *C. elegans* genome, a process that is readily seen with many different transgene constructs that are introduced into *C. elegans* (Kelly et al., 1997; Hsieh and Fire, 2000, which are herein incorporated by reference in their entireties). The process of injected transgene silencing in *C. elegans* is not completely understood but is thought to involve the progressive recruitment of heterochromatin-related histone modifications to the extrachromosomal array structures into which the foreign DNA is incorporated (Bean et al., 2005; Hsieh and Fire, 2000, which are herein incorporated by reference in their entireties). Several different vectors are available that seem to partially limit germline silencing of injected *C. elegans* transgenes; intriguingly the majority of these vectors are derived from genes with substantial phasing scores (let-858, mex-3, pie-1, smu-2, smu-1, ama-1) (Kelly et al., 1997, which is herein incorporated by reference in its entirety). ;ftp://ftp-.wonnbase.org/pub/wonnbase/datasets/fire_vectors/> Reese et al., 2000; Sparz et al., 2004, which is herein incorporated by reference in its entirety). For comparison, phasing diagrams for these genes are shown in FIG. 12.

Given that a large number of germline-expressed *C. elegans* genes lack any detectable phasing signals, one expects that the phasing is not the only force that can prevent heterochromatinization. The location of many of the non-periodic germline-expressed genes in the autosomal centers may give these genes a significant advantage in using whatever mechanism they employ to resist silencing. A number of germline-expressed genes without strong phasing have been investigated in designing potential vectors for driving germline reporter expression; interestingly, these experiments have been almost uniformly unsuccessful (no germline reporter expression was seen with the following fusions that were otherwise functional as assayed by phenotypic rescue: glp-1, dcr-1, mes-1, rde-1, fem-1; (A. Fire, I. Priess, S. Eddy, A. Zahler, J. Fleenor, S. Xu, S. Parrish and D. Blanchard, unpublished). The one exception to this rule has been the gene gna-2 (W. Johnston and I. Dennis, personal communication; Lee and Schedl, 2004), where germline expression has been reported from extrachromosomal arrays in the absence of any evident phasing. These observations indicate the possibility that the non-periodic germline-expressed genes in autosomal centers may use alternative means to prevent heterochromatization that are less effective in the relatively "harsh" genomic environment of autosomal arms and of the extrachromosomal and somewhat repetitive transgene arrays.

Defense mechanisms that rely on species-specific properties of DNA could in principle be quite general. While the key feature in this case could be unusual patterns of nucleosome positioning or mobility, one expects that other species could use features such as base composition (GC %), presence of specific protein binding sites, or conserved DNA/miRNA interactions to provide a layer of self-nonself contribution and thus to protect their cells (and most importantly germline cells) from invasion or activity by unwanted information.

Tools that manipulate gene expression in a specific cell type are critical for many experimental and therapeutic manipulations. For manipulation of *C. elegans*, a suggestion from this analysis is certainly that we should be aware of the periodic character of potential vectors in designing experiments. Consequences of this might include the choice of periodic promoters and coding regions for intended expression of reporters and other factors in the animal and in particular in the germline. Pushing this proposal one step further, reporter sequences for germline expression might also be improved by incorporation of phasing signals to conform more closely to structures in native genes expressed in this environment. Studies to evaluate the efficacy of such strategies are underway for *C. elegans*.

For manipulations of non-nematode species (e.g. human cell lines and transgenic mice some of the same challenges of transgene silencing have been described and discussed (e.g., Bacheler et al. 1979; see Bestor, 2000, which are herein incorporated by reference in their entireties). Although the structures described in this paper are directed to *C. elegans*, they are applicable to other systems. As an example, two suggestions for potential application in other system could be made. First, the type of AA/TT phasing described in this paper, if it fundamentally alters nucleosome positioning or mobility, might be useful in other systems to avoid silencing. Non-nematode species may use alternative mechanisms (some of which may be evolutionarily less expensive in terms of number of affected base pairs) to avoid silencing for the majority of important endogenous genes. Despite this, the AA/TT phasing may still produce a functional effect in these systems and could in principle be used but be less evident in sequence analysis or be used only for a small number of genes. Either way, it should be possible to evaluate the ability of periodic sequences of the character seen in *C. elegans* to block silencing of transgenes in vertebrates.

Use of Highly Periodic Segments of Transcribed DNA as an Expression Vector

As a test of the hypothesis that highly periodic segments of transcribed DNA could function as expression vectors, we first produced two segments of highly periodic DNA which were designed to encode *Aequora Victoria* green fluorescent protein (gfp) (Chalfie et al., 1994, which is herein incorporated by reference in its entirety). Each of these segments contained a start codon (ATG) followed by 237 codons for the remaining amino acids in gfp, followed by a stop codon (TAG) for construct spgfp-1 and by a short nuclear localization signal for segment spgfp-2.

The first periodic gfp construct, designated spgfp-1 (FIG. 13), was interrupted with four intron sequences of 83, 76, 82, and 83 bases respectively. These sequences are shown in FIG. 14.

Each of the four introns in spgfp-1 begins and ends with splice site consensus sequences (gtaagttt and tttttcag, respectively) designed to match splice site consensus sequences previously described for both invertebrates and mammals (Fields, 1990; Mount, 1982, which are herein incorporated by reference in their entireties). Intron positions in the construct were chosen to approximately equalize the lengths of the five resulting exons (175, 160, and 158 for the three internal exons, 151+5'UTR and 73+3'UTR for initial and terminal exons). Introns were placed where it was possible to flank them in adjacent coding sequences with AG (upstream in the coding region) and G (downstream in the coding region), as is common for animal genes. Starting 31-33 bases upstream of the 3' splice site of each intron sequence is a consensus splice "Branch Point" sequence (TACTAACTAAC) derived from studies of the yeast *Sacchromyces cerevisiae* (Newman et al., 1985, which is herein incorporated by reference in its entirety). Although these four intron sequences carry exact matches to the various consensus splice-guiding sequences, it should be stressed that natural introns have frequent mismatches to all but sequences immediately adjacent to the splice junction (Fields, 1990; Mount, 1982, which are herein incorporated by reference in their entireties). Thus one could certainly construct such introns without requiring perfect matches to the splice consensus.

Each intron in spgfp-1 was designed with a high degree of internal periodicity, with six TTTTT segments arranged at 10-11 base intervals. Such an arrangement of AA/TT polymers would be vanishingly rare in random DNA sequence of a comparable length and A+T content. This precisely periodic arrangement would be present in $<1/10^8$ individual intron sequences of comparable length and AT content. This gives a likelihood of $<1/10^{32}$ for four consecutive introns. In principal, we could have used either An or Tn strings on the coding strand to enforce the periodicity. Only Tn strings were chosen for this particular construct; this was to avoid self complementarity during gene assembly.

Choices of codons for the spgfp-1 construct allowed additional flexibility. Each amino acid can be encoded by several different triplet codons, yielding a flexibility in which of the relevant codons would be chosen for each amino acid. We chose codons as much as possible to contribute to the AA/TT periodicity. Where this was not possible, common codons for *C. elegans* were chosen. In all cases, codons were chosen to minimize potential cryptic splice, junctions in the final primary transcript and mRNA.

For a protein coding sequence constrained to match a specified protein sequence, codon choice allows at most a modest degree of periodicity in the coding region. This modest periodicity, however, might be expected to maintain and reinforce structural constraints on chromatin-based silencing that may initiate from sequences in the much more structurally distinct intron sequences that periodically interrupt the synthetic genes.

Spgfp-1 encodes gfp in which amino acid 65 has been changed from serine to cytosine (Heim et al., 1995, which is herein incorporated by reference in its entirety). This variant of gfp (and the comparable 135T variant) shows improved kinetics of protein folding and photo-stability during illumination with a strong fluorescence light source. The 135C variant has been the basis for many of the most commonly used vectors for *C. elegans* gene expression assays (Fire et al., 1998, which is herein incorporated by reference in its entirety).

The entire coding region for spgfp-1 is 1041 base pairs (including start and stop codons). To facilitate insertion of this coding region into diverse expression vectors, a unique AgeI restriction endonuclease site is placed at the 5' end and a unique EcoRI restriction endonuclease site at the 3' end (beyond the stop codon). Numerous additional restriction sites flank the coding region in the variety of expression vectors that have been produced from this original vector and these sites provide a broad flexibility in terms of future insertions of the coding region into additional expression vectors.

Driven from a body muscle-specific promoter in transgenic *C. elegans* (FIG. 15), we observed expression of a functional GFP protein from the spgfp-1 coding region in body muscle; driven from a promoter in germline tissue, we observed expression in the *C. elegans* germline.

A separate set of constructs, in which a spgfp-1 coding region was driven by the cytomegalovirus immediate early promoter (CMVp), (Boshart et al., 1985, which is herein incorporated by reference in its entirety) was tested in both transgenic mice derived from microinjection of DNA into mouse zygotes, and tissue culture cells transfected with the DNA. FIGS. 16 and 17 show the relevant constructs (L7152 [spgfp-1] and L7148 [a standard gfp expression vector with EGFP (Fukumura et al., 1998, which is herein incorporated by reference in its entirety)]) in detail and FIG. 18 shows gfp expression in transgenic mice. Although a detailed characterization of the expression pattern in mice awaits further analysis, the ability of this construct to express in numerous mouse tissues is evident.

Given that experiments in *C. elegans* and mice confirmed the ability of the spgfp-1 coding region to function properly, we sought a quantitative system in which this coding region could be compared with gfp expression vectors which are currently standard for following gene expression in vertebrate cells. To carry out these experiments, we transfected tissue culture cells from a variety of human tumors with the constructs shown in FIGS. 16 and 17. Antibiotic selection (G418) (Davies et al., 1980, which is herein incorporated by reference in its entirety) was then imposed to maintain the presence of the DNA (FIG. 19). Expression of GFP by cells in the population was monitored by use of a fluorescence activated cell sorter; GFP expression was also evident by fluorescence of the cells when viewed in a standard epifluorescence microscope (FIG. 20).

As the reference for measuring expression, we examined the fluorescence of cells following transfection of an equivalent construct 'EGFP' (Fukumura et al., 1998, which is herein incorporated by reference in its entirety) which is currently the state-of-the-art construct, in which a widely used synthetic gfp coding region with human codon preferences has been utilized. Cells transformed with the two constructs were grown on Petri plates in standard media, passaged twice per week, and maintained in drug selection for periods of 2-4 months. GFP levels were assayed as a function of passage number, normalized where possible to the initial transfection efficiencies in each experiment. For each transfection experiment, three independent groups of transfected cells were examined and followed over time. Passaging of each cell population was independent, so that three independent populations of cells were followed for each combination of DNA construct and cell line.

As shown in FIGS. 21, 22, and 23, gfp expression tended in some cases to decrease with continued passage of each of the transfected cell populations. It should be stressed that this decrease occurred even in the presence of continued antibiotic selection on each cell line for the presence of the transfected DNA. This type of gene silencing phenomenon for transfected DNA has reproducibly been observed by us and by numerous others using such assays. For two of the three cell lines, ME180 (Sykes et al., 1970, which is herein incorporated by reference in its entirety) and Caski (Pattillo et al., 1977), we found that the gfp expression persisted substantially longer in assays using the spgfp-1 reporter than in comparable assays using the standard humanized gfp (e.g. egfp; Fukumura et al., 1998, which is herein incorporated by reference in its entirety). A third cell line, HTH83 (Dahlman et al., 2000, which is herein incorporated by reference in its entirety), derived from an anaplastic thyroid cancer, appeared to show a reverse bias, indicating that sequence effects on persistence of gene expression in transgenic strains may have cell-type-specific characteristics. This observation is also consistent with our observations in C. elegans that high degrees of periodicity in DNA sequence appear to preferentially associate with expression in a subset of cells in the animal.

A second gfp reporter construct, spgfp-2 was prepared by a process similar to that used for spgfp-1. Spgfp-2 (FIGS. 24 and 25) differs from spgfp-1 in the details of the individual codons and introns used and in the choice of shorter T-runs to enforce periodicity in the introns (spgfp-2 has periodic runs of four T residues, while spgfp-1 has periodic runs of five T residues). Expression of the spgfp-2 gfp construct was tested in C. elegans. Although substantially less intense when viewed in the microscope than spgfp-1, expression from this construct was certainly visible. Activity spgfp-2 in transgenic lines was confirmed both by the appearance of fluorescent cells in transgenic animals (FIG. 15) and by the production of spliced RNA with the expected structure of the gfp transcript (FIG. 26).

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents, and patent applications referred to in this application are herein incorporated by reference in their entirety.

REFERENCES

Ahmed, S., and Hodgkin, L. (2000). MRT-2 checkpoint protein is required for germline immortality and telomere replication in C. elegans. Nature 403:159-164.

Ahringer, J. (2000). NuRD and SIN3 bistone deacetylase complexes in development. Trends Genet 16:351-356.

Bacheler, L., Jaenisch, R, and Fan, H. (1979) Highly inducible cell lines derived from mice genetically transmitting the Moloney murine leukemia virus genome. J Virol 29:899-906.

Barnes, T. M., Kohara, Y., Coulson, A, and Hekimi, S. (1995). Meiotic recombination, noncoding DNA and genomic organization in Caenorhabditis elegans. Genetics, 141: 159-179.

Bean, C. J., Schaner, C. E, and Kelly, W. G. (2004) Meiotic pairing and imprinted X chromatin assembly in Caenorhabditis elegans. Nat Genet, 36:100-105.

Bestor, T. H. (2000) Gene silencing as a threat to the success of gene therapy. J Clin Invest. 105:409-411.

Blacque, O. E, Perens, E. A, Boroevich, K. A., Inglis, P. N., Li, C., Warner, A, Khattra, J., Holt, R A, Ou, G., Mah, A K, McKay, S. I., Huang, P., Swoboda, P., Jones, S. J., Marra, M. A., Baillie, D. L., Moerman, D. G., Shahamn, S., and Leroux, M. R. (2005). Functional genomics of the cilium, a sensory organelle. Curr. Biol., 15:935-941.

Blumenthal, T. and Gleason, K. S. (2003) Caenorhabditis elegans operons: form and function. Nat Rev Genet, 4: 112-120.

Bolshoy, A, McNamara, P., Harrington, R E., and Trifonov, E N. (1991). Curved DNA without A-A: experimental estimation of all 16 DNA wedge angles. Proc Natl Acad Sci USA, 88:2312-2316.

Boshart M, Weber F, Jahn O, Dorsch-Häsler K, Fleckenstein B, Schaffner W. (1985) A very strong enhancer is located upstream of an immediate early gene of human cytomegalovirus. Cell 41:521-530.

Brenner, S. (1974) The genetics of Caenorhabditis elegans. Genetics 77:71-94.

C. elegans sequencing consortium (1998). Genome sequence of the nematode C. elegans: a platform for investigating biology. Science 282:2012-2018.

Calladine, C. R., and Drew, H. R. (1986). Principles of sequence-dependent flexure of DNA J Mol Biol, 192:907-918.

Chalfie, M., Tu, Y., Euskirchen, G., Ward, W. W., and Prasher, D. C. (1994) Green fluorescent protein as a marker for gene expression. Science 263:802-805.

Chen, N., Harris, T. W., Antoshechkin, I., Bastiani, C., Bieri, T., Blasiar, D., Bradnam, K., Canaran, P., Chan, J., Chen, C. K., Chen, W. J., Cunningham, E, Davis, P., Kenny, E., Kishore, R., Lawson, D., Lee, R., Muller, H. M., Nakamura, C., Pai, S., Ozersky, P., Petcherski, A, Rogers, A, Sabo, A, Schwarz, E. M., Van, Au.k.e.n.., Wang, Q., Durbin, R., Spieth, J., Sternberg, P. W., and Stein, L. D. (2005). WormBase: a comprehensive data resource for Caenorhabditis biology and genomics. Nucleic Acids Res 33:D383-D389.

Chen, N., Pai, S., Zhao, Z., Mah, A, Newbury, R., Johnsen, R. C., Altun, Z., Moerman, D. G., Baillie, D. L., and Stein, L. D. (2005). Identification of a nematode chemosensory gene family. Proc Natl Acad Sci USA, 102:146-151.

Colaiacovo, M. P., MacQueen, A J., Martinez-Perez, E., McDonald, K., Adamo, A, LaVolpe, A, and Villeneuve, A M. (2003). Synaptonemal complex assembly in C. elegans is dispensable for loading strand-exchange proteins but critical for proper completion of recombination. Dev Cell, 5:463-474.

Costa, M., Raich, W., Agbunag, C., Leung, B., Hardin, J., and Priess, J. R. (1998). A putative catenin-cadherin system mediates morphogenesis of the Caenorhabditis elegans embryo. J Cell Biol., 141:297-308.

Crothers, D. M., Haran, T. E., and Nadeau, I. G. (1990). Intrinsically bent DNA. J Biol Chem., 265:7093-7096.

Dahlman, T., Lammerts, E., Wik, M., Bergstrom, D., Grimelius, L., Westermark, K., Rubin, K., and Heldin, N. E. (2000) Fibrosis in undifferentiated (anaplastic) thyroid carcinomas: evidence for a dual action of tumour cells in collagen type I synthesis. J Pathol 191:376-386.

Dai, L., Chuang, R Y., and Kelly, T. J. (2005) DNA replication origins in the Schizosaccharomyces pombe genome. Proc Natl Acad Sci USA, 102:337-342.

Davies, J. and Jimenez, A. (1980) A new selective agent for eukaryotic cloning vectors. Am J Trop Med Hyg 29:1089-1092.

Dernburg, A. F., McDonald, K., Moulder, G., Barstead, R., Dresser, M., and Villeneuve, A. M. (1998). Meiotic recombination in *C. elegans* initiates by a conserved mechanism and is dispensable for homologous chromosome synopsis. Cell, 94:387-398.

Diekmann, S. (1987). Temperature and salt dependence of the gel migration anomaly of curved DNA fragments. Nucleic Acids Res., 15:247-265.

Dixon, D. K., Jones, D., and Candido, E. P. (1990). The differentially expressed 16-kD heat shock genes of *Caenorhabditis elegans* exhibit differential changes in chromatin structure during heat shock. DNA Cell Biol., 9:177-191.

Duret, L., Marais, C., and Biemont, C. (2000). Transposons but not retrotransposons are located preferentially in regions of high recombination rate in *Caenorhabditis elegans*. Cenetics, 156:1661-1669.

Ellis, R E., Jacobson, D. M., and Horvitz, H R (1991). Genes required for the engulfment of cell corpses during programmed cell death in *Caenorhabditis elegans*. Genetics, 129:79-94.

Fields, C. (1990) Information content of *Caenorhabditis elegans* splice site sequences varies with intron length. Nucleic Acids Res 18:1509-1512.

Fire, A., Ahnn, J., Kelly, W., Harfe, B., Kostas, S., Hsieh, J., Hsu, M., and Xu, S. (1998) GFP applications in *C. elegans*. in GFP Strategies and Applications, M. Chalfie and S. Kain eds, John Wiley and Sons, NY. pages 153-168.

Fukumura, D., R. Xavier, T. Sugiura, Y. Chen, E. Park, N. Lu, M. Selig, G. Nielsen, T. Taksir, R. Jain and B. Seed (1998) Tumor induction of VEGF promoter activity in stromal cells. *Cell* 94: 715-725.

Fukushima, A, Ikemura, T., Kinouchi, M., Oshinia, T., Kudo, Y., Mori, H, and Kanaya, S. (2002). Periodicity in prokaryotic and eukaryotic genomes identified by power spectrum analysis. Gene, 300:203-211.

Gall, L. G., Wu, Z., Murphy, c., and Gao, H (2004). Structure in the amphibian germinal vesicle. Exp Cell Res., 296:28-34.

Goodsell, D. S., and Dickerson, R E. (1994). Bending and curvature calculations in B-DNA Nucleic Acids Res., 22:5497-5503.

Gruenbaum, Y, Margalit, A, Goldman, R D., Shuinaker, D. K, and Wilson, K L. (2005). The nuclear lamina comes of age. Nat Rev Mol Cell Biol., 6:21-31.

Hayes, J. J., Clark, D J., and Wolffe, A P. (1991). Histone contributions to the structure of DNA in the nucleosome. Proc Natl Acad Sci USA, 88:6829-6833.

Heim, R., Cubitt, A. B., and Tsien, R. Y. (1995) Improved green fluorescence. Nature 373:663-664.

Holmquist, G. P. (1994). Chromatin self-organization by mutation bias. J Mol Evol 39:436-438.

Hsieh, L., and Fire, A (2000). Recognition and silencing of repeated DNA Annu Rev Genet., 34:187-204.

Hwang, H. Y., Olson, S. K, Brown, J. R, Esko, J. D., and Horvitz, H. R (2003). The *Caenorhabditis elegans* genes sqv-2 and sqv-6, which are required for vulval morphogeriesis, encode glycosaminoglycan galactosyltransferase II and xylosyltransferase. J Biol Chern., 278: 11735-11738.

Ioshikhes, I., Bolshoy, A, Derenshteyn, K, Borodovsky, M., and Trifonov, E. N. (1996). Nucleosome DNA sequence pattern revealed by multiple alignment of experimentally mapped sequences. J Mol Bio., 1262:129-139.

Kelly, W. G., Schaner, C. E., Dernburg, A F., Lee, M. H., Kim, S. K, Villeneuve, A M., and Reinke, V. (2002). X-chromosome silencing in the germline of *C. elegans*. Development, 129:479-492.

Kelly, W. G., Xu, S., Montgomery, M., and Fire, A. (1997) Distinct Requirements for Somatic and Germline Expression of a Generally Expressed *C. elegans* Gene. Genetics, 146: 227-238.

Kemphues, K J., Priess, I. R, Morton, D. G., and Cheng, N. S. (1988). Identification of genes required for cytoplasmic localization in early *C. elegans* embryos. Cell, 52:311-320.

Kent, W. L, and Zahler, A. M. (2000). The intronerator: exploring introns and alternative splicing in *Caenorhabditis elegans*. Nucleic Acids Res., 28:91-93.

Kim, S. K., Lund, L, Kiraly, M., Duke, K., Jiang, M., Stuart, I M., Eizinger, A., Wylie, B. N., and Davidson, G. S. (2001). A gene exprcssion map for *Caenorhabditis elegans*. Science, 293:2087-2092.

Kiyama, R, and Trifonov, E. N. (2002). What positions nucleosomes?—A model. FEBS Lett., 523:7-11.

Klug, A., and Lutter, L. C. (1981). The helical periodicity of DNA on the nucleosome. Nucleic Acids Res., 9:4267-4283.

Koo, H. S., Wu, H. M., and Crothers, D. M. (1986). DNA bending at adenine. thymine tracts. Nature, 320:501-506.

Kornberg, R D., and Lorch, Y. (1999). Twenty-five years of the nucleosoire, fundamental particle of the eukaryote chromosome. Cell, 98:285-294.

Kullback, S. and Leibler, R A. (1951) On information and sufficiency. Annals of Mathematical Statistics, 22:79-86.

Kurtz, S. and Schleiermacher, C. (1999). REPuter: fast computation of maximal repeats in complete genomes. Bioinformatics, 15:426-427.

Lee, M. H. and Schedl, T. (2004) Translation repression by GLD-1 protects its mRNA targets from nonsense-mediated mRNA decay in *C. elegans*. Genes Dev., 18:1047-1059.

L'Hemault, S. W. and Roberts, T. M. (1995). Cell biology of nematode sperm. Methods Cell Biol., 48:273-301.

Marini, L. E., Levene, S. D., Crothers, D. M., and Englund, P. T. (1982) Bent helical structure in kinetoplast DNA. Proc Natl Acad Sci USA, 79:7664-7668.

McClintock, R (1984). The significance of responses of the genome to challenge. Science, 226:792-801.

McKay, S. J., Johnsen, R., Khattra, J., Asano, J., Baillie, D. L., Chan, S., Dube, N., Fang, L., Goszezynski, B., Ha, E., Halfnight, E., Hollebakken, R., Huang, P., Hung, K., Jensen, V., Jones, S J., Kai, H., Li, D., Mah, A., Marra, M., McGhee, J., Newbury, R., Pouzyrev, A., Riddle, D. L., Sonnhammer, E., Tian, H., Tu, D., Tyson, J. R., Vatcher, G., Warner, A., Wong, K., Zhao, Z., and Moerman, D. G. (2003). Gene expression profiling of cells, tissues, and developmental stages of the nematode *C. elegans*. Cold Spring Harb Symp Quant Biol., 68:159-169.

Mello, C. C., Draper, R W., and Priess, J. R. (1994). The maternal genes apx-1 and glp-1 and establishment of dorsal-ventral polarity in the early *C. elegans* embryo. Cell, 77:95-106.

Mello, C. C., Kramer, J. M., Stinchcomb, D. & Anibros, V. (1991) Efficient gene transfer in *C. elegans*: extrachromosomal maintenance and integration of transforming sequences. Embo J 10, 3959-3970.

Mellon, I. (2005). Transcription-coupled repair: a complex affair. Mutat Res., 577: 155-161.

Minsky, A. (2004). Information content and complexity in the high-order organization of DNA. Annu Rev Biophys Biomol Struct., 33:317-442.

Mount, S. M. (1982) A catalogue of splice junction sequences. Nucleic Acids Res 10:459-472.

Nelson, H. C., Finch, J. T., Luisi, R F., and Klug, A. (1987). The structure of an oligo(dA) . . . oligo(dT). tract and its biological implications. Nature, 330:221-226.

Newman, A. J., Lin, R. J., Cheng, S. C., and Abelson, J. (1985) Molecular consequences of specific intron mutations on yeast mRNA splicing in vivo and in vitro. Cell 42:335-344.

Okkema, P., White-Harrison, S., Plunger, V., Aryana, A., and Fire, A. (1993). Sequence requirements for myosin gene expression and regulation in C. elegans. Genetics 135, 385-404.

Pattillo, R. A., Hussa, R. O., Story, M. T., Ruckert, A. C., Shalaby, M. R., and Mattingly, R. F. (1977) Tumor antigen and human chorionic gonadotropin in CaSki cells: a new epidernoid cervical cancer cell line. Science 196:1456-1458.

pCDNA3 documentation. Invitrogen life sciences Inc, San Diego, Calif.

Pulak, R. and P Anderson (1993) mRNA surveillance by the Caenorhabditis elegans smg genes. Genes & Development 7:1885-1897.

Reddy, K. C., and Villeneuve, A. M. (2004). C. elegans HIM-17 links chromatin modification and competence for initiation of meiofic recombination. Cell, 118:439-452.

Rhodes, D., and Klug, A. (1981). Sequence-dependent helical periodicity of DNA. Nature, 292:378-380.

Richards, E J., and Elgin, S. C. (2002). Epigenetic codes for heterochromatin formation and silencing: rounding up the usual suspects. Cell, 108:489-500.

Richmond, T J., and Davey, e. A (2003). The structure of DNA in the nucleosome core. Nature, 423:145-150.

Sambrook, J., Fritsch, E., and Maniatis, T. (1989) Molecular Cloning: A Laboratory Manual, 2nd Ed., Cold Spring Harbor Laboratory, Cold Spring Harbor, N.Y.

Sarai, A, Mazur, J., Nussinov, R, and Jernigan, R L. (1989). Sequence dependence of DNA conformational flexibility. Biochemistry, 28:7842-7849.

Satchwell, S. C., Drew, H. R, and Travers, A A (1986). Sequence periodicities in chicken nucleosome core DNA J Mol Biol., 191:659-675.

Schieferstein, D., and Thoma, P. (1996). Modulation of cyclobutane pyrimidine dimmer formation in a positioned nucleosome containing poly(dAdT). tracts. Biochemistry, 35:7705-7714.

Selker, E. D. (2002). Repeat-induced gene silencing in fungi. Adv Genet., 46: 439-450.

Shannon, C. E. 1948. A mathematical theory of communication. The Bell System Technical Journal, 27:379-423; 623-656.

Shin, T. H., and Mello, e.C. (2003). Chromatin regulation during C. elegans germline development. Curr Opin Genet Dev., 13:455-462.

Spartz, A K., Herman, R K., and Shaw, J. E. (2004). SMU-2 and SMU-1, Caenorhabditis elegans homologs of mammalian spliceosome-associated proteins RED and fSAP57, work together to affect splice site choice. Mol Cell Biol., 24:6811-6823.

Stinchcomb, D. T., Shaw, J. E., Carr, S. H., and Hirsh, D. (1985) Extrachromosomal DNA transformation of Caenorhabditis elegans. Mol Cell Biol., 5:3484-3496.

Sykes, J. A., Whitescarver, J., Jernstrom, P., Nolan, J. F., and Byatt, P. (1970) Some properties of a new epithelial cell line of human origin. J Natl Cancer Inst 45:107-122.

Taddei, A, Hediger, F., Neumann, P. R, and Gasser, S. M. (2004) The function of nuclear architecture: a genetic approach. Annu Rev Genet., 38:305-45.

Taketo, M., Schroeder, A. C., Mobraaten, L. E., Gunning, K. B., Hanten, G., Fox, R. R., Roderick, T. H., Stewart, C. L., Lilly, F., Hansen, C. T., and Overbeek, P. (1991) FVB/N: an inbred mouse strain preferable for trasngenic analyses. Proc Natl Acad Sci USA 88:2065-2069.

Thomas, J. W., Touchman, J. W., Blakesley, R W., Bouffard, G. G., Beckstrom-Sternberg, S. M., Margulies, E. H., Blanchette, M., Siepel, A. C., Thomas, P. J., McDowell, J. C., Maskeri, B., Hansen, N. F., Schwartz, M. S., Weber, R J., Kent, W. J., Karolchik, D., Bruen, T. C., Bevan, R., Cutler, D. J., Schwartz, S., Elnitski, L., Idol, J. R., Prasad, A B., Lee-Lin, S. Q., Maduro, V. V., Summers, T. J., Portnoy, M. E., Dietrich, N. L., Akhter, N., Ayele, K., Benjamin, B., Cariaga, K., Brinkley, e.P., Brooks, S. Y., Granite, S., Guan, X., Gupta, J., Haghighi, P., Ho, S. L., Huang, M. C., Karlins, E., Laric, P L., Legaspi, R., Lim, M. J., Maduro, Q. L., Masiello, C. A, Mastrian, S. D., McCloskey, J. C., Pearson, R., Stantripop, S., Tiongson, E. E., Tran, J. T., Tsurgeon, C., Vogt, J. L., Walker, M. A, Wetherby, K. D., Wiggins, L. S., Young, A C., Zhang, L. H., Osoegawa, K., Zhu, B., Zhao, B., Shu, C. L., Dejong, P. J., Lawrence, C. E., Smit, A. F., Chakravarti, A, Haussler, D., Green, P., Miller, W., and Green, E. D. (2003). Comparative analyses of multi-species sequences from targeted genomic regions. Nature, 424:788-793.

Trifonov, E. N. (1989). The multiple codes of nucleotide sequences. Bull Math Biol., 51:417-432.

Trifonov, E. N., Konopka, A K., and Jovin, T. M. (1985). Unusual frequencies of certain alternating purine-pyrinidine runs in natural DNA sequences: relation to Z-DNA FEBS Lett., 185:197-202.

Turker, M. S., and Bestor, T. H. (1997), Formation of methylation patterns in the mammalian genome. Mutat Res., 386: 119-130.

Ulanovsky, L. E., and Trifonov, E. N. (1987). Estimation of wedge components in curved DNA Nature, 326:720-722.

VanWye, J. D., Bronson, E.e., and Anderson, J. N. (1991). Species-specific patterns of DNA bending and sequence. Nucleic Acids Res., 19:5253-5261.

Velculescu, V. E., Zhang, L., Vogelstein, B., and Kinzler, K W. (I 995). Serial analysis of gene expression. Science, 270: 484-487.

Wheeler, D. L., Barrett, T., Benson, D. A., Bryant, S. H., Canese, K, Church, D. M., DiCuccio, M., Edgar, R., Federhen, S., Helmberg, W., Kenton, D. L., Khovayko, O., Lipman, D. I, Madden, T. L., Maglott, D. R., Ostell, J., Pontius, J. U., Pruitt, K. D., Schuler, G. D., Schriml, L. M., Sequeira, E., Sherry, S. T., Sirotkin, K, Starchenko, G., Suzek, T. O., Tatusov, R., Tatusova, T. A., Wagner, L., and Yaschenko, E. (2005) Database resources of the National Center for Biotechnology Information. Nucleic Acids Res., 33:D39-D45.

Widom, J. (1992). A relationship between the helical twist of DNA and the ordered positioning of nucleosomes in all eukaryotic cells. Proc Natl Acad Sci USA, 89: 1095-1099.

Widom, J. (1996). Short-range order in two eukaryotic genomes: relation to chromosome structure. J Mol Biol., 259:579-588.

The invention claimed is:

1. A DNA molecule encoding green fluorescent protein (GFP), the DNA molecule being double stranded with one strand comprising a coding sequence encoding the GFP with the coding sequence being interrupted by at least one synthetic intron, wherein the at least one synthetic intron is at least 20 bases in length and comprises at least two consecutive inserts that are 10 to 11 bases in length, wherein the inserts are on the same DNA strand as the strand encoding the GFP and comprise a sequence of 2-5 consecutive bases of adenine (A) and/or thymine (T).

2. The DNA molecule of claim 1, wherein at least one of the at least one synthetic introns comprises at least three consecutive inserts of 10 or 11 bases in length.

3. The DNA molecule of claim 2, wherein at least one of the at least one synthetic introns is 90 bases in length or less.

4. The DNA molecule of claim 3, wherein the coding sequence that encodes the GFP is interrupted by 2, 3, 4, 5, 6, 7, 8, 9 or 10 synthetic introns.

5. The DNA molecule of claim 1, wherein at least one of the at least one synthetic introns comprises the nucleotide sequence of SEQ ID NO: 8.

6. The DNA molecule of claim 5, wherein the DNA molecule comprises a nucleotide sequence that is at least 80% identical to the nucleotide sequence of SEQ ID NO:2.

7. The DNA molecule of claim 6, wherein the DNA molecule comprises the nucleotide sequence of SEQ ID NO:2.

8. The DNA molecule of claim 1, wherein the DNA molecule is contained in an expression vector.

9. The DNA molecule of claim 8, wherein the expression vector is adenovirus vector.

10. The DNA molecule of claim 8, wherein the expression vector comprises a constitutive promoter.

11. The DNA molecule of claim 8, wherein the expression vector comprises an inducible promoter.

12. The DNA molecule of claim 8, wherein the expression vector is contained within a eukaryotic cell.

13. The DNA molecule of claim 8, wherein the expression vector comprises a nucleic acid sequence that is at least 80% identical to the nucleic acid sequence of SEQ ID NO:12.

14. The DNA molecule of claim 13, wherein the expression vector comprises the nucleic acid sequence of SEQ ID NO:12.

15. A method of expressing green fluorescent protein (GFP) in a eukaryotic cell, the method comprising:
   a) introducing into the eukaryotic cell a DNA molecule encoding green fluorescent protein (GFP), the DNA molecule being double stranded with one strand comprising a coding sequence encoding the GFP with the coding sequence being interrupted by least one synthetic intron, wherein the at least one synthetic intron is at least 20 bases in length and comprises at least two consecutive inserts that are 10 to 11 bases in length, wherein the inserts are on the same DNA molecule strand as the strand encoding the GFP and comprise a sequence of 2-5 consecutive bases of adenine (A) and/or thymine (T), and
   b) providing conditions to the eukaryotic cell that are suitable for protein expression, wherein the eukaryotic cell expresses the GFP.

16. The method of claim 15, wherein the GFP is expressed longer than standard humanized GFP.

17. The method of claim 15, wherein the at least one synthetic intron of the introduced DNA molecule comprises at least three consecutive inserts of 10 or 11 bases in length.

18. The method of claim 15, wherein the at least one synthetic intron in the introduced DNA molecule is 90 bases in length or less.

19. The method of claim 15, wherein the coding sequence that encodes the GFP in the introduced DNA molecule is interrupted by 2, 3, 4, 5, 6, 7, 8, 9 or 10 synthetic introns.

20. The method of claim 15, wherein at least one of the at least one synthetic introns of the introduced DNA molecule comprises the nucleotide sequence of SEQ ID NO: 8.

21. The method of claim 15, wherein the introduced DNA molecule comprises a nucleic acid sequence at least 80% identical to nucleic acid sequence of SEQ ID NO:2.

22. The method of claim 21, wherein the introduced DNA molecule comprises the nucleic acid sequence of SEQ ID NO:2.

23. The method of claim 15, wherein the introduced DNA molecule is contained in an expression vector.

24. The method of claim 23, wherein the expression vector comprises a nucleic acid sequence that is at least 80% identical to the nucleic acid sequence of SEQ ID NO:12.

25. The method of claim 24, wherein the expression vector comprises the nucleic acid sequence of SEQ ID NO:12.

26. The method of claim 24, wherein the expression vector is an adenovirus vector.

27. The method of claim 26, wherein the expression vector comprises a constitutive promoter.

28. The method of claim 23, wherein the expression vector comprises an inducible promoter.

* * * * *